(12) United States Patent
Stone et al.

(10) Patent No.: US 11,612,391 B2
(45) Date of Patent: Mar. 28, 2023

(54) SOFT TISSUE REPAIR DEVICE AND ASSOCIATED METHODS

(71) Applicant: Biomet Sports Medicine, LLC, Warsaw, IN (US)

(72) Inventors: Kevin T. Stone, Winona Lake, IN (US); Ryan A. Kaiser, Leesburg, IN (US); Nathan M. Sautter, North Manchester, IN (US); Andrew Holst, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 507 days.

(21) Appl. No.: 16/806,611

(22) Filed: Mar. 2, 2020

(65) Prior Publication Data
US 2020/0197002 A1 Jun. 25, 2020

Related U.S. Application Data

(60) Continuation of application No. 15/412,676, filed on Jan. 23, 2017, now abandoned, which is a
(Continued)

(51) Int. Cl.
*A61B 17/04* (2006.01)
*A61B 90/00* (2016.01)
(Continued)

(52) U.S. Cl.
CPC .......... *A61B 17/0483* (2013.01); *A61B 17/04* (2013.01); *A61B 17/0401* (2013.01);
(Continued)

(58) Field of Classification Search
CPC ............ A61B 17/0401; A61B 17/0469; A61B 17/0482; A61B 17/04; A61B 17/0483;
(Continued)

(56) References Cited

U.S. PATENT DOCUMENTS

| 26,501 A | 12/1859 | Kendrick et al. |
| 64,499 A | 5/1867 | Daubert |

(Continued)

FOREIGN PATENT DOCUMENTS

| AU | 4957264 A | 3/1966 |
| AU | 440266 A1 | 10/1967 |

(Continued)

OTHER PUBLICATIONS

US 6,238,418 B1, 05/2001, Schwartz (withdrawn)
(Continued)

*Primary Examiner* — Dianne Dornbusch
(74) *Attorney, Agent, or Firm* — Schwegman Lundberg & Woessner, P.A.

(57) ABSTRACT

A fibrous tissue repair device includes first and second tubular anchors having corresponding longitudinal passages. The tissue repair device includes corresponding first and second inserters. Each inserter has a shaft with a distal portion received in the longitudinal passage of the corresponding tubular anchor. A flexible strand couples the first and second anchors.

24 Claims, 29 Drawing Sheets

Related U.S. Application Data continuation of application No. 13/833,567, filed on Mar. 15, 2013, now Pat. No. 9,561,025, which is a continuation of application No. 13/721,970, filed on Dec. 20, 2012, now Pat. No. 8,632,569, which is a division of application No. 13/045,689, filed on Mar. 11, 2011, now Pat. No. 8,337,525, which is a division of application No. 12/014,340, filed on Jan. 15, 2008, now Pat. No. 7,905,904.

(51) Int. Cl.
  *A61B 17/06* (2006.01)
  *A61B 17/064* (2006.01)

(52) U.S. Cl.
  CPC ...... *A61B 17/0469* (2013.01); *A61B 17/0482* (2013.01); *A61B 17/0485* (2013.01); *A61B 17/0493* (2013.01); *A61B 2017/042* (2013.01); *A61B 2017/0404* (2013.01); *A61B 2017/0406* (2013.01); *A61B 2017/0409* (2013.01); *A61B 2017/0414* (2013.01); *A61B 2017/0445* (2013.01); *A61B 2017/0472* (2013.01); *A61B 2017/0475* (2013.01); *A61B 2017/0496* (2013.01); *A61B 2017/0646* (2013.01); *A61B 2017/06052* (2013.01); *A61B 2090/036* (2016.02)

(58) Field of Classification Search
  CPC ............ A61B 17/0485; A61B 17/0493; A61B 17/0642; A61B 17/06109; A61B 2017/0406; A61B 2017/0417; A61B 2017/2923; A61B 2017/0464; A61B 2017/042; A61B 2017/0438; A61B 2017/0445; A61B 2017/0409; A61B 2017/0469; A61B 2017/0472; A61B 2017/0488; A61B 2017/06052; A61F 2/0811; A61F 2/0817
  See application file for complete search history.

(56) References Cited

U.S. PATENT DOCUMENTS

| | | | |
|---|---|---|---|
| 65,499 A | 6/1867 | Milter |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A | 11/1885 | Binns |
| 394,739 A | 12/1888 | Toulmin |
| 401,677 A | 4/1889 | Autenrieth |
| 417,805 A | 12/1889 | Beaman |
| 445,875 A | 2/1891 | Brickell |
| 487,304 A | 12/1892 | Todd |
| 687,221 A | 11/1901 | Gaff et al. |
| 762,710 A | 6/1904 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,505,470 A | 8/1924 | Kelm |
| 1,635,066 A | 7/1927 | Wells |
| 1,950,799 A | 3/1934 | Jones |
| 2,042,403 A | 5/1936 | Hrivnak |
| 2,065,659 A | 12/1936 | Cullen |
| 2,108,206 A | 2/1938 | Meeker |
| 2,121,193 A | 6/1938 | Erich |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,379,629 A | 7/1945 | Eweson |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Thomas |
| 2,549,382 A | 4/1951 | Mitterway |
| 2,562,419 A | 7/1951 | Ferris |
| 2,581,564 A | 1/1952 | Jaime |
| 2,600,395 A | 6/1952 | Joseph et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Moe |
| 2,860,393 A | 11/1958 | Brook |
| 2,880,728 A | 4/1959 | Rights |
| 2,881,762 A | 4/1959 | Lowrie |
| 2,883,096 A | 4/1959 | Horace |
| 2,913,042 A | 11/1959 | John |
| 2,947,504 A | 8/1960 | Ruhlman |
| 3,000,009 A | 9/1961 | Selstad |
| 3,003,155 A | 10/1961 | Mieizynski |
| 3,013,559 A | 12/1961 | Thomas |
| 3,037,619 A | 6/1962 | Ernest |
| 3,039,460 A | 6/1962 | Chandler |
| 3,081,781 A | 3/1963 | Stermer |
| 3,090,386 A | 5/1963 | William |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,223,083 A | 12/1965 | Cobey |
| 3,234,938 A | 2/1966 | Robinson |
| 3,240,379 A | 3/1966 | Bremer et al. |
| 3,250,271 A | 5/1966 | Jack |
| 3,399,432 A | 9/1968 | Merser |
| 3,409,014 A | 11/1968 | Grant |
| RE26,501 E | 12/1968 | Himmeistein et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | Mcknight |
| 3,522,803 A | 8/1970 | Majzlln |
| 3,527,223 A | 9/1970 | Shein |
| 3,533,406 A | 10/1970 | Tatum |
| 3,541,591 A | 11/1970 | Hoegerman |
| 3,545,008 A | 12/1970 | Bader, Jr. |
| 3,547,389 A | 12/1970 | Mitchell |
| 3,579,831 A | 5/1971 | Stevens et al. |
| 3,590,616 A | 7/1971 | Schussler |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,650,274 A | 3/1972 | Edwards et al. |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |

(56) References Cited

U.S. PATENT DOCUMENTS

| | | |
|---|---|---|
| 3,786,801 A | 1/1974 | Sartorius |
| 3,802,438 A | 4/1974 | Wolvek |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,896,810 A | 7/1975 | Akiyama |
| 3,907,442 A | 9/1975 | Reid |
| 3,910,281 A | 10/1975 | Kletschka |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,949,755 A | 4/1976 | Vauquois |
| 3,953,896 A | 5/1976 | Treace |
| 3,954,103 A | 5/1976 | Garcia-roel et al. |
| 3,961,632 A | 6/1976 | Moossun |
| 3,973,560 A | 8/1976 | Emmett |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | Mcgrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes |
| 4,144,876 A | 3/1979 | Deleo |
| 4,146,022 A | 3/1979 | Johnson et al. |
| 4,149,277 A | 4/1979 | Bokros |
| 4,157,714 A | 6/1979 | Foltz et al. |
| 4,158,250 A | 6/1979 | Ringwald |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert |
| 4,185,636 A | 1/1980 | Gabbay et al. |
| 4,196,883 A | 4/1980 | Einhorn et al. |
| 4,207,627 A | 6/1980 | Cloutier |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser |
| 4,275,490 A | 6/1981 | Bivins |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,302,397 A | 11/1981 | Frainier et al. |
| 4,307,723 A | 12/1981 | Finney |
| 4,312,337 A | 1/1982 | Donohue |
| 4,316,469 A | 2/1982 | Kapitanov |
| 4,319,428 A | 3/1982 | Fox |
| 4,326,531 A | 4/1982 | Shimonaka |
| 4,344,193 A | 8/1982 | Kenny |
| 4,345,601 A | 8/1982 | Fukuda |
| 4,349,027 A | 9/1982 | Difrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland et al. |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A | 12/1984 | Massari et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,597,766 A | 7/1986 | Hilal et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | Mcgarry et al. |
| 4,632,100 A | 12/1986 | Somers et al. |
| 4,635,637 A | 1/1987 | Schreiber |
| 4,636,121 A | 1/1987 | Miller |
| 4,640,271 A | 2/1987 | Lower |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maaie |
| 4,653,489 A | 3/1987 | Tronzo |
| 4,655,771 A | 4/1987 | Wallsten |
| 4,655,777 A | 4/1987 | Dunn |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |

(56) References Cited

U.S. PATENT DOCUMENTS

| | | |
|---|---|---|
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,711,639 A | 12/1987 | Grundei |
| 4,714,474 A | 12/1987 | Brooks, Jr. et al. |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,329 A | 3/1988 | Mansat |
| 4,728,332 A | 3/1988 | Albrektsson |
| 4,730,615 A | 3/1988 | Sutherland et al. |
| 4,736,746 A | 4/1988 | Anderson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | Mcfarland |
| 4,744,793 A | 5/1988 | Parr et al. |
| 4,750,492 A | 6/1988 | Jacobs |
| 4,751,922 A | 6/1988 | Dipietropolo |
| 4,754,685 A | 7/1988 | Kite et al. |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hansiik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,779,372 A | 10/1988 | Pozo Obeso |
| 4,781,190 A | 11/1988 | Lee |
| 4,784,126 A | 11/1988 | Hourahane |
| 4,787,882 A | 11/1988 | Claren |
| 4,790,297 A | 12/1988 | Luque |
| 4,790,850 A | 12/1988 | Dunn et al. |
| 4,793,363 A | 12/1988 | Ausherman et al. |
| 4,795,468 A | 1/1989 | Hodorek et al. |
| 4,809,695 A | 3/1989 | Gwathmey et al. |
| 4,813,406 A | 3/1989 | Ogle, II |
| 4,813,416 A | 3/1989 | Pollak et al. |
| 4,823,780 A | 4/1989 | Odensten et al. |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,836,080 A | 6/1989 | Kite, III et al. |
| 4,838,282 A | 6/1989 | Strasser et al. |
| 4,841,960 A | 6/1989 | Garner |
| 4,846,835 A | 7/1989 | Grande |
| 4,851,005 A | 7/1989 | Hunt et al. |
| 4,858,601 A | 8/1989 | Glisson |
| 4,858,603 A | 8/1989 | Clemow et al. |
| 4,858,608 A | 8/1989 | Mcquilkin |
| 4,860,513 A | 8/1989 | Whitman |
| 4,863,383 A | 9/1989 | Grafelmann |
| 4,863,471 A | 9/1989 | Mansat |
| 4,870,957 A | 10/1989 | Goble et al. |
| 4,872,450 A | 10/1989 | Austad |
| 4,873,976 A | 10/1989 | Schreiber |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,917,700 A | 4/1990 | Aikins |
| 4,919,667 A | 4/1990 | Richmond |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,467 A | 8/1990 | Ohi et al. |
| 4,946,468 A | 8/1990 | Li |
| 4,950,270 A | 8/1990 | Bowman et al. |
| 4,950,285 A | 8/1990 | Wilk |
| 4,959,069 A | 9/1990 | Brennan et al. |
| 4,960,381 A | 10/1990 | Niznick |
| 4,961,741 A | 10/1990 | Hayhurst |
| 4,962,929 A | 10/1990 | Melton, Jr. |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,974,656 A | 12/1990 | Judkins |
| 4,976,736 A | 12/1990 | White et al. |
| 4,978,350 A | 12/1990 | Wagenknecht |
| 4,979,956 A | 12/1990 | Silvestrini |
| 4,983,176 A | 1/1991 | Cushman et al. |
| 4,983,184 A | 1/1991 | Steinemann |
| 4,983,240 A | 1/1991 | Orkin et al. |
| 4,988,351 A | 1/1991 | Paulos et al. |
| 4,994,074 A | 2/1991 | Bezwada et al. |
| 4,997,433 A | 3/1991 | Goble et al. |
| 5,002,545 A | 3/1991 | Whiteside et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,019,093 A | 5/1991 | Kaplan et al. |
| 5,020,713 A | 6/1991 | Kunreuther |
| 5,026,398 A | 6/1991 | May et al. |
| 5,028,569 A | 7/1991 | Cihon |
| 5,030,224 A | 7/1991 | Wright |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,067,962 A | 11/1991 | Campbell et al. |
| 5,071,420 A | 12/1991 | Paulos et al. |
| 5,074,874 A | 12/1991 | Yoon, Inbae et al. |
| 5,078,731 A | 1/1992 | Hayhurst |
| 5,078,843 A | 1/1992 | Pratt |
| 5,080,050 A | 1/1992 | Dale |
| 5,080,675 A | 1/1992 | Lawes et al. |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,727 A | 3/1992 | Moghe |
| 5,092,866 A | 3/1992 | Breard et al. |
| 5,098,433 A | 3/1992 | Freedland |
| 5,098,435 A | 3/1992 | Stednitz |
| 5,100,415 A | 3/1992 | Hayhurst |
| 5,100,417 A | 3/1992 | Cerier |
| 5,108,433 A | 4/1992 | May et al. |
| 5,112,335 A | 5/1992 | Laboureau et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |

(56) References Cited

U.S. PATENT DOCUMENTS

| | | |
|---|---|---|
| 5,123,914 A | 6/1992 | Cope |
| 5,127,783 A | 7/1992 | Moghe et al. |
| 5,127,785 A | 7/1992 | Faucher |
| 5,129,901 A | 7/1992 | Decoste |
| 5,129,902 A | 7/1992 | Goble et al. |
| 5,129,904 A | 7/1992 | Illi |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,171,274 A | 12/1992 | Fluckiger et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,217,495 A | 6/1993 | Kaplan et al. |
| 5,219,359 A | 6/1993 | McQuilkin et al. |
| 5,222,976 A | 6/1993 | Yoon |
| 5,224,940 A | 7/1993 | Dann et al. |
| 5,224,946 A | 7/1993 | Hayhurst et al. |
| 5,226,914 A | 7/1993 | Caplan et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | Dipoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,282,868 A | 2/1994 | Bahler |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,330,534 A | 7/1994 | Herrington et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,344,460 A | 9/1994 | Turanyi et al. |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,354,299 A | 10/1994 | Coleman |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,358,530 A | 10/1994 | Hodorek |
| 5,358,531 A | 10/1994 | Goodfellow et al. |
| 5,360,431 A | 11/1994 | Puno et al. |
| 5,362,294 A | 11/1994 | Seitzinger |
| 5,362,911 A | 11/1994 | Cevasco et al. |
| 5,364,400 A | 11/1994 | Rego, Jr. et al. |
| 5,366,461 A | 11/1994 | Blasnik |
| 5,368,599 A | 11/1994 | Hirsch et al. |
| 5,370,646 A | 12/1994 | Reese et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,376,118 A | 12/1994 | Kaplan et al. |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | De La Torre |
| 5,391,182 A | 2/1995 | Chin |
| 5,393,302 A | 2/1995 | Clark et al. |
| RE34,871 E | 3/1995 | Mcguire et al. |
| 5,395,374 A | 3/1995 | Miller et al. |
| 5,395,401 A | 3/1995 | Bahler |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,824 A | 6/1995 | Akerfeldt et al. |
| 5,423,860 A | 6/1995 | Lizardi et al. |
| 5,425,733 A | 6/1995 | Schmieding |
| 5,425,766 A | 6/1995 | Bowald |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |

(56) References Cited

U.S. PATENT DOCUMENTS

| | | |
|---|---|---|
| 5,443,468 A | 8/1995 | Johnson |
| 5,443,482 A | 8/1995 | Stone et al. |
| 5,443,483 A | 8/1995 | Kirsch |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,721 A | 10/1995 | Legrand |
| 5,456,722 A | 10/1995 | Mcleod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,470,354 A | 11/1995 | Hershberger et al. |
| 5,472,452 A | 12/1995 | Trott |
| 5,474,565 A | 12/1995 | Trott |
| 5,474,568 A | 12/1995 | Scott et al. |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,480,446 A | 1/1996 | Goodfellow et al. |
| 5,484,442 A | 1/1996 | Melker et al. |
| 5,486,197 A | 1/1996 | Le et al. |
| 5,486,359 A | 1/1996 | Caplan et al. |
| 5,489,210 A | 2/1996 | Hanosh |
| 5,490,750 A | 2/1996 | Gundy |
| 5,495,974 A | 3/1996 | Deschenes et al. |
| 5,496,290 A | 3/1996 | Ackerman |
| 5,496,331 A | 3/1996 | Xu et al. |
| 5,496,348 A | 3/1996 | Bonutti |
| 5,498,302 A | 3/1996 | Davidson |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,514,059 A | 5/1996 | Romney |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,011 A | 7/1996 | Greene, Jr. et al. |
| 5,534,012 A | 7/1996 | Bonutti |
| 5,534,033 A | 7/1996 | Simpson |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,664 A | 10/1996 | Duriacher et al. |
| 5,562,668 A | 10/1996 | Johnson |
| 5,562,669 A | 10/1996 | Mcguire |
| 5,562,683 A | 10/1996 | Chan |
| 5,562,685 A | 10/1996 | Mollenauer et al. |
| 5,562,686 A | 10/1996 | Sauer et al. |
| 5,569,252 A | 10/1996 | Justin et al. |
| 5,569,269 A | 10/1996 | Hart et al. |
| 5,569,305 A | 10/1996 | Bonutti |
| 5,569,306 A | 10/1996 | Thal |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,547 A | 11/1996 | LeVeen et al. |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,745 A | 5/1997 | Schwartz |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | Mcdevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A | 7/1997 | Pavletic |
| 5,649,963 A | 7/1997 | Mcdevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,677 A | 9/1997 | Wimmer |
| 5,662,681 A | 9/1997 | Nash et al. |
| 5,665,112 A | 9/1997 | Thai |
| 5,667,513 A | 9/1997 | Torrie et al. |

(56) References Cited

U.S. PATENT DOCUMENTS

| | | |
|---|---|---|
| 5,671,695 A | 9/1997 | Schroeder |
| 5,673,546 A | 10/1997 | Abraham et al. |
| 5,674,224 A | 10/1997 | Howell et al. |
| 5,679,723 A | 10/1997 | Cooper |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada |
| 5,690,655 A | 11/1997 | Hart et al. |
| 5,690,676 A | 11/1997 | Dipoto et al. |
| 5,690,678 A | 11/1997 | Johnson |
| 5,693,046 A | 12/1997 | Songer et al. |
| 5,695,497 A | 12/1997 | Stahelin |
| 5,697,929 A | 12/1997 | Mellinger |
| 5,697,969 A | 12/1997 | Schmitt et al. |
| 5,699,657 A | 12/1997 | Paulson |
| 5,700,277 A | 12/1997 | Nash et al. |
| 5,702,397 A | 12/1997 | Goble et al. |
| 5,702,422 A | 12/1997 | Stone |
| 5,702,462 A | 12/1997 | Oberlander |
| 5,702,464 A | 12/1997 | Lackey et al. |
| 5,707,373 A | 1/1998 | Sevrain et al. |
| 5,709,708 A | 1/1998 | Thal et al. |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,716,616 A | 2/1998 | Prockop et al. |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,723,331 A | 3/1998 | Tubo et al. |
| 5,725,529 A | 3/1998 | Nicholson et al. |
| 5,725,549 A | 3/1998 | Lam |
| 5,725,556 A | 3/1998 | Moser et al. |
| 5,725,557 A | 3/1998 | Gatturna et al. |
| 5,725,581 A | 3/1998 | Branemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | De La Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,776,200 A | 7/1998 | Johnson et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,782,925 A | 7/1998 | Collazo et al. |
| 5,785,714 A | 7/1998 | Morgan et al. |
| 5,786,217 A | 7/1998 | Tubo et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor |
| 5,800,447 A | 9/1998 | Wenstrom, Jr. |
| 5,800,543 A | 9/1998 | Mcleod et al. |
| 5,810,824 A | 9/1998 | Chan |
| 5,810,848 A | 9/1998 | Hayhurst |
| 5,811,094 A | 9/1998 | Caplan et al. |
| 5,814,056 A | 9/1998 | Prosst et al. |
| 5,814,069 A | 9/1998 | Schulze et al. |
| 5,814,070 A | 9/1998 | Borzone et al. |
| 5,814,071 A | 9/1998 | Mcdevitt et al. |
| 5,814,072 A | 9/1998 | Bonutti |
| 5,814,073 A | 9/1998 | Bonutti |
| 5,817,095 A | 10/1998 | Smith |
| 5,823,980 A | 10/1998 | Kopfer |
| 5,824,011 A | 10/1998 | Stone et al. |
| 5,824,066 A | 10/1998 | Gross |
| 5,827,285 A | 10/1998 | Bramlet |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,947 A | 1/1999 | Stamler |
| 5,860,973 A | 1/1999 | Michelson |
| 5,860,978 A | 1/1999 | Mcdevitt et al. |
| 5,868,740 A | 2/1999 | LaVeen et al. |
| 5,868,748 A | 2/1999 | Burke |
| 5,868,789 A | 2/1999 | Huebner |
| 5,871,456 A | 2/1999 | Armstrong et al. |
| 5,871,484 A | 2/1999 | Spievack et al. |
| 5,871,486 A | 2/1999 | Huebner |
| 5,871,490 A | 2/1999 | Schulze et al. |
| 5,871,542 A | 2/1999 | Goodfellow et al. |
| 5,871,543 A | 2/1999 | Hofmann |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,920 A | 5/1999 | Desatnick et al. |
| 5,899,938 A | 5/1999 | Sklar et al. |
| 5,906,934 A | 5/1999 | Grande et al. |
| 5,908,421 A | 6/1999 | Beger |
| 5,908,436 A | 6/1999 | Cuschieri et al. |
| 5,910,148 A | 6/1999 | Reimels et al. |
| 5,911,721 A | 6/1999 | Nicholson et al. |
| 5,916,557 A | 6/1999 | Berlowitz-tarrant et al. |
| 5,918,604 A | 7/1999 | Whelan |
| 5,919,232 A | 7/1999 | Chaffringeon et al. |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| 5,928,286 A | 7/1999 | Ashby et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,129 A | 8/1999 | Mcdevitt et al. |
| 5,935,133 A | 8/1999 | Wagner et al. |
| 5,935,134 A | 8/1999 | Pedlick et al. |
| 5,935,149 A | 8/1999 | Ek |

(56) References Cited

U.S. PATENT DOCUMENTS

| | | |
|---|---|---|
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Ciark |
| 5,957,953 A | 9/1999 | Dipoto et al. |
| 5,961,520 A | 10/1999 | Beck, Jr. et al. |
| 5,961,521 A | 10/1999 | Roger |
| 5,961,524 A | 10/1999 | Crombie |
| 5,963,869 A | 10/1999 | Fehnel |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,964,808 A | 10/1999 | Blaha et al. |
| 5,968,045 A | 10/1999 | Frazier |
| 5,968,047 A | 10/1999 | Reed |
| 5,968,077 A | 10/1999 | Wojciechowicz et al. |
| 5,968,078 A | 10/1999 | Grotz |
| 5,968,099 A | 10/1999 | Badorf et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A | 11/1999 | Evans et al. |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,989,294 A | 11/1999 | Marlow |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,004,351 A | 12/1999 | Tomita et al. |
| 6,004,352 A | 12/1999 | Buni |
| 6,007,538 A | 12/1999 | Levin |
| 6,007,567 A | 12/1999 | Bonutti |
| 6,010,525 A | 1/2000 | Bonutti et al. |
| 6,013,103 A | 1/2000 | Kaufman et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,023,661 A | 2/2000 | Sottery |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,036,695 A | 3/2000 | Smith |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,146 A | 5/2000 | Carroll et al. |
| 6,066,173 A | 5/2000 | Mckernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,083,257 A | 7/2000 | Taylor et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan et al. |
| 6,110,128 A | 8/2000 | Andelin et al. |
| 6,110,207 A | 8/2000 | Eichhorn et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,127,596 A | 10/2000 | Brown et al. |
| 6,132,433 A | 10/2000 | Whelan |
| 6,132,437 A | 10/2000 | Omurtag |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,150,163 A | 11/2000 | McPherson et al. |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,174,324 B1 | 1/2001 | Egan et al. |
| 6,179,840 B1 | 1/2001 | Bowman |
| 6,183,461 B1 | 2/2001 | Matsuura et al. |
| 6,183,737 B1 | 2/2001 | Zaleske et al. |
| 6,187,025 B1 | 2/2001 | Machek |
| 6,190,348 B1 | 2/2001 | Tiemann |
| 6,190,401 B1 | 2/2001 | Green et al. |
| 6,190,411 B1 | 2/2001 | Lo |
| 6,190,415 B1 | 2/2001 | Cooke et al. |
| 6,193,754 B1 | 2/2001 | Seedhom |
| 6,200,318 B1 | 3/2001 | Har-shai et al. |
| 6,200,329 B1 | 3/2001 | Fung et al. |
| 6,200,330 B1 | 3/2001 | Benderev et al. |
| 6,200,606 B1 | 3/2001 | Peterson et al. |
| 6,200,685 B1 | 3/2001 | Davidson |
| 6,203,556 B1 | 3/2001 | Evans et al. |
| 6,203,563 B1 | 3/2001 | Fernandez |
| 6,203,565 B1 | 3/2001 | Bonutti et al. |
| 6,203,572 B1 | 3/2001 | Johnson et al. |
| 6,203,576 B1 | 3/2001 | Afriat et al. |

(56) References Cited

U.S. PATENT DOCUMENTS

| | | |
|---|---|---|
| 6,206,883 B1 | 3/2001 | Tunc |
| 6,210,376 B1 | 4/2001 | Grayson |
| 6,210,381 B1 | 4/2001 | Morse |
| 6,210,445 B1 | 4/2001 | Zawadzki |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner |
| 6,228,096 B1 | 5/2001 | Marchand |
| 6,231,592 B1 | 5/2001 | Bonutti et al. |
| 6,234,980 B1 | 5/2001 | Bell |
| 6,235,057 B1 | 5/2001 | Roger et al. |
| 6,235,058 B1 | 5/2001 | Huene |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,024 B1 | 6/2001 | Montagnino et al. |
| 6,245,081 B1 | 6/2001 | Bowman |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,929 B1 | 9/2001 | Smith et al. |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,302,915 B1 | 10/2001 | Cooney, III et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,124 B1 | 10/2001 | Gueret |
| 6,309,405 B1 | 10/2001 | Bonutti |
| 6,312,448 B1 | 11/2001 | Bonutti |
| 6,315,788 B1 | 11/2001 | Roby |
| 6,319,224 B1 | 11/2001 | Stout et al. |
| 6,319,271 B1 | 11/2001 | Schwartz et al. |
| 6,328,758 B1 | 12/2001 | Tornier et al. |
| 6,334,064 B1 | 12/2001 | Fiddian-green |
| 6,342,060 B1 | 1/2002 | Adams |
| 6,343,531 B2 | 2/2002 | Amis |
| 6,355,066 B1 | 3/2002 | Kim et al. |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,111 B1 | 5/2002 | Barber |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,456 B1 | 6/2002 | Slate et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,425,924 B1 | 7/2002 | Rousseau |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,458,161 B1 | 10/2002 | Gibbs et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| 6,500,208 B1 | 12/2002 | Metzger et al. |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | Mcdevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'addario |
| 6,544,281 B2 | 4/2003 | Elattrache et al. |
| 6,547,564 B1 | 4/2003 | Hansson |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,551,353 B1 | 4/2003 | Baker et al. |
| 6,553,802 B1 | 4/2003 | Jacob |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Järvinen |
| 6,565,572 B2 | 5/2003 | Chappius |
| 6,565,573 B1 | 5/2003 | Ferrante |
| 6,569,167 B1 | 5/2003 | Bobechko et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,572,655 B1 | 6/2003 | Johnson |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |

(56) References Cited

U.S. PATENT DOCUMENTS

| | | |
|---|---|---|
| 6,592,609 B1 | 7/2003 | Bonutti |
| 6,592,622 B1 | 7/2003 | Ferguson |
| 6,595,911 B2 | 7/2003 | Lovuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,064 B1 | 8/2003 | Gobie et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,626,930 B1 | 9/2003 | Allen et al. |
| 6,629,977 B1 | 10/2003 | Wolf |
| 6,629,997 B2 | 10/2003 | Mansmann |
| 6,632,245 B2 | 10/2003 | Kim |
| 6,635,073 B2 | 10/2003 | Bonutti |
| 6,638,279 B2 | 10/2003 | Bonutti |
| 6,638,286 B1 | 10/2003 | Burbank et al. |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,169 B1 | 11/2003 | Slate et al. |
| 6,645,211 B2 | 11/2003 | Magana |
| 6,645,227 B2 | 11/2003 | Fallin et al. |
| 6,648,903 B1 | 11/2003 | Pierson, III |
| 6,648,921 B2 | 11/2003 | Anderson et al. |
| 6,652,450 B2 | 11/2003 | Neisz et al. |
| 6,652,533 B2 | 11/2003 | O'neil |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,669,707 B1 | 12/2003 | Swanstrom et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,712,859 B2 | 3/2004 | Rousseau |
| 6,716,190 B1 | 4/2004 | Glines et al. |
| 6,716,224 B1 | 4/2004 | Singhatat |
| 6,716,234 B2 | 4/2004 | Grafton et al. |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,780 B2 | 6/2004 | Stout et al. |
| 6,752,810 B1 | 6/2004 | Gao et al. |
| 6,752,831 B2 | 6/2004 | Sybert et al. |
| 6,755,836 B1 | 6/2004 | Lewis |
| 6,755,868 B2 | 6/2004 | Rousseau |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,790,210 B1 | 9/2004 | Cragg et al. |
| 6,793,595 B1 | 9/2004 | Monnet |
| 6,802,862 B1 | 10/2004 | Roger et al. |
| 6,808,502 B2 | 10/2004 | Nguyen |
| 6,808,526 B1 | 10/2004 | Magerl et al. |
| 6,814,741 B2 | 11/2004 | Bowman et al. |
| 6,830,572 B2 | 12/2004 | Mcdevitt et al. |
| 6,833,005 B1 | 12/2004 | Mantas |
| 6,835,377 B2 | 12/2004 | Goldberg et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,243 B2 | 5/2005 | Culbert |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,911,202 B2 | 6/2005 | Amir et al. |
| 6,916,292 B2 | 7/2005 | Morawski et al. |
| 6,916,321 B2 | 7/2005 | Tenhuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,923,832 B1 | 8/2005 | Sharkey et al. |
| 6,939,379 B2 | 9/2005 | Sklar |
| 6,946,001 B2 | 9/2005 | Sanford et al. |
| 6,949,102 B2 | 9/2005 | Andrews |
| 6,951,565 B2 | 10/2005 | Keane et al. |
| 6,960,214 B2 | 11/2005 | Burkinshaw |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,011,682 B2 | 3/2006 | Lashinski et al. |
| 7,033,397 B2 | 4/2006 | Webster et al. |
| 7,048,754 B2 | 5/2006 | Martin et al. |
| 7,052,499 B2 | 5/2006 | Steger et al. |
| 7,060,101 B2 | 6/2006 | O'Connor et al. |
| 7,066,942 B2 | 6/2006 | Treace |
| 7,066,944 B2 | 6/2006 | Laufer et al. |
| 7,081,126 B2 | 7/2006 | Mcdevitt et al. |
| 7,083,638 B2 | 8/2006 | Foerster |
| 7,087,064 B1 | 8/2006 | Hyde |
| 7,087,073 B2 | 8/2006 | Bonutti |
| 7,090,690 B2 | 8/2006 | Foerster et al. |
| 7,097,654 B1 | 8/2006 | Freedland |
| 7,101,395 B2 | 9/2006 | Tremulis et al. |
| 7,105,010 B2 | 9/2006 | Hart et al. |
| 7,105,026 B2 | 9/2006 | Johnson et al. |

(56) References Cited

U.S. PATENT DOCUMENTS

| | | |
|---|---|---|
| 7,112,221 B2 | 9/2006 | Harris |
| 7,118,578 B2 | 10/2006 | West, Jr. et al. |
| 7,118,583 B2 | 10/2006 | O'quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,148,209 B2 | 12/2006 | Hoemann et al. |
| 7,153,127 B2 | 12/2006 | Struble et al. |
| 7,153,307 B2 | 12/2006 | Scribner |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,179,259 B1 | 2/2007 | Gibbs |
| 7,201,722 B2 | 4/2007 | Krueger |
| 7,207,993 B1 | 4/2007 | Baldwin et al. |
| 7,229,441 B2 | 6/2007 | Trieu et al. |
| 7,235,091 B2 | 6/2007 | Thornes |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,291,177 B2 | 11/2007 | Gibbs |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,354,354 B2 | 4/2008 | Palumbo et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,462,198 B2 | 12/2008 | Webster et al. |
| 7,463,198 B2 | 12/2008 | Deaett et al. |
| 7,465,308 B2 | 12/2008 | Sikora et al. |
| 7,468,074 B2 | 12/2008 | Caborn |
| 7,481,814 B1 | 1/2009 | Metzger |
| 7,484,539 B1 | 2/2009 | Huang |
| 7,485,149 B1 | 2/2009 | White |
| 7,494,496 B2 | 2/2009 | Swain et al. |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,517,357 B2 | 4/2009 | Abrams et al. |
| 7,572,275 B2 | 8/2009 | Fallin et al. |
| 7,572,298 B2 | 8/2009 | Roller et al. |
| 7,578,825 B2 | 8/2009 | Huebner |
| 7,585,311 B2 | 9/2009 | Green et al. |
| 7,588,587 B2 | 9/2009 | Barbieri et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 * | 10/2009 | Schaffhausen ..... A61B 17/0401 606/232 |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,686,810 B2 | 3/2010 | West, Jr. et al. |
| 7,691,112 B2 | 4/2010 | Chanduszko et al. |
| 7,695,493 B2 | 4/2010 | Saadat et al. |
| 7,695,503 B1 | 4/2010 | Kaiser |
| 7,703,372 B1 | 4/2010 | Shakespeare |
| 7,713,188 B2 | 5/2010 | Bouffier |
| 7,713,285 B1 | 5/2010 | Stone et al. |
| 7,717,929 B2 | 5/2010 | Failman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,762,942 B2 | 7/2010 | Neisz et al. |
| 7,771,482 B1 | 8/2010 | Karmon |
| 7,776,041 B1 | 8/2010 | Walters |
| 7,780,701 B1 | 8/2010 | Meridew et al. |
| 7,790,945 B1 | 9/2010 | Watson, Jr. |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |
| 7,867,252 B2 | 1/2011 | Criscuolo et al. |
| 7,867,264 B2 | 1/2011 | Mcdevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,896,907 B2 | 3/2011 | Mcdevitt et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,938,847 B2 | 5/2011 | Fanton et al. |
| 7,951,198 B2 | 5/2011 | Sucec et al. |
| 7,955,388 B2 | 6/2011 | Jensen et al. |
| 7,959,650 B2 | 6/2011 | Kaiser et al. |
| 7,976,565 B1 | 7/2011 | Meridew |
| 7,981,140 B2 | 7/2011 | Burkhart |
| 7,998,203 B2 | 8/2011 | Blum |
| 8,034,090 B2 | 10/2011 | Stone et al. |
| 8,062,334 B2 | 11/2011 | Green et al. |
| 8,066,776 B2 | 11/2011 | O'Connor et al. |
| 8,075,574 B2 | 12/2011 | May et al. |
| 8,075,626 B2 | 12/2011 | Dun |
| 8,088,108 B2 | 1/2012 | Kraft |
| 8,088,130 B2 | 1/2012 | Kaiser et al. |
| 8,109,867 B2 | 2/2012 | Rosenblatt |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,118,868 B2 | 2/2012 | May et al. |
| 8,128,658 B2 | 3/2012 | Kaiser et al. |
| 8,137,354 B2 | 3/2012 | Stone |
| 8,137,382 B2 | 3/2012 | Denham et al. |
| 8,137,407 B2 | 3/2012 | Todd et al. |
| 8,142,510 B2 | 3/2012 | Lee et al. |
| 8,147,557 B2 | 4/2012 | Lee et al. |
| 8,147,558 B2 | 4/2012 | Lee et al. |
| 8,162,997 B2 | 4/2012 | Struhl |
| 8,167,906 B2 | 5/2012 | Cauldwell et al. |
| 8,177,810 B2 | 5/2012 | Ferree |
| 8,202,295 B2 | 6/2012 | Kaplan |
| 8,202,318 B2 | 6/2012 | Willobee |
| 8,221,454 B2 | 7/2012 | Schaffhasen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,589 B2 | 11/2012 | Tyber et al. |
| 8,303,604 B2 | 11/2012 | Stone et al. |
| 8,317,825 B2 | 11/2012 | Stone |
| 8,328,806 B2 | 12/2012 | Tyber et al. |
| 8,333,788 B2 | 12/2012 | Maiorino |

(56) References Cited

U.S. PATENT DOCUMENTS

| | | |
|---|---|---|
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,054 B2 | 1/2013 | Ducharme et al. |
| 8,361,113 B2 | 1/2013 | Stone et al. |
| 8,409,253 B2 | 4/2013 | Stone et al. |
| 8,454,635 B2 | 6/2013 | Paolitto et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,545,535 B2 | 10/2013 | Hirotsuka et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,574,235 B2 | 11/2013 | Stone |
| 8,579,901 B1 | 11/2013 | Foerster |
| 8,579,944 B2 | 11/2013 | Holloway et al. |
| 8,591,544 B2 | 11/2013 | Jolly et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,904 B1 | 3/2014 | Schultz |
| 8,672,968 B2 | 3/2014 | Stone et al. |
| 8,672,969 B2 | 3/2014 | Stone et al. |
| 8,702,718 B2 | 4/2014 | Bhatnagar et al. |
| 8,715,297 B1 | 5/2014 | Foerster et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,808,374 B2 | 8/2014 | Eggli |
| 8,814,903 B2 | 8/2014 | Sengun et al. |
| 8,828,067 B2 | 9/2014 | Tipirneni et al. |
| 8,840,645 B2 | 9/2014 | Denham et al. |
| 8,858,642 B2 | 10/2014 | Metzger et al. |
| 8,894,715 B2 | 11/2014 | Metzger et al. |
| 8,900,314 B2 | 12/2014 | Metzger et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,961,548 B2 | 2/2015 | Buser |
| 8,968,364 B2 | 3/2015 | Berelsman |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 | 5/2015 | Jaramillo et al. |
| 9,028,509 B2 | 5/2015 | Chu et al. |
| 9,078,644 B2 | 7/2015 | Stone |
| 9,149,267 B2 | 10/2015 | Norton et al. |
| 9,173,651 B2 | 11/2015 | Stone et al. |
| 9,179,950 B2 | 11/2015 | Zajac et al. |
| 9,198,673 B2 | 12/2015 | Stone |
| 9,216,078 B2 | 12/2015 | Conner et al. |
| 9,271,713 B2 | 3/2016 | Denham et al. |
| 9,271,826 B2 | 3/2016 | Eggli et al. |
| 9,289,285 B2 | 3/2016 | Eggli |
| 9,314,235 B2 | 4/2016 | Bojarski et al. |
| 9,314,241 B2 | 4/2016 | Stone et al. |
| 9,357,991 B2 | 6/2016 | Denham et al. |
| 9,357,992 B2 | 6/2016 | Stone et al. |
| 9,370,350 B2 | 6/2016 | Norton |
| 9,381,013 B2 | 7/2016 | Norton |
| 9,402,621 B2 | 8/2016 | Stone et al. |
| 9,408,599 B2 | 8/2016 | Kaiser et al. |
| 9,414,833 B2 | 8/2016 | Stone et al. |
| 9,414,925 B2 | 8/2016 | Metzger et al. |
| 9,468,433 B2 | 10/2016 | Denham et al. |
| 9,486,211 B2 | 11/2016 | Stone et al. |
| 9,492,158 B2 | 11/2016 | Stone et al. |
| 9,498,204 B2 | 11/2016 | Denham et al. |
| 9,504,460 B2 | 11/2016 | Stone et al. |
| 9,510,819 B2 | 12/2016 | Stone et al. |
| 9,510,821 B2 | 12/2016 | Denham et al. |
| 9,532,777 B2 | 1/2017 | Kaiser et al. |
| 9,538,998 B2 | 1/2017 | Stone et al. |
| 9,539,003 B2 | 1/2017 | Stone et al. |
| 9,561,025 B2 | 2/2017 | Stone et al. |
| 9,572,655 B2 | 2/2017 | Denham |
| 9,585,651 B2 | 3/2017 | Lam et al. |
| 9,603,591 B2 | 3/2017 | Denham et al. |
| 9,622,736 B2 | 4/2017 | Stone et al. |
| 9,642,661 B2 | 5/2017 | Stone et al. |
| 9,681,940 B2 | 6/2017 | Stone et al. |
| 9,724,090 B2 | 8/2017 | Kaiser et al. |
| 9,743,919 B2 | 8/2017 | Manos et al. |
| 9,757,119 B2 | 9/2017 | Norton et al. |
| 9,763,656 B2 | 9/2017 | Stone et al. |
| 9,782,245 B2 | 10/2017 | Mujwid et al. |
| 9,788,876 B2 | 10/2017 | Stone |
| 9,801,620 B2 | 10/2017 | Kaiser et al. |
| 9,801,708 B2 | 10/2017 | Denham et al. |
| 9,833,230 B2 | 12/2017 | Stone |
| 9,861,351 B2 | 1/2018 | Kaiser et al. |
| 9,918,826 B2 | 3/2018 | Berelsman et al. |
| 9,918,827 B2 | 3/2018 | Berelsman et al. |
| 9,993,241 B2 | 6/2018 | Denham et al. |
| 10,004,489 B2 | 6/2018 | Kaiser et al. |
| 10,004,493 B2 | 6/2018 | Stone et al. |
| 10,004,588 B2 | 6/2018 | Berelsman et al. |
| 10,022,118 B2 | 7/2018 | Norton et al. |
| 10,092,288 B2 | 10/2018 | Denham et al. |
| 10,098,629 B2 | 10/2018 | Kaiser et al. |
| 10,154,837 B2 | 12/2018 | Stone et al. |
| 10,167,582 B1 | 1/2019 | Pilgeram et al. |
| 10,251,637 B2 | 4/2019 | Stone et al. |
| 10,265,064 B2 | 4/2019 | Stone et al. |
| 10,265,159 B2 | 4/2019 | Denham et al. |
| 10,321,906 B2 | 6/2019 | Stone et al. |
| 10,349,931 B2 | 7/2019 | Stone |
| 10,363,028 B2 | 7/2019 | Norton |
| 10,368,856 B2 | 8/2019 | Stone et al. |
| 10,398,428 B2 | 9/2019 | Denham et al. |
| 10,398,430 B2 | 9/2019 | Stone et al. |
| 10,441,264 B2 | 10/2019 | Stone et al. |
| 10,517,587 B2 | 12/2019 | Denham et al. |
| 10,517,714 B2 | 12/2019 | Stone et al. |
| 10,542,967 B2 | 1/2020 | Kaiser et al. |
| 10,595,851 B2 | 3/2020 | Kaiser et al. |
| 10,603,029 B2 | 3/2020 | Kaiser et al. |
| 10,610,217 B2 | 4/2020 | Stone et al. |
| 10,675,073 B2 | 6/2020 | Stone et al. |
| 10,687,803 B2 | 6/2020 | Denham et al. |
| 10,695,045 B2 | 6/2020 | Kaiser et al. |
| 10,695,052 B2 | 6/2020 | Denham et al. |
| 10,702,259 B2 | 7/2020 | Stone et al. |
| 10,716,557 B2 | 7/2020 | Denham et al. |
| 10,729,421 B2 | 8/2020 | Stone et al. |
| 10,729,423 B2 | 8/2020 | Kaiser et al. |
| 10,729,430 B2 | 8/2020 | Denham et al. |
| 10,743,925 B2 | 8/2020 | Stone et al. |
| 10,758,221 B2 | 9/2020 | Berelsman et al. |
| 10,835,232 B2 | 11/2020 | Stone et al. |
| 10,932,770 B2 | 3/2021 | Stone et al. |
| 10,973,507 B2 | 4/2021 | Stone et al. |
| 10,987,099 B2 | 4/2021 | Stone et al. |
| 11,039,826 B2 | 6/2021 | Denham et al. |
| 11,065,103 B2 | 7/2021 | Berelsman et al. |
| 11,096,684 B2 | 8/2021 | Stone et al. |
| 11,109,857 B2 | 9/2021 | Stone et al. |
| 11,116,495 B2 | 9/2021 | Stone et al. |
| 11,185,320 B2 | 11/2021 | Kaiser et al. |
| 11,241,305 B2 | 2/2022 | Denham et al. |
| 11,259,792 B2 | 3/2022 | Denham et al. |
| 11,259,794 B2 | 3/2022 | Stone et al. |
| 11,284,884 B2 | 3/2022 | Denham et al. |
| 11,311,287 B2 | 4/2022 | Stone et al. |
| 11,317,907 B2 | 5/2022 | Denham et al. |
| 11,376,115 B2 | 7/2022 | Stone et al. |
| 11,446,019 B2 | 9/2022 | Stone et al. |

(56) References Cited

U.S. PATENT DOCUMENTS

| | | |
|---|---|---|
| 11,471,147 B2 | 10/2022 | Kaiser et al. |
| 2001/0002439 A1 | 5/2001 | Bonutti et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0027341 A1 | 10/2001 | Gianotti |
| 2001/0029387 A1 | 10/2001 | Wolf et al. |
| 2001/0037131 A1 | 11/2001 | Schmieding et al. |
| 2001/0037153 A1 | 11/2001 | Charles, Jr. et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044627 A1 | 11/2001 | Justin |
| 2001/0044639 A1 | 11/2001 | Levinson |
| 2001/0047206 A1 | 11/2001 | Sklar et al. |
| 2001/0051815 A1 | 12/2001 | Esplin |
| 2001/0051816 A1 | 12/2001 | Enzerink et al. |
| 2001/0053934 A1 | 12/2001 | Schmieding |
| 2001/0056299 A1 | 12/2001 | Thompson |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | Elattrache et al. |
| 2002/0019649 A1* | 2/2002 | Sikora ............... A61B 17/0401 606/232 |
| 2002/0029048 A1 | 3/2002 | Miller |
| 2002/0029066 A1 | 3/2002 | Foerster |
| 2002/0032465 A1 | 3/2002 | Lemer |
| 2002/0045902 A1 | 4/2002 | Bonutti |
| 2002/0052628 A1 | 5/2002 | Bowman |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077629 A1 | 6/2002 | Hoffman et al. |
| 2002/0077659 A1 | 6/2002 | Johnson et al. |
| 2002/0082220 A1 | 6/2002 | Hoemann et al. |
| 2002/0091391 A1 | 7/2002 | Cole et al. |
| 2002/0099411 A1 | 7/2002 | Bartlett |
| 2002/0111591 A1 | 8/2002 | Mckinnon et al. |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0050667 A1 | 3/2003 | Grafton et al. |
| 2003/0065361 A1 | 4/2003 | Dreyfuss |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Archibald, III |
| 2003/0088251 A1 | 5/2003 | Braun et al. |
| 2003/0088272 A1 | 5/2003 | Smith |
| 2003/0093156 A1 | 5/2003 | Metzger et al. |
| 2003/0105477 A1 | 6/2003 | Schwartz et al. |
| 2003/0105489 A1 | 6/2003 | Eichhorn et al. |
| 2003/0114929 A1 | 6/2003 | Knudsen |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | Mcdevitt et al. |
| 2003/0135214 A1 | 7/2003 | Fetto |
| 2003/0135239 A1 | 7/2003 | Gabriel et al. |
| 2003/0135265 A1 | 7/2003 | Stinson |
| 2003/0135963 A1 | 7/2003 | Holbrook et al. |
| 2003/0139752 A1 | 7/2003 | Pasricha et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0018751 A1 | 10/2003 | Hyde |
| 2003/0195528 A1 | 10/2003 | Ritchart |
| 2003/0195564 A1 | 10/2003 | Tran et al. |
| 2003/0195565 A1 | 10/2003 | Bonutti |
| 2003/0020821 A1 | 11/2003 | Dreyfuss et al. |
| 2003/0208209 A1 | 11/2003 | Gambale et al. |
| 2003/0212456 A1 | 11/2003 | Lipchitz et al. |
| 2003/0216809 A1 | 11/2003 | Ferguson |
| 2003/0220646 A1 | 11/2003 | Thelen et al. |
| 2003/0220660 A1 | 11/2003 | Kortenbach et al. |
| 2003/0225459 A1 | 12/2003 | Hammer et al. |
| 2003/0229361 A1 | 12/2003 | Jackson |
| 2003/0229396 A1 | 12/2003 | Andrews |
| 2003/0236555 A1 | 12/2003 | Thornes |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0013380 A1 | 1/2004 | Jimenez |
| 2004/0015171 A1 | 1/2004 | Bojarski et al. |
| 2004/0015172 A1 | 1/2004 | Biedermann et al. |
| 2004/0024456 A1 | 2/2004 | Charles, Jr. et al. |
| 2004/0024457 A1 | 2/2004 | Boyce et al. |
| 2004/0039389 A1 | 2/2004 | Hugh, Jr. et al. |
| 2004/0044351 A1 | 3/2004 | Searle |
| 2004/0044391 A1 | 3/2004 | Porter |
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0098099 A1 | 5/2004 | McCullagh et al. |
| 2004/0111117 A1 | 6/2004 | Colleran et al. |
| 2004/0122431 A1 | 6/2004 | Biedermann et al. |
| 2004/0122454 A1 | 6/2004 | Wang et al. |
| 2004/0122456 A1 | 6/2004 | Saadat et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0133238 A1 | 7/2004 | Cerier |
| 2004/0133239 A1 | 7/2004 | Singhatat |
| 2004/0138664 A1 | 7/2004 | Bowman |
| 2004/0138683 A1* | 7/2004 | Shelton ............... A61B 17/0401 606/232 |
| 2004/0138704 A1 | 7/2004 | Gambale et al. |
| 2004/0138706 A1 | 7/2004 | Abrams et al. |
| 2004/0138747 A1 | 7/2004 | Kaladelfos |

(56) References Cited

U.S. PATENT DOCUMENTS

| | | |
|---|---|---|
| 2004/0138755 A1 | 7/2004 | O'connor et al. |
| 2004/0143344 A1 | 7/2004 | Malaviya et al. |
| 2004/0144535 A1 | 7/2004 | Kalman et al. |
| 2004/0147932 A1 | 7/2004 | Burkinshaw et al. |
| 2004/0147958 A1 | 7/2004 | Lam et al. |
| 2004/0148030 A1 | 7/2004 | Ek |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | Mcdevitt et al. |
| 2004/0182968 A1 | 9/2004 | Gentry |
| 2004/0187314 A1 | 9/2004 | Johnson |
| 2004/0193185 A1 | 9/2004 | Mcbrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0230302 A1 | 11/2004 | May et al. |
| 2004/0236353 A1 | 11/2004 | Bain et al. |
| 2004/0236373 A1 | 11/2004 | William, III |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1 | 12/2004 | Hwang et al. |
| 2005/0004670 A1 | 1/2005 | Gebhardt et al. |
| 2005/0021087 A1 | 1/2005 | Koseki |
| 2005/0021148 A1 | 1/2005 | Gibbs |
| 2005/0027307 A1 | 2/2005 | Schwartz et al. |
| 2005/0033289 A1 | 2/2005 | Warren et al. |
| 2005/0033362 A1 | 2/2005 | Grafton |
| 2005/0033363 A1 | 2/2005 | Bojarski et al. |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer, Jr. |
| 2005/0064042 A1 | 3/2005 | Vunjak-novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1 | 4/2005 | Gedebou |
| 2005/0090828 A1 | 4/2005 | Alford |
| 2005/0090862 A1 | 4/2005 | Mcdevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0107882 A1 | 5/2005 | Stone et al. |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0130301 A1 | 6/2005 | Mckay et al. |
| 2005/0131413 A1 | 6/2005 | O'driscoll et al. |
| 2005/0137600 A1 | 6/2005 | Jacobs et al. |
| 2005/0137624 A1 | 6/2005 | Fallman |
| 2005/0143734 A1 | 6/2005 | Cachia et al. |
| 2005/0149033 A1 | 7/2005 | Mcguire et al. |
| 2005/0149118 A1 | 7/2005 | Koyfman et al. |
| 2005/0149119 A1 | 7/2005 | Koyfman et al. |
| 2005/0149122 A1 | 7/2005 | Mcdevitt et al. |
| 2005/0149187 A1 | 7/2005 | Clark et al. |
| 2005/0154471 A1 | 7/2005 | Aram et al. |
| 2005/0159812 A1 | 7/2005 | Dinger, III et al. |
| 2005/0160656 A1 | 7/2005 | Satwat et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0171604 A1 | 8/2005 | Michalow |
| 2005/0177237 A1 | 8/2005 | Shappley et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192581 A1 | 9/2005 | Molz et al. |
| 2005/0192632 A1 | 9/2005 | Geissler et al. |
| 2005/0197711 A1 | 9/2005 | Cachia |
| 2005/0203620 A1 | 9/2005 | Steiner et al. |
| 2005/0209703 A1 | 9/2005 | Fell |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0229433 A1 | 10/2005 | Cachia |
| 2005/0234549 A1 | 10/2005 | Kladakis et al. |
| 2005/0240198 A1 | 10/2005 | Albertson et al. |
| 2005/0025121 A1 | 11/2005 | Westra et al. |
| 2005/0251153 A1 | 11/2005 | Sakamoto et al. |
| 2005/0251159 A1 | 11/2005 | Ewers et al. |
| 2005/0251177 A1 | 11/2005 | Saadat et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0261642 A1 | 11/2005 | Weston |
| 2005/0028871 A1 | 12/2005 | Fallin et al. |
| 2005/0267479 A1 | 12/2005 | Morgan et al. |
| 2005/0267533 A1 | 12/2005 | Gertner |
| 2005/0277088 A1 | 12/2005 | Fischer et al. |
| 2005/0277939 A1 | 12/2005 | Miller, III |
| 2005/0277961 A1 | 12/2005 | Stone et al. |
| 2005/0277985 A1 | 12/2005 | Wert et al. |
| 2005/0283040 A1 | 12/2005 | Greenhalgh |
| 2005/0283156 A1 | 12/2005 | Schmieding et al. |
| 2005/0283158 A1 | 12/2005 | West, Jr. |
| 2005/0283192 A1 | 12/2005 | Torrie et al. |
| 2005/0283220 A1 | 12/2005 | Gobran et al. |
| 2006/0000441 A1 | 1/2006 | Nobis et al. |
| 2006/0004364 A1 | 1/2006 | Green et al. |
| 2006/0004460 A1 | 1/2006 | Engh et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant et al. |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089525 A1 | 4/2006 | Mamo et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli |

(56) References Cited

U.S. PATENT DOCUMENTS

| | | |
|---|---|---|
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0178701 A1 | 8/2006 | Schmieding |
| 2006/0178743 A1 | 8/2006 | Carter |
| 2006/0189993 A1 | 8/2006 | Stone |
| 2006/0190041 A1 | 8/2006 | Fallin et al. |
| 2006/0190042 A1* | 8/2006 | Stone ............... A61B 17/0401 606/232 |
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1 | 9/2006 | Karabey et al. |
| 2006/0229623 A1 | 10/2006 | Bonutti et al. |
| 2006/0229671 A1 | 10/2006 | Steiner et al. |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0241776 A1 | 10/2006 | Brown et al. |
| 2006/0241781 A1 | 10/2006 | Brown et al. |
| 2006/0247642 A1 | 11/2006 | Stone et al. |
| 2006/0253130 A1 | 11/2006 | Wolniewicz, III |
| 2006/0259048 A1 | 11/2006 | Koseki |
| 2006/0259076 A1 | 11/2006 | Burkhart |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276818 A1 | 12/2006 | Buser et al. |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0280803 A1 | 12/2006 | Kumar et al. |
| 2006/0282082 A1 | 12/2006 | Fanton et al. |
| 2006/0282083 A1 | 12/2006 | Fanton et al. |
| 2006/0282085 A1 | 12/2006 | Stone |
| 2006/0293709 A1* | 12/2006 | Bojarski ............ A61B 17/0401 606/232 |
| 2007/0005068 A1 | 1/2007 | Sklar |
| 2007/0005080 A1 | 1/2007 | Wolniewicz, III et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0032823 A1 | 2/2007 | Tegg |
| 2007/0038218 A1 | 2/2007 | Grevious |
| 2007/0043371 A1 | 2/2007 | Teague |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0078517 A1 | 4/2007 | Engh et al. |
| 2007/0083236 A1 | 4/2007 | Sikora et al. |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0129809 A1 | 6/2007 | Meridew et al. |
| 2007/0135843 A1 | 6/2007 | Burkhart |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0162120 A1 | 7/2007 | Bouffier |
| 2007/0167926 A1 | 7/2007 | Blott et al. |
| 2007/0167950 A1 | 7/2007 | Tauro et al. |
| 2007/0173948 A1 | 7/2007 | Meridew et al. |
| 2007/0185488 A1 | 8/2007 | Pohjonen et al. |
| 2007/0185532 A1* | 8/2007 | Stone ............... A61B 17/0482 606/232 |
| 2007/0185568 A1 | 8/2007 | Schwartz |
| 2007/0191849 A1 | 8/2007 | Elattrache et al. |
| 2007/0191853 A1 | 8/2007 | Stone |
| 2007/0198022 A1 | 8/2007 | Lang et al. |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1 | 9/2007 | Stone et al. |
| 2007/0225763 A1 | 9/2007 | Zwolinski et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0244565 A1 | 10/2007 | Stchur |
| 2007/0250059 A1 | 10/2007 | Weisshaupt et al. |
| 2007/0250163 A1 | 10/2007 | Cassani |
| 2007/0250175 A1 | 10/2007 | Meridew et al. |
| 2007/0255282 A1 | 11/2007 | Simonton et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0288023 A1 | 12/2007 | Pellegrino et al. |
| 2008/0009904 A1 | 1/2008 | Bourque et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051834 A1 | 2/2008 | Mazzocca et al. |
| 2008/0051836 A1 | 2/2008 | Foerster et al. |
| 2008/0058787 A1 | 3/2008 | Gertner |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0086138 A1 | 4/2008 | Stone et al. |
| 2008/0097430 A1 | 4/2008 | Bernstein et al. |
| 2008/0103528 A1 | 5/2008 | Zirps et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0137624 A1 | 6/2008 | Silverstrim et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0147127 A1 | 6/2008 | Tipirneni et al. |
| 2008/0147187 A1 | 6/2008 | Bollinger et al. |
| 2008/0154260 A1 | 6/2008 | Hoof |
| 2008/0154314 A1 | 6/2008 | Mcdevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0166421 A1 | 7/2008 | Buhr et al. |
| 2008/0172097 A1 | 7/2008 | Lerch et al. |

(56) References Cited

U.S. PATENT DOCUMENTS

| | | |
|---|---|---|
| 2008/0177302 A1 | 7/2008 | Shumas |
| 2008/0183290 A1 | 7/2008 | Baird et al. |
| 2008/0188933 A1 | 8/2008 | Koob et al. |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0217263 A1 | 9/2008 | Higgins et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0228271 A1 | 9/2008 | Stone et al. |
| 2008/0234730 A1 | 9/2008 | Cotton et al. |
| 2008/0243260 A1 | 10/2008 | Lee et al. |
| 2008/0243261 A1 | 10/2008 | Wyss et al. |
| 2008/0243262 A1 | 10/2008 | Lee |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-may |
| 2008/0269674 A1 | 10/2008 | Stone |
| 2008/0275469 A1 | 11/2008 | Fanton et al. |
| 2008/0275477 A1 | 11/2008 | Sterrett et al. |
| 2008/0281428 A1 | 11/2008 | Meyers et al. |
| 2008/0288070 A1 | 11/2008 | Lo |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |
| 2009/0018654 A1 | 1/2009 | Schmieding et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062847 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0084491 A1 | 4/2009 | Uthgenannt et al. |
| 2009/0099598 A1 | 4/2009 | Mcdevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teaguex et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0182335 A1 | 7/2009 | Struhl |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0216325 A1 | 8/2009 | May et al. |
| 2009/0228015 A1 | 9/2009 | Ellis |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0234451 A1 | 9/2009 | Manderson |
| 2009/0240251 A1 | 9/2009 | Gabele |
| 2009/0240335 A1 | 9/2009 | Arcenio et al. |
| 2009/0241497 A1 | 10/2009 | Imai et al. |
| 2009/0248091 A1 | 10/2009 | Teague et al. |
| 2009/0254089 A1 | 10/2009 | Tipirneni et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2009/0318965 A1 | 12/2009 | Burkhart |
| 2010/0016891 A1 | 1/2010 | Kennedy et al. |
| 2010/0016899 A1 | 1/2010 | Gelfand |
| 2010/0030321 A1 | 2/2010 | Mach |
| 2010/0042114 A1 | 2/2010 | Schaffhausen et al. |
| 2010/0063540 A1 | 3/2010 | Maiorino |
| 2010/0063541 A1 | 3/2010 | Brunelle et al. |
| 2010/0087857 A1 | 4/2010 | Stone et al. |
| 2010/0094341 A1 | 4/2010 | Raju |
| 2010/0094355 A1 | 4/2010 | Trenhaile |
| 2010/0106254 A1 | 4/2010 | Delsignore |
| 2010/0121348 A1 | 5/2010 | Van Der Burg et al. |
| 2010/0145384 A1 | 6/2010 | Stone et al. |
| 2010/0152752 A1 | 6/2010 | Denove et al. |
| 2010/0191319 A1 | 7/2010 | Lilburn et al. |
| 2010/0191342 A1 | 7/2010 | Byrd et al. |
| 2010/0204700 A1 | 8/2010 | Falahee |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0274282 A1 | 10/2010 | Olson |
| 2010/0292792 A1 | 11/2010 | Stone et al. |
| 2010/0298872 A1 | 11/2010 | Berndt et al. |
| 2010/0298952 A1 | 11/2010 | Busold et al. |
| 2010/0030571 A1 | 12/2010 | Metzger |
| 2010/0305698 A1 | 12/2010 | Metzger et al. |
| 2010/0305709 A1 | 12/2010 | Metzger et al. |
| 2010/0312245 A1 | 12/2010 | Tipirneni et al. |
| 2010/0312341 A1 | 12/2010 | Kaiser et al. |
| 2010/0324676 A1 | 12/2010 | Albertorio |
| 2010/0331881 A1 | 12/2010 | Hart |
| 2011/0009885 A1 | 1/2011 | Graf et al. |
| 2011/0022083 A1 | 1/2011 | Dimatteo et al. |
| 2011/0026141 A1 | 2/2011 | Barrows |
| 2011/0040387 A1 | 2/2011 | Ries et al. |
| 2011/0046733 A1 | 2/2011 | Eggli |
| 2011/0087225 A1 | 4/2011 | Fritzinger |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'oca |
| 2011/0124954 A1 | 5/2011 | Ogdahl et al. |
| 2011/0125153 A1 | 5/2011 | Tyber et al. |
| 2011/0160767 A1 | 6/2011 | Stone et al. |
| 2011/0160768 A1 | 6/2011 | Stone et al. |
| 2011/0166608 A1 | 7/2011 | Duggal et al. |
| 2011/0184227 A1 | 7/2011 | Altman et al. |
| 2011/0208239 A1 | 8/2011 | Stone et al. |
| 2011/0208240 A1 | 8/2011 | Stone et al. |
| 2011/0213367 A1 | 9/2011 | Tyber et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2011/0295284 A1 | 12/2011 | Purdue et al. |
| 2011/0319932 A1 | 12/2011 | Avelar et al. |
| 2012/0004669 A1 | 1/2012 | Overes et al. |
| 2012/0024134 A1 | 2/2012 | Dow et al. |
| 2012/0029561 A1 | 2/2012 | Olson |
| 2012/0041485 A1 | 2/2012 | Kaiser et al. |
| 2012/0041486 A1 | 2/2012 | Stone et al. |
| 2012/0041496 A1 | 2/2012 | Walker |
| 2012/0042768 A1 | 2/2012 | Chou et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0060278 A1 | 3/2012 | Mccurdy |
| 2012/0083837 A1 | 4/2012 | Ferragamo et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |

(56) References Cited

U.S. PATENT DOCUMENTS

| | | |
|---|---|---|
| 2012/0116450 A1 | 5/2012 | Mcdevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0130423 A1 | 5/2012 | Sengun et al. |
| 2012/0130492 A1 | 5/2012 | Eggli et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165864 A1 | 6/2012 | Hernandez et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0192455 A1 | 8/2012 | Hansen et al. |
| 2012/0197271 A1 | 8/2012 | Astorino et al. |
| 2012/0215257 A1 | 8/2012 | Mcdevitt et al. |
| 2012/0239159 A1 | 9/2012 | Metzger et al. |
| 2012/0245585 A1 | 9/2012 | Kaiser et al. |
| 2012/0265219 A1 | 10/2012 | Rushdy et al. |
| 2012/0265294 A1 | 10/2012 | Nishigishi |
| 2012/0271403 A1 | 10/2012 | Gries |
| 2012/0273085 A1 | 11/2012 | David et al. |
| 2012/0290002 A1 | 11/2012 | Astorino |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone |
| 2013/0035722 A1 | 2/2013 | Mcdevitt et al. |
| 2013/0046341 A1 | 2/2013 | Stone et al. |
| 2013/0060323 A1 | 3/2013 | Mchugo |
| 2013/0090720 A1 | 4/2013 | Mahr et al. |
| 2013/0090731 A1 | 4/2013 | Walker |
| 2013/0103082 A1 | 4/2013 | Kaiser et al. |
| 2013/0012381 A1 | 5/2013 | Brown et al. |
| 2013/0110165 A1 | 5/2013 | Burkhart et al. |
| 2013/0110251 A1 | 5/2013 | Metzger et al. |
| 2013/0116730 A1 | 5/2013 | Denham |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158599 A1 | 6/2013 | Hester et al. |
| 2013/0158601 A1 | 6/2013 | Stone et al. |
| 2013/0172942 A1 | 7/2013 | Lewis et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0231700 A1 | 9/2013 | Gedet et al. |
| 2013/0237997 A1 | 9/2013 | Arai et al. |
| 2013/0245761 A1 | 9/2013 | Conner et al. |
| 2013/0267956 A1 | 10/2013 | Terrill |
| 2013/0274812 A1 | 10/2013 | Dell'oca |
| 2013/0289564 A1 | 10/2013 | Bernstein et al. |
| 2013/0317621 A1 | 11/2013 | Metzger et al. |
| 2013/0331742 A1 | 12/2013 | Aupperle et al. |
| 2013/0331848 A1 | 12/2013 | Kaiser et al. |
| 2014/0005754 A1 | 1/2014 | Finley et al. |
| 2014/0018804 A1 | 1/2014 | Foerster |
| 2014/0046367 A1 | 2/2014 | Stone et al. |
| 2014/0046368 A1 | 2/2014 | Kaiser et al. |
| 2014/0052179 A1 | 2/2014 | Dreyfuss et al. |
| 2014/0058436 A1 | 2/2014 | Rosenbluth et al. |
| 2014/0067081 A1 | 3/2014 | Stone |
| 2014/0081322 A1 | 3/2014 | Sengun et al. |
| 2014/0088655 A1 | 3/2014 | Stone et al. |
| 2014/0094913 A1 | 4/2014 | Berelsman et al. |
| 2014/0128985 A1 | 5/2014 | Sanders et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0336760 A1 | 11/2014 | Eggli |
| 2014/0350674 A1 | 11/2014 | Stone et al. |
| 2015/0012094 A1 | 1/2015 | Denham et al. |
| 2015/0032216 A1 | 1/2015 | Metzger et al. |
| 2015/0057665 A1 | 2/2015 | Neal et al. |
| 2015/0057757 A1 | 2/2015 | Metzger et al. |
| 2015/0066081 A1 | 3/2015 | Martin |
| 2015/0119890 A1 | 4/2015 | Kaiser et al. |
| 2015/0127051 A1 | 5/2015 | Kaiser et al. |
| 2015/0128792 A1 | 5/2015 | Zachariades et al. |
| 2015/0134000 A1 | 5/2015 | Denham et al. |
| 2015/0143981 A1 | 5/2015 | Dunker |
| 2015/0148888 A1 | 5/2015 | Milner et al. |
| 2015/0173753 A1 | 6/2015 | Spivey et al. |
| 2015/0173887 A1 | 6/2015 | Berelsman et al. |
| 2015/0257750 A1 | 9/2015 | Kaiser et al. |
| 2015/0320026 A1 | 11/2015 | Toddes |
| 2016/0000483 A1 | 1/2016 | Stone |
| 2016/0022261 A1 | 1/2016 | Stone et al. |
| 2016/0038187 A1 | 2/2016 | Mcdonnell |
| 2016/0058436 A1 | 3/2016 | Stone et al. |
| 2016/0058484 A1 | 3/2016 | Mccombs-stearnes et al. |
| 2016/0074049 A1 | 3/2016 | Russell et al. |
| 2016/0081789 A1 | 3/2016 | Denham et al. |
| 2016/0106414 A1 | 4/2016 | Stone et al. |
| 2016/0128684 A1 | 5/2016 | Stone et al. |
| 2016/0183935 A1 | 6/2016 | Stone |
| 2016/0199053 A1 | 7/2016 | Norton et al. |
| 2016/0213369 A1 | 7/2016 | Stone et al. |
| 2016/0242760 A1 | 8/2016 | Kaiser et al. |
| 2017/0014225 A1 | 1/2017 | Denham et al. |
| 2017/0020507 A1 | 1/2017 | Denham et al. |
| 2017/0020569 A1 | 1/2017 | Grant |
| 2017/0035411 A1 | 2/2017 | Kaiser et al. |
| 2017/0049557 A1 | 2/2017 | Denham et al. |
| 2017/0065278 A1 | 3/2017 | Stone |
| 2017/0071593 A1 | 3/2017 | Stone |
| 2017/0071595 A1 | 3/2017 | Stone et al. |
| 2017/0086816 A1 | 3/2017 | Norton |
| 2017/0119382 A1 | 5/2017 | Denham et al. |
| 2017/0128061 A1 | 5/2017 | Stone et al. |
| 2017/0181746 A1 | 6/2017 | Denham et al. |
| 2017/0189011 A1 | 7/2017 | Stone et al. |
| 2017/0189197 A1 | 7/2017 | Werber et al. |
| 2017/0202587 A1 | 7/2017 | Stone et al. |
| 2017/0273686 A1 | 9/2017 | Denham et al. |
| 2017/0311947 A1 | 11/2017 | Kaiser et al. |
| 2017/0319194 A1 | 11/2017 | Mayeski et al. |
| 2017/0319195 A1 | 11/2017 | Denham et al. |
| 2017/0319204 A1 | 11/2017 | Norton et al. |
| 2017/0325808 A1 | 11/2017 | Stone et al. |
| 2017/0333176 A1 | 11/2017 | Stone et al. |
| 2017/0360425 A1 | 12/2017 | Stone et al. |
| 2018/0000477 A1 | 1/2018 | Kaiser et al. |
| 2018/0014864 A1 | 1/2018 | Stone et al. |
| 2018/0020762 A1 | 1/2018 | Jamison |
| 2018/0021036 A1 | 1/2018 | Kaiser et al. |
| 2018/0021125 A1 | 1/2018 | Berelsman et al. |
| 2018/0042609 A1 | 2/2018 | Denham et al. |
| 2018/0098858 A1 | 4/2018 | Valderrabano et al. |
| 2018/0125476 A1 | 5/2018 | Kaiser et al. |
| 2018/0125477 A1 | 5/2018 | Stone |
| 2018/0153538 A1 | 6/2018 | Kaiser et al. |
| 2018/0153558 A1 | 6/2018 | Bake et al. |
| 2018/0161030 A1 | 6/2018 | Stone et al. |
| 2018/0177501 A1 | 6/2018 | Kaiser et al. |
| 2018/0193015 A1 | 7/2018 | Denham et al. |
| 2018/0221017 A1 | 8/2018 | Stone et al. |

(56) References Cited

U.S. PATENT DOCUMENTS

| | | |
|---|---|---|
| 2018/0235747 A1 | 8/2018 | Berelsman et al. |
| 2018/0249997 A1 | 9/2018 | Stone et al. |
| 2018/0256153 A1 | 9/2018 | Stone et al. |
| 2019/0083233 A1 | 3/2019 | Denham et al. |
| 2019/0150909 A1 | 5/2019 | Stone et al. |
| 2019/0150923 A1 | 5/2019 | Stone et al. |
| 2019/0231348 A1 | 8/2019 | Stone et al. |
| 2019/0254652 A1 | 8/2019 | Stone et al. |
| 2019/0274681 A1 | 9/2019 | Denham et al. |
| 2019/0282227 A1 | 9/2019 | Norton |
| 2019/0290258 A1 | 9/2019 | Denham et al. |
| 2019/0298345 A1 | 10/2019 | Denham |
| 2019/0328382 A1 | 10/2019 | Stone et al. |
| 2019/0365376 A1 | 12/2019 | Stone et al. |
| 2020/0029955 A1 | 1/2020 | Stone et al. |
| 2020/0085562 A1 | 3/2020 | Stone et al. |
| 2020/0178959 A1 | 6/2020 | Denham et al. |
| 2020/0187932 A1 | 6/2020 | Kaiser et al. |
| 2020/0187933 A1 | 6/2020 | Kaiser et al. |
| 2020/0297338 A1 | 9/2020 | Stone et al. |
| 2020/0367880 A1 | 11/2020 | Stone et al. |
| 2021/0177397 A1 | 6/2021 | Stone et al. |
| 2021/0228203 A1 | 7/2021 | Denham et al. |
| 2021/0361286 A1 | 11/2021 | Stone et al. |
| 2022/0015757 A1 | 1/2022 | Stone et al. |
| 2022/0054123 A1 | 2/2022 | Kaiser et al. |
| 2022/0096074 A1 | 3/2022 | Denham et al. |
| 2022/0096081 A1 | 3/2022 | Denham et al. |
| 2022/0133296 A1 | 5/2022 | Stone et al. |

FOREIGN PATENT DOCUMENTS

| | | |
|---|---|---|
| AU | 4381268 A | 4/1970 |
| AU | 5850469 A | 1/1971 |
| AU | 5963869 A | 2/1971 |
| AU | 1505470 A | 11/1971 |
| AU | 2223767 A | 5/1973 |
| AU | 3615171 A | 5/1973 |
| AU | 440266 B2 | 9/1973 |
| AU | 5028569 A | 9/1973 |
| AU | 7110887 A | 10/1987 |
| AU | 639410 A | 11/1989 |
| AU | 1713188 A | 11/1989 |
| AU | 651929 B2 | 8/1994 |
| AU | 3877493 B2 | 8/1994 |
| BE | 1010569 A6 | 10/1998 |
| CN | 1720872 A | 1/2006 |
| CN | 1777450 A | 5/2006 |
| CN | 101083954 A | 12/2007 |
| CN | 101584592 A | 11/2009 |
| CN | 105208970 A | 12/2015 |
| DE | 2529669 A1 | 3/1976 |
| DE | 2747312 A1 | 4/1979 |
| DE | 2818254 A1 | 10/1979 |
| DE | 2919009 A1 | 11/1979 |
| DE | 3027138 A1 | 12/1981 |
| DE | 3225620 A1 | 2/1983 |
| DE | 3136083 A1 | 3/1983 |
| DE | 233303 A1 | 2/1986 |
| DE | 4127550 A1 | 2/1993 |
| DE | 4302397 A | 7/1993 |
| DE | 29621340 U1 | 4/1998 |
| DE | 19841252 A1 | 3/2000 |
| DE | 29922088 U1 | 4/2000 |
| DE | 20207781 U1 | 8/2002 |
| EP | 0019062 A1 | 11/1980 |
| EP | 0108912 A2 | 5/1984 |
| EP | 0129422 A2 | 12/1984 |
| EP | 0129442 A1 | 12/1984 |
| EP | 0172130 A2 | 2/1986 |
| EP | 0241240 A2 | 10/1987 |
| EP | 0241792 A1 | 10/1987 |
| EP | 0260970 A2 | 3/1988 |
| EP | 0270704 A1 | 6/1988 |
| EP | 0282789 A2 | 9/1988 |
| EP | 0315371 A2 | 5/1989 |
| EP | 0317406 A1 | 5/1989 |
| EP | 0340159 A1 | 11/1989 |
| EP | 0346183 A1 | 12/1989 |
| EP | 0349173 A1 | 1/1990 |
| EP | 0374088 A1 | 6/1990 |
| EP | 0409364 A2 | 1/1991 |
| EP | 0415915 A1 | 3/1991 |
| EP | 0440991 A1 | 8/1991 |
| EP | 0441065 A2 | 8/1991 |
| EP | 0447065 A2 | 9/1991 |
| EP | 0451932 A1 | 10/1991 |
| EP | 0464480 A1 | 1/1992 |
| EP | 0490417 A1 | 6/1992 |
| EP | 0497079 A1 | 8/1992 |
| EP | 0502509 A1 | 9/1992 |
| EP | 0502698 A1 | 9/1992 |
| EP | 0520177 A1 | 12/1992 |
| EP | 520177 A1 | 12/1992 |
| EP | 0546726 A1 | 6/1993 |
| EP | 0552950 A1 | 7/1993 |
| EP | 0574707 A1 | 12/1993 |
| EP | 0582514 A1 | 2/1994 |
| EP | 0591991 A2 | 4/1994 |
| EP | 0598219 A2 | 5/1994 |
| EP | 0611551 A1 | 8/1994 |
| EP | 0627203 A2 | 12/1994 |
| EP | 0651979 A1 | 5/1995 |
| EP | 0669110 A2 | 8/1995 |
| EP | 0686373 A1 | 12/1995 |
| EP | 0702933 A1 | 3/1996 |
| EP | 0775473 A1 | 5/1997 |
| EP | 0913123 A1 | 5/1999 |
| EP | 0913131 A2 | 5/1999 |
| EP | 0995409 A1 | 4/2000 |
| EP | 1013229 A2 | 6/2000 |
| EP | 1093773 A1 | 4/2001 |
| EP | 1093774 A1 | 4/2001 |
| EP | 1555945 A2 | 7/2005 |
| EP | 1741412 A2 | 1/2007 |
| EP | 1864617 A2 | 12/2007 |
| EP | 2238944 A2 | 10/2010 |
| EP | 2544607 A1 | 1/2013 |
| EP | 2709557 A1 | 3/2014 |
| EP | 2895112 A1 | 7/2015 |
| EP | 2934379 A1 | 10/2015 |
| EP | 2434987 B1 | 6/2016 |
| EP | 2775935 B1 | 5/2017 |
| FR | 2622790 A1 | 5/1989 |
| FR | 2634373 A1 | 1/1990 |
| FR | 2655840 A1 | 6/1991 |
| FR | 2663837 A1 | 1/1992 |
| FR | 2682867 A1 | 4/1993 |
| FR | 2687911 A1 | 9/1993 |
| FR | 2688689 A1 | 9/1993 |
| FR | 2704140 A3 | 10/1994 |
| FR | 2717070 A1 | 9/1995 |
| FR | 2723528 A1 | 2/1996 |
| FR | 2734709 A1 | 12/1996 |
| FR | 2744010 A1 | 8/1997 |
| FR | 2745999 A1 | 9/1997 |
| FR | 2770764 A1 | 5/1999 |
| GB | 401677 A | 11/1933 |
| GB | 1413477 A | 11/1975 |
| GB | 1485681 A | 9/1977 |
| GB | 2083751 A | 3/1982 |
| GB | 2118474 A | 11/1983 |
| GB | 2129306 A | 5/1984 |
| GB | 2227175 A | 7/1990 |
| GB | 2253147 A | 9/1992 |
| GB | 2312376 A | 10/1997 |
| GB | 2403416 A | 1/2005 |
| GB | 2454251 A | 5/2009 |
| JP | 5362911 U | 5/1978 |
| JP | 5362912 U | 5/1978 |
| JP | 5374942 U | 6/1978 |
| JP | 5378230 U | 6/1978 |
| JP | 54166092 U | 11/1979 |
| JP | 54166093 U | 11/1979 |

(56) References Cited

FOREIGN PATENT DOCUMENTS

| | | | |
|---|---|---|---|
| JP | 54176284 U | 12/1979 | |
| JP | 54178988 U | 12/1979 | |
| JP | 5362911 A | 7/1987 | |
| JP | 62159647 A | 7/1987 | |
| JP | 62159647 U | 10/1987 | |
| JP | 62295657 A | 12/1987 | |
| JP | 5269160 A | 10/1993 | |
| JP | 5300917 A | 11/1993 | |
| JP | 751292 A | 2/1995 | |
| JP | 10127672 A | 5/1998 | |
| JP | 10211213 A | 8/1998 | |
| JP | 5362911 B2 | 12/2013 | |
| JP | 5362912 B2 | 12/2013 | |
| JP | 5374942 B2 | 12/2013 | |
| JP | 5378230 B2 | 12/2013 | |
| RU | 2051647 C1 | 1/1996 | |
| RU | 2076667014 C1 | 4/1997 | |
| WO | WO-8300615 A1 | 3/1983 | |
| WO | WO-8603666 A1 | 7/1986 | |
| WO | WO-8701270 A1 | 3/1987 | |
| WO | WO-8901767 A1 | 3/1989 | |
| WO | WO-8909030 A1 | 10/1989 | |
| WO | WO-8910096 A1 | 11/1989 | |
| WO | WO-9008510 A1 | 8/1990 | |
| WO | WO-9203980 A1 | 3/1992 | |
| WO | WO-9314705 A1 | 8/1993 | |
| WO | WO-9315694 A1 | 8/1993 | |
| WO | WO-9502373 A1 | 1/1995 | |
| WO | WO-9503003 A1 | 2/1995 | |
| WO | WO-9529637 A1 | 11/1995 | |
| WO | WO-9532670 A1 | 12/1995 | |
| WO | WO-9609797 A1 | 4/1996 | |
| WO | WO-9629029 A1 | 9/1996 | |
| WO | WO-9737603 A1 | 10/1997 | |
| WO | WO-9812991 A1 | 4/1998 | |
| WO | WO-9812992 A1 | 4/1998 | |
| WO | WO-9822047 A1 | 5/1998 | |
| WO | WO-9822048 A1 | 5/1998 | |
| WO | WO-9901084 A2 | 1/1999 | |
| WO | WO-9912480 A1 | 3/1999 | |
| WO | WO-9937219 A1 | 7/1999 | |
| WO | WO-9944544 A1 | 9/1999 | |
| WO | WO-9952472 A1 | 10/1999 | |
| WO | WO-0004159 A1 | 1/2000 | |
| WO | WO-0040159 A1 | 7/2000 | |
| WO | WO-0139671 A1 | 6/2001 | |
| WO | WO-0236020 A1 | 5/2002 | |
| WO | WO-03005914 A1 | 1/2003 | |
| WO | WO-03071962 A2 | 9/2003 | |
| WO | WO-03077772 A1 | 9/2003 | |
| WO | WO-03092551 A1 | 11/2003 | |
| WO | WO-2004091412 A1 | 10/2004 | |
| WO | WO-05104992 A1 | 11/2005 | |
| WO | WO-2005122954 A1 | 12/2005 | |
| WO | WO-2006011786 A1 | 2/2006 | |
| WO | WO-2006023661 A2 | 3/2006 | |
| WO | WO-2006055823 A2 | 5/2006 | |
| WO | WO-2007045460 A2 | 4/2007 | |
| WO | WO-2007103562 A2 | 9/2007 | |
| WO | WO-2007109280 A2 | 9/2007 | |
| WO | WO-2007119057 A1 | 10/2007 | |
| WO | WO-2008002550 A2 | 1/2008 | |
| WO | WO-2008015171 A1 | 2/2008 | |
| WO | WO-2008073588 A2 | 6/2008 | |
| WO | WO-2009012021 A1 | 1/2009 | |
| WO | WO-2009083047 A1 | 7/2009 | |
| WO | WO-2009131820 A1 | 10/2009 | |
| WO | WO-2010138832 A1 | 12/2010 | |
| WO | WO-2011112371 A1 | 9/2011 | |
| WO | WO-2011150238 A1 | 12/2011 | |
| WO | WO-2012134999 A1 | 10/2012 | |
| WO | WO-2012158583 A1 | 11/2012 | |
| WO | WO-2013066974 A1 | 5/2013 | |
| WO | WO-2013074525 A1 | 5/2013 | |
| WO | WO-2014043078 A1 | 3/2014 | |
| WO | WO-2014100109 A1 | 6/2014 | |
| WO | WO-2014151766 A1 | 9/2014 | |

OTHER PUBLICATIONS

U.S. Appl. No. 11/541,506 U.S. Pat. No. 7,601,165, filed Sep. 29, 2006, Method and Apparatus for Forming a Self-Locking Adjustable Suture Loop.

U.S. Appl. No. 11/784,821 U.S. Pat. No. 9,017,381, filed Apr. 10, 2007, Adjustable Knotless Loops.

U.S. Appl. No. 14/697,140 U.S. Pat. No. 9,861,351, filed Apr. 27, 2015, Adjustable Knotless Loops.

U.S. Appl. No. 15/720,997, filed Sep. 29, 2017, Adjustable Knotless Loops.

U.S. Appl. No. 11/347,661 U.S. Pat. No. 7,749,250, filed Feb. 3, 2006, Soft Tissue Repair Assembly and Associated Method.

U.S. Appl. No. 15/903,261, filed Feb. 23, 2018, Adjustable Knotless Loops.

U.S. Appl. No. 12/828,977 U.S. Pat. No. 8,409,253, filed Jul. 1, 2010, Soft Tissue Repair Assembly and Associated Method.

U.S. Appl. No. 13/767,401 U.S. Pat. No. 9,414,833, filed Feb. 14, 2013, Soft Tissue Repair Assembly and Associated Method.

U.S. Appl. No. 14/936,831 U.S. Pat. No. 10,441,264, filed Nov. 10, 2015, Soft Tissue Repair Assembly and Associated Method.

U.S. Appl. No. 15/361,917, filed Nov. 28, 2016, Soft Tissue Repair Assembly and Associated Method.

U.S. Appl. No. 16/251,342, filed Jan. 18, 2019, Soft Tissue Repair Assembly and Associated Method.

U.S. Appl. No. 16/544,293, filed Aug. 19, 2019, Soft Tissue Repair Assembly and Associated Method.

U.S. Appl. No. 11/541,505 U.S. Pat. No. 7,658,751, filed Sep. 9, 2006, Method for Implanting Soft Tissue.

U.S. Appl. No. 12/702,067 U.S. Pat. No. 8,672,968, filed Feb. 8, 2010, Method for Implanting Soft Tissue.

U.S. Appl. No. 14/211,977 U.S. Pat. No. 9,486,211, filed Mar. 14, 2014, Method for Implanting Soft Tissue.

U.S. Appl. No. 15/061,352 U.S. Pat. No. 10,004,493, filed Mar. 4, 2016, Method for Implanting Soft Tissue.

U.S. Appl. No. 15/664,572 U.S. Pat. No. 10,398,430, filed Jul. 31, 2017, Method for Implanting Soft Tissue.

U.S. Appl. No. 16/508,764, filed Jul. 11, 2019, Method for Implanting Soft Tissue.

U.S. Appl. No. 11/935,681 U.S. Pat. No. 7,905,903, filed Nov. 6, 2007, Method for Tissue Fixation.

U.S. Appl. No. 12/196,398 U.S. Pat. No. 7,959,650, filed Aug. 22, 2008, Adjustable Knotless Loops.

U.S. Appl. No. 13/102,182 U.S. Pat. No. 8,231,654, filed May 6, 2011, Adjustable Knotless Loops.

U.S. Appl. No. 10/984,624 U.S. Pat. No. 7,608,098, filed Nov. 9, 2004, Bone Fixation Device.

U.S. Appl. No. 11/294,694 U.S. Pat. No. 7,914,539, filed Dec. 5, 2005, Tissue Fixation Device.

U.S. Appl. No. 11/408,282, filed Apr. 20, 2006, Soft Tissue Conduit Device.

U.S. Appl. No. 12/419,491 U.S. Pat. No. 8,317,825, filed Apr. 7, 2009, Soft Tissue Conduit Device and Method.

U.S. Appl. No. 11/869,440 U.S. Pat. No. 7,857,830, filed Oct. 9, 2007, Soft Tissue Repair and Conduit Device.

U.S. Appl. No. 12/976,328 U.S. Pat. No. 8,273,106, filed Dec. 22, 2010, Soft Tissue Repair and Conduit Device.

U.S. Appl. No. 12/498,168 U.S. Pat. No. 8,361,113, filed Jun. 22, 2009, Method and Apparatus for Coupling Soft Tissue to a Bone.

U.S. Appl. No. 13/751,846 U.S. Pat. No. 9,492,158, filed Jan. 28, 2013, Method and Apparatus for Coupling Soft Tissue to a Bone.

U.S. Appl. No. 14/983,747 U.S. Pat. No. 10,154,837, filed Dec. 30, 2015, Method and Apparatus for Coupling Soft Tissue to a Bone.

U.S. Appl. No. 15/941,481, filed Mar. 30, 2018, Method and Apparatus for Coupling Soft Tissue to a Bone.

U.S. Appl. No. 16/400,199, May 1, 2019, Method and Apparatus for Coupling Soft Tissue to a Bone.

(56) References Cited

OTHER PUBLICATIONS

U.S. Appl. No. 12/014,399 U.S. Pat. No. 7,909,851, filed Jan. 15, 2008, Soft Tissue Repair Assembly and Associated Method.
U.S. Appl. No. 13/045,691 U.S. Pat. 8,292,921, filed Mar. 11, 2011, Soft Tissue Repair Assembly and Associated Method.
U.S. Appl. No. 13/656,821 U.S. Pat. No. 9,173,651, filed Oct. 22, 2012, Soft Tissue Repair Device and Associated Methods.
U.S. Appl. No. 14/876,167 U.S. Pat. No. 10,251,637, filed Oct. 6, 2015, Soft Tissue Repair Device and Associated Methods.
U.S. Appl. No. 15/891,049, filed Feb. 7, 2018, Soft Tissue Repair Device and Associated Methods.
U.S. Appl. No. 16/593,022, filed Oct. 4, 2019, Soft Tissue Repair Device and Associated Methods.
U.S. Appl. No. 12/014,340 U.S. Pat. No. 7,905,904, filed Jan. 15, 2008, Soft Tissue Repair Assembly and Associated Method.
U.S. Appl. No. 13/045,689 U.S. Pat. No. 8,337,525, filed Mar. 11, 2011, Soft Tissue Repair Assembly and Associated Method.
U.S. Appl. No. 13/721,970 U.S. Pat. No. 8,632,569, filed Dec. 20, 2012, Soft Tissue Repair Assembly and Associated Method.
U.S. Appl. No. 13/838,755 U.S. Pat. No. 9,510,819, filed Mar. 15, 2013, Soft Tissue Repair Device and Associated Methods.
U.S. Appl. No. 13/833,567 U.S. Pat. No. 9,561,025, filed Mar. 15, 2013, Soft Tissue Repair Device and Associated Methods.
U.S. Appl. No. 14/159,094 U.S. Pat. No. 9,622,736, filed Jan. 20, 2014, Soft Tissue Repair Device and Associated Methods.
U.S. Appl. No. 15/412,676, filed Jan. 23, 2017, Soft Tissue Repair Device and Associated Methods.
U.S. Appl. No. 12/489,181 U.S. Pat. No. 8,298,262, filed Jun. 22, 2009, Method for Tissue Fixation.
U.S. Appl. No. 13/625,413 U.S. Pat. No. 9,402,621, filed Sep. 24, 2012, Method for Tissue Fixation.
U.S. Appl. No. 14/983,108 U.S. Pat. No. 10,321,906, filed Dec. 29, 2015, Method for Tissue Fixation.
U.S. Appl. No. 15/945,425, filed Apr. 4, 2018, Method for Tissue Fixation.
U.S. Appl. No. 16/380,742, filed Apr. 10, 2019, Method for Tissue Fixation.
U.S. Appl. No. 10/983,236, filed Nov. 5, 2004, Tissue Repair Assembly.
U.S. Appl. No. 11/347,662, filed Feb. 3, 2006, Tissue Repair Assembly.
U.S. Appl. No. 16/795,181, filed Feb. 19, 2020, Method and Apparatus for Coupling Soft Tissue to a Bone.
U.S. Appl. No. 12/196,410 U.S. Pat. No. 8,118,836, filed Aug. 22, 2008, Method and Apparatus for Coupling Soft Tissue to a Bone.
U.S. Appl. No. 13/399,125 U.S. Pat. No. 8,840,645, filed Feb. 17, 2012, Method and Apparatus for Coupling Soft Tissue to a Bone.
U.S. Appl. No. 14/492,590 U.S. Pat. No. 9,572,655, filed Sep. 22, 2014, Method and Apparatus for Coupling Soft Tissue to a Bone.
U.S. Appl. No. 14,956,724 U.S. Pat. No. 9,801,708, filed Dec. 2, 2015, Method and Apparatus for Coupling Soft Tissue to a Bone.
U.S. Appl. No. 15/278,777 U.S. Pat. No. 10,092,288, filed Sep. 28, 2016, Method and Apparatus for Coupling Soft Tissue to a Bone.
U.S. Appl. No. 15/455,895, filed Mar. 10, 2017, Method and Apparatus for Coupling Soft Tissue to a Bone.
U.S. Appl. No. 15/622,718, filed Jun. 14, 2017, Method and Apparatus for Coupling Soft Tissue to a Bone.
U.S. Appl. No. 15/793,216, filed Oct. 25, 2017, Method and Apparatus for Coupling Soft Tissue to a Bone.
U.S. Appl. No. 16/420,676, filed May 23, 2019, Method and Apparatus for Coupling Soft Tissue to a Bone.
U.S. Appl. No. 12/196,407 U.S. Pat. No. 8,137,382, filed Aug. 22, 2008, Method and Apparatus for Forming a Self-Locking Adjustable Suture Loop.
U.S. Appl. No. 13/412,116 U.S. Pat. No. 8,771,316, filed Mar. 5, 2012, Method and Apparatus for Coupling Anatomical Features.
U.S. Appl. No. 14/324,688 U.S. Pat. No. 9,498,204, filed Jul. 7, 2014, Method and Apparatus for Coupling Anatomical Features.
U.S. Appl. No. 13/412,127 U.S. Pat. No. 8,721,684, filed Mar. 5, 2012, Method and Apparatus for Coupling Anatomical Features.
U.S. Appl. No. 14/275,548 U.S. Pat. No. 9,510,821, filed May 12, 2014, Method and Apparatus for Coupling Anatomical Features.
U.S. Appl. No. 15/288,183 U.S. Pat. No. 10,398,428, filed Oct. 7, 2016, Method and Apparatus for Coupling Anatomical Features.
U.S. Appl. No. 15/662,572, filed Jul. 28, 2017, Method and Apparatus for Coupling Anatomical Features.
U.S. Appl. No. 16/436,023, filed Jun. 10, 2019, Method and Apparatus for Coupling Anatomical Features.
U.S. Appl. No. 12/196,405 U.S. Pat. No. 8,128,658, filed Aug. 22, 2008, Method and Apparatus for Coupling Soft Tissue to Bone.
U.S. Appl. No. 13/181,729 U.S. Pat. No. 8,551,14, filed Jul. 13, 2011, Method and Apparatus for Coupling Soft Tissue to Bone.
U.S. Appl. No. 13/412,105 U.S. Pat. No. 8,932,331, filed Mar. 5, 2012, Method and Apparatus for Coupling Soft Tissue to Bone.
U.S. Appl. No. 14/594,285 U.S. Pat. No. 9,801,620, filed Jan. 12, 2015, Method and Apparatus for Coupling Soft Tissue to Bone.
U.S. Appl. No. 15/703,727, filed Sep. 13, 2017, Method and Apparatus for Coupling Soft Tissue to Bone.
U.S. Appl. No. 16/802,248, filed Feb. 26, 2020, Method and Apparatus for Coupling Soft Tissue to Bone.
U.S. Appl. No. 12/474,802 U.S. Pat. No. 8,088,130, filed May 29, 2009, Method and Apparatus for Coupling Soft Tissue to a Bone.
U.S. Appl. No. 13/278,341 U.S. Pat. No. 8,608,777, filed Oct. 21, 2011, Method and Apparatus for Coupling Soft Tissue to a Bone.
U.S. Appl. No. 14/107,350 U.S. Pat. No. 9,532,777, filed Dec. 16, 2013, Method and Apparatus for Coupling Soft Tissue to a Bone.
U.S. Appl. No. 15/074,553 U.S. Pat. No. 10,004,489, filed Mar. 18, 2016, Method and Apparatus for Coupling Soft Tissue to a Bone.
U.S. Appl. No. 15/297,844 U.S. Pat. No. 10,098,629, filed Oct. 19, 2016, Method and Apparatus for Coupling Soft Tissue to a Bone.
U.S. Appl. No. 15/865,938 U.S. Pat. No. 10,542,967, filed Jan. 9, 2018, Method and Apparatus for Coupling Soft Tissue to a Bone.
U.S. Appl. No. 15/886,712, filed Feb. 1, 2018, Method and Apparatus for Coupling Soft Tissue to a Bone.
U.S. Appl. No. 16/802,228, filed Feb. 26, 2020, Method and Apparatus for Coupling Soft Tissue to a Bone.
U.S. Appl. No. 12/570,854 U.S. Pat. No. 8,303,604, filed Sep. 30, 2009, Soft Tissue Repair Device and Method.
U.S. Appl. No. 13/645,964 U.S. Pat. No. 9,504,460, filed Oct. 5, 2012, Soft Tissue Repair Device and Method.
U.S. Appl. No. 15/332,590 U.S. Pat. No. 10,265,064, filed Oct. 24, 2016, Soft Tissue Repair Device and Method.
U.S. Appl. No. 16/255,300, filed Jan. 23, 2019, Soft Tissue Repair Device and Method.
U.S. Appl. No. 12/719,337 U.S. Pat. No. 9,078,644, filed Mar. 8, 2010, Fracture Fixation Device.
U.S. Appl. No. 14/794,309 U.S. Pat. No. 9,833,230, filed Jul. 8, 2015, Fracture Fixation Device.
U.S. Appl. No. 15/060,007 U.S. Pat. No. 10,349,931, filed Mar. 3, 2016, Fracture Fixation Device.
U.S. Appl. No. 15/866,089, filed Jan. 9, 2018, Fracture Fixation Device.
U.S. Appl. No. 12/915,962 U.S. Pat. No. 8,562,647, filed Oct. 29, 2010, Method and Apparatus for Securing Soft Tissue to bone.
U.S. Appl. No. 14/055,172 U.S. Pat. No. 9,724,390, filed Oct. 16, 2013, Method and Apparatus for Attaching Soft Tissue to Bone.
U.S. Appl. No. 15/654,386, filed Jul. 19, 2017, Method and Apparatus for Attaching Soft Tissue to Bone.
U.S. Appl. No. 12/938,902 U.S. Pat. No. 8,591,327, filed Nov. 3, 2010, Method and Apparatus for Securing Soft Tissue to Bone.
U.S. Appl. No. 14/094,311 U.S. Pat. No. 9,642,661, filed Dec. 2, 2013, Method and Apparatus for Sternal Closure.
U.S. Appl. No. 15/461,675, filed Mar. 17, 2017, Method and Apparatus for Sternal Closure.
U.S. Appl. No. 11/504,882 U.S. Pat. No. 8,998,949, filed Aug. 16, 2006, Soft Tissue Conduit Device.
U.S. Appl. No. 12/029,861 U.S. Pat. No. 8,251,998, filed Feb. 12, 2008, Chondral Defect Repair.
U.S. Appl. No. 13/587,374 U.S. Pat. No. 8,777,956, filed Aug. 16, 2012, Chondral Defect Repair.
U.S. Appl. No. 11/740,035, filed Apr. 25, 2007, Method for Treating Cartilage Defects.

(56) References Cited

OTHER PUBLICATIONS

U.S. Appl. No. 11/739,768, U.S. Pat. No. 8,137,354, filed Apr. 25, 2007, Localized Cartilage Defect Therapy.
U.S. Appl. No. 13/350,935 U.S. Pat. No. 9,198,673, filed Jan. 16, 2012, Localized Cartilage Defect Therapy.
U.S. Appl. No. 14/923,506, filed Oct. 27, 2015, Localized Cartilage Defect Therapy.
U.S. Appl. No. 13/111,564 U.S. Pat. No. 8,574,235, filed May 19, 2011, Method for Trochanteric Reattachment.
U.S. Appl. No. 14/071,295 U.S. Pat. No. 9,005,287, filed Nov. 4, 2013, Method for Bone Reattachment.
U.S. Appl. No. 13/288,459 U.S. Pat. No. 9,468,433, filed Nov. 3, 2011, Method and Apparatus for Forming a Self-Locking Adjustable Loop.
U.S. Appl. No. 15/294,994 U.S. Pat. No. 10,517,587, filed Oct. 17, 2016, Method and Apparatus for Forming a Self-Locking Adjustable Loop.
U.S. Appl. No. 16/443,391, filed Jun. 17, 2019, Method and Apparatus for Forming a Self-Locking Adjustable Loop.
U.S. Appl. No. 13/288,463 U.S. Pat. No. 8,936,621, filed Nov. 3, 2011, Method and Apparatus for Forming a Self-Locking Adjustable Loop.
U.S. Appl. No. 14/599,909 U.S. Pat. No. 9,993,241, filed Jan. 19, 2015, Method and Apparatus for Forming a Self-Locking Adjustable Loop.
U.S. Appl. No. 15/917,143, filed Mar. 9, 2018, Method and Apparatus for Forming a Self-Locking Adjustable Loop.
U.S. Appl. No. 13/720,648 U.S. Pat. No. 9,357,991, filed Dec. 19, 2012, Method and Apparatus for Stitching Tendons.
U.S. Appl. No. 15/166,480 U.S. Pat. No. 10,265,159, filed May 27, 2016, Method and Apparatus for Stitching Tendons.
U.S. Appl. No. 16/160,559, filed Oct. 15, 2018, Method and Apparatus for Stitching Tendons.
U.S. Appl. No. 14/095,639 U.S. Pat. No. 9,918,827, filed Dec. 3, 2013, Scaffold for Spring Ligament Repair.
U.S. Appl. No. 14/095,614 U.S. Pat. No. 9,918,826, filed Dec. 3, 2013, Scaffold for Spring Ligament Repair.
U.S. Appl. No. 15/722,002, filed Oct. 2, 2017, Scaffold for Spring Ligament Repair.
U.S. Appl. No. 13/098,897 U.S. Pat. No. 8,562,645, filed May 2, 2011, Method and Apparatus for Forming a Self-Locking Adjustable Loop.
U.S. Appl. No. 14/055,191 U.S. Pat. No. 9,539,003, filed Oct. 16, 2013, Method and Apparatus for Forming a Self-Locking Adjustable Loop.
U.S. Appl. No. 15/401,768, filed Jan. 9, 2017, Method and Apparatus for Forming a Self-Locking Adjustable Loop.
U.S. Appl. No. 15/972,646, filed May 7, 2018, Method and Apparatus for Forming a Self-Locking Adjustable Loop.
U.S. Appl. No. 13/098,927 U.S. Pat. No. 8,652,171, filed May 2, 2011, Method and Apparatus for Soft Tissue Fixation.
U.S. Appl. No. 14/182,035 U.S. Pat. No. 9,763,656, filed Feb. 17, 2014, Method and Apparatus for Soft Tissue Fixation.
U.S. Appl. No. 15/682,187, filed Aug. 21, 2017, Method and Apparatus for Soft Tissue Fixation.
U.S. Appl. No. 12/788,978 U.S. Pat. No. 8,801,783, filed May 27, 2010, Prosthetic Ligament System for Knee Joint.
U.S. Appl. No. 14/456,286 U.S. Pat. No. 9,681,940, filed Aug. 11, 2014, Ligament System for Knee Joint.
U.S. Appl. No. 15/626,384 U.S. Pat. No. 10,517,714, filed Jun. 19, 2017, Ligament System for Knee Joint.
U.S. Appl. No. 16/690,671, filed Nov. 21, 2019, Prosthetic Ligament System for Knee Joint.
U.S. Appl. No. 11/386,071 U.S. Pat. No. 8,034,090, filed Mar. 21, 2006, Bone Fixation Device.
U.S. Appl. No. 13/293,825 U.S. Appl. No. 9,149,267, filed Nov. 10, 2011, Method and Apparatus for Coupling Soft Tissue to a Bone.
U.S. Appl. No. 14/854,308 U.S. Pat. No. 10,022,118, filed Sep. 15, 2015, Method and Apparatus for Coupling Soft Tissue to a Bone.
U.S. Appl. No. 13/071,563 U.S. Pat. No. 8,926,613, filed Mar. 25, 2011, Method and Apparatus for Forming a Bone Hole.
U.S. Appl. No. 14/589,101, filed Jan. 5, 2015, Method and Apparatus for Forming a Bone Hole.
U.S. Appl. No. 13/311,936 U.S. Pat. No. 9,408,599, filed Dec. 6, 2011, Method and Apparatus for Coupling Soft Tissue to a Bone.
U.S. Appl. No. 15/231,074, filed Aug. 8, 2016, Method and Apparatus for Coupling Soft Tissue to a Bone.
U.S. Appl. No. 13/757,003 U.S. Pat. No. 9,357,992, filed Feb. 1, 2013, Method for Coupling Soft Tissue to a Bone.
U.S. Appl. No. 13/295,126 U.S. Pat. No. 9,271,713, filed Nov. 14, 2011, Method and Apparatus for Tensioning a Suture.
U.S. Appl. No. 13/281,009 U.S. Pat. No. 9,538,998, filed Oct. 25, 2011, Method and Apparatus for Fracture Fixation.
U.S. Appl. No. 13/269,097 U.S. Pat. No. 8,672,969, filed Oct. 7, 2011, Fracture Fixation Device.
U.S. Appl. No. 14/215,550 U.S. Pat. No. 9,788,876, filed Mar. 17, 2014, Fracture Fixation Device.
U.S. Appl. No. 15/715,731, filed Sep. 26, 2017, Fracture Fixation Device.
U.S. Appl. No. 13/757,019 U.S. Pat. No. 9,314,241, filed Feb. 1, 2013, Apparatus for Coupling Soft Tissue to a Bone.
U.S. Appl. No. 15/131,663 U.S. Pat. No. 10,368,856, filed Apr. 18, 2016, Apparatus for Coupling Soft Tissue to a Bone.
U.S. Appl. No. 13/790,982 U.S. Pat. No. 9,370,350, filed Mar. 8, 2013, Apparatus for Coupling Soft Tissue to a Bone.
U.S. Appl. No. 13/790,997 U.S. Pat. No. 9,381,013, filed Mar. 8, 2013, Method for Coupling Soft Tissue to a Bone.
U.S. Appl. No. 15/200,546 U.S. Pat. No. 10,363,028, filed Jul. 1, 2016, Method for Coupling Soft Tissue to a Bone.
U.S. Appl. No. 16/428,277, filed May 31, 2019, Method for Coupling Soft Tissue to a Bone.
U.S. Appl. No. 12/788,973 U.S. Pat. No. 8,500,818, filed May 27, 2010, Knee Prosthesis Assembly With Ligament Link.
U.S. Appl. No. 13/959,145 U.S. Pat. No. 9,414,925, filed Aug. 5, 2013, Method of Implanting a Knee Prosthesis Assembly With a Ligament Link.
U.S. Appl. No. 13/109,672 U.S. Pat. No. 8,968,364, filed May 17, 2011, Method and Apparatus for Fixation of an ACL Graft.
U.S. Appl. No. 14/635,055 U.S. Pat. No. 10,004,588, filed Mar. 2, 2015, Method and Apparatus for Fixation of an ACL Graft.
U.S. Appl. No. 15/956,444, filed Apr. 18, 2018, Method and Apparatus for Fixation of an ACL Graft.
U.S. Appl. No. 13/109,667 U.S. Pat. No. 8,771,352, filed May 17, 2011, Method and Apparatus for Tibial Fixation of an ACL Graft.
U.S. Appl. No. 13/889,851 U.S. Pat. No. 9,216,078, filed May 8, 2013, Method and Apparatus for Tibial Fixation of an ACL Graft.
U.S. Appl. No. 14/974,516, filed Dec. 18, 2015, Method and Apparatus for Tibial Fixation of an ACL Graft.
U.S. Appl. No. 13/177,153 U.S. Pat. No. 8,652,172, filed Jul. 6, 2011, Flexible Anchors for Tissue Fixation.
U.S. Appl. No. 14/182,046 U.S. Pat. No. 9,603,591, filed Feb. 17, 2014, Flexible Anchors for Tissue Fixation.
U.S. Appl. No. 12/107,437, filed Apr. 22, 2008, Method and Apparatus for Attaching Soft Tissue to Bone.
U.S. Appl. No. 12/398,548 U.S. Pat. No. 8,118,868, filed Mar. 5, 2009, Method and Apparatus for Attaching Soft Tissue to Bone.
U.S. Appl. 17/516,664, filed Nov. 1, 2021, Adjustable Knotless Loops.
U.S. Appl. No. 17/492,082, filed Oct. 1, 2021, Method for Implantlng Soft Tissue.
U.S. Appl. No. 15/941,481 U.S. Pat. No. 10,973,507, filed Mar. 30, 2018, Method and Apparatus for Coupling Soft Tissue to a Bone.
U.S. Appl. No. 17/190,686, filed Mar. 3, 2021, Method and Apparatus for Coupling Soft Tissue to a Bone.
U.S. Appl. No. 16/989,386, filed Aug. 10, 2020, Soft Tissue Repair Device and Associated Methods.
U.S. Appl. No. 15/945,425 U.S. Pat. No. 10,987,099, filed Apr. 4, 2018, Method for Tissue Fixation.
U.S. Appl. No. 17/577,188, filed Jan. 17, 2022, Method for Tissue Fixation.
U.S. Appl. No. 17/550,074, filed Dec. 14, 2021, Method and Apparatus Coupling Soft Tissue to a Bone.

(56) References Cited

OTHER PUBLICATIONS

U.S. Appl. No. 17/392,971, filed Aug. 3, 2021, Soft Tissue Repair Device and Method.
U.S. Appl. No. 17/545,668, filed Dec. 8, 2021, Method and Apparatus for Coupling Anatomical Features.
U.S. Appl. No. 17/232,672, filed Apr. 16, 2021, Method and Apparatus for Forming a Self-Locking Adjustable Loop.
U.S. Appl. No. 16/895,246, filed Jun. 8, 2020, Method and Apparatus for Soft Tissue Fixation.
"U.S. Appl. No. 16/428,277, Corrected Notice of Allowability dated Sep. 16, 2022", 6 pgs.
"U.S. Appl. No. 16/544,293, Non Final Office Action dated Sep. 21, 2022", 14 pgs.
"U.S. Appl. No. 16/593,022, Response filed Sep. 9, 2022 to Restriction Requirement dated Sep. 6, 2022", 8 pgs.
"U.S. Appl. No. 16/593,022, Response filed Nov. 4, 2022 to Restriction Requirement dated Oct. 31, 2022", 8 pgs.
"U.S. Appl. No. 16/593,022, Restriction Requirement dated Oct. 31, 2022", 6 pgs.
"U.S. Appl. No. 16/802,248, Notice of Allowance dated Oct. 28, 2022", 9 pgs.
"U.S. Appl. No. 16/802,248, Response filed Sep. 14, 2022 to Non Final Office Action dated Jun. 17, 2022", 12 pgs.
"U.S. Appl. No. 16/895,246, Response filed Sep. 28, 2022 to Restriction Requirement dated Sep. 9, 2022", 7 pgs.
"U.S. Appl. No. 16/895,246, Restriction Requirement dated Sep. 9, 2022", 6 pgs.
"U.S. Appl. No. 17/940,022, Preliminary Amendment filed Sep. 26, 2022", 6 pgs.
"U.S. Appl. No. 16/428,277, Non Final Office Action dated May 24, 2022", 7 pgs.
"U.S. Appl. No. 16/428,277, Notice of Allowance dated Aug. 25, 2022", 9 pgs.
"U.S. Appl. No. 16/428,277, Response filed Aug. 3, 2022 to Non Final Office Action dated May 24, 2022", 8 pgs.
"U.S. Appl. No. 16/544,293, Response filed Aug. 15, 2022 to Restriction Requirement dated Jul. 7, 2022", 7 pgs.
"U.S. Appl. No. 16/544,293, Restriction Requirement dated Jul. 7, 2022", 6 pgs.
"U.S. Appl. No. 16/593,022, Restriction Requirement dated Sep. 6, 2022", 6 pgs.
"U.S. Appl. No. 16/795,181, Final Office Action dated Jun. 7, 2022", 12 pgs.
"U.S. Appl. No. 16/795,181, Notice of Allowance dated Aug. 25, 2022", 7 pgs.
"U.S. Appl. No. 16/795,181, Response filed Aug. 3, 2022 to Final Office Action dated Jun. 7, 2022", 8 pgs.
"U.S. Appl. No. 16/802,228, Notice of Allowance dated Jun. 15, 2022", 10 pgs.
"U.S. Appl. No. 16/802,248, Non Final Office Action dated Jun. 17, 2022", 18 pgs.
"U.S. Appl. No. 15/361,917, Notice of Allowance dated Mar. 4, 2020", 8 pgs.
"U.S. Appl. No. 15/662,572, Notice of Allowance dated Mar. 11, 2020", 9 pgs.
"U.S. Appl. No. 15/682,187, Notice of Allowance dated Mar. 25, 2020", 9 pgs.
"U.S. Appl. No. 15/715,731, Notice of Allowance dated Apr. 8, 2020", 9 pgs.
"U.S. Appl. No. 15/720,997, Advisory Action dated Jun. 15, 2021", 3 pgs.
"U.S. Appl. No. 15/720,997, Advisory Action dated Oct. 13, 2020", 2 pgs.
"U.S. Appl. No. 15/720,997, Final Office Action dated Apr. 7, 2021", 9 pgs.
"U.S. Appl. No. 15/720,997, Final Office Action dated Aug. 4, 2020", 10 pgs.
"U.S. Appl. No. 15/720,997, Non Final Office Action dated Nov. 23, 2020", 7 pgs.
"U.S. Appl. No. 15/720,997, Notice of Allowance dated Jul. 29, 2021", 7 pgs.
"U.S. Appl. No. 15/720,997, Response filed Jan. 25, 2021 to Non Final Office Action dated Nov. 23, 2020", 9 pgs.
"U.S. Appl. No. 15/720,997, Response filed Mar. 27, 2020 to Non Final Office Action dated Jan. 6, 2020", 10 pgs.
"U.S. Appl. No. 15/720,997, Response filed Jun. 2, 2021 to Final Office Action dated Apr. 7, 2021", 9 pgs.
"U.S. Appl. No. 15/720,997, Response filed Jul. 7, 2021 to Advisory Action dated Jun. 15, 2021", 6 pgs.
"U.S. Appl. No. 15/720,997, Response filed Sep. 30, 2020 to Final Office Action dated Aug. 4, 2020", 11 pgs.
"U.S. Appl. No. 15/722,002, Notice of Allowance dated Apr. 8, 2020", 7 pgs.
"U.S. Appl. No. 15/722,002, Response filed Mar. 5, 2020 to Non Final Office Action dated Feb. 4, 2020", 7 pgs.
"U.S. Appl. No. 15/793,216, Notice of Allowance dated Mar. 23, 2020", 7 pgs.
"U.S. Appl. No. 15/866,089, Corrected Notice of Allowability dated Aug. 27, 2020", 2 pgs.
"U.S. Appl. No. 15/866,089, Final Office Action dated Mar. 25, 2020", 15 pgs.
"U.S. Appl. No. 15/866,089, Notice of Allowance dated Jul. 15, 2020", 5 pgs.
"U.S. Appl. No. 15/866,089, Response filed Jun. 18, 2020 to Final Office Action dated Mar. 25, 2020", 11 pgs.
"U.S. Appl. No. 15/891,049, Examiner Interview Summary dated Aug. 10, 2020", 3 pgs.
"U.S. Appl. No. 15/891,049, Examiner Interview Summary dated Dec. 4, 2020", 2 pgs.
"U.S. Appl. No. 15/891,049, Final Office Action dated Nov. 10, 2020", 10 pgs.
"U.S. Appl. No. 15/891,049, Non Final Office Action dated Jul. 14, 2020", 16 pgs.
"U.S. Appl. No. 15/891,049, Notice of Allowance dated Dec. 22, 2020", 8 pgs.
"U.S. Appl. No. 15/891,049, Response filed May 29, 2020 to Restriction Requirement dated May 5, 2020", 9 pgs.
"U.S. Appl. No. 15/891,049, Response filed Aug. 17, 2020 to Non Final Office Action dated Jul. 14, 2020", 18 pgs.
"U.S. Appl. No. 15/891,049, Response filed Dec. 1, 2020 to Final Office Action dated Nov. 10, 2020", 12 pgs.
"U.S. Appl. No. 15/891,049, Restriction Requirement dated May 5, 2020", 6 pgs.
"U.S. Appl. No. 15/903,261, Notice of Allowance dated Mar. 26, 2020", 9 pgs.
"U.S. Appl. No. 15/917,143, Non Final Office Action dated Aug. 7, 2020", 6 pgs.
"U.S. Appl. No. 15/917,143, Notice of Allowance dated Feb. 24, 2021", 8 pgs.
"U.S. Appl. No. 15/917,143, Response filed Jun. 17, 2020 to Restriction Requirement dated May 5, 2020", 8 pgs.
"U.S. Appl. No. 15/917,143, Response filed Oct. 29, 2020 to Non Final Office Action dated Aug. 7, 2020", 11 pgs.
"U.S. Appl. No. 15/917,143, Restriction Requirement dated May 5, 2020", 6 pgs.
"U.S. Appl. No. 15/941,481, Non Final Office Action dated Aug. 14, 2020", 21 pgs.
"U.S. Appl. No. 15/941,481, Notice of Allowance dated Dec. 3, 2020", 8 pgs.
"U.S. Appl. No. 15/941,481, Response filed Jun. 24, 2020 to Restriction Requirement dated May 19, 2020", 8 pgs.
"U.S. Appl. No. 15/941,481, Response filed Nov. 16, 2020 to Non Final Office Action dated Aug. 14, 2020", 15 pgs.
"U.S. Appl. No. 15/941,481, Restriction Requirement dated May 19, 2020", 7 pgs.
"U.S. Appl. No. 15/945,425, Non Final Office Action dated Aug. 25, 2020", 11 pgs.
"U.S. Appl. No. 15/945,425, Notice of Allowance dated Dec. 24, 2020", 8 pgs.
"U.S. Appl. No. 15/945,425, Response filed Jun. 24, 2020 to Restriction Requirement dated May 19, 2020", 7 pgs.

(56) References Cited

OTHER PUBLICATIONS

"U.S. Appl. No. 15/945,425, Response filed Nov. 23, 2020 to Non Final Office Action dated Aug. 25, 2020", 10 pgs.
"U.S. Appl. No. 15/945,425, Restriction Requirement dated May 19, 2020", 7 pgs.
"U.S. Appl. No. 15/956,444, Non Final Office Action dated Dec. 7, 2020", 7 pgs.
"U.S. Appl. No. 15/956,444, Notice of Allowance dated Mar. 11, 2021", 8 pgs.
"U.S. Appl. No. 15/956,444, PTO Response to Rule 312 Communication dated Jun. 8, 2021", 2 pgs.
"U.S. Appl. No. 15/956,444, Response filed Feb. 23, 2021 to Non Final Office Action dated Dec. 7, 2020", 11 pgs.
"U.S. Appl. No. 15/956,444, Response filed Sep. 14, 2020 to Restriction Requirement dated Jul. 14, 2020", 8 pgs.
"U.S. Appl. No. 15/956,444, Restriction Requirement dated Jul. 14, 2020", 7 pgs.
"U.S. Appl. No. 15/972,646, Non Final Office Action dated Dec. 7, 2020", 11 pgs.
"U.S. Appl. No. 15/972,646, Notice of Allowance dated Apr. 21, 2021", 8 pgs.
"U.S. Appl. No. 15/972,646, Response filed Feb. 22, 2021 to Non Final Office Action dated Dec. 7, 2020", 13 pgs.
"U.S. Appl. No. 15/972,646, Response filed Sep. 21, 2020 to Restriction Requirement dated Jul. 27, 2020", 7 pgs.
"U.S. Appl. No. 15/972,646, Restriction Requirement dated Jul. 27, 2020", 6 pgs.
"U.S. Appl. No. 16/160,559, Non Final Office Action dated May 14, 2021", 12 pgs.
"U.S. Appl. No. 16/160,559, Notice of Allowance dated Sep. 16, 2021", 14 pgs.
"U.S. Appl. No. 16/160,559, PTO Response to Rule 312 Communication dated Dec. 24, 2021", 2 pgs.
"U.S. Appl. No. 16/160,559, Response filed Mar. 2, 2021 to Restriction Requirement dated Jan. 27, 2021", 7 pgs.
"U.S. Appl. No. 16/160,559, Response filed Aug. 11, 2021 to Non Final Office Action dated May 14, 2021", 10 pgs.
"U.S. Appl. No. 16/160,559, Restriction Requirement dated Jan. 27, 2021", 6 pgs.
"U.S. Appl. No. 16/251,342, Notice of Allowance dated Jul. 26, 2021", 8 pgs.
"U.S. Appl. No. 16/251,342, Response filed May 3, 2021 to Restriction Requirement dated Apr. 30, 2021", 8 pgs.
"U.S. Appl. No. 16/251,342, Restriction Requirement dated Apr. 30, 2021", 6 pgs.
"U.S. Appl. No. 16/251,342, Supplemental Preliminary Amendment filed Oct. 28, 2020", 7 pgs.
"U.S. Appl. No. 16/251,342, Supplemental Preliminary Amendment filed Nov. 4, 2020", 7 pgs.
"U.S. Appl. No. 16/255,300 Supplemental Preliminary Amendment Filed Nov. 12, 2020", 8 pgs.
"U.S. Appl. No. 16/255,300, Notice of Allowance dated Jul. 19, 2021", 10 pgs.
"U.S. Appl. No. 16/380,742, Notice of Allowance dated Jan. 3, 2022", 13 pgs.
"U.S. Appl. No. 16/380,742, Response filed Oct. 20, 2021 to Restriction Requirement dated Aug. 20, 2021", 6 pgs.
"U.S. Appl. No. 16/380,742, Restriction Requirement dated Aug. 20, 2021", 7 pgs.
"U.S. Appl. No. 16/380,742, Supplemental Preliminary Amendment filed Mar. 1, 2021", 5 pgs.
"U.S. Appl. No. 16/400,199, Non Final Office Action dated Feb. 10, 2022", 8 pgs.
"U.S. Appl. No. 16/400,199, Notice of Allowance dated May 11, 2022", 8 pgs.
"U.S. Appl. No. 16/400,199, Response filed Apr. 13, 2022 to Non Final Office Action dated Feb. 10, 2022", 11 pgs.
"U.S. Appl. No. 16/400,199, Response filed Nov. 15, 2021 to Restriction Requirement dated Oct. 1, 2021", 8 pgs.

"U.S. Appl. No. 16/400,199, Restriction Requirement dated Oct. 1, 2021", 7 pgs.
"U.S. Appl. No. 16/420,676, Non Final Office Action dated Jul. 20, 2021", 11 pgs.
"U.S. Appl. No. 16/420,676, Notice of Allowance dated Nov. 15, 2021", 9 pgs.
"U.S. Appl. No. 16/420,676, Response filed Oct. 20, 2021 to Non Final Office Action dated Jul. 20, 2021", 14 pgs.
"U.S. Appl. No. 16/428,277, Response filed Apr. 11, 2022 to Restriction Requirement dated Feb. 11, 2022", 8 pgs.
"U.S. Appl. No. 16/428,277, Restriction Requirement dated Feb. 11, 2022", 6 pgs.
"U.S. Appl. No. 16/436,023, Examiner Interview Summary dated Aug. 23, 2021", 2 pgs.
"U.S. Appl. No. 16/436,023, Non Final Office Action dated May 19, 2021", 18 pgs.
"U.S. Appl. No. 16/436,023, Notice of Allowance dated Oct. 27, 2021", 8 pgs.
"U.S. Appl. No. 16/436,023, Response filed Aug. 19, 2021 to Non Final Office actio dated May 19, 2021", 9 pgs.
"U.S. Appl. No. 16/443,391, Non Final Office Action dated Aug. 31, 2021", 11 pgs.
"U.S. Appl. No. 16/443,391, Notice of Allowance dated Jan. 7, 2022", 5 pgs.
"U.S. Appl. No. 16/443,391, Response filed Nov. 15, 2021 to Non Final Office Action dated Aug. 31, 2021", 9 pgs.
"U.S. Appl. No. 16/508,764, Notice of Allowance dated Oct. 20, 2021", 10 pgs.
"U.S. Appl. No. 16/508,764, Supplemental Amendment filed Sep. 30, 2021", 6 pgs.
"U.S. Appl. No. 16/544,293, Supplemental Preliminary Amendment filed Oct. 28, 2020", 6 pgs.
"U.S. Appl. No. 16/593,022, Supplemental Preliminary Amendment filed Oct. 21, 2020", 8 pgs.
"U.S. Appl. No. 16/690,671, Non Final Office Action dated Nov. 15, 2021", 8 pgs.
"U.S. Appl. No. 16/690,671, Notice of Allowance dated Mar. 2, 2022", 7 pgs.
"U.S. Appl. No. 16/690,671, Response filed Feb. 4, 2022 to Non Final Office Action dated Nov. 15, 2021", 10 pgs.
"U.S. Appl. No. 16/795,181, Examiner Interview Summary dated Apr. 15, 2022", 2 pgs.
"U.S. Appl. No. 16/795,181, Non Final Office Action dated Jan. 24, 2022", 12 pgs.
"U.S. Appl. No. 16/795,181, Response filed Apr. 14, 2022 to Non Final Office Action dated Jan. 24, 2022", 9 pgs.
"U.S. Appl. No. 16/802,228, Preliminary Amendment filed Mar. 4, 2020", 7 pgs.
"U.S. Appl. No. 16/802,248, Preliminary Amendment filed Mar. 5, 2020", 8 pgs.
"U.S. Appl. No. 16/895,246, Preliminary Amendment filed Jun. 9, 2020", 6 pgs.
"U.S. Appl. No. 16/989,386, Supplemental Preliminary Amendment filed Oct. 21, 2020", 8 pgs.
"U.S. Appl. No. 17/190,686, Preliminary Amendment filed Mar. 10, 2021", 7 pgs.
"U.S. Appl. No. 17/392,971, Preliminary Amendment filed Aug. 18, 2021", 9 pgs.
"U.S. Appl. No. 17/492,082, Preliminary Amendment filed Oct. 25, 2021", 6 pgs.
"U.S. Appl. No. 17/516,664, Preliminary Amendment filed Nov. 10, 2021", 6 pgs.
"U.S. Appl. No. 17/545,668, Preliminary Amendment filed Dec. 9, 2021", 5 pgs.
"U.S. Appl. No. 17/550,074, Preliminary Amendment filed Dec. 15, 2021", 5 pgs.
"U.S. Appl. No. 17/577,188, Preliminary Amendment filed Jan. 19, 2022", 7 pgs.
"European Application Serial No. 14716173.1, Communication Pursuant to Article 94(3) EPC dated Jul. 13, 2020", 4 pgs.
"AperFix® System Surgical Technique Guide. Single Tunnel Double Bundle.™", Cayenne Medical brochure, (Aug. 2008), 8 pgs.

(56) References Cited

OTHER PUBLICATIONS

"U.S. Appl. No. 10/984,624, Final Office Action dated Jan. 5, 2009", 9 pgs.
"U.S. Appl. No. 10/984,624, Non Final Office Action dated Jul. 10, 2008", 9 pgs.
"U.S. Appl. No. 10/984,624, Notice of Allowance dated Jun. 12, 2009", 9 pgs.
"U.S. Appl. No. 10/984,624, Response filed Apr. 1, 2009 to Final Office Action dated Jan. 5, 2009", 16 pgs.
"U.S. Appl. No. 10/984,624, Response filed Apr. 15, 2008 to Restriction Requirement dated Mar. 24, 2008", 1 pg.
"U.S. Appl. No. 10/984,624, Response filed Oct. 10, 2008 to Non Final Office Action dated Jul. 10, 2008", 12 pgs.
"U.S. Appl. No. 10/984,624, Restriction Requirement dated Mar. 24, 2008", 5 pgs.
"U.S. Appl. No. 11/294,694, Final Office Action dated Sep. 1, 2010", 14 pgs.
"U.S. Appl. No. 11/294,694, Non Final Office Action dated Mar. 16, 2010", 19 pgs.
"U.S. Appl. No. 11/294,694, Notice of Allowance dated Nov. 17, 2010", 4 pgs.
"U.S. Appl. No. 11/294,694, Preliminary Amendment filed Jan. 13, 2010", 9 pgs.
"U.S. Appl. No. 11/294,694, Response filed Jun. 16, 2010 to Non Final Office Action dated Mar. 16, 2010", 16 pgs.
"U.S. Appl. No. 11/294,694, Response filed Nov. 1, 2010 to Final Office Action dated Sep. 1, 2010", 10 pgs.
"U.S. Appl. No. 11/294,694, Response filed Dec. 22, 2009 to Restriction Requirement dated Nov. 25, 2009", 1 pg.
"U.S. Appl. No. 11/294,694, Restriction Requirement dated Nov. 25, 2009", 9 pgs.
"U.S. Appl. No. 11/347,661, Examiner Interview Summary dated Sep. 11, 2009", 2 pgs.
"U.S. Appl. No. 11/347,661, Final Office Action dated Mar. 3, 2009", 15 pgs.
"U.S. Appl. No. 11/347,661, Non Final Office Action dated Aug. 13, 2009", 19 pgs.
"U.S. Appl. No. 11/347,661, Non Final Office Action dated Aug. 21, 2008", 11 pgs.
"U.S. Appl. No. 11/347,661, Notice of Allowance dated Feb. 24, 2010", 8 pgs.
"U.S. Appl. No. 11/347,661, Notice of Allowance dated May 5, 2010", 8 pgs.
"U.S. Appl. No. 11/347,661, Response filed May 29, 2008 to Restriction Requirement dated Apr. 30, 2008", 1 pg.
"U.S. Appl. No. 11/347,661, Response filed Jun. 3, 2009 to Final Office Action dated Mar. 3, 2009", 19 pgs.
"U.S. Appl. No. 11/347,661, Response filed Nov. 6, 2009 to Non Final Office Action dated Aug. 13, 2009", 16 pgs.
"U.S. Appl. No. 11/347,661, Response filed Nov. 19, 2008 to Non Final Office Action dated Aug. 21, 2008", 12 pgs.
"U.S. Appl. No. 11/347,661, Restriction Requirement dated Apr. 30, 2008", 6 pgs.
"U.S. Appl. No. 11/347,662, Examiner Interview Summary dated Jun. 24, 2010", 3 pgs.
"U.S. Appl. No. 11/347,662, Examiner Interview Summary dated Nov. 9, 2009", 3 pgs.
"U.S. Appl. No. 11/347,662, Final Office Action dated Sep. 16, 2009", 13 pgs.
"U.S. Appl. No. 11/347,662, Final Office Action dated Oct. 26, 2010", 10 pgs.
"U.S. Appl. No. 11/347,662, Non Final Office Action dated Mar. 9, 2009", 11 pgs.
"U.S. Appl. No. 11/347,662, Non Final Office Action dated May 21, 2010", 19 pgs.
"U.S. Appl. No. 11/347,662, Non Final Office Action dated Oct. 28, 2008", 13 pgs.
"U.S. Appl. No. 11/347,662, Response filed Jan. 16, 2009 to Non Final Office Action dated Oct. 28, 2008", 16 pgs.
"U.S. Appl. No. 11/347,662, Response filed Feb. 12, 2010 to Final Office Action dated Sep. 16, 2009", 21 pgs.
"U.S. Appl. No. 11/347,662, Response filed Jun. 5, 2009 to Non Final Office Action dated Mar. 9, 2009", 13 pgs.
"U.S. Appl. No. 11/347,662, Response filed Aug. 20, 2010 to Non Final Office Action dated May 21, 2010", 13 pgs.
"U.S. Appl. No. 11/386,071, Advisory Action dated Dec. 23, 2010", 3 pgs.
"U.S. Appl. No. 11/386,071, Examiner Interview Summary dated Jan. 31, 2011", 3 pgs.
"U.S. Appl. No. 11/386,071, Examiner Interview Summary dated Jul. 21, 2010", 3 pgs.
"U.S. Appl. No. 11/386,071, Final Office Action dated Oct. 27, 2010", 10 pgs.
"U.S. Appl. No. 11/386,071, Non Final Office Action dated May 12, 2010", 13 pgs.
"U.S. Appl. No. 11/386,071, Notice of Allowance dated Jun. 6, 2011", 6 pgs.
"U.S. Appl. No. 11/386,071, Response filed Jan. 26, 2011 to Advisory Action dated Dec. 23, 2010", 13 pgs.
"U.S. Appl. No. 11/386,071, Response filed Aug. 12, 2010 to Non Final Office Action dated May 12, 2010", 14 pgs.
"U.S. Appl. No. 11/386,071, Response filed Dec. 15, 2010 to Final Office Action dated Oct. 27, 2010", 14 pgs.
"U.S. Appl. No. 11/408,282, Final Office Action dated Dec. 15, 2008", 8 pgs.
"U.S. Appl. No. 11/408,282, Non Final Office Action dated May 23, 2008", 12 pgs.
"U.S. Appl. No. 11/408,282, Response filed Aug. 21, 2008 to Non Final Office Action dated May 23, 2008", 10 pgs.
"U.S. Appl. No. 11/504,882, Examiner Interview Summary dated Sep. 2, 2010", 3 pgs.
"U.S. Appl. No. 11/504,882, Final Office Action dated Dec. 21, 2010", 7 pgs.
"U.S. Appl. No. 11/504,882, Non Final Office Action dated Jun. 19, 2014", 11 pgs.
"U.S. Appl. No. 11/504,882, Non Final Office Action dated Jun. 23, 2010", 8 pgs.
"U.S. Appl. No. 11/504,882, Non Final Office Action dated Nov. 13, 2013", 13 pgs.
"U.S. Appl. No. 11/504,882, Notice of Allowance dated Dec. 1, 2014", 9 pgs.
"U.S. Appl. No. 11/504,882, Response filed Feb. 10, 2014 to Non Final Office Action dated Nov. 13, 2013", 11 pgs.
"U.S. Appl. No. 11/504,882, Response filed Mar. 18, 2011 to Final Office Action dated Dec. 21, 2010", 11 pgs.
"U.S. Appl. No. 11/504,882, Response filed Sep. 17, 2014 to Non Final Office Action dated Jun. 19, 2014", 14 pgs.
"U.S. Appl. No. 11/504,882, Response filed Sep. 23, 2010 to Non Final Office Action dated Jun. 23, 2010", 12 pgs.
"U.S. Appl. No. 11/504,882, Supplemental Notice of Allowability dated Mar. 12, 2015", 5 pgs.
"U.S. Appl. No. 11/541,505, Non Final Office Action dated May 19, 2009", 7 pgs.
"U.S. Appl. No. 11/541,505, Notice of Allowance dated Sep. 18, 2009", 8 pgs.
"U.S. Appl. No. 11/541,505, Response filed Apr. 9, 2009 to Restriction Requirement dated Mar. 9, 2009", 1 pg.
"U.S. Appl. No. 11/541,505, Response filed Jun. 18, 2009 to Non Final Office Action dated May 19, 2009", 5 pgs.
"U.S. Appl. No. 11/541,505, Restriction Requirement dated Mar. 9, 2009", 9 pgs.
"U.S. Appl. No. 11/541,506, Notice of Allowance dated Jun. 1, 2009", 10 pgs.
"U.S. Appl. No. 11/541,506, Notice of Allowance dated Jun. 29, 2009", 8 pgs.
"U.S. Appl. No. 11/541,506, Response filed Apr. 9, 2009 to Restriction Requirement dated Mar. 9, 2009", 1 pg.
"U.S. Appl. No. 11/541,506, Restriction Requirement dated Mar. 9, 2009", 6 pgs.
"U.S. Appl. No. 11/739,768, Examiner Interview Summary dated May 11, 2011", 3 pgs.

(56) References Cited

OTHER PUBLICATIONS

"U.S. Appl. No. 11/739,768, Examiner Interview Summary dated Oct. 4, 2011", 3 pgs.
"U.S. Appl. No. 11/739,768, Final Office Action dated Aug. 22, 2011", 14 pgs.
"U.S. Appl. No. 11/739,768, Non Final Office Action dated Mar. 4, 2011", 11 pgs.
"U.S. Appl. No. 11/739,768, Notice of Allowance dated Nov. 15, 2011", 5 pgs.
"U.S. Appl. No. 11/739,768, Response filed Jun. 6, 2011 to Non Final Office Action dated Mar. 4, 2011", 15 pgs.
"U.S. Appl. No. 11/739,768, Response filed Oct. 26, 2011 to Final Office Action dated Aug. 22, 2011", 14 pgs.
"U.S. Appl. No. 11/740,035, Final Office Action dated Aug. 7, 2008", 9 pgs.
"U.S. Appl. No. 11/740,035, Non Final Office Action dated Jan. 3, 2008", 9 pgs.
"U.S. Appl. No. 11/740,035, Response filed Apr. 3, 2008 to Non Final Office Action dated Jan. 3, 2008", 6 pgs.
"U.S. Appl. No. 11/784,821, Corrected Notice of Allowance dated Dec. 24, 2014", 4 pgs.
"U.S. Appl. No. 11/784,821, Examiner Interview Summary dated Jun. 26, 2014", 3 pgs.
"U.S. Appl. No. 11/784,821, Examiner Interview Summary dated Nov. 17, 2009", 3 pgs.
"U.S. Appl. No. 11/784,821, Final Office Action dated Mar. 10, 2010", 11 pgs.
"U.S. Appl. No. 11/784,821, Non Final Office Action dated Mar. 28, 2014", 14 pgs.
"U.S. Appl. No. 11/784,821, Non Final Office Action dated Sep. 4, 2009", 12 pgs.
"U.S. Appl. No. 11/784,821, Notice of Allowance dated Oct. 21, 2014", 10 pgs.
"U.S. Appl. No. 11/784,821, Response filed Jun. 10, 2010 to Final Office Action dated Mar. 10, 2010", 20 pgs.
"U.S. Appl. No. 11/784,821, Response filed Jun. 15, 2009 to Restriction Requirement dated May 13, 2009", 2 pgs.
"U.S. Appl. No. 11/784,821, Response filed Jun. 26, 2014 to Non Final Office Action dated Mar. 28, 2014", 16 pgs.
"U.S. Appl. No. 11/784,821, Response filed Nov. 23, 2009 to Non Final Office Action dated Sep. 4, 2009", 17 pgs.
"U.S. Appl. No. 11/784,821, Restriction Requirement dated May 13, 2009", 6 pgs.
"U.S. Appl. No. 11/869,440, Examiner Interview Summary dated Mar. 25, 2010", 3 pgs.
"U.S. Appl. No. 11/869,440, Non Final Office Action dated Mar. 1, 2010", 13 pgs.
"U.S. Appl. No. 11/869,440, Notice of Allowance dated Aug. 19, 2010", 10 pgs.
"U.S. Appl. No. 11/869,440, Response filed Jun. 1, 2010 to Non Final Office Action dated Mar. 1, 2010", 14 pgs.
"U.S. Appl. No. 11/935,681, Examiner Interview Summary dated Jul. 19, 2010", 3 pgs.
"U.S. Appl. No. 11/935,681, Non Final Office Action dated May 24, 2010", 12 pgs.
"U.S. Appl. No. 11/935,681, Notice of Allowance dated Nov. 8, 2010", 10 pgs.
"U.S. Appl. No. 11/935,681, Response filed Apr. 19, 2010 to Restriction Requirement dated Mar. 17, 2010", 4 pgs.
"U.S. Appl. No. 11/935,681, Response filed Aug. 24, 2010 to Non Final Office Action dated May 24, 2010", 13 pgs.
"U.S. Appl. No. 11/935,681, Restriction Requirement dated Mar. 17, 2010", 6 pgs.
"U.S. Appl. No. 12/014,340, Examiner Interview Summary dated Jun. 22, 2010", 3 pgs.
"U.S. Appl. No. 12/014,340, Non Final Office Action dated May 25, 2010", 12 pgs.
"U.S. Appl. No. 12/014,340, Notice of Allowance dated Nov. 8, 2010", 9 pgs.
"U.S. Appl. No. 12/014,340, Preliminary Amendment filed May 21, 2010", 11 pgs.
"U.S. Appl. No. 12/014,340, Response filed Apr. 26, 2010 to Restriction Requirement dated Mar. 25, 2010", 2 pgs.
"U.S. Appl. No. 12/014,340, Response filed Aug. 25, 2010 to Non Final Office Action dated May 25, 2010", 16 pgs.
"U.S. Appl. No. 12/014,340, Restriction Requirement dated Mar. 25, 2010", 9 pgs.
"U.S. Appl. No. 12/014,399, Examiner Interview Summary dated Jun. 23, 2010", 3 pgs.
"U.S. Appl. No. 12/014,399, Non Final Office Action dated May 26, 2010", 13 pgs.
"U.S. Appl. No. 12/014,399, Notice of Allowance dated Nov. 12, 2010", 11 pgs.
"U.S. Appl. No. 12/014,399, Preliminary Amendment filed May 25, 2010", 10 pgs.
"U.S. Appl. No. 12/014,399, Response filed May 5, 2010 to Restriction Requirement dated Apr. 6, 2010", 2 pgs.
"U.S. Appl. No. 12/014,399, Response filed Aug. 25, 2010 to Non Final Office Action dated May 26, 2010", 14 pgs.
"U.S. Appl. No. 12/014,399, Restriction Requirement dated Apr. 6, 2010", 9 pgs.
"U.S. Appl. No. 12/029,861, Examiner Interview Summary dated Jan. 27, 2012", 3 pgs.
"U.S. Appl. No. 12/029,861, Final Office Action dated Dec. 8, 2011", 11 pgs.
"U.S. Appl. No. 12/029,861, Non Final Office Action dated Jul. 26, 2011", 11 pgs.
"U.S. Appl. No. 12/029,861, Notice of Allowance dated Apr. 26, 2012", 5 pgs.
"U.S. Appl. No. 12/029,861, Response filed Jan. 26, 2012 to Final Office Action dated Dec. 8, 2011", 15 pgs.
"U.S. Appl. No. 12/029,861, Response filed May 6, 2011 to Restriction Requirement dated Apr. 7, 2011", 10 pgs.
"U.S. Appl. No. 12/029,861, Response filed Jun. 23, 2011 to Restriction Requirement dated May 24, 2011", 1 pgs.
"U.S. Appl. No. 12/029,861, Response filed Oct. 14, 2011 to Non Final Office Action dated Jul. 26, 2011", 11 pgs.
"U.S. Appl. No. 12/029,861, Restriction Requirement dated Apr. 7, 2011", 8 pgs.
"U.S. Appl. No. 12/029,861, Restriction Requirement dated May 24, 2011", 6 pgs.
"U.S. Appl. No. 12/107,437, Examiner Interview Summary dated May 10, 2010", 4 pgs.
"U.S. Appl. No. 12/107,437, Non Final Office Action dated Mar. 17, 2010", 9 pgs.
"U.S. Appl. No. 12/107,437, Preliminary Amendment filed Feb. 23, 2010", 9 pgs.
"U.S. Appl. No. 12/107,437, Response filed Jan. 29, 2010 to Restriction Requirement dated Jan. 13, 2010", 1 pgs.
"U.S. Appl. No. 12/107,437, Restriction Requirement dated Jan. 13, 2010", 7 pgs.
"U.S. Appl. No. 12/196,398, Examiner Interview Summary dated Nov. 8, 2010", 3 pgs.
"U.S. Appl. No. 12/196,398, Notice of Allowance dated Feb. 3, 2011", 12 pgs.
"U.S. Appl. No. 12/196,398, Preliminary Amendment filed Nov. 10, 2008", 3 pgs.
"U.S. Appl. No. 12/196,398, Preliminary Amendment filed Dec. 1, 2010", 12 pgs.
"U.S. Appl. No. 12/196,398, Preliminary Amendment filed Dec. 9, 2008", 46 pgs.
"U.S. Appl. No. 12/196,398, Response filed Oct. 29, 2010 to Restriction Requirement dated Sep. 29, 2010", 2 pgs.
"U.S. Appl. No. 12/196,398, Restriction Requirement dated Sep. 29, 2010", 6 pgs.
"U.S. Appl. No. 12/196,398, Supplemental Notice of Allowability dated Mar. 9, 2011", 4 pgs.
"U.S. Appl. No. 12/196,398, Supplemental Notice of Allowability dated Apr. 15, 2011", 4 pgs.
"U.S. Appl. No. 12/196,405, Examiner Interview Summary dated Jun. 20, 2011", 3 pgs.

(56) References Cited

OTHER PUBLICATIONS

"U.S. Appl. No. 12/196,405, Non Final Office Action dated Apr. 11, 2011", 13 pgs.
"U.S. Appl. No. 12/196,405, Notice of Allowance dated Oct. 26, 2011", 11 pgs.
"U.S. Appl. No. 12/196,405, Preliminary Amendment filed Nov. 10, 2008", 3 pgs.
"U.S. Appl. No. 12/196,405, Response filed Mar. 16, 2011 to Restriction Requirement dated Feb. 14, 2011", 1 pgs.
"U.S. Appl. No. 12/196,405, Response filed Jul. 12, 2011 to Non Final Office Action dated Apr. 11, 2011", 19 pgs.
"U.S. Appl. No. 12/196,405, Restriction Requirement dated Feb. 14, 2011", 6 pgs.
"U.S. Appl. No. 12/196,405, Supplemental Amendment filed Oct. 3, 2011", 12 pgs.
"U.S. Appl. No. 12/196,407, Examiner Interview Summary dated Jul. 14, 2011", 3 pgs.
"U.S. Appl. No. 12/196,407, Non Final Office Action dated May 4, 2011", 11 pgs.
"U.S. Appl. No. 12/196,407, Notice of Allowance dated Oct. 26, 2011", 10 pgs.
"U.S. Appl. No. 12/196,407, Preliminary Amendment filed Nov. 10, 2008", 3 pgs.
"U.S. Appl. No. 12/196,407, Response filed Apr. 20, 2011 to Restriction Requirement dated Mar. 22, 2011", 12 pgs.
"U.S. Appl. No. 12/196,407, Response filed Aug. 2, 2011 to Non Final Office Action dated May 4, 2011", 27 pgs.
"U.S. Appl. No. 12/196,407, Restriction Requirement dated Mar. 22, 2011", 6 pgs.
"U.S. Appl. No. 12/196,407, Supplemental Response to Non Final Office Action filed Oct. 3, 2011", 18 pgs.
"U.S. Appl. No. 12/196,410, Examiner Interview Summary dated Jul. 14, 2011", 3 pgs.
"U.S. Appl. No. 12/196,410, Non Final Office Action dated May 9, 2011", 9 pgs.
"U.S. Appl. No. 12/196,410, Notice of Allowance dated Oct. 13, 2011", 8 pgs.
"U.S. Appl. No. 12/196,410, Response filed Apr. 20, 2011 to Restriction Requirement dated Mar. 22, 2011", 13 pgs.
"U.S. Appl. No. 12/196,410, Response filed Aug. 1, 2011 to Non Final Office Action dated May 9, 2011", 23 pgs.
"U.S. Appl. No. 12/196,410, Restriction Requirement dated Mar. 22, 2011", 6 pgs.
"U.S. Appl. No. 12/196,410, Supplemental Amendment filed Oct. 3, 2011", 15 pgs.
"U.S. Appl. No. 12/398,548, Examiner Interview Summary dated Jul. 12, 2011", 3 pgs.
"U.S. Appl. No. 12/398,548, Non Final Office Action dated Apr. 12, 2011", 7 pgs.
"U.S. Appl. No. 12/398,548, Notice of Allowance dated Oct. 18, 2011", 7 pgs.
"U.S. Appl. No. 12/398,548, Response filed Jul. 12, 2011 to Non Final Office Action dated Apr. 12, 2011", 15 pgs.
"U.S. Appl. No. 12/398,548, Supplemental Preliminary Amendment filed Sep. 7, 2010", 11 pgs.
"U.S. Appl. No. 12/419,491, Examiner Interview Summary dated May 30, 2012", 3 pgs.
"U.S. Appl. No. 12/419,491, Examiner Interview Summary dated Nov. 29, 2011", 3 pgs.
"U.S. Appl. No. 12/419,491, Final Office Action dated Apr. 12, 2012", 12 pgs.
"U.S. Appl. No. 12/419,491, Non Final Office Action dated Sep. 22, 2011", 12 pgs.
"U.S. Appl. No. 12/419,491, Notice of Allowance dated Jul. 13, 2012", 10 pgs.
"U.S. Appl. No. 12/419,491, Response filed May 30, 2012 to Final Office Action dated Apr. 12, 2012", 12 pgs.
"U.S. Appl. No. 12/419,491, Response filed Dec. 9, 2011 to Non Final Office Action dated Sep. 22, 2011", 17 pgs.
"U.S. Appl. No. 12/474,802, Notice of Allowance dated Aug. 31, 2011", 13 pgs.
"U.S. Appl. No. 12/474,802, Notice of Allowance dated Oct. 26, 2011", 4 pgs.
"U.S. Appl. No. 12/474,802, Response filed Mar. 28, 2011 to Restriction Requirement dated Feb. 24, 2011", 12 pgs.
"U.S. Appl. No. 12/474,802, Restriction Requirement dated Feb. 24, 2011", 6 pgs.
"U.S. Appl. No. 12/489,168, Examiner Interview Summary dated Feb. 21, 2012", 3 pgs.
"U.S. Appl. No. 12/489,168, Non Final Office Action dated Dec. 7, 2011", 10 pgs.
"U.S. Appl. No. 12/489,168, Notice of Allowance dated Apr. 26, 2012", 8 pgs.
"U.S. Appl. No. 12/489,168, Notice of Allowance dated Sep. 5, 2012", 8 pgs.
"U.S. Appl. No. 12/489,168, Preliminary Amendment filed Oct. 22, 2009", 3 pgs.
"U.S. Appl. No. 12/489,168, Response filed Feb. 27, 2012 to Non Final Office Action dated Dec. 7, 2011", 15 pgs.
"U.S. Appl. No. 12/489,168, Response filed Nov. 11, 2011 to Restriction Requirement dated Oct. 20, 2011", 1 pg.
"U.S. Appl. No. 12/489,168, Restriction Requirement dated Oct. 20, 2011", 8 pgs.
"U.S. Appl. No. 12/489,181, Examiner Interview Summary dated Feb. 13, 2012", 3 pgs.
"U.S. Appl. No. 12/489,181, Non Final Office Action dated Jan. 3, 2012", 9 pgs.
"U.S. Appl. No. 12/489,181, Notice of Allowance dated May 23, 2012", 9 pgs.
"U.S. Appl. No. 12/489,181, Preliminary Amendment filed Mar. 31, 2011", 10 pgs.
"U.S. Appl. No. 12/489,181, Preliminary Amendment filed Oct. 22, 2009", 3 pgs.
"U.S. Appl. No. 12/489,181, Response filed Mar. 27, 2012 to Non Final Office Action dated Jan. 3, 2012", 12 pgs.
"U.S. Appl. No. 12/489,181, Response filed Dec. 5, 2011 to Restriction Requirement dated Nov. 4, 2011", 1 pg.
"U.S. Appl. No. 12/489,181, Restriction Requirement dated Nov. 4, 2011", 7 pgs.
"U.S. Appl. No. 12/570,854, Examiner Interview Summary dated Apr. 16, 2012", 3 pgs.
"U.S. Appl. No. 12/570,854, Non Final Office Action dated Feb. 10, 2012", 8 pgs.
"U.S. Appl. No. 12/570,854, Notice of Allowance dated Jun. 29, 2012", 10 pgs.
"U.S. Appl. No. 12/570,854, Notice of Allowance dated Sep. 19, 2012", 6 pgs.
"U.S. Appl. No. 12/570,854, Response filed May 10, 2012 to Non Final Office Action dated Feb. 10, 2012", 27 pgs.
"U.S. Appl. No. 12/570,854, Response filed Dec. 20, 2011 to Restriction Requirement dated Dec. 14, 2011", 1 pg.
"U.S. Appl. No. 12/570,854, Restriction Requirement dated Dec. 14, 2011", 6 pgs.
"U.S. Appl. No. 12/702,067, Non Final Office Action dated Mar. 5, 2013", 8 pgs.
"U.S. Appl. No. 12/702,067, Notice of Allowance dated Oct. 7, 2013", 11 pgs.
"U.S. Appl. No. 12/702,067, Preliminary Amendment filed Jan. 11, 2011", 13 pgs.
"U.S. Appl. No. 12/702,067, Response filed Jun. 5, 2013 to Non Final Office Action dated Mar. 5, 2013", 17 pgs.
"U.S. Appl. No. 12/702,067, Response filed Oct. 2, 2012 to Restriction Requirement dated Sep. 4, 2012", 1 pg.
"U.S. Appl. No. 12/702,067, Restriction Requirement dated Sep. 4, 2012", 9 pgs.
"U.S. Appl. No. 12/719,337, Advisory Action dated Sep. 30, 2014", 4 pgs.
"U.S. Appl. No. 12/719,337, Examiner Interview Summary dated Apr. 4, 2014", 4 pgs.
"U.S. Appl. No. 12/719,337, Examiner Interview Summary dated May 14, 2013", 3 pgs.

(56) References Cited

OTHER PUBLICATIONS

"U.S. Appl. No. 12/719,337, Examiner Interview Summary dated Sep. 18, 2014", 3 pgs.
"U.S. Appl. No. 12/719,337, Final Office Action dated Mar. 12, 2013", 8 pgs.
"U.S. Appl. No. 12/719,337, Final Office Action dated Jul. 18, 2014", 15 pgs.
"U.S. Appl. No. 12/719,337, Non Final Office Action dated Jan. 10, 2014", 14 pgs.
"U.S. Appl. No. 12/719,337, Non Final Office Action dated Sep. 5, 2012", 7 pgs.
"U.S. Appl. No. 12/719,337, Notice of Allowance dated Mar. 11, 2015", 10 pgs.
"U.S. Appl. No. 12/719,337, Notice of Non-Compliant Amendment dated May 2, 2014", 3 pgs.
"U.S. Appl. No. 12/719,337, Response filed Apr. 10, 2014 to Non Final Office Action dated Jan. 10, 2014", 16 pgs.
"U.S. Appl. No. 12/719,337, Response filed May 25, 2012 to Restriction Requirement dated Apr. 26, 2012", 9 pgs.
"U.S. Appl. No. 12/719,337, Response filed Jun. 5, 2013 to Final Office Action dated Mar. 12, 2013", 16 pgs.
"U.S. Appl. No. 12/719,337, Response filed Jun. 25, 2014 to Notice of Non-Compliant Amendment dated May 2, 2014", 10 pgs.
"U.S. Appl. No. 12/719,337, Response filed Sep. 18, 2014 to Final Office Action dated Jul. 18, 2014", 13 pgs.
"U.S. Appl. No. 12/719,337, Response filed Nov. 28, 2012 to Non Final Office Action dated Sep. 5, 2012", 14 pgs.
"U.S. Appl. No. 12/719,337, Restriction Requirement dated Apr. 26, 2012", 8 pgs.
"U.S. Appl. No. 12/788,966, Examiner Interview Summary dated Jun. 1, 2012", 3 pgs.
"U.S. Appl. No. 12/788,966, Final Office Action dated May 4, 2012", 16 pgs.
"U.S. Appl. No. 12/788,966, Non Final Office Action dated Jan. 4, 2012", 12 pgs.
"U.S. Appl. No. 12/788,966, Notice of Allowance dated Aug. 16, 2012", 10 pgs.
"U.S. Appl. No. 12/788,966, Notice of Allowance dated Nov. 23, 2012", 2 pgs.
"U.S. Appl. No. 12/788,966, Response filed Apr. 4, 2012 to Non Final Office Action dated Jan. 4, 2012", 15 pgs.
"U.S. Appl. No. 12/788,966, Response filed Aug. 6, 2012 to Final Office Action dated May 4, 2012", 12 pgs.
"U.S. Appl. No. 12/788,966, Response filed Dec. 16, 2011 to Restriction Requirement dated Dec. 7, 2011", 11 pgs.
"U.S. Appl. No. 12/788,966, Restriction Requirement dated Dec. 7, 2011", 9 pgs.
"U.S. Appl. No. 12/788,973, Advisory Action dated Jan. 23, 2013", 3 pgs.
"U.S. Appl. No. 12/788,973, Advisory Action dated Dec. 27, 2012", 8 pgs.
"U.S. Appl. No. 12/788,973, Final Office Action dated Sep. 18, 2012", 16 pgs.
"U.S. Appl. No. 12/788,973, Non Final Office Action dated May 8, 2012", 12 pgs.
"U.S. Appl. No. 12/788,973, Notice of Allowance dated Mar. 21, 2013", 6 pgs.
"U.S. Appl. No. 12/788,973, Response filed Jan. 16, 2013 to Advisory Action dated Dec. 27, 2012", 9 pgs.
"U.S. Appl. No. 12/788,973, Response filed Jul. 19, 2012 to Non Final Office Action dated May 8, 2012", 21 pgs.
"U.S. Appl. No. 12/788,973, Response filed Dec. 16, 2011 to Restriction Requirement dated Dec. 6, 2011", 11 pgs.
"U.S. Appl. No. 12/788,973, Response filed Dec. 17, 2012 to Final Office Action dated Sep. 18, 2012", 15 pgs.
"U.S. Appl. No. 12/788,973, Restriction Requirement dated Dec. 6, 2011", 9 pgs.
"U.S. Appl. No. 12/788,973, Supplemental Notice of Allowance dated May 24, 2013", 2 pgs.
"U.S. Appl. No. 12/788,978, Advisory Action dated Dec. 24, 2013", 4 pgs.
"U.S. Appl. No. 12/788,978, Applicant's Summary of Examiner Interview filed Dec. 12, 2013", 2 pgs.
"U.S. Appl. No. 12/788,978, Corrected Notice of Allowance dated Apr. 30, 2014", 2 pgs.
"U.S. Appl. No. 12/788,978, Examiner Interview Summary dated Jan. 28, 2014", 3 pgs.
"U.S. Appl. No. 12/788,978, Examiner Interview Summary dated Mar. 22, 2013", 3 pgs.
"U.S. Appl. No. 12/788,978, Examiner Interview Summary dated Sep. 11, 2012", 3 pgs.
"U.S. Appl. No. 12/788,978, Examiner Interview Summary dated Oct. 29, 2013", 4 pgs.
"U.S. Appl. No. 12/788,978, Examiner Interview Summary dated Dec. 16, 2013", 3 pgs.
"U.S. Appl. No. 12/788,978, Examiner Interview Summary dated Dec. 27, 2012", 3 pgs.
"U.S. Appl. No. 12/788,978, Final Office Action dated Aug. 20, 2013", 17 pgs.
"U.S. Appl. No. 12/788,978, Final Office Action dated Nov. 2, 2012", 14 pgs.
"U.S. Appl. No. 12/788,978, Non Final Office Action dated Jan. 11, 2013", 16 pgs.
"U.S. Appl. No. 12/788,978, Non Final Office Action dated Jul. 13, 2012", 17 pgs.
"U.S. Appl. No. 12/788,978, Notice of Allowance dated Jan. 24, 2014", 9 pgs.
"U.S. Appl. No. 12/788,978, Notice of Non-Compliant Amendment dated Jun. 6, 2013", 3 pgs.
"U.S. Appl. No. 12/788,978, Response filed Jan. 2, 2013 to Final Office Action dated Nov. 2, 2012", 13 pgs.
"U.S. Appl. No. 12/788,978, Response filed Jan. 20, 2014 to Advisory Action dated Dec. 24, 2013", 4 pgs.
"U.S. Appl. No. 12/788,978, Response filed Apr. 8, 2013 to Non Final Office Action dated Jan. 11, 2013", 16 pgs.
"U.S. Appl. No. 12/788,978, Response filed May 21, 2012 to Restriction Requirement dated Apr. 20, 2012", 12 pgs.
"U.S. Appl. No. 12/788,978, Response filed Jul. 3, 2013 to Notice of Non-Compliant Amendment dated Jun. 6, 2013", 17 pgs.
"U.S. Appl. No. 12/788,978, Response filed Oct. 5, 2012 to Non Final Office Action dated Jul. 13, 2012", 20 pgs.
"U.S. Appl. No. 12/788,978, Response filed Nov. 20, 2013 to Final Office Action dated Aug. 20, 2013", 15 pgs.
"U.S. Appl. No. 12/788,978, Restriction Requirement dated Apr. 20, 2012", 8 pgs.
"U.S. Appl. No. 12/828,977, Examiner Interview Summary dated Jul. 9, 2012", 3 pgs.
"U.S. Appl. No. 12/828,977, Non Final Office Action dated May 3, 2012", 9 pgs.
"U.S. Appl. No. 12/828,977, Notice of Allowance dated Sep. 5, 2012", 9 pgs.
"U.S. Appl. No. 12/828,977, Preliminary Amendment filed Jul. 19, 2011", 10 pgs.
"U.S. Appl. No. 12/828,977, Response filed Mar. 14, 2012 to Restriction Requirement dated Feb. 13, 2012", 9 pgs.
"U.S. Appl. No. 12/828,977, Response filed Jul. 25, 2012 to Non Final Office Action dated May 3, 2012", 11 pgs.
"U.S. Appl. No. 12/828,977, Restriction Requirement dated Feb. 13, 2012", 7 pgs.
"U.S. Appl. No. 12/915,962, Examiner Interview Summary dated Jul. 25, 2012", 3 pgs.
"U.S. Appl. No. 12/915,962, Non Final Office Action dated May 7, 2012", 11 pgs.
"U.S. Appl. No. 12/915,962, Non Final Office Action dated Oct. 15, 2012", 9 pgs.
"U.S. Appl. No. 12/915,962, Notice of Allowance dated Jun. 10, 2013", 12 pgs.
"U.S. Appl. No. 12/915,962, Response filed Jan. 10, 2013 to Non Final Office Action dated Oct. 15, 2012", 21 pgs.
"U.S. Appl. No. 12/915,962, Response filed Mar. 16, 2012 to Restriction Requirement dated Feb. 15, 2012", 15 pgs.

(56) References Cited

OTHER PUBLICATIONS

"U.S. Appl. No. 12/915,962, Response filed Aug. 7, 2012 to Non Final Office Action dated May 7, 2012", 26 pgs.
"U.S. Appl. No. 12/915,962, Restriction Requirement dated Feb. 15, 2012", 8 pgs.
"U.S. Appl. No. 12/938,902, Examiner Interview Summary dated Dec. 3, 2012", 3 pgs.
"U.S. Appl. No. 12/938,902, Non Final Office Action dated Sep. 17, 2012", 11 pgs.
"U.S. Appl. No. 12/938,902, Notice of Allowance dated Jun. 21, 2013", 13 pgs.
"U.S. Appl. No. 12/938,902, Notice of Allowance dated Oct. 1, 2013", 9 pgs.
"U.S. Appl. No. 12/938,902, Response filed Aug. 6, 2012 to Restriction Requirement dated Jul. 6, 2012", 14 pgs.
"U.S. Appl. No. 12/938,902, Response filed Dec. 10, 2012 to Non Final Office Action dated Sep. 17, 2012", 20 pgs.
"U.S. Appl. No. 12/938,902, Restriction Requirement dated Jul. 6, 2012", 8 pgs.
"U.S. Appl. No. 12/976,328, Examiner Interview Summary dated Feb. 13, 2012", 3 pgs.
"U.S. Appl. No. 12/976,328, Non Final Office Action dated Dec. 15, 2011", 13 pgs.
"U.S. Appl. No. 12/976,328, Notice of Allowance dated Apr. 30, 2012", 9 pgs.
"U.S. Appl. No. 12/976,328, Response filed Mar. 2, 2012 to Non Final Office Action dated Dec. 15, 2011", 15 pgs.
"U.S. Appl. No. 13/045,689, Examiner Interview Summary dated May 14, 2012", 3 pgs.
"U.S. Appl. No. 13/045,689, Non Final Office Action dated Mar. 20, 2012", 11 pgs.
"U.S. Appl. No. 13/045,689, Notice of Allowance dated Aug. 10, 2012", 10 pgs.
"U.S. Appl. No. 13/045,689, Notice of Allowance dated Sep. 24, 2012", 7 pgs.
"U.S. Appl. No. 13/045,689, Response filed Jan. 30, 2012 to Restriction Requirement dated Dec. 29, 2011", 13 pgs.
"U.S. Appl. No. 13/045,689, Response filed Jun. 8, 2012 to Non Final Office Action dated Mar. 20, 2012", 15 pgs.
"U.S. Appl. No. 13/045,689, Restriction Requirement dated Dec. 29, 2011", 6 pgs.
"U.S. Appl. No. 13/045,691, Examiner Interview Summary dated May 14, 2012", 3 pgs.
"U.S. Appl. No. 13/045,691, Non Final Office Action dated Mar. 20, 2012", 12 pgs.
"U.S. Appl. No. 13/045,691, Notice of Allowance dated Jun. 19, 2012", 10 pgs.
"U.S. Appl. No. 13/045,691, Response filed Feb. 9, 2012 to Restriction Requirement dated Jan. 9, 2012", 1 pg.
"U.S. Appl. No. 13/045,691, Response filed Jun. 8, 2012 to Non Final Office Action dated Mar. 20, 2012", 17 pgs.
"U.S. Appl. No. 13/045,691, Restriction Requirement dated Jan. 9, 2012", 6 pgs.
"U.S. Appl. No. 13/071,563, Final Office Action dated May 23, 2014", 13 pgs.
"U.S. Appl. No. 13/071,563, Non Final Office Action dated Oct. 23, 2013", 18 pgs.
"U.S. Appl. No. 13/071,563, Notice of Allowance dated Aug. 15, 2014", 7 pgs.
"U.S. Appl. No. 13/071,563, Preliminary Amendment filed May 1, 2012", 8 pgs.
"U.S. Appl. No. 13/071,563, Preliminary Amendment filed Dec. 6, 2011", 7 pgs.
"U.S. Appl. No. 13/071,563, Response filed Jan. 21, 2014 to Non Final Office Action dated Oct. 23, 2013", 13 pgs.
"U.S. Appl. No. 13/071,563, Response filed Jul. 23, 2014 to Final Office Action dated May 23, 2014", 14 pgs.
"U.S. Appl. No. 13/071,563, Response filed Sep. 19, 2013 to Restriction Requirement dated Aug. 19, 2013", 11 pgs.
"U.S. Appl. No. 13/071,563, Restriction Requirement dated Aug. 19, 2013", 7 pgs.
"U.S. Appl. No. 13/098,897, Examiner Interview Summary dated Nov. 27, 2012", 3 pgs.
"U.S. Appl. No. 13/098,897, Non Final Office Action dated Sep. 21, 2012", 9 pgs.
"U.S. Appl. No. 13/098,897, Notice of Allowance dated Jun. 11, 2013", 13 pgs.
"U.S. Appl. No. 13/098,897, Response filed Aug. 30, 2012 to Restriction Requirement dated Jul. 30, 2012", 16 pgs.
"U.S. Appl. No. 13/098,897, Response filed Dec. 18, 2012 to Non Final Office Action dated Sep. 21, 2012", 21 pgs.
"U.S. Appl. No. 13/098,897, Restriction Requirement dated Jul. 30, 2012", 8 pgs.
"U.S. Appl. No. 13/098,927, Advisory Action dated Aug. 8, 2013", 3 pgs.
"U.S. Appl. No. 13/098,927, Applicant's Summary of Examiner Interview filed Sep. 23, 2013", 12 pgs.
"U.S. Appl. No. 13/098,927, Examiner Interview Summary dated Jun. 28, 2013", 3 pgs.
"U.S. Appl. No. 13/098,927, Examiner Interview Summary dated Sep. 20, 2013", 3 pgs.
"U.S. Appl. No. 13/098,927, Final Office Action dated May 22, 2013", 10 pgs.
"U.S. Appl. No. 13/098,927, Non Final Office Action dated Sep. 24, 2012", 12 pgs.
"U.S. Appl. No. 13/098,927, Notice of Allowance dated Jan. 8, 2014", 5 pgs.
"U.S. Appl. No. 13/098,927, Notice of Allowance dated Sep. 26, 2013", 14 pgs.
"U.S. Appl. No. 13/098,927, Response filed Jul. 22, 2015 to Final Office Action dated May 22, 2013", 17 pgs.
"U.S. Appl. No. 13/098,927, Response filed Aug. 27, 2012 to Restriction Requirement dated Jul. 25, 2012", 14 pgs.
"U.S. Appl. No. 13/098,927, Response filed Dec. 21, 2012 to Non Final Office Action dated Sep. 24, 2012", 21 pgs.
"U.S. Appl. No. 13/098,927, Restriction Requirement dated Jul. 25, 2012", 8 pgs.
"U.S. Appl. No. 13/102,182, Notice of Allowance dated Mar. 22, 2012", 10 pgs.
"U.S. Appl. No. 13/109,667, Advisory Action dated Feb. 4, 2014", 4 pgs.
"U.S. Appl. No. 13/109,667, Examiner Interview Summary dated Dec. 20, 2013", 3 pgs.
"U.S. Appl. No. 13/109,667, Final Office Action dated Oct. 11, 2013", 19 pgs.
"U.S. Appl. No. 13/109,667, Non Final Office Action dated May 21, 2013", 21 pgs.
"U.S. Appl. No. 13/109,667, Notice of Allowance dated Feb. 18, 2014", 10 pgs.
"U.S. Appl. No. 13/109,667, Response filed Jan. 13, 2014 to Final Office Action dated Oct. 11, 2013", 20 pgs.
"U.S. Appl. No. 13/109,667, Response filed May 2, 2013 to Restriction Requirement dated Apr. 2, 2013", 1 pg.
"U.S. Appl. No. 13/109,667, Response filed Aug. 21, 2013 to Non Final Office Action dated May 21, 2013", 27 pgs.
"U.S. Appl. No. 13/109,667, Restriction Requirement dated Apr. 2, 2013", 8 pgs.
"U.S. Appl. No. 13/109,667, Supplemental Notice of Allowability dated Jun. 12, 2014", 3 pgs.
"U.S. Appl. No. 13/109,667, Supplemental Notice of Allowance dated May 28, 2014", 2 pgs.
"U.S. Appl. No. 13/109,667, Supplemental Preliminary Amendment filed Feb. 4, 2014", 16 pgs.
"U.S. Appl. No. 13/109,672, 312 Amendment filed Jan. 15, 2015", 3 pgs.
"U.S. Appl. No. 13/109,672, Non Final Office Action dated May 15, 2014", 10 pgs.
"U.S. Appl. No. 13/109,672, Notice of Allowance dated Feb. 3, 2015", 2 pgs.
"U.S. Appl. No. 13/109,672, Notice of Allowance dated Sep. 29, 2014", 9 pgs.

(56) References Cited

OTHER PUBLICATIONS

"U.S. Appl. No. 13/109,672, PTO Response to Rule 312 Communication dated Jan. 27, 2015", 2 pgs.
"U.S. Appl. No. 13/109,672, Response filed Apr. 14, 2014 to Restriction Requirement dated Feb. 14, 2014", 15 pgs.
"U.S. Appl. No. 13/109,672, Response filed Aug. 15, 2014 to Non Final Office Action dated May 15, 2014", 20 pgs.
"U.S. Appl. No. 13/109,672, Response filed Nov. 4, 2013 to Restriction Requirement dated Oct. 2, 2013", 10 pgs.
"U.S. Appl. No. 13/109,672, Restriction Requirement dated Feb. 14, 2014", 7 pgs.
"U.S. Appl. No. 13/109,672, Restriction Requirement dated Oct. 2, 2013", 7 pgs.
"U.S. Appl. No. 13/111,564, Corrected Notice of Allowance dated Oct. 9, 2013", 2 pgs.
"U.S. Appl. No. 13/111,564, Examiner Interview Summary dated Jun. 18, 2013", 3 pgs.
"U.S. Appl. No. 13/111,564, Non Final Office Action dated Mar. 18, 2013", 8 pgs.
"U.S. Appl. No. 13/111,564, Notice of Allowance dated Jun. 28, 2013", 12 pgs.
"U.S. Appl. No. 13/111,564, Response filed Feb. 4, 2013 to Restriction Requirement dated Jan. 3, 2013", 20 pgs.
"U.S. Appl. No. 13/111,564, Response filed Jun. 18, 2013 to Non Final Office Action dated Mar. 18, 2013", 25 pgs.
"U.S. Appl. No. 13/111,564, Restriction Requirement dated Jan. 3, 2013", 5 pgs.
"U.S. Appl. No. 13/177,153, Final Office Action dated May 28, 2013", 11 pgs.
"U.S. Appl. No. 13/177,153, Non Final Office Action dated Oct. 2, 2012", 11 pgs.
"U.S. Appl. No. 13/177,153, Notice of Allowance dated Jan. 7, 2014", 4 pgs.
"U.S. Appl. No. 13/177,153, Notice of Allowance dated Sep. 17, 2013", 13 pgs.
"U.S. Appl. No. 13/177,153, Response filed Aug. 28, 2013 to Final Office Action dated May 28, 2013", 19 pgs.
"U.S. Appl. No. 13/177,153, Response filed Sep. 4, 2012 to Restriction Requirement dated Aug. 2, 2012", 15 pgs.
"U.S. Appl. No. 13/177,153, Response filed Dec. 20, 2012 to Non Final Office Action dated Oct. 2, 2012", 16 pgs.
"U.S. Appl. No. 13/177,153, Restriction Requirement dated Aug. 2, 2012", 9 pgs.
"U.S. Appl. No. 13/181,729, Examiner Interview Summary dated May 9, 2013", 3 pgs.
"U.S. Appl. No. 13/181,729, Final Office Action dated Mar. 13, 2013", 14 pgs.
"U.S. Appl. No. 13/181,729, Non Final Office Action dated Oct. 2, 2012", 7 pgs.
"U.S. Appl. No. 13/181,729, Notice of Allowance dated May 23, 2013", 9 pgs.
"U.S. Appl. No. 13/181,729, Response filed May 13, 2013 to Final Office Action dated Mar. 13, 2013", 13 pgs.
"U.S. Appl. No. 13/181,729, Response filed Dec. 20, 2012 to Non Final Office Action dated Oct. 2, 2012", 15 pgs.
"U.S. Appl. No. 13/269,097, Final Office Action dated Aug. 8, 2013", 7 pgs.
"U.S. Appl. No. 13/269,097, Non Final Office Action dated Feb. 12, 2013", 10 pgs.
"U.S. Appl. No. 13/269,097, Notice of Allowance dated Feb. 3, 2014", 5 pgs.
"U.S. Appl. No. 13/269,097, Notice of Allowance dated Oct. 21, 2013", 9 pgs.
"U.S. Appl. No. 13/269,097, Response filed May 13, 2013 to Non Final Office Action dated Feb. 12, 2013", 17 pgs.
"U.S. Appl. No. 13/269,097, Response filed Oct. 8, 2013 to Final Office Action dated Aug. 8, 2013", 12 pgs.
"U.S. Appl. No. 13/269,097, Response filed Nov. 13, 2012 to Restriction Requirement dated Oct. 17, 2012", 1 pg.

"U.S. Appl. No. 13/269,097, Restriction Requirement dated Oct. 17, 2012", 8 pgs.
"U.S. Appl. No. 13/278,341, Notice of Allowance dated Jun. 18, 2013", 10 pgs.
"U.S. Appl. No. 13/278,341, Response filed Mar. 8, 2013 to Restriction Requirement dated Feb. 11, 2013", 1 pg.
"U.S. Appl. No. 13/278,341, Restriction Requirement dated Feb. 11, 2013", 6 pgs.
"U.S. Appl. No. 13/281,009, Corrected Notice of Allowance dated Nov. 18, 2016", 4 pgs.
"U.S. Appl. No. 13/281,009, Corrected Notice of Allowance dated Dec. 12, 2016", 2 pgs.
"U.S. Appl. No. 13/281,009, Examiner Interview Summary dated Nov. 18, 2016", 2 pgs.
"U.S. Appl. No. 13/281,009, Non Final Office Action dated Jun. 2, 2015", 9 pgs.
"U.S. Appl. No. 13/281,009, Notice of Allowance dated Feb. 24, 2016", 9 pgs.
"U.S. Appl. No. 13/281,009, Notice of Allowance dated Jun. 23, 2016", 9 pgs.
"U.S. Appl. No. 13/281,009, Notice of Allowance dated Oct. 29, 2015", 8 pgs.
"U.S. Appl. No. 13/281,009, Response filed Sep. 2, 2015 to Non Final Office Action dated Jun. 2, 2015", 13 pgs.
"U.S. Appl. No. 13/281,009, Restriction Requirement dated Feb. 11, 2015", 6 pgs.
"U.S. Appl. No. 13/288,459, Corrected Notice of Allowance dated Aug. 3, 2016", 4 pgs.
"U.S. Appl. No. 13/288,459, Corrected Notice of Allowance dated Sep. 9, 2016", 4 pgs.
"U.S. Appl. No. 13/288,459, Corrected Notice of Allowance dated Sep. 23, 2016", 4 pgs.
"U.S. Appl. No. 13/288,459, Examiner Interview Summary dated Feb. 6, 2015", 3 pgs.
"U.S. Appl. No. 13/288,459, Examiner Interview Summary dated Jan. 11, 2016", 1 pg.
"U.S. Appl. No. 13/288,459, Non Final Office Action dated Jun. 24, 2015", 10 pgs.
"U.S. Appl. No. 13/288,459, Non Final Office Action dated Nov. 4, 2014", 15 pgs.
"U.S. Appl. No. 13/288,459, Notice of Allowance dated Jan. 11, 2016", 13 pgs.
"U.S. Appl. No. 13/288,459, Notice of Allowance dated May 10, 2016", 7 pgs.
"U.S. Appl. No. 13/288,459, Response filed Mar. 3, 2015 to Non Final Office Action dated Nov. 4, 2014", 16 pgs.
"U.S. Appl. No. 13/288,459, Response filed Oct. 13, 2014 to Restriction Requirement dated Aug. 11, 2014", 15 pgs.
"U.S. Appl. No. 13/288,459, Response filed Oct. 23, 2015 to Non Final Office Action dated Jun. 24, 2015", 14 pgs.
"U.S. Appl. No. 13/288,459, Restriction Requirement dated Aug. 11, 2014", 9 pgs.
"U.S. Appl. No. 13/288,463, Examiner Interview Summary dated Jun. 3, 2014", 3 pgs.
"U.S. Appl. No. 13/288,463, Non Final Office Action dated Feb. 24, 2014", 13 pgs.
"U.S. Appl. No. 13/288,463, Notice of Allowance dated Aug. 27, 2014", 9 pgs.
"U.S. Appl. No. 13/288,463, Response filed May 27, 2014 to Non Final Office Action dated Feb. 24, 2014", 15 pgs.
"U.S. Appl. No. 13/288,463, Supplemental Notice of Allowability dated Dec. 8, 2014", 5 pgs.
"U.S. Appl. No. 13/288,463, Supplemental Notice of Allowability dated Dec. 19, 2014", 5 pgs.
"U.S. Appl. No. 13/293,825, Notice of Allowability dated Jun. 22, 2015", 7 pgs.
"U.S. Appl. No. 13/293,825, Notice of Allowance dated May 19, 2015", 9 pgs.
"U.S. Appl. No. 13/293,825, Response filed Apr. 15, 2015 to Restriction Requirement dated Feb. 12, 2015", 17 pgs.
"U.S. Appl. No. 13/293,825, Restriction Requirement dated Feb. 12, 2015", 9 pgs.

(56) References Cited

OTHER PUBLICATIONS

"U.S. Appl. No. 13/295,126, Non Final Office Action dated May 19, 2015", 9 pgs.
"U.S. Appl. No. 13/295,126, Notice of Allowance dated Oct. 22, 2015", 9 pgs.
"U.S. Appl. No. 13/295,126, Response filed Apr. 13, 2015 to Restriction Requirement dated Feb. 12, 2015", 1 pgs.
"U.S. Appl. No. 13/295,126, Response filed Aug. 17, 2015 to Non Final Office Action dated May 19, 2015", 21 pgs.
"U.S. Appl. No. 13/295,126, Restriction Requirement dated Feb. 12, 2015", 9 pgs.
"U.S. Appl. No. 13/311,936, Examiner Interview Summary dated Feb. 12, 2015", 2 pgs.
"U.S. Appl. No. 13/311,936, Non Final Office Action dated Feb. 9, 2015", 13 pgs.
"U.S. Appl. No. 13/311,936, Non Final Office Action dated Oct. 19, 2015", 8 pgs.
"U.S. Appl. No. 13/311,936, Notice of Allowance dated Mar. 29, 2016", 8 pgs.
"U.S. Appl. No. 13/311,936, PTO Response to Rule 312 Communication dated May 10, 2016", 2 pgs.
"U.S. Appl. No. 13/311,936, Response filed Jan. 18, 2016 to Non Final Office Action dated Oct. 19, 2015", 8 pgs.
"U.S. Appl. No. 13/311,936, Response filed Jun. 9, 2015 to Non Final Office Action dated Feb. 9, 2015", 12 pgs.
"U.S. Appl. No. 13/311,936, Response filed Oct. 3, 2014 to Restriction Requirement dated Aug. 5, 2014", 10 pgs.
"U.S. Appl. No. 13/311,936, Restriction Requirement dated Aug. 5, 2014", 7 pgs.
"U.S. Appl. No. 13/350,985, Final Office Action dated Apr. 16, 2015", 8 pgs.
"U.S. Appl. No. 13/350,985, Non Final Office Action dated Dec. 15, 2014", 8 pgs.
"U.S. Appl. No. 13/350,985, Notice of Allowance dated Jul. 27, 2015", 5 pgs.
"U.S. Appl. No. 13/350,985, Response filed Mar. 13, 2015 to Non Final Office Action dated Dec. 15, 2014", 10 pgs.
"U.S. Appl. No. 13/350,985, Response filed Jul. 9, 2015 to Final Office Action dated Apr. 16, 2015", 8 pgs.
"U.S. Appl. No. 13/350,985, Response filed Dec. 2, 2014 to Restriction Requirement dated Oct. 2, 2014", 9 pgs.
"U.S. Appl. No. 13/350,985, Restriction Requirement dated Oct. 2, 2014", 6 pgs.
"U.S. Appl. No. 13/399,125, Corrected Notice of Allowance dated Aug. 28, 2014", 2 pgs.
"U.S. Appl. No. 13/399,125, Examiner Interview Summary dated May 17, 2013", 3 pgs.
"U.S. Appl. No. 13/399,125, Final Office Action dated Mar. 20, 2013", 12 pgs.
"U.S. Appl. No. 13/399,125, Non Final Office Action dated Oct. 24, 2012", 12 pgs.
"U.S. Appl. No. 13/399,125, Notice of Allowance dated May 16, 2014", 8 pgs.
"U.S. Appl. No. 13/399,125, Response filed Jan. 10, 2013 to Non Final Office Action dated Oct. 24, 2012", 15 pgs.
"U.S. Appl. No. 13/399,125, Response filed May 20, 2013 to Final Office Action dated Mar. 20, 2013", 14 pgs.
"U.S. Appl. No. 13/412,105, Advisory Action dated Feb. 24, 2014", 3 pgs.
"U.S. Appl. No. 13/412,105, Examiner Interview Summary dated Feb. 6, 2014", 3 pgs.
"U.S. Appl. No. 13/412,105, Examiner Interview Summary dated Oct. 11, 2013", 3 pgs.
"U.S. Appl. No. 13/412,105, Final Office Action dated Dec. 13, 2013", 9 pgs.
"U.S. Appl. No. 13/412,105, Non Final Office Action dated Jul. 15, 2013", 10 pgs.
"U.S. Appl. No. 13/412,105, Notice of Allowance dated Aug. 18, 2014", 9 pgs.
"U.S. Appl. No. 13/412,105, Response filed Feb. 10, 2014 to Final Office Action dated Dec. 13, 2013", 14 pgs.
"U.S. Appl. No. 13/412,105, Response filed Mar. 13, 2014 to Advisory Action dated Feb. 24, 2014", 19 pgs.
"U.S. Appl. No. 13/412,105, Response filed May 6, 2013 to Restriction Requirement dated Apr. 5, 2013", 9 pgs.
"U.S. Appl. No. 13/412,105, Response filed Oct. 14, 2013 to Non Final Office Action dated Jul. 15, 2013", 13 pgs.
"U.S. Appl. No. 13/412,105, Restriction Requirement dated Apr. 5, 2013", 9 pgs.
"U.S. Appl. No. 13/412,116, Corrected Notice of Allowance dated Jun. 2, 2014", 2 pgs.
"U.S. Appl. No. 13/412,116, Examiner Interview Summary dated Dec. 13, 2013", 3 pgs.
"U.S. Appl. No. 13/412,116, Non Final Office Action dated Sep. 11, 2013", 9 pgs.
"U.S. Appl. No. 13/412,116, Notice of Allowance dated Feb. 19, 2014", 9 pgs.
"U.S. Appl. No. 13/412,116, Response filed Jul. 3, 2013 to Restriction Requirement dated Jun. 19, 2013", 1 pg.
"U.S. Appl. No. 13/412,116, Response filed Dec. 11, 2013 to Non Final Office Action dated Sep. 11, 2013", 11 pgs.
"U.S. Appl. No. 13/412,116, Restriction Requirement dated Jun. 19, 2013", 9 pgs.
"U.S. Appl. No. 13/412,127, Examiner Interview Summary dated Nov. 5, 2013", 3 pgs.
"U.S. Appl. No. 13/412,127, Non Final Office Action dated Aug. 7, 2013", 15 pgs.
"U.S. Appl. No. 13/412,127, Notice of Allowance dated Dec. 24, 2013", 10 pgs.
"U.S. Appl. No. 13/412,127, Response filed May 23, 2013 to Restriction Requirement dated Apr. 24, 2013", 2 pgs.
"U.S. Appl. No. 13/412,127, Response filed Nov. 5, 2013 to Non Final Office Action dated Aug. 7, 2013", 16 pgs.
"U.S. Appl. No. 13/412,127, Restriction Requirement dated Apr. 24, 2013", 10 pgs.
"U.S. Appl. No. 13/587,374, Final Office Action dated Nov. 6, 2013", 9 pgs.
"U.S. Appl. No. 13/587,374, Non Final Office Action dated Ju. 17, 2013", 8 pgs.
"U.S. Appl. No. 13/587,374, Notice of Allowance dated Feb. 28, 2014", 5 pgs.
"U.S. Appl. No. 13/587,374, Preliminary Amendment filed Jun. 21, 2013", 9 pgs.
"U.S. Appl. No. 13/587,374, Response filed Jan. 24, 2014 to Final Office Action dated Nov. 6, 2013", 15 pgs.
"U.S. Appl. No. 13/587,374, Response filed Oct. 14, 2013 to Non Final Office Action dated Jul. 17, 2013", 14 pgs.
"U.S. Appl. No. 13/609,389, 312 Amendment filed Sep. 15, 2014", 4 pgs.
"U.S. Appl. No. 13/609,389, Examiner interview Summary dated Feb. 4, 2014", 4 pgs.
"U.S. Appl. No. 13/609,389, Final Office Action dated May 5, 2014", 14 pgs.
"U.S. Appl. No. 13/609,389, Non Final Office Action dated Nov. 27, 2013", 12 pgs.
"U.S. Appl. No. 13/609,389, Notice of Allowance dated Jul. 23, 2014", 5 pgs.
"U.S. Appl. No. 13/609,389, PTO Response to Rule 312 Communication dated Oct. 16, 2014", 2 pgs.
"U.S. Appl. No. 13/609,389, Response filed Feb. 27, 2014 to Non Final Office Action dated Nov. 27, 2013", 18 pgs.
"U.S. Appl. No. 13/609,389, Response filed Jul. 10, 2014 to Final Office Action dated May 5, 2014", 12 pgs.
"U.S. Appl. No. 13/625,413, Final Office Action dated Oct. 30, 2015", 8 pgs.
"U.S. Appl. No. 13/625,413, Non Final Office Action dated Jun. 8, 2015", 11 pgs.
"U.S. Appl. No. 13/625,413, Notice of Allowance dated Apr. 1, 2016", 8 pgs.
"U.S. Appl. No. 13/625,413, Notice of Allowance dated Dec. 11, 2015", 9 pgs.

(56) References Cited

OTHER PUBLICATIONS

"U.S. Appl. No. 13/625,413, Response filed May 11, 2015 to Restriction Requirement dated Mar. 10, 2015", 1 pg.
"U.S. Appl. No. 13/625,413, Response filed Sep. 8, 2015 to Non Final Office Action dated Jun. 8, 2015", 16 pgs.
"U.S. Appl. No. 13/625,413, Response filed Dec. 1, 2015 to Final Office Action dated Oct. 30, 2015", 9 pgs.
"U.S. Appl. No. 13/625,413, Restriction Requirement dated Mar. 10, 2015", 7 pgs.
"U.S. Appl. No. 13/645,964, Advisory Action dated Feb. 4, 2016", 2 pgs.
"U.S. Appl. No. 13/645,964, Final Office Action dated Oct. 6, 2015", 17 pgs.
"U.S. Appl. No. 13/645,964, Non Final Office Action dated Mar. 15, 2016", 15 pgs.
"U.S. Appl. No. 13/645,964, Non Final Office Action dated Mar. 17, 2015", 15 pgs.
"U.S. Appl. No. 13/645,964, Notice of Allowance dated Jul. 21, 2016", 9 pgs.
"U.S. Appl. No. 13/645,964, Response filed Jun. 13, 2016 to Non Final Office Action dated Mar. 15, 2016", 11 pgs.
"U.S. Appl. No. 13/645,964, Response filed Jul. 17, 2015 to Non Final Office Action dated Mar. 17, 2015", 17 pgs.
"U.S. Appl. No. 13/645,964, Response filed Dec. 4, 2015 to Final Office Action dated Oct. 6, 2015", 14 pgs.
"U.S. Appl. No. 13/656,821, Notice of Allowance dated Jun. 18, 2015", 11 pgs.
"U.S. Appl. No. 13/656,821, Response filed May 11, 2015 to Restriction Requirement dated Mar. 10, 2015", 1 pg.
"U.S. Appl. No. 13/656,821, Restriction Requirement dated Mar. 10, 2015", 6 pgs.
"U.S. Appl. No. 13/720,631, Final Office Action dated Jun. 25, 2014", 10 pgs.
"U.S. Appl. No. 13/720,631, Non Final Office Action dated Mar. 6, 2014", 7 pgs.
"U.S. Appl. No. 13/720,631, Notice of Allowance dated Jul. 25, 2014", 5 pgs.
"U.S. Appl. No. 13/720,631, Response filed Jun. 6, 2014 to Non Final Office Action dated Mar. 6, 2014", 11 pgs.
"U.S. Appl. No. 13/720,631, Response filed Jul. 14, 2014 to Final Office Action dated Jun. 25, 2014", 6 pgs.
"U.S. Appl. No. 13/720,631, Supplemental Notice of Allowance dated Sep. 8, 2014", 2 pgs.
"U.S. Appl. No. 13/720,648, Final Office Action dated Nov. 16, 2015", 7 pgs.
"U.S. Appl. No. 13/720,648, Non Final Office Action dated Jun. 10, 2015", 11 pgs.
"U.S. Appl. No. 13/720,648, Notice of Allowance dated Feb. 5, 2016", 11 pgs.
"U.S. Appl. No. 13/720,648, Response filed Jan. 13, 2016 to Final Office Action dated Nov. 16, 2015", 9 pgs.
"U.S. Appl. No. 13/720,648, Response filed May 11, 2015 to Restriction Requirement dated Mar. 10, 2015", 8 pgs.
"U.S. Appl. No. 13/720,648, Response filed Oct. 9, 2015 to Non Final Office Action dated Jun. 10, 2015", 12 pgs.
"U.S. Appl. No. 13/720,648, Restriction Requirement dated Mar. 10, 2015", 8 pgs.
"U.S. Appl. No. 13/721,970, Notice of Allowance dated Aug. 12, 2013", 13 pgs.
"U.S. Appl. No. 13/721,970, Preliminary Amendment filed Mar. 15, 2013", 13 pgs.
"U.S. Appl. No. 13/721,970, Response filed May 8, 2013 to Restriction Requirement dated Apr. 11, 2013", 1 pgs.
"U.S. Appl. No. 13/721,970, Restriction Requirement dated Apr. 11, 2013", 6 pgs.
"U.S. Appl. No. 13/751,846, Final Office Action dated Nov. 17, 2015", 9 pgs.
"U.S. Appl. No. 13/751,846, Non Final Office Action dated Jun. 15, 2015", 10 pgs.
"U.S. Appl. No. 13/751,846, Notice of Allowance dated Mar. 16, 2016", 11 pgs.
"U.S. Appl. No. 13/751,846, Notice of Allowance dated Jul. 6, 2016", 9 pgs.
"U.S. Appl. No. 13/751,846, Response filed Feb. 5, 2016 to Final Office Action dated Nov. 17, 2015", 14 pgs.
"U.S. Appl. No. 13/751,846, Response filed May 11, 2015 to Restriction Requirement dated Mar. 10, 2015", 15 pgs.
"U.S. Appl. No. 13/751,846, Response filed Oct. 9, 2015 to Non Final Office Action dated Jun. 15, 2015", 20 pgs.
"U.S. Appl. No. 13/751,846, Restriction Requirement dated Mar. 10, 2015", 7 pgs.
"U.S. Appl. No. 13/757,003, Non Final Office Action dated Jun. 25, 2015", 8 pgs.
"U.S. Appl. No. 13/757,003, Notice of Allowance dated Feb. 8, 2016", 10 pgs.
"U.S. Appl. No. 13/757,003, Response filed May 12, 2015 to Restriction Requirement dated Mar. 12, 2015", 9 pgs.
"U.S. Appl. No. 13/757,003, Response filed Oct. 26, 2015 to Non Final Office Action dated Jul. 25, 2015", 8 pgs.
"U.S. Appl. No. 13/757,003, Restriction Requirement dated Mar. 12, 2015", 6 pgs.
"U.S. Appl. No. 13/757,019, Non Final Office Action dated Jun. 25, 2015", 11 pgs.
"U.S. Appl. No. 13/757,019, Notice of Allowance dated Dec. 10, 2015", 10 pgs.
"U.S. Appl. No. 13/757,019, Response filed May 11, 2015 to Restriction Requirement dated Mar. 11, 2015", 9 pgs.
"U.S. Appl. No. 13/757,019, Response filed Oct. 26, 2015 to Non Final Office Action dated Jun. 25, 2015", 9 pgs.
"U.S. Appl. No. 13/757,019, Restriction Requirement dated Mar. 11, 2015", 10 pgs.
"U.S. Appl. No. 13/767,401, Non Final Office Action dated Aug. 26, 2015", 9 pgs.
"U.S. Appl. No. 13/767,401, Notice of Allowance dated Apr. 8, 2016", 9 pgs.
"U.S. Appl. No. 13/767,401, Notice of Allowance dated Dec. 30, 2015", 9 pgs.
"U.S. Appl. No. 13/767,401, Response filed May 18, 2015 to Restriction Requirement dated Mar. 17, 2015", 15 pgs.
"U.S. Appl. No. 13/767,401, Response filed Nov. 6, 2015 to Non Final Office Action dated Aug. 26, 2015", 12 pgs.
"U.S. Appl. No. 13/767,401, Restriction Requirement dated Mar. 17, 2015", 8 pgs.
"U.S. Appl. No. 13/790,982, Examiner Interview Summary dated Jun. 9, 2015", 3 pgs.
"U.S. Appl. No. 13/790,982, Non Final Office Action dated Sep. 16, 2015", 11 pgs.
"U.S. Appl. No. 13/790,982, Notice of Allowance dated Feb. 24, 2016", 10 pgs.
"U.S. Appl. No. 13/790,982, Response filed Jun. 2, 2015 to Restriction Requirement dated Apr. 2, 2015", 11 pgs.
"U.S. Appl. No. 13/790,982, Response filed Dec. 16, 2015 to Non Final Office Action dated Sep. 16, 2015", 10 pgs.
"U.S. Appl. No. 13/790,982, Restriction Requirement dated Apr. 2, 2015", 10 pgs.
"U.S. Appl. No. 13/790,997, Examiner Interview Summary dated Jun. 8, 2015", 3 pgs.
"U.S. Appl. No. 13/790,997, Non Final Office Action dated Sep. 21, 2015", 8 pgs.
"U.S. Appl. No. 13/790,997, Notice of Allowance dated Mar. 2, 2016", 9 pgs.
"U.S. Appl. No. 13/790,997, Response filed Jun. 2, 2015 to Restriction Requirement dated Apr. 2, 2015", 12 pgs.
"U.S. Appl. No. 13/790,997, Response filed Dec. 18, 2015 to Non Final Office Action dated Sep. 21, 2015", 9 pgs.
"U.S. Appl. No. 13/790,997, Restriction Requirement dated Apr. 2, 2015", 8 pgs.
"U.S. Appl. No. 13/791,014, Final Office Action dated Jan. 8, 2016", 11 pgs.
"U.S. Appl. No. 13/791,014, Non Final Office Action dated Aug. 14, 2015", 9 pgs.

(56) References Cited

OTHER PUBLICATIONS

"U.S. Appl. No. 13/791,014, Notice of Allowability dated Jul. 27, 2017", 2 pgs.
"U.S. Appl. No. 13/791,014, Notice of Allowance dated Jan. 10, 2017", 15 pgs.
"U.S. Appl. No. 13/791,014, Notice of Allowance dated Apr. 27, 2017", 8 pgs.
"U.S. Appl. No. 13/791,014, Response filed Jun. 6, 2016 to Final Office Action dated Jan. 8, 2016", 13 pgs.
"U.S. Appl. No. 13/791,014, Response filed Aug. 3, 2015 to Restriction Requirement dated May 1, 2015", 9 pgs.
"U.S. Appl. No. 13/791,014, Response filed Nov. 10, 2015 to Non Final Office Action dated Aug. 14, 2015", 13 pgs.
"U.S. Appl. No. 13/791,014, Restriction Requirement dated May 1, 2015", 6 pgs.
"U.S. Appl. No. 13/833,567, Advisory Action dated Apr. 28, 2016", 3 pgs.
"U.S. Appl. No. 13/833,567, Final Office Action dated Mar. 9, 2016", 9 pgs.
"U.S. Appl. No. 13/833,567, Non Final Office Action dated May 27, 2016", 9 pgs.
"U.S. Appl. No. 13/833,567, Non Final Office Action dated Oct. 23, 2015", 10 pgs.
"U.S. Appl. No. 13/833,567, Notice of Allowance dated Sep. 27, 2016", 9 pgs.
"U.S. Appl. No. 13/833,567, Response filed Jan. 22, 2016 to Non Final Office Action dated Oct. 23, 2015", 11 pgs.
"U.S. Appl. No. 13/833,567, Response filed Apr. 20, 2016 to Final Office Action dated Mar. 9, 2016", 10 pgs.
"U.S. Appl. No. 13/833,567, Response filed Jun. 25, 2015 to Restriction Requirement dated Apr. 3, 2015", 10 pgs.
"U.S. Appl. No. 13/833,567, Response filed Aug. 4, 2016 to Non Final Office Action dated May 27, 2016", 11 pgs.
"U.S. Appl. No. 13/833,567, Restriction Requirement dated Apr. 3, 2015", 6 pgs.
"U.S. Appl. No. 13/838,755, Final Office Action dated Feb. 22, 2016", 9 pgs.
"U.S. Appl. No. 13/838,755, Non Final Office Action dated Sep. 17, 2015", 11 pgs.
"U.S. Appl. No. 13/838,755, Notice of Allowance dated Apr. 27, 2016", 7 pgs.
"U.S. Appl. No. 13/838,755, Notice of Allowance dated Aug. 3, 2016", 8 pgs.
"U.S. Appl. No. 13/838,755, Response filed Apr. 15, 2016 to Final Office Action dated Feb. 22, 2016", 11 pgs.
"U.S. Appl. No. 13/838,755, Response filed Jun. 8, 2015 to Restriction Requirement dated Apr. 6, 2015", 1 pg.
"U.S. Appl. No. 13/838,755, Response filed Dec. 1, 2015 to Non Final Office Action dated Sep. 17, 2015", 13 pgs.
"U.S. Appl. No. 13/838,755, Restriction Requirement dated Apr. 6, 2015", 6 pgs.
"U.S. Appl. No. 13/889,851, Non Final Office Action dated Apr. 6, 2015", 10 pgs.
"U.S. Appl. No. 13/889,851, Notice of Allowance dated Aug. 12, 2015", 8 pgs.
"U.S. Appl. No. 13/889,851, Response filed Feb. 26, 2015 to Restriction Requirement dated Jan. 21, 2015", 12 pgs.
"U.S. Appl. No. 13/889,851, Response filed Jul. 6, 2015 to Non Final Office Action dated Apr. 6, 2015", 14 pgs.
"U.S. Appl. No. 13/889,851, Restriction Requirement dated Jan. 21, 2015", 6 pgs.
"U.S. Appl. No. 13/889,851, Supplemental Amendment and Response filed Jul. 6, 2015 to Non Final Office Action dated Apr. 6, 2015", 8 pgs.
"U.S. Appl. No. 13/959,145, Examiner Interview Summary dated Sep. 16, 2015", 3 pgs.
"U.S. Appl. No. 13/959,145, Final Office Action dated Jan. 29, 2016", 16 pgs.
"U.S. Appl. No. 13/959,145, Final Office Action dated Feb. 5, 2015", 22 pgs.
"U.S. Appl. No. 13/959,145, Non Final Office Action dated Jul. 31, 2015", 21 pgs.
"U.S. Appl. No. 13/959,145, Non Final Office Action dated Sep. 15, 2014", 20 pgs.
"U.S. Appl. No. 13/959,145, Notice of Allowability dated Jun. 14, 2016", 2 pgs.
"U.S. Appl. No. 13/959,145, Notice of Allowance dated Apr. 13, 2016", 5 pgs.
"U.S. Appl. No. 13/959,145, Response filed Mar. 28, 2016 to Final Office Action dated Jan. 29, 2016", 10 pgs.
"U.S. Appl. No. 13/959,145, Response filed Jul. 6, 2015 to Final Office Action dated Feb. 5, 2015", 18 pgs.
"U.S. Appl. No. 13/959,145, Response filed Oct. 30, 2015 to Non Final Office Action dated Jul. 31, 2015", 14 pgs.
"U.S. Appl. No. 13/959,145, Response filed Dec. 15, 2014 to Non Final Office Action dated Sep. 15, 2014", 21 pgs.
"U.S. Appl. No. 14/055,172, Final Office Action dated Dec. 22, 2016", 8 pgs.
"U.S. Appl. No. 14/055,172, Non Final Office Action dated Jul. 14, 2016", 12 pgs.
"U.S. Appl. No. 14/055,172, Notice of Allowance dated Mar. 29, 2017", 10 pgs.
"U.S. Appl. No. 14/055,172, Response filed Feb. 22, 2017 to Final Office Action dated Dec. 22, 2016", 11 pgs.
"U.S. Appl. No. 14/055,172, Response filed May 4, 2016 to Restriction Requirement dated Mar. 4, 2016", 8 pgs.
"U.S. Appl. No. 14/055,172, Response filed Nov. 14, 2016 to Non Final Office Action dated Jul. 14, 2016", 19 pgs.
"U.S. Appl. No. 14/055,172, Restriction Requirement dated Mar. 4, 2016", 6 pgs.
"U.S. Appl. No. 14/055,191, Non Final Office Action dated May 16, 2016", 8 pgs.
"U.S. Appl. No. 14/055,191, Notice of Allowability dated Sep. 8, 2016", 7 pgs.
"U.S. Appl. No. 14/055,191, Notice of Allowance dated Aug. 31, 2016", 13 pgs.
"U.S. Appl. No. 14/055,191, Response filed Apr. 29, 2016 to Restriction Requirement dated Mar. 7, 2016", 8 pgs.
"U.S. Appl. No. 14/055,191, Response filed Aug. 3, 2016 to Non Final Office Action dated May 16, 2016", 11 pgs.
"U.S. Appl. No. 14/055,191, Restriction Requirement dated Mar. 7, 2016", 6 pgs.
"U.S. Appl. No. 14/071,295, Non Final Office Action dated Aug. 15, 2014", 6 pgs.
"U.S. Appl. No. 14/071,295, Notice of Allowance dated Dec. 10, 2014", 8 pgs.
"U.S. Appl. No. 14/071,295, Response filed Nov. 17, 2014 to Non Final Office Action dated Aug. 15, 2014", 14 pgs.
"U.S. Appl. No. 14/071,295, Supplemental Notice of Allowability dated Jan. 26, 2015", 2 pgs.
"U.S. Appl. No. 14/094,311, Corrected Notice of Allowance dated Mar. 28, 2017", 5 pgs.
"U.S. Appl. No. 14/094,311, Notice of Allowance dated Aug. 16, 2016", 12 pgs.
"U.S. Appl. No. 14/094,311, Notice of Allowance dated Dec. 27, 2016", 8 pgs.
"U.S. Appl. No. 14/094,311, Response filed Jul. 26, 2016 to Restriction Requirement dated Jun. 22, 2016", 10 pgs.
"U.S. Appl. No. 14/094,311, Restriction Requirement dated Jun. 22, 2016", 6 pgs.
"U.S. Appl. No. 14/095,614, Non Final Office Action dated Jan. 19, 2017", 9 pgs.
"U.S. Appl. No. 14/095,614, Notice of Allowance dated May 8, 2017", 8 pgs.
"U.S. Appl. No. 14/095,614, Notice of Allowance dated Nov. 6, 2017", 9 pgs.
"U.S. Appl. No. 14/095,614, Preliminary Amendment filed Apr. 15, 2014", 17 pgs.
"U.S. Appl. No. 14/095,614, Response filed Mar. 2, 2017 to Non Final Office Action dated Jan. 19, 2017", 14 pgs.
"U.S. Appl. No. 14/095,614, Response filed Sep. 12, 2016 to Restriction Requirement dated Jul. 11, 2016", 11 pgs.

(56) References Cited

OTHER PUBLICATIONS

"U.S. Appl. No. 14/095,614, Restriction Requirement dated Jul. 11, 2016", 8 pgs.
"U.S. Appl. No. 14/095,639, Non Final Office Action dated Jan. 18, 2017", 10 pgs.
"U.S. Appl. No. 14/095,639, Notice of Allowance dated Apr. 13, 2017", 9 pgs.
"U.S. Appl. No. 14/095,639, Notice of Allowance dated Oct. 30, 2017", 9 pgs.
"U.S. Appl. No. 14/095,639, Response filed Mar. 2, 2017 to Non Final Office Action dated Jan. 18, 2017", 9 pgs.
"U.S. Appl. No. 14/095,639, Response filed Sep. 12, 2016 to Restriction Requirement dated Jul. 19, 2016", 7 pgs.
"U.S. Appl. No. 14/095,639, Restriction Requirement dated Jul. 19, 2016", 8 pgs.
"U.S. Appl. No. 14/107,350, Notice of Allowance dated Feb. 26, 2016", 11 pgs.
"U.S. Appl. No. 14/107,350, Notice of Allowance dated Jul. 27, 2016", 7 pgs.
"U.S. Appl. No. 14/107,350, Preliminary Amendment filed Feb. 28, 2014", 4 pgs.
"U.S. Appl. No. 14/159,094, Examiner Interview Summary dated Nov. 29, 2016", 1 pg.
"U.S. Appl. No. 14/159,094, Non Final Office Action dated Jun. 29, 2016", 15 pgs.
"U.S. Appl. No. 14/159,094, Notice of Allowance dated Nov. 29, 2016", Examiner Interview Summary dated Nov. 29, 2016 included, 11 pgs.
"U.S. Appl. No. 14/159,094, Response filed Jun. 3, 2016 to Restriction Requirement dated Apr. 20, 2016", 9 pgs.
"U.S. Appl. No. 14/159,094, Response filed Sep. 19, 2016 to Non Final Office Action dated Jun. 29, 2016", 13 pgs.
"U.S. Appl. No. 14/159,094, Restriction Requirement dated Apr. 20, 2016", 6 pgs.
"U.S. Appl. No. 14/182,038, Advisory Action dated Mar. 1, 2017", 3 pgs.
"U.S. Appl. No. 14/182,038, Final Office Action dated Dec. 19, 2016", 8 pgs.
"U.S. Appl. No. 14/182,038, Non Final Office Action dated Jul. 19, 2016", 10 pgs.
"U.S. Appl. No. 14/182,038, Notice of Allowance dated May 24, 2017", 9 pgs.
"U.S. Appl. No. 14/182,038, Response filed Feb. 20, 2017 to Final Office Action dated Dec. 19, 2016", 11 pgs.
"U.S. Appl. No. 14/182,038, Response filed Jun. 27, 2016 to Restriction Requirement dated Apr. 26, 2016", 8 pgs.
"U.S. Appl. No. 14/182,038, Response filed Oct. 19, 2016 to Non Final Office Action dated Jul. 19, 2016", 15 pgs.
"U.S. Appl. No. 14/182,038, Restriction Requirement dated Apr. 26, 2016", 7 pgs.
"U.S. Appl. No. 14/182,046, Corrected Notice of Allowance dated Jan. 20, 2017", 6 pgs.
"U.S. Appl. No. 14/182,046, Non Final Office Action dated Jul. 15, 2016", 9 pgs.
"U.S. Appl. No. 14/182,046, Notice of Allowance dated Dec. 8, 2016", 7 pgs.
"U.S. Appl. No. 14/182,046, Response filed Jun. 27, 2016 to Restriction Requirement dated Apr. 26, 2016", 7 pgs.
"U.S. Appl. No. 14/182,046, Response filed Oct. 17, 2016 to Non Final Office Action dated Jul. 15, 2016", 11 pgs.
"U.S. Appl. No. 14/182,046, Restriction Requirement dated Apr. 26, 2016", 6 pgs.
"U.S. Appl. No. 14/211,977, Notice of Allowance dated Jul. 12, 2016", 9 pgs.
"U.S. Appl. No. 14/211,977, Preliminary Amendment filed Mar. 2, 2016", 7 pgs.
"U.S. Appl. No. 14/211,977, Response filed Apr. 29, 2016 to Restriction Requirement dated Mar. 11, 2016", 8 pgs.
"U.S. Appl. No. 14/211,977, Restriction Requirement dated Mar. 11, 2016", 6 pgs.
"U.S. Appl. No. 14/215,550, Corrected Notice of Allowance dated Jul. 27, 2017", 2 pgs.
"U.S. Appl. No. 14/215,550, Examiner Interview Summary dated Mar. 9, 2017", 3 pgs.
"U.S. Appl. No. 14/215,550, Final Office Action dated Feb. 1, 2017", 11 pgs.
"U.S. Appl. No. 14/215,550, Non Final Office Action dated Jul. 19, 2016", 12 pgs.
"U.S. Appl. No. 14/215,550, Notice of Allowance dated Jun. 21, 2017", 8 pgs.
"U.S. Appl. No. 14/215,550, Response filed May 1, 2017 to Final Office Action dated Feb. 1, 2017", 10 pgs.
"U.S. Appl. No. 14/215,550, Response filed Jun. 22, 2016 to Restriction Requirement dated Apr. 28, 2016", 7 pgs.
"U.S. Appl. No. 14/215,550, Response filed Dec. 5, 2016 to Non Final Office Action dated Jul. 19, 2016", 13 pgs.
"U.S. Appl. No. 14/215,550, Restriction Requirement dated Apr. 28, 2016", 6 pgs.
"U.S. Appl. No. 14/275,548, Examiner Interview Summary dated May 25, 2016", 3 pgs.
"U.S. Appl. No. 14/275,548, Non Final Office Action dated Feb. 19, 2016", 14 pgs.
"U.S. Appl. No. 14/275,548, Notice of Allowance dated Jul. 27, 2016", 7 pgs.
"U.S. Appl. No. 14/275,548, Response filed May 19, 2016 to Non Final Office Action dated Feb. 19, 2016", 19 pgs.
"U.S. Appl. No. 14/324,688, Corrected Notice of Allowance dated Sep. 22, 2016", 2 pgs.
"U.S. Appl. No. 14/324,688, Non Final Office Action dated Jan. 8, 2016", 18 pgs.
"U.S. Appl. No. 14/324,688, Notice of Allowance dated Jun. 9, 2016", 7 pgs.
"U.S. Appl. No. 14/324,688, Response filed Apr. 8, 2016 to Non Final Office Action dated Jan. 8, 2016", 15 pgs.
"U.S. Appl. No. 14/456,286, Advisory Action dated Jun. 21, 2016", 3 pgs.
"U.S. Appl. No. 14/456,286, Final Office Action dated May 27, 2016", 15 pgs.
"U.S. Appl. No. 14/456,286, Non Final Office Action dated Oct. 17, 2016", 17 pgs.
"U.S. Appl. No. 14/456,286, Non Final Office Action dated Dec. 30, 2015", 16 pgs.
"U.S. Appl. No. 14/456,286, Notice of Allowance dated Feb. 15, 2017", 9 pgs.
"U.S. Appl. No. 14/456,286, Response filed Mar. 30, 2016 to Non Final Office Action dated Dec. 30, 2015", 15 pgs.
"U.S. Appl. No. 14/456,286, Response filed Jun. 13, 2016 to Final Office Action dated May 27, 2016", 10 pgs.
"U.S. Appl. No. 14/456,286, Response filed Nov. 16, 2016 to Non Final Office Action dated Oct. 17, 2016", 9 pgs.
"U.S. Appl. No. 14/456,286, Response filed Dec. 11, 2015 to Restriction Requirement dated Oct. 29, 2015", 6 pgs.
"U.S. Appl. No. 14/456,286, Restriction Requirement dated Oct. 29, 2015", 9 pgs.
"U.S. Appl. No. 14/492,590, Notice of Allowance dated Oct. 5, 2016", 10 pgs.
"U.S. Appl. No. 14/492,590, Response filed Sep. 15, 2016 to Restriction Requirement dated Jul. 25, 2015", 7 pgs.
"U.S. Appl. No. 14/492,590, Restriction Requirement dated Jul. 25, 2016", 6 pgs.
"U.S. Appl. No. 14/492,590, Supplemental Response filed Sep. 26, 2016 to Restriction Requirement dated Jul. 25, 2016", 10 pgs.
"U.S. Appl. No. 14/514,453, Final Office Action dated Mar. 17, 2016", 17 pgs.
"U.S. Appl. No. 14/514,453, Non Final Office Action dated Sep. 24, 2015", 11 pgs.
"U.S. Appl. No. 14/514,453, Response filed Dec. 16, 2015 to Non Final Office Action dated Sep. 24, 2015", 14 pgs.
"U.S. Appl. No. 14/532,333, Response filed Apr. 7, 2016 to Restriction Requirement dated Feb. 8, 2016", 10 pgs.
"U.S. Appl. No. 14/532,333, Restriction Requirement dated Feb. 8, 2016", 6 pgs.

(56) References Cited

OTHER PUBLICATIONS

"U.S. Appl. No. 14/589,101, Advisory Action dated Feb. 21, 2017", 5 pgs.
"U.S. Appl. No. 14/589,101, Advisory Action dated May 22, 2018", 3 pgs.
"U.S. Appl. No. 14/589,101, Examiner Interview Summary dated Jan. 30, 2017", 3 pgs.
"U.S. Appl. No. 14/589,101, Final Office Action dated Feb. 22, 2018", 15 pgs.
"U.S. Appl. No. 14/589,101, Final Office Action dated Oct. 2, 2015", 10 pgs.
"U.S. Appl. No. 14/589,101, Final Office Action dated Nov. 16, 2016", 12 pgs.
"U.S. Appl. No. 14/589,101, Non Final Office Action dated Feb. 12, 2015", 10 pgs.
"U.S. Appl. No. 14/589,101, Non Final Office Action dated May 5, 2016", 14 pgs.
"U.S. Appl. No. 14/589,101, Non Final Office Action dated Sep. 14, 2017", 13 pgs.
"U.S. Appl. No. 14/589,101, Response filed Jan. 23, 2017 to Final Office Action dated Nov. 16, 2016", 9 pgs.
"U.S. Appl. No. 14/589,101, Response filed Apr. 10, 2018 to Final Office Action dated Feb. 22, 2018", 10 pgs.
"U.S. Appl. No. 14/589,101, Response filed Jun. 12, 2015 to Non Final Office Action dated Feb. 12, 2015", 11 pgs.
"U.S. Appl. No. 14/589,101, Response filed Nov. 13, 2017 to Non Final Office Action dated Sep. 14, 2017", 13 pgs.
"U.S. Appl. No. 14/589,101, Response filed Dec. 29, 2015 to Final Office Action dated Oct. 2, 2015", 15 pgs.
"U.S. Appl. No. 14/589,191, Response filed Aug. 5, 2016 to Non Final Office Action dated May 5, 2016", 16 pgs.
"U.S. Appl. No. 14/594,285, Final Office Action dated May 22, 2017", 12 pgs.
"U.S. Appl. No. 14/594,285, Non Final Office Action dated Jan. 11, 2017", 15 pgs.
"U.S. Appl. No. 14/594,285, Notice of Allowance dated Jun. 27, 2017", 10 pgs.
"U.S. Appl. No. 14/594,285, Response filed Apr. 11, 2017 to Non Final Office Action dated Jan. 11, 2017", 12 pgs.
"U.S. Appl. No. 14/594,285, Response filed Jun. 14, 2017 to Final Office Action dated May 22, 2017", 9 pgs.
"U.S. Appl. No. 14/594,285, Response filed Dec. 14, 2016 to Restriction Requirement dated Nov. 7, 2016", 8 pgs.
"U.S. Appl. No. 14/594,285, Restriction Requirement dated Nov. 7, 2016", 6 pgs.
"U.S. Appl. No. 14/599,909, Non Final Office Action dated Jul. 27, 2017", 18 pgs.
"U.S. Appl. No. 14/599,909, Notice of Allowance dated Feb. 13, 2018", 9 pgs.
"U.S. Appl. No. 14/599,909, Response filed Sep. 21, 2017 to Non Final Office Action dated Jul. 27, 2017", 10 pgs.
"U.S. Appl. No. 14/635,055, Non Final Office Action dated Aug. 28, 2017", 8 pgs.
"U.S. Appl. No. 14/635,055, Notice of Allowance dated Feb. 28, 2018", 11 pgs.
"U.S. Appl. No. 14/635,055, Response filed Jun. 27, 2017 to Restriction Requirement dated Apr. 27, 2017", 11 pgs.
"U.S. Appl. No. 14/635,055, Response filed Nov. 28, 2017 to Non Final Office Action dated Aug. 28, 2017", 13 pgs.
"U.S. Appl. No. 14/635,055, Restriction Requirement dated Apr. 27, 2017", 7 pgs.
"U.S. Appl. No. 14/697,140, Advisory Action dated Aug. 11, 2017", 3 pgs.
"U.S. Appl. No. 14/697,140, Final Office Action dated Jun. 30, 2017", 13 pgs.
"U.S. Appl. No. 14/697,140, Final Office Action dated Sep. 23, 2016", 10 pgs.
"U.S. Appl. No. 14/697,140, Non Final Office Action dated Jan. 10, 2017", 12 pgs.
"U.S. Appl. No. 14/697,140, Non Final Office Action dated Apr. 8, 2016", 8 pgs.
"U.S. Appl. No. 14/697,140, Notice of Allowance dated Sep. 5, 2017", 7 pgs.
"U.S. Appl. No. 14/697,140, Response filed Mar. 1, 2017 to Non Final Office Action dated Jan. 10, 2017", 11 pgs.
"U.S. Appl. No. 14/697,140, Response filed Jun. 13, 2016 to Non Final Office Action dated Apr. 8, 2016", 10 pgs.
"U.S. Appl. No. 14/697,140, Response filed Jul. 27, 2017 to Final Office Action dated Jun. 30, 2017", 10 pgs.
"U.S. Appl. No. 14/697,140, Response filed Nov. 16, 2016 to Final Office Action dated Sep. 23, 2016", 13 pgs.
"U.S. Appl. No. 14/794,309, Final Office Action dated Mar. 20, 2017", 18 pgs.
"U.S. Appl. No. 14/794,309, Non Final Office Action dated Jun. 20, 2017", 16 pgs.
"U.S. Appl. No. 14/794,309, Non Final Office Action dated Nov. 22, 2016", 13 pgs.
"U.S. Appl. No. 14/794,309, Notice of Allowance dated Sep. 18, 2017", 5 pgs.
"U.S. Appl. No. 14/794,309, Preliminary Amendment filed Sep. 22, 2015", 6 pgs.
"U.S. Appl. No. 14/794,309, Response filed Feb. 22, 2017 to Non Final Office Action dated Nov. 22, 2016", 12 pgs.
"U.S. Appl. No. 14/794,309, Response filed May 22, 2017 to Final Office Action dated Mar. 20, 2017", 13 pgs.
"U.S. Appl. No. 14/794,309, Response filed Aug. 17, 2017 to Non Final Office Action dated Jun. 20, 2017", 12 pgs.
"U.S. Appl. No. 14/794,309, Supplemental Preliminary Amendment filed Mar. 3, 2016", 8 pgs.
"U.S. Appl. No. 14/854,308, Notice of Allowance dated Mar. 16, 2018", 11 pgs.
"U.S. Appl. No. 14/854,308, Response filed Dec. 20, 2017 to Restriction Requirement dated Oct. 20, 2017", 8 pgs.
"U.S. Appl. No. 14/854,308, Restriction Requirement dated Oct. 20, 2017", 8 pgs.
"U.S. Appl. No. 14/854,308, Supplemental Preliminary Amendment filed Aug. 31, 2017", 3 pgs.
"U.S. Appl. No. 14/876,167, Final Office Action dated Jul. 31, 2018", 8 pgs.
"U.S. Appl. No. 14/876,167, Non Final Office Action dated Mar. 13, 2018", 8 pgs.
"U.S. Appl. No. 14/876,167, Notice of Allowance dated Dec. 10, 2018", 8 pgs.
"U.S. Appl. No. 14/876,167, Preliminary Amendment filed Oct. 27, 2015", 8 pgs.
"U.S. Appl. No. 14/876,167, Response filed Jan. 9, 2018 to Restriction Requirement dated Nov. 22, 2017", 6 pgs.
"U.S. Appl. No. 14/876,167, Response filed Jun. 6, 2018 to Non Final Office Action dated Mar. 13, 2018", 9 pgs.
"U.S. Appl. No. 14/876,167, Response filed Sep. 28, 2018 to Final Office Action dated Jul. 31, 2018", 10 pgs.
"U.S. Appl. No. 14/876,167, Restriction Requirement dated Nov. 22, 2017", 9 pgs.
"U.S. Appl. No. 14/936,831, Advisory Action dated Jan. 29, 2019", 3 pgs.
"U.S. Appl. No. 14/936,831, Final Office Action dated Nov. 20, 2018", 8 pgs.
"U.S. Appl. No. 14/936,831, Non Final Office Action mailed May 16, 18", 11 pgs.
"U.S. Appl. No. 14/936,831, Notice of Allowance mailed Jul. 3, 19", 8 pgs.
"U.S. Appl. No. 14/936,831, Notice of Non-Compliant Amendment mailed Mar. 14, 18", 2 pgs.
"U.S. Appl. No. 14/936,831, Preliminary Amendment filed Nov. 11, 2015", 6 pgs.
"U.S. Appl. No. 14/936,831, Response filed Jan. 10, 2018 to Restriction Requirement dated Nov. 22, 2017", 6 pgs.
"U.S. Appl. No. 14/936,831, Response filed Jan. 21, 2019 to Final Office Action dated Nov. 20, 2018", 9 pgs.
"U.S. Appl. No. 14/936,831, Response filed Mar. 26, 2018 to Notice of Non-Compliant Amendment dated Mar. 14, 2018", 6 pgs.

(56) References Cited

OTHER PUBLICATIONS

"U.S. Appl. No. 14/936,831, Response filed Aug. 16, 2018 to Non Final Office Action dated May 16, 2018", 9 pgs.
"U.S. Appl. No. 14/936,831, Restriction Requirement dated Nov. 22, 2017", 8 pgs.
"U.S. Appl. No. 14/956,724, Examiner Interview Summary dated Jun. 20, 2017", 3 pgs.
"U.S. Appl. No. 14/956,724, Non Final Office Action dated Mar. 31, 2017", 17 pgs.
"U.S. Appl. No. 14/956,724, Notice of Allowance dated Aug. 23, 2017", 9 pgs.
"U.S. Appl. No. 14/956,724, Preliminary Amendment filed Dec. 7, 2015", 8 pgs.
"U.S. Appl. No. 14/956,724, Response filed Jun. 16, 2017 to Non Final Office Action dated Mar. 31, 2017", 12 pgs.
"U.S. Appl. No. 14/956,724, Supplemental Preliminary Amendment filed Feb. 11, 16", 7 pgs.
"U.S. Appl. No. 14/956,724, Supplemental Preliminary Amendment filed Oct. 3, 16", 8 pgs.
"U.S. Appl. No. 14/983,108, Final Office Action mailed Aug. 30, 18", 9 pgs.
"U.S. Appl. No. 14/983,108, Non Final Office Action mailed Apr. 10, 18", 7 pgs.
"U.S. Appl. No. 14/983,108, Non Final Office Action mailed Nov. 5, 18", 8 pgs.
"U.S. Appl. No. 14/983,108, Notice of Allowance daated Mar. 8, 2019", 8 pgs.
"U.S. Appl. No. 14/983,108, Preliminary Amendment filed Dec. 30, 2015", 7 pgs.
"U.S. Appl. No. 14/983,108, Response filed Jan. 24, 2018 to Restriction Requirement dated Dec. 4, 2017", 6 pgs.
"U.S. Appl. No. 14/983,108, Response filed Feb. 4, 2019 to Non Final Office Action dated Nov. 5, 2018", 8 pgs.
"U.S. Appl. No. 14/983,108, Response filed Jun. 13, 2018 to Non Final Office Action dated Apr. 10, 2018", 10 pgs.
"U.S. Appl. No. 14/983,108, Response filed Oct. 22, 2018 to Final Office Action dated Aug. 30, 2018", 9 pgs.
"U.S. Appl. No. 14/983,108, Restriction Requirement dated Dec. 4, 2017", 7 pgs.
"U.S. Appl. No. 14/983,747, Non Final Office Action dated Apr. 9, 2018", 13 pgs.
"U.S. Appl. No. 14/983,747, Notice of Allowance dated Sep. 24, 2018", 14 pgs.
"U.S. Appl. No. 14/983,747, Preliminary Amendment filed Jan. 4, 2016", 5 pgs.
"U.S. Appl. No. 14/983,747, Response filed Jan. 24, 2018 to Restriction Requirement dated Dec. 20, 2017", 5 pgs.
"U.S. Appl. No. 14/983,747, Response filed Jun. 13, 2018 to Non Final Office Action dated Apr. 9, 2018", 9 pgs.
"U.S. Appl. No. 14/983,747, Restriction Requirement dated Dec. 20, 2017", 7 pgs.
"U.S. Appl. No. 14/983,747, Supplemental Response to Restriction Requirement filed Jan. 24, 2018", 5 pgs.
"U.S. Appl. No. 15/060,007, Corrected Notice of Allowability dated May 1, 2019", 2 pgs.
"U.S. Appl. No. 15/060,007, Final Office Action dated Jan. 3, 2019", 9 pgs.
"U.S. Appl. No. 15/060,007, Non Final Office Action dated Nov. 9, 2018", 17 pgs.
"U.S. Appl. No. 15/060,007, Notice of Allowance dated Mar. 6, 2019", 5 pgs.
"U.S. Appl. No. 15/060,007, Preliminary Amendment filed Mar. 9, 2016", 9 pgs.
"U.S. Appl. No. 15/060,007, Response filed Feb. 15, 2019 to Final Office Action dated Jan. 3, 2019", 9 pgs.
"U.S. Appl. No. 15/060,007, Response filed Nov. 26, 2018 to Non Final Office Action dated Nov. 9, 2018", 10 pgs.
"U.S. Appl. No. 15/061,352, Corrected Notice of Allowance dated Feb. 12, 2018", 2 pgs.
"U.S. Appl. No. 15/061,352, Non Final Office Action dated Nov. 17, 2017", 6 pgs.
"U.S. Appl. No. 15/061,352, Notice of Allowance dated Jan. 19, 2018", 10 pgs.
"U.S. Appl. No. 15/061,352, Preliminary Amendment filed Mar. 7, 2016", 8 pgs.
"U.S. Appl. No. 15/061,352, Response filed Dec. 12, 2017 to Non Final Office Action dated Nov. 17, 2017", 9 pgs.
"U.S. Appl. No. 15/074,553, Corrected Notice of Allowance dated Feb. 12, 2018", 2 pgs.
"U.S. Appl. No. 15/074,553, Non Final Office Action dated Nov. 17, 2017", 6 pgs.
"U.S. Appl. No. 15/074,553, Notice of Allowance dated Jan. 19, 2018", 10 pgs.
"U.S. Appl. No. 15/074,553, Preliminary Amendment filed Mar. 21, 2016", 8 pgs.
"U.S. Appl. No. 15/074,553, Response filed Dec. 12, 2017 to Non Final Office Action dated Nov. 17, 2017", 8 pgs.
"U.S. Appl. No. 15/131,663, Non Final Office Action dated Oct. 2, 2018", 7 pgs.
"U.S. Appl. No. 15/131,663, Notice of Allowance dated Mar. 19, 2019", 8 pgs.
"U.S. Appl. No. 15/131,663, Preliminary Amendment filed Dec. 21, 2016", 6 pgs.
"U.S. Appl. No. 15/131,663, Response filed Jan. 2, 2019 to Non-Final Office Action dated Oct. 2, 2018", 9 pgs.
"U.S. Appl. No. 15/131,663, Response filed Jul. 13, 2018 to Restriction Requirement dated May 18, 2018", 8 pgs.
"U.S. Appl. No. 15/131,663, Restriction Requirement dated May 18, 2018", 7 pgs.
"U.S. Appl. No. 15/166,480, Notice of Allowance dated Sep. 20, 2018", 12 pgs.
"U.S. Appl. No. 15/166,480, Response filed Jul. 18, 2018 to Restriction Requirement dated May 21, 2018", 6 pgs.
"U.S. Appl. No. 15/166,480, Restriction Requirement dated May 21, 2018", 6 pgs.
"U.S. Appl. No. 15/166,480, Supplemental Preliminary Amendment filed Jul. 18, 2017", 7 pgs.
"U.S. Appl. No. 15/200,546, Non Final Office Action dated Oct. 15, 2018", 10 pgs.
"U.S. Appl. No. 15/200,546, Notice of Allowance dated Mar. 19, 2019", 7 pgs.
"U.S. Appl. No. 15/200,546, Preliminary Amendment filed Dec. 21, 2016", 6 pgs.
"U.S. Appl. No. 15/200,546, Response filed Jan. 15, 2019 to Non-Final Office Action dated Oct. 15, 2018", 10 pgs.
"U.S. Appl. No. 15/200,546, Response filed Sep. 17, 2018 to Restriction Requirement dated Jul. 16, 2018", 8 pgs.
"U.S. Appl. No. 15/200,546, Restriction Requirement dated Jul. 16, 2018", 6 pgs.
"U.S. Appl. No. 15/278,777, Non Final Office Action dated Feb. 28, 2018", 14 pgs.
"U.S. Appl. No. 15/278,777, Notice of Allowance dated Jul. 16, 2018", 8 pgs.
"U.S. Appl. No. 15/278,777, Preliminary Amendment filed Oct. 3, 2016", 7 pgs.
"U.S. Appl. No. 15/278,777, Response filed May 29, 2018 to Non Final Office action dated Feb. 28, 2018", 11 pgs.
"U.S. Appl. No. 15/288,183, Corrected Notice of Allowability dated Jun. 21, 2019", 7 pgs.
"U.S. Appl. No. 15/288,183, Non Final Office Action dated Dec. 10, 2018", 13 pgs.
"U.S. Appl. No. 15/288,183, Notice of Allowance dated May 9, 2019", 11 pgs.
"U.S. Appl. No. 15/288,183, Preliminary Amendment filed Oct. 31, 2016", 7 pgs.
"U.S. Appl. No. 15/288,183, Response filed Feb. 27, 2019 to Non Final Office Action dated Dec. 10, 2018", 11 pgs.
"U.S. Appl. No. 15/288,183, Response filed Oct. 25, 2018 to Restriction Requirement dated Sep. 12, 2018", 7 pgs.
"U.S. Appl. No. 15/288,183, Restriction Requirement dated Sep. 12, 2018", 6 pgs.

(56) References Cited

OTHER PUBLICATIONS

"U.S. Appl. No. 15/288,183, Supplemental Preliminary Amendment filed Jul. 27, 2017", 7 pgs.
"U.S. Appl. No. 15/294,994, Examiner Interview Summary dated Feb. 26, 2019", 3 pgs.
"U.S. Appl. No. 15/294,994, Final Office Action dated Jan. 25, 2019", 13 pgs.
"U.S. Appl. No. 15/294,994, Non Final Office Action dated Aug. 9, 2018", 9 pgs.
"U.S. Appl. No. 15/294,994, Notice of Allowance dated May 22, 2019", 10 pgs.
"U.S. Appl. No. 15/294,994, Preliminary Amendment filed Jan. 25, 2017", 8 pgs.
"U.S. Appl. No. 15/294,994, Response filed Feb. 27, 2019 to Final Office Action dated Jan. 25, 2019", 9 pgs.
"U.S. Appl. No. 15/294,994, Response filed Oct. 25, 2018 to Non Final Office Action dated Aug. 9, 2018", 10 pgs.
"U.S. Appl. No. 15/294,994, Supplemental Preliminary Amendment filed May 31, 2017", 6 pgs,.
"U.S. Appl. No. 15/297,844, Notice of Allowance dated Aug. 30, 2018", 10 pgs.
"U.S. Appl. No. 15/297,844, Preliminary Amendment filed Oct. 20, 2016", 7 pgs.
"U.S. Appl. No. 15/297,844, Supplemental Preliminary Amendment filed Jan. 25, 2018", 6 pgs.
"U.S. Appl. No. 15/332,590, Notice of Allowance dated Dec. 5, 2018", 13 pgs.
"U.S. Appl. No. 15/332,590, Preliminary Amendment filed Nov. 22, 2016", 5 pgs.
"U.S. Appl. No. 15/361,917, Advisory Action dated Nov. 19, 2019", 3 pgs.
"U.S. Appl. No. 15/361,917, Final Office Action dated Sep. 3, 2019", 8 pgs.
"U.S. Appl. No. 15/361,917, Non Final Office Action dated Apr. 19, 2019", 11 pgs.
"U.S. Appl. No. 15/361,917, Preliminary Amendment filed Nov. 30, 2016", 6 pgs.
"U.S. Appl. No. 15/361,917, Response filed Feb. 14, 2019 to Restriction Requirement dated Jan. 3, 2019", 6 pgs.
"U.S. Appl. No. 15/361,917, Response filed Jun. 19, 2019 to Non Final Office Action dated Apr. 19, 2019", 9 pgs.
"U.S. Appl. No. 15/361,917, Response filed Nov. 4, 2019 to Final Office Action dated Sep. 3, 2019", 8 pgs.
"U.S. Appl. No. 15/361,917, Restriction Requirement dated Jan. 3, 2019", 6 pgs.
"U.S. Appl. No. 15/401,768, Non Final Office Action dated Jul. 22, 2019", 10 pgs.
"U.S. Appl. No. 15/401,768, Notice of Allowance dated Nov. 20, 2019", 9 pgs.
"U.S. Appl. No. 15/401,768, Preliminary Amendment filed Mar. 23, 2017", 6 pgs.
"U.S. Appl. No. 15/401,768, Response filed May 15, 2019 to Restriction Requirement dated Mar. 15, 2019", 7 pgs.
"U.S. Appl. No. 15/401,768, Response filed Aug. 28, 2019 to Non Final Office Action dated Jul. 22, 2019", 10 pgs.
"U.S. Appl. No. 15/401,768, Restriction Requirement dated Mar. 15, 2019", 6 pgs.
"U.S. Appl. No. 15/401,768, Supplemental Preliminary Amendment filed Jun. 22, 2017", 7 pgs.
"U.S. Appl. No. 15/412,676, Non Final Office Action dated Jul. 23, 2019", 11 pgs.
"U.S. Appl. No. 15/412,676, Notice of Allowance dated Dec. 30, 2019", 8 pgs.
"U.S. Appl. No. 15/412,676, Preliminary Amendment filed Jul. 3, 2017", 7 pgs.
"U.S. Appl. No. 15/412,676, Response filed May 15, 2019 to Restriction Requirement dated Mar. 15, 2019", 7 pgs.
"U.S. Appl. No. 15/412,676, Response filed Oct. 23, 2019 to Non Final Office Action dated Jul. 23, 2019", 12 pgs.
"U.S. Appl. No. 15/412,676, Restriction Requirement dated Mar. 15, 2019", 6 pgs.
"U.S. Appl. No. 15/455,895, Examiner Interview Summary dated Nov. 25, 2019", 3 pgs.
"U.S. Appl. No. 15/455,895, Non Final Office Action dated Sep. 5, 2019", 11 pgs.
"U.S. Appl. No. 15/455,895, Notice of Allowance dated Feb. 13, 2020", 7 pgs.
"U.S. Appl. No. 15/455,895, Preliminary Amendment filed Mar. 13, 2017", 6 pgs.
"U.S. Appl. No. 15/455,895, Response filed Jan. 28, 2020 to Non Final Office Action dated Sep. 5, 2019", 14 pgs.
"U.S. Appl. No. 15/455,895, Supplemental Preliminary Amendment filed May 24, 2019", 6 pgs.
"U.S. Appl. No. 15/461,675, Non Final Office Action dated Aug. 9, 2019", 10 pgs.
"U.S. Appl. No. 15/461,675, Notice of Allowance dated Jan. 30, 2020", 7 pgs.
"U.S. Appl. No. 15/461,675, Preliminary Amendment filed Jun. 24, 2017", 6 pgs.
"U.S. Appl. No. 15/461,675, Response filed May 24, 2019 to Restriction Requirement dated Mar. 26, 2019", 6 pgs.
"U.S. Appl. No. 15/461,675, Response filed Nov. 12, 2019 to Non Final Office Action dated Aug. 9, 2019", 11 pgs.
"U.S. Appl. No. 15/461,675, Restriction Requirement dated Mar. 26, 2019", 6 pgs.
"U.S. Appl. No. 15/461,675, Supplemental Preliminary Amendment filed Jun. 28, 2018", 7 pgs.
"U.S. Appl. No. 15/622,718, Examiner Interview Summary dated Nov. 22, 2019", 3 pgs.
"U.S. Appl. No. 15/622,718, Non Final Office Action dated Aug. 28, 2019", 14 pgs.
"U.S. Appl. No. 15/622,718, Notice of Allowance dated Feb. 13, 2020", 8 pgs.
"U.S. Appl. No. 15/622,718, Preliminary Amendment filed Jun. 15, 2017", 7 pgs.
"U.S. Appl. No. 15/622,718, Response filed Jan. 28, 2020 to Non Final Office Action dated Aug. 28, 2019", 11 pgs.
"U.S. Appl. No. 15/622,718, Response filed Jul. 31, 2019 to Restriction Requirement dated Jun. 7, 2019", 8 pgs.
"U.S. Appl. No. 15/622,718, Restriction Requirement dated Jun. 7, 2019", 6 pgs.
"U.S. Appl. No. 15/626,384, Non Final Office Action dated May 3, 2019", 14 pgs.
"U.S. Appl. No. 15/626,384, Notice of Allowability dated Oct. 18, 2019", 2 pgs.
"U.S. Appl. No. 15/626,384, Notice of Allowance dated Aug. 21, 2019", 7 pgs.
"U.S. Appl. No. 15/626,384, Preliminary Amendment filed Aug. 10, 2018", 11 pgs.
"U.S. Appl. No. 15/626,384, Response filed Jul. 31, 2019 to Non-Final Office Action dated May 3, 2019", 13 pgs.
"U.S. Appl. No. 15/654,386, Non Final Office Action dated Nov. 7, 2019", 10 pgs.
"U.S. Appl. No. 15/654,386, Notice of Allowance dated Feb. 20, 2020", 8 pgs.
"U.S. Appl. No. 15/654,386, Preliminary Amendment filed Aug. 30, 2017", 11 pgs.
"U.S. Appl. No. 15/654,386, Response filed Feb. 5, 2020 to Non Final Office Action dated Nov. 7, 2019", 12 pgs.
"U.S. Appl. No. 15/654,386, Response filed Aug. 23, 2019 to Restriction Requirement dated Jul. 16, 2019", 9 pgs.
"U.S. Appl. No. 15/654,386, Restriction Requirement dated Jul. 16, 2019", 6 pgs.
"U.S. Appl. No. 15/659,689, Non Final Office Action dated Oct. 31, 2018", 13 pgs.
"U.S. Appl. No. 15/659,689, Preliminary Amendment filed Jul. 26, 2017", 7 pgs.
"U.S. Appl. No. 15/662,572, Non Final Office Action dated Oct. 10, 2019", 14 pgs.
"U.S. Appl. No. 15/662,572, Preliminary Amendment filed Jul. 31, 2017", 7 pgs.

(56) References Cited

OTHER PUBLICATIONS

"U.S. Appl. No. 15/662,572, Response filed Jan. 8, 2020 to Non Final Office Action dated Oct. 10, 2019", 10 pgs.
"U.S. Appl. No. 15/662,572, Response filed Aug. 23, 2019 to Restriction Requirement dated Jul. 1, 2019", 8 pgs.
"U.S. Appl. No. 15/662,572, Restriction Requirement dated Jul. 1, 2019", 6 pgs.
"U.S. Appl. No. 15/664,572, Non Final Office Action dated May 15, 2019", 8 pgs.
"U.S. Appl. No. 15/664,572, Notice of Allowance dated Jun. 12, 2019", 8 pgs.
"U.S. Appl. No. 15/664,572, Preliminary Amendment filed Aug. 3, 2017", 7 pgs.
"U.S. Appl. No. 15/664,572, Response filed May 17, 2019 to Non Final Office Action dated May 15, 2019", 9 pgs.
"U.S. Appl. No. 15/682,187, Non Final Office Action dated Dec. 16, 2019", 10 pgs.
"U.S. Appl. No. 15/682,187, Preliminary Amendment filed Sep. 7, 2017", 6 pgs.
"U.S. Appl. No. 15/682,187, Response filed Feb. 27, 2020 to Non Final Office Action dated Dec. 16, 2019", 11 pages.
"U.S. Appl. No. 15/682,187, Response filed Sep. 18, 2019 to Restriction Requirement dated Aug. 9, 2019", 7 pgs.
"U.S. Appl. No. 15/682,187, Restriction Requirement dated Aug. 9, 2019", 6 pgs.
"U.S. Appl. No. 15/703,727, Non Final Office Action dated Aug. 1, 2019", 11 pgs.
"U.S. Appl. No. 15/703,727, Notice of Allowance dated Nov. 20, 2019", 7 pgs.
"U.S. Appl. No. 15/703,727, Preliminary Amendment filed Sep. 14, 2017", 7 pgs.
"U.S. Appl. No. 15/703,727, Response filed Nov. 1, 2019 to Non Final Office Action dated Aug. 1, 2019", 10 pgs.
"U.S. Appl. No. 15/715,731, Non Final Office Action mailed Jan. 21, 20", 8 pgs.
"U.S. Appl. No. 15/715,731, Preliminary Amendment Filed Sep. 26, 17", 9 pgs.
"U.S. Appl. No. 15/715,731, Response filed Feb. 27, 20 to Non Final Office Action mailed Jan. 21, 20", 12 pgs.
"U.S. Appl. No. 15/715,731, Response Filed Nov. 4, 19 to Restriction Requirement Mailed Sep. 4, 19", 9 pgs.
"U.S. Appl. No. 15/715,731, Restriction Requirement mailed Sep. 4, 19", 6 pgs.
"U.S. Appl. No. 15/715,731, Supplemental Preliminary Amendment filed Dec. 29, 17", 8 pgs.
"U.S. Appl. No. 15/720,997, Non Final Office Action mailed Jan. 6, 20", 10 pgs.
"U.S. Appl. No. 15/720,997, Non Final Office Action mailed Jul. 16, 19", 11 pgs.
"U.S. Appl. No. 15/720,997, Preliminary Amendment filed Oct. 2, 17", 6 pgs.
"U.S. Appl. No. 15/720,997, Response filed Oct. 3, 19 to Non-Final Office Action mailed Jul. 16, 19", 9 pgs.
"U.S. Appl. No. 15/722,002, Non Final Office Action dated Feb. 4, 2020", 8 pgs.
"U.S. Appl. No. 15/722,002, Preliminary Amendment filed Jun. 29, 2018", 5 pgs.
"U.S. Appl. No. 15/722,002, Response filed Nov. 14, 2019 to Restriction Requirement dated Sep. 17, 2019", 6 pgs.
"U.S. Appl. No. 15/722,002, Restriction Requirement dated Sep. 17, 2019", 6 pgs.
"U.S. Appl. No. 15/793,216, Examiner Interview Summary dated Nov. 4, 2019", 4 pgs.
"U.S. Appl. No. 15/793,216, Non Final Office Action dated Aug. 1, 2019", 21 pgs.
"U.S. Appl. No. 15/793,216, Preliminary Amendment filed Oct. 26, 2017", 8 pgs.
"U.S. Appl. No. 15/793,216, Response filed Jan. 28, 2020 to Non Final Office Action dated Aug. 1, 2019", 13 pgs.
"U.S. Appl. No. 15/865,938, Notice of Allowance dated Sep. 17, 2019", 11 pgs.
"U.S. Appl. No. 15/865,938, Preliminary Amendment filed Jan. 10, 2018", 7 pgs.
"U.S. Appl. No. 15/866,089, Non Final Office Action dated Dec. 4, 2019", 16 pgs.
"U.S. Appl. No. 15/866,089, Preliminary Amendment filed Jan. 10, 2018", 10 pgs.
"U.S. Appl. No. 15/866,089, Response filed Feb. 27, 2020 to Non Final Office Action dated Dec. 4, 2019", 10 pgs.
"U.S. Appl. No. 15/886,712, Non Final Office Action dated Sep. 27, 2019", 8 pgs.
"U.S. Appl. No. 15/886,712, Notice of Allowance dated Nov. 14, 2019", 7 pgs.
"U.S. Appl. No. 15/886,712, Preliminary Amendment filed Feb. 2, 2018", 8 pgs.
"U.S. Appl. No. 15/886,712, Response filed Oct. 18, 2019 to Non Final Office Action dated Sep. 27, 2019", 9 pgs.
"U.S. Appl. No. 15/891,049, Preliminary Amendment filed Feb. 8, 2018", 6 pgs.
"U.S. Appl. No. 15/891,049, Supplemental Preliminary Amendment filed Dec. 20, 2019", 8 pgs.
"U.S. Appl. No. 15/903,261, Preliminary Amendment filed Feb. 28, 2018", 6 pgs.
"U.S. Appl. No. 15/917,143, Preliminary Amendment filed Mar. 14, 2018", 7 pgs.
"U.S. Appl. No. 15/941,481, Preliminary Amendment filed Mar. 30, 2018", 7 pgs.
"U.S. Appl. No. 15/945,425, Preliminary Amendment filed Apr. 5, 2018", 8 pgs.
"U.S. Appl. No. 15/945,425, Supplemental Preliminary Amendment filed May 10, 2018", 6 pgs.
"U.S. Appl. No. 15/956,444, Preliminary Amendment filed Apr. 19, 2018", 7 pgs.
"U.S. Appl. No. 15/972,646, Preliminary Amendment filed May 9, 2018", 6 pgs.
"U.S. Appl. No. 16/160,559, Preliminary Amendment filed Oct. 17, 2018", 6 pgs.
"U.S. Appl. No. 16/251,342, Preliminary Amendment filed Jan. 21, 2019", 6 pgs.
"U.S. Appl. No. 16/255,300, Preliminary Amendment filed Jan. 24, 2019", 6 pgs.
"U.S. Appl. No. 16/380,742, Preliminary Amendment filed Apr. 12, 2019", 6 pgs.
"U.S. Appl. No. 16/400,199, Preliminary Amendment filed May 7, 2019", 7 pgs.
"U.S. Appl. No. 16/420,676, Preliminary Amendment filed Jun. 3, 2019", 5 pgs.
"U.S. Appl. No. 16/428,277, Preliminary Amendment filed Jun. 3, 2019", 5 pgs.
"U.S. Appl. No. 16/436,023, Preliminary Amendment filed Jun. 12, 2019", 6 pgs.
"U.S. Appl. No. 16/443,391, Preliminary Amendment filed Jun. 19, 2019", 6 pgs.
"U.S. Appl. No. 16/508,764, Preliminary Amendment filed Jul. 12, 2019", 7 pgs.
"U.S. Appl. No. 16/544,293, Preliminary Amendment filed Aug. 21, 2019", 7 pgs.
"U.S. Appl. No. 16/593,022, Preliminary Amendment filed Oct. 30, 2019", 8 pgs.
"U.S. Appl. No. 16/593,022, Supplemental Preliminary Amendment filed Dec. 5, 2019", 8 pgs.
"U.S. Appl. No. 16/593,022, Supplemental Preliminary Amendment filed Dec. 20, 2019", 5 pgs.
"U.S. Appl. No. 16/690,671, Preliminary Amendment filed Dec. 11, 2019", 7 pgs.
"U.S. Appl. No. 16/795,181, Preliminary Amendment filed Feb. 20, 2020", 6 pgs.
"Arthroscopic Meniscal Repair using the Meniscal Cinch™", Surgical Technique brochure. Arthrex®, 6 sheets, (2008), 6 sheets.
"Australian Application Serial No. 2014236885, First Examination Report dated Dec. 11, 2017", 2 pgs.

(56) References Cited

OTHER PUBLICATIONS

"Australian Application Serial No. 2014236885, Response filed Feb. 14, 2018 to First Examination Report dated Dec. 11, 2017", 6 pgs.
"Bio-Intrafix Tibial Soft Tissue Fastener, Building on the Legacy of IntraFix", DePuy Mitek brochure, (Feb. 2007), 6 pgs.
"Bio-Intrafix (TCP/PLA) & Intrafix, Tibial Soft Tissue Fasteners", DePuy Mitek, ((date unknown)), 6 pgs.
"Biomechanical Evaluation of the Biomet Sports Medicine JurggerKnot™ Soft Anchor in Porcine Bone", Study completed Jan. 2010. Biomet Sports Medicine Research and Develo ment, Warsaw, Indiana, (Jan. 2010), 2 pgs.
"Canadian Application Serial No. 2906596, Office Action dated Feb. 26, 2018", 3 pgs.
"Chinese Application Serial No. 201480027708.4, Office Action dated Feb. 14, 2017", (W/English Translation), 18 pgs.
"Chinese Application Serial No. 201480027708.4, Office Action dated May 26, 2016", W/English Translation, 15 pgs.
"Chinese Application Serial No. 201480027708.4, Office Action dated Aug. 18, 2017", (W/English Translation), 8 pgs.
"Chinese Application Serial No. 201480027708.4, Response filed May 2, 2017 to Office Action dated Feb. 14, 2017", (W/ English Translation), 17 pgs.
"Chinese Application Serial No. 201480027708.4, Response filed Oct. 10, 2016 to Office Action dated May 26, 2016", (W/ English Translation of Claims), 14 pgs.
"Chinese Application Serial No. 201480027708.4, Response filed Oct. 31, 2017 to Office Action dated Aug. 18, 2017", (W/ English Claims), 7 pgs.
"Declaration of John White regarding PSCD and Customized Device and Exhibits 1-5".
"Do your next distal tendon repair with . . . The Lubbers Technique", Teno Fix® brochure, Ortheon® Medical, (2003), 2 pgs.
"European Application No. 16168202.6, Extended European Search Report dated Aug. 16, 2017", 11 pgs.
"European Application No. 16168202.6, Response filed Nov. 3, 2017 to Extended European Search Report dated Aug. 16, 2017", 9 pgs.
"European Application Serial No. 10727548.9, Examination Notification Art. 94(3) dated Sep. 18, 2014", 6 pgs.
"European Application Serial No. 10727548.9, Office Action dated Jan. 11, 2016", 6 pgs.
"European Application Serial No. 10727548.9, Office Action dated Jan. 19, 2012", 2 pgs.
"European Application Serial No. 10727548.9, Response filed Mar. 19, 2015 to Examination Notification Art. 94(3) dated Sep. 18, 2014", 23 pgs.
"European Application Serial No. 11707316.3, Examination Notification Art. 94(3) dated Feb. 4, 2014", 3 pgs.
"European Application Serial No. 11707316.3, Examination Notification Art. 94(3) dated Dec. 17, 2014", 5 pgs.
"European Application Serial No. 11707316.3, Office Action dated Nov. 10, 2015", 6 pgs.
"European Application Serial No. 11707316.3, Response filed Jun. 5, 2014 to Examination Notification Art. 94(3) dated Feb. 4, 2014", 7 pgs.
"European Application Serial No. 11707316.3, Response filed Jun. 29, 2015 to Examination Notification Art. 94(3) dated Dec. 17, 2014", 25 pgs.
"European Application Serial No. 12721676.0, Communication pursuant to Article 94(3) EPC dated Sep. 30, 2015", 4 pgs.
"European Application Serial No. 12/21676.0, Office Action dated Jan. 3, 2014", 2 pgs.
"European Application Serial No. 12721676.0, Preliminary Amendment filed Nov. 19, 2013", 9 pgs.
"European Application Serial No. 1221676.0, Response filed Apr. 11, 2016 to Communication pursuant to Article 94(3) EPC dated Sep. 30, 2015", 38 pgs.
"European Application Serial No. 12721676.0, Response filed Jul. 10, 2014 to Office Action dated Jan. 3, 2014", 2 pgs.

"European Application Serial No. 12791902.5, Examination Notification Art. 94(3) dated Aug. 14, 2015", 4 pgs.
"European Application Serial No. 12791902.5, Office Action dated Jul. 15, 2014", 2 pgs.
"European Application Serial No. 12791902.5, Response filed Feb. 23, 2016 to Examination Notification Art. 94(3) dated Aug. 14, 2015", 12 pgs.
"European Application Serial No. 12806211.4, Examination Notification Art. 94(3) dated Aug. 13, 2015", 5 pgs.
"European Application Serial No. 12806211.4, Office Action dated Jul. 18, 2014", 2 pgs.
"European Application Serial No. 12806211.4, Response filed Feb. 23, 2016 to Communication Pursuant to Article 94(3) EPC dated Aug. 13, 2015", 11 pgs.
"European Application Serial No. 13818131.8, Office Action dated Jul. 28, 2015", 2 pgs.
"European Application Serial No. 13818131.8, Response filed Feb. 8, 2016 to Office Action dated Jul. 28, 2015", 14 pgs.
"European Application Serial No. 14716173.1, Office Action dated Nov. 5, 2015", 2 pgs.
"European Application Serial No. 14716173.1, Response filed May 16, 2016 to Communication pursuant to Rules 161(1) and 162 EPC dated Nov. 5, 2015", 10 pgs.
"European Application Serial No. 14716173.1, Response filed Sep. 25, 2017 to Office Action dated Mar. 14, 2017", 12pgs.
"European Application Serial No. 16168202.6, Communication Pursuant to Article 94(3) EPC dated Apr. 25, 2018", 5 pgs.
"European Application Serial No. 16168202.6, Communication pursuant to Article 94(3) EPC dated Dec. 11, 2018", 6 pgs.
"European Application Serial No. 16168202.6, Partial European Search Report dated May 9, 2017", 12 pgs.
"European Application Serial No. 16168202.6, Response filed Sep. 5, 2018 to Communication Pursuant to Article 94(3) EPC dated Apr. 25, 2018", 13 pgs.
"European Application Serial No. 17169003.5, Extended European Search Report dated May 11, 2018", 8 pgs.
"European Application Serial No. 17169003.5, Response Filed Dec. 19, 2018 to Extended European Search Report dated May 11, 2018", 22 pgs.
"European Application Serial No. 12806211.4, Communication Pursuant to Article 94(3) EPC dated Jun. 23, 2016", 4 pgs.
"EZ Log Femoral Fixation Device", copyright 2005 Arthrotek, Inc, (2005), 8 pgs.
"Information of Polydioxanone", Dolphin Sutures, [Online] Retrieved from the internet: <https://www.dolphinsutures.com/resoucres/information-on-polydioxanone>, (2018), 2 pgs.
"International Application Serial No. PCT/US2009/039580, International Preliminary Report on Patentability dated Nov. 4, 2010", 9 pgs.
"International Application Serial No. PCT/US2009/039580, International Search Report dated Jul. 30, 2009", 4 pgs.
"international Application Serial No. PCT/US2009/039580, Written Opinion dated Jul. 30, 2009", 7 pgs.
"International Application Serial No. PCT/US2010/036602, International Preliminary Report on Patentability dated Dec. 8, 2011", 9 pgs.
"International Application Serial No. PCT/US2010/036602, International Search Report dated Nov. 8, 2010", 6 pgs.
"International Application Serial No. PCT/US2010/036602, Written Opinion dated Nov. 8, 2010", 7 pgs.
"International Application Serial No. PCT/US2011/026349, International Preliminary Report on Patentability dated Sep. 20, 2012", 11 pgs.
"International Application Serial No. PCT/US2011/026349, International Search Report dated Jul. 28, 2011", 6 pgs.
"International Application Serial No. PCT/US2011/026349, Invitation to Pay Additional Fees dated Jun. 9, 2011", 5 pgs.
"International Application Serial No. PCT/US2011/026349, Written Opinion dated Jul. 28, 2011", 9 pgs.
"international Application Serial No. PCT/US2011/038188, International Preliminary Report on Patentability dated Dec. 6, 2012", 14 pgs.

(56) References Cited

OTHER PUBLICATIONS

"International Application Serial No. PCT/US2011/038188, International Search Report dated Oct. 14, 2011", 6 pgs.
"International Application Serial No. PCT/US2011/038188, Invitation to Pay Additional Fees dated Aug. 5, 2011", 5 pgs.
"International Application Serial No. PCT/US2011/038188, Written Opinion dated Oct. 14, 2011", 12 pgs.
"International Application Serial No. PCT/US2012/030294, International Preliminary Report on Patentability dated Oct. 10, 2013", 9 pgs.
"International Application Serial No. PCT/US2012/030294, International Search Report dated May 23, 2012", 6 pgs.
"International Application Serial No. PCT/US2012/030294, Written Opinion dated May 23, 2012", 7 pgs.
"International Application Serial No. PCT/US2012/037703, International Preliminary Report on Patentability dated Nov. 28, 2013", 10 pgs.
"International Application Serial No. PCT/US2012/037703, International Search Report dated Sep. 21, 2012", 6 pgs.
"International Application Serial No. PCT/US2012/037703, Invitation to Pay Additional Fees dated Jul. 19, 2012", 7 pgs.
"international Application Serial No. PCT/US2012/037703, Written Opinion dated Sep. 21, 2012", 8 pgs.
"International Application Serial No. PCT/US2012/062738, International Preliminary Report on Patentability dated May 15, 2014", 9 pgs.
"International Application Serial No. PCT/US2012/062738, International Search Report dated Mar. 6, 2013", 6 pgs.
"International Application Serial No. PCT/US2012/062738, Written Opinion dated Mar. 6, 2013", 7 pgs.
"International Application Serial No. PCT/US2012/064832, International Preliminary Report on Patentability dated May 30, 2014", 9 pgs.
"International Application Serial No. PCT/US2012/064832, International Search Report dated Feb. 6, 2013", 3 pgs.
"International Application Serial No. PCT/US2012/064832, Written Opinion dated Feb. 6, 2013", 7 pqs.
"International Application Serial No. PCT/US2013/058921, International Preliminary Report on Patentability dated Mar. 26, 2015", 9 pgs.
"International Application Serial No. PCT/US2013/058921, International Search Report dated Oct. 21, 2013", 5 pgs.
"International Application Serial No. PCT/US2013/058921, Written Opinion dated Oct. 21, 2013", 6 pgs.
"International Application Serial No. PCT/US2013/075989, International Preliminary Report on Patentability dated Jul. 2, 2015", 10 pgs.
"International Application Serial No. PCT/US2013/075989, International Search Report dated Mar. 6, 2014", 4 pgs.
"International Application Serial No. PCT/US2013/075989, Written Opinion dated Mar. 6, 2014", 7 pgs.
"International Application Serial No. PCT/US2014/026413, International Preliminary Report on Patentability dated Sep. 24, 2015", 10 pgs.
"International Application Serial No. PCT/US2014/026413, International Search Report dated Jun. 6, 2014", 5 pgs.
"International Application Serial No. PCT/US2014/026413, Written Opinion dated Jun. 6, 2014", 8 pgs.
"JuggerKnot™ Soft Anchor Midfoot Repair", brochure. Biomet Sports Medicine, (Jul. 2011), 12 pgs.
"JuggerKnot™ Soft Anchor. It's Small. It's strong. And it's all suture . . . ", Ordering Information brochure. Biomet Sports Medicine, (Jun. 2011), 2 pgs.
"JuggerKnot™ Soft Anchor. Labral Repair", brochure. Biomet Sports Medicine, (Apr. 2011), 12 pgs.
"JuggerKnot™ Soft Anchor: Arthroscopic and Mini-Open Rotator Cuff Repair Using JuggerKnot™ Soft Anchor-2,9mm with ALLthread™ Knotless Anchor Surgical Technique", brochure, Biomet® Sports Medicine, (2013), 16 pgs.

"Make your next tendon repair an open-and-shut case. The Teno Fix® Tendon Repair System", Teno Fix® brochure, Ortheon® Medical, (2003), 2 pgs.
"Mallory-Head Modular Calcar Revision System", Biomet Orthopedics, Inc., (2006), 20 pgs.
"Next Generation in Knee Ligament Reconstruction & Repair Technology", Suture Tensioner w/Tensiometer, Arthrex®, Inc. catalog, (2009).
"Panalok Anchor with PDS II and Ethibond Suture", Mitek Products Ethicon, (1997), 2 pgs.
"Rapid Sternal Closure", KLS Martin L.P., [Online] retrieved from the internet: U.S. Appl. No. 13/645,964 , (2006).
"Rotator Cuff Fixation", Acufex Fastenator System: Shoulder Arthroscopy; H-2-H-22, 22 pgs.
"SE Graft Tensioning System Surgical Technique", Linvatec Corporation copyright 2003, (2004), 12 pgs.
"SportMesh™ Soft Tissue Reinforcment, Made from . . . Artelon® optimal tissue repair", Biomet® Sports Medicine, Inc., (2007), 8 pgs.
"Sternal Cable System", Pioneer®, [Online] retrieved from the internet: U.S. Appl. No. 13/645,964 , (2010).
"The AutoCuff System", Opus Medical, [Online]. Retrieved from the Internet: <www.opusmedical.com>, (2003), 4 pgs.
"Toggleloc™ Femoral Fixation Device", Arthrotek, (Mar. 31, 2006), 8 pgs.
"TriTis™ Tibial Fixation System and Implant", brochure. Scandius Biomedical, (2006).
Albritton, Mark J, et al., "Toggleloc Fixation Device with Ziploop Technology: Biceps Tendon Reattachment", Biomet Sports Medicine, a Biomet Company Brochure 2099, (2011), 1-12.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Andrews, James R, "Toggleloc™ Fixation Device with Ziploop™ Technology: ACL Reconstruction Bone-Tendon-Bone", Biomet Sports Medicine, a Biomet Company Brochure, (2013), 1-20.
Anitua, Eduardo, et al., "Autologous platelets as a source of proteins for healing and tissue regeneration", Thromb Haemost, vol. 91, (2004), 4-15.
Arthrotek, "A Biomet Company; Sure fire Hybrid Meniscal Device", Fall AANA, (2004), 37 pgs.
Barber, Alan F, "Uses and Abuses of Sutures and Anchors", Shoulder Scope, San Diego Shoulder Arthroscopy Library, (Jul. 1999), 6 pgs.
Barber, Alan F, "Using Sutures and Anchors", San Diego Shoulder Arthroscopy Course, 17th Annual Meetina, (Jun. 14, 2000), 9 pgs.
Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Flavia, Namie Azato, "Traction endurance biomechanical study of metallic suture anchors at different insertion angles", Acta Ortop. Bras., vol. 11, No. 1, Sao Paulo, (Jan./Mar. 2003), pp. 25-31.
Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.
Fromm, Stuart M.D. E, "", Rapidloc, Meniscal Repair System, Mitek Products, Ethicon, (2001), 6 pgs.
Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Hecker, AT, et al., "Pull-out strength of suture anchors for rotator cuff and Bankart lesion repairs", The American Journal of Sports Medicine 21(6), (1993), 874-879.

(56) References Cited

OTHER PUBLICATIONS

Hunt, Patrick, et al., "Development of a Perforated Biodegradable Interference Screw; Arthroscopy:", The Journal of Arthroscopic and Related Surgery, vol. 21, No. 3;, (Mar. 2005), 258-265.

Lawhorn, M D, et al., "MaxFire™ Meniscal Repair Device with Zip Loop™ Technology", Biomet Sports Medicine, (Feb. 29, 2008), 12 pgs.

Majors, MD, Roy Alan, "Meniscal repairs: proven techniques and current trends", Lippincott Williams & Wilkins, Inc.;, (2002), 30-36.

Miller, Mark D, et al., "Pitfalls Associated with FasT-Fix Meniscal Repair", Arthroscopy: The Journal of Arthroscopic and Related Surgery, vol. 18 No. 8 :, (Oct. 2002), 939-943.

Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.

Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.

Roseberg, MD, Thomas D, "ACL Reconstruction with Acufex Director Drill Guide and Endobutton CL Fixation System", Smith & Nephew: Knee Series, Technique Guide, (2005), 12 pgs.

Saxena, Pankaj, et al., "Use of Double Wires in Sternal Closure, A Useful Technique", Texas Heart® Institute. Journal List> Tex Heart Inst J > v.33(4), (2006).

Smith, et al., "Endoscopic Meniscal Repair Using the T-Fix", (1996), 16 pgs.

Smith, et al., "Fast-Fix", Meniscal Repair System;, (2001), 3 pgs.

Steadman, et al., "Microfracture: Surgical Technique and Rehabilitation to Treat Chondral Defects", Clinical Orthopaedics and Related Research 391, (2001), S362-S369.

Thomas, Roseberg D, "Technique for ACL Reconstruction with Acufex Director Drill Guide and Endobutton CL", Smith & Nephew, Technique Guide, (1999), 18 pgs.

Weiler, A, et al., "Biodegradierbare Interferenzschrauben in der Kreuzbandchirurgie", Opjournal 14, (1998), 278-284.

Zeitani, Jacob M.D, "A New Sternal Reinforcement Device to Prevent and Treat Sternal Dehiscence", CTSNet, [Online]. Retrieved from the Internet: <URL: http://www.ctsnet.org/print/article/new-sternal-reinforcement-device-prevent-and-treat-sternal-dehiscence>, (Jun. 30, 2008), 6 pgs.

* cited by examiner

SOFT TISSUE REPAIR DEVICE AND ASSOCIATED METHODS

CROSS-REFERENCE TO RELATED APPLICATIONS

This application is a continuation of U.S. patent application Ser. No. 15/412,676 filed on Jan. 23, 2017, which is a continuation of U.S. patent application Ser. No. 13/833,567 filed on Mar. 15, 2013, now U.S. Pat. No. 9,561,025 issued on Feb. 7, 2017, which is a continuation of U.S. patent application Ser. No. 13/721,970 filed on Dec. 20, 2012, now U.S. Pat. No. 8,632,569 issued on Jan. 21, 2014, which is a divisional of U.S. patent application Ser. No. 13/045,689 filed on Mar. 11, 2011, now U.S. Pat. No. 8,337,525 issued on Dec. 25, 2012, which is a divisional of U.S. patent application Ser. No. 12/014,340 filed on Jan. 15, 2008, now U.S. Pat. No. 7,905,904 issued on Mar. 15, 2011.

The disclosures of the above applications are incorporated wherein by reference.

INTRODUCTION

Tears caused by trauma or disease in fibrous soft tissue, such as cartilage, ligament, or muscle, can be repaired by suturing. Various repair devices have been developed for facilitating suturing and are effective for their intended purposes. Nevertheless, tissue repair devices for facilitating suturing are still desirable.

SUMMARY

The present teachings provide a fibrous tissue repair device that includes first and second tubular anchors having corresponding longitudinal passages. The tissue repair device includes corresponding first and second inserters. Each inserter has a shaft with a distal portion received in the longitudinal passage of the corresponding tubular anchor. A flexible strand couples the first and second anchors.

In some embodiments the anchors are non-deformable in some embodiments, the tissue repair device includes a cannula having a handle and a passage receiving the first and second inserters.

In some embodiments, the fibrous repair device includes a handle, first and second inserters movable relative to the handle, and first and second anchors pre-loaded on corresponding external surfaces of the first and second inserters. The repair device also includes a control mechanism operable to control a deployment sequence of the first and second inserters for deploying the corresponding first and second anchors, such that the second inserter is prevented from deploying the second anchor until the first anchor is deployed by the first inserter.

In some embodiments, the fibrous tissue repair device includes a handle, a first inserter movable relative to the handle, a first anchor pre-loaded on an external surface of the first inserter, and a first slider coupled to the handle for moving the first inserter between deployment and retraction positions. The repair device can also include a second inserter movable relative to the handle, a second anchor pre-loaded on an external surface of the second inserter, and a second slider coupled to the handle for moving the second inserter between deployment and retraction positions. Further, the repair device can include a slider control mechanism coupled to the first and second sliders and operable to control a motion sequence of the first and second inserters, such that the first inserter is constrained to move to a deployment position before the second inserter. The repair device can also include a flexible strand coupling the first and second anchors. The flexible strand can pass through portions of the first and second anchors and form an adjustable knotless loop.

The present teachings also provide a method of repairing fibrous tissue. The method includes preloading a first anchor externally onto a first inserter, passing the first inserter from a first side to a second side of the fibrous tissue at a first location, delivering the first anchor on the second side of the fibrous tissue, and retracting the first inserter away from the tissue.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DESCRIPTION OF VARIOUS ASPECTS

The following description is merely exemplary in nature and is in no way intended to limit the invention, its application, or uses. For example, although the present teachings are illustrated in an application for meniscus repair in knee surgery, the present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic or other procedures.

Figure 1:
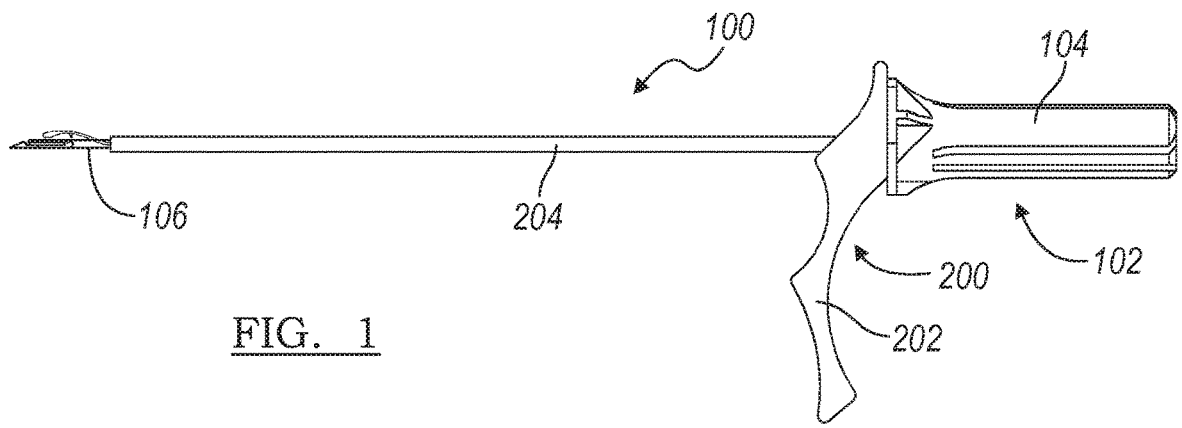
FIG. 1 is side view of a tissue repair device according to the present teachings.
Figure 1A:
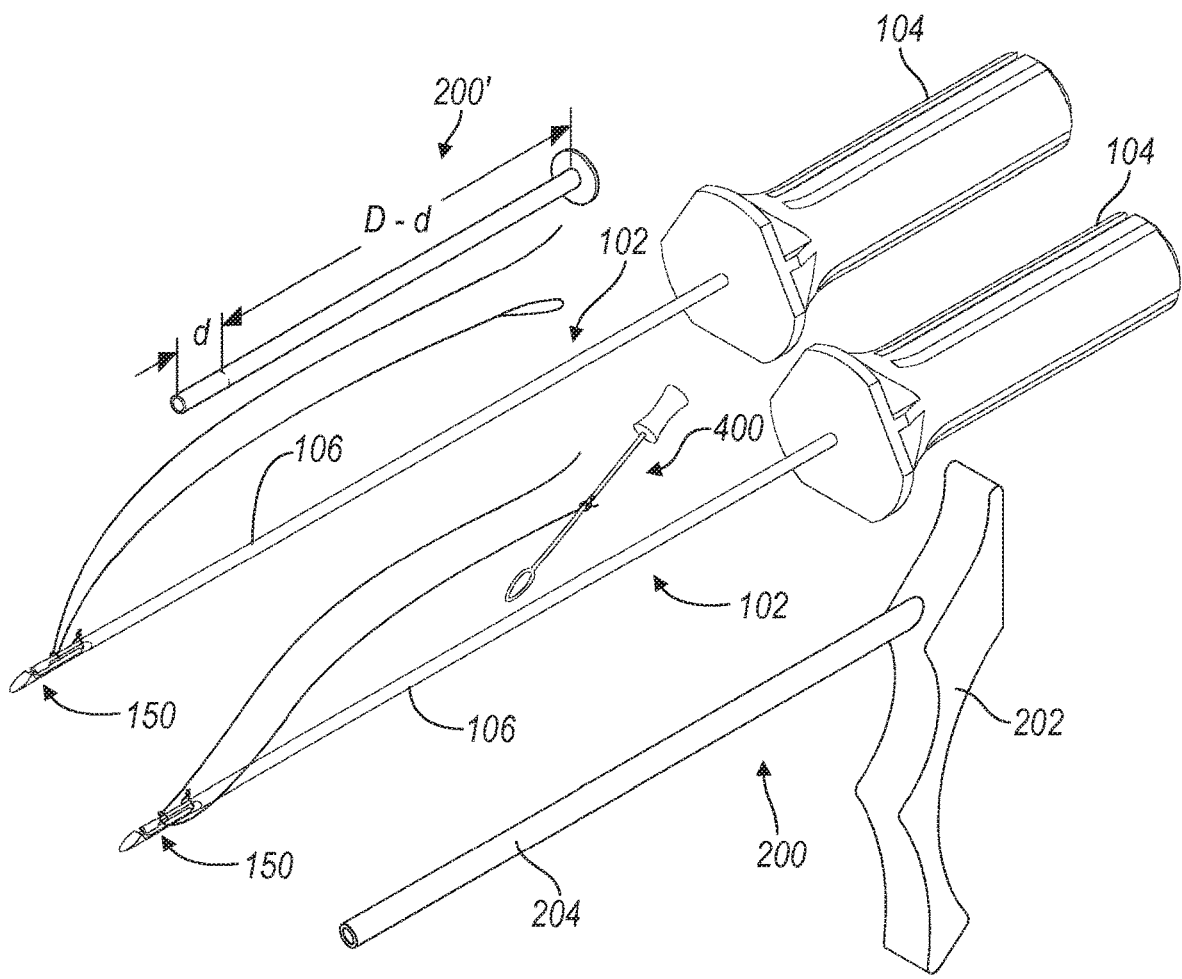
FIG. 1A is a perspective view of a tissue repair kit according to the present teachings.
Figure 2:
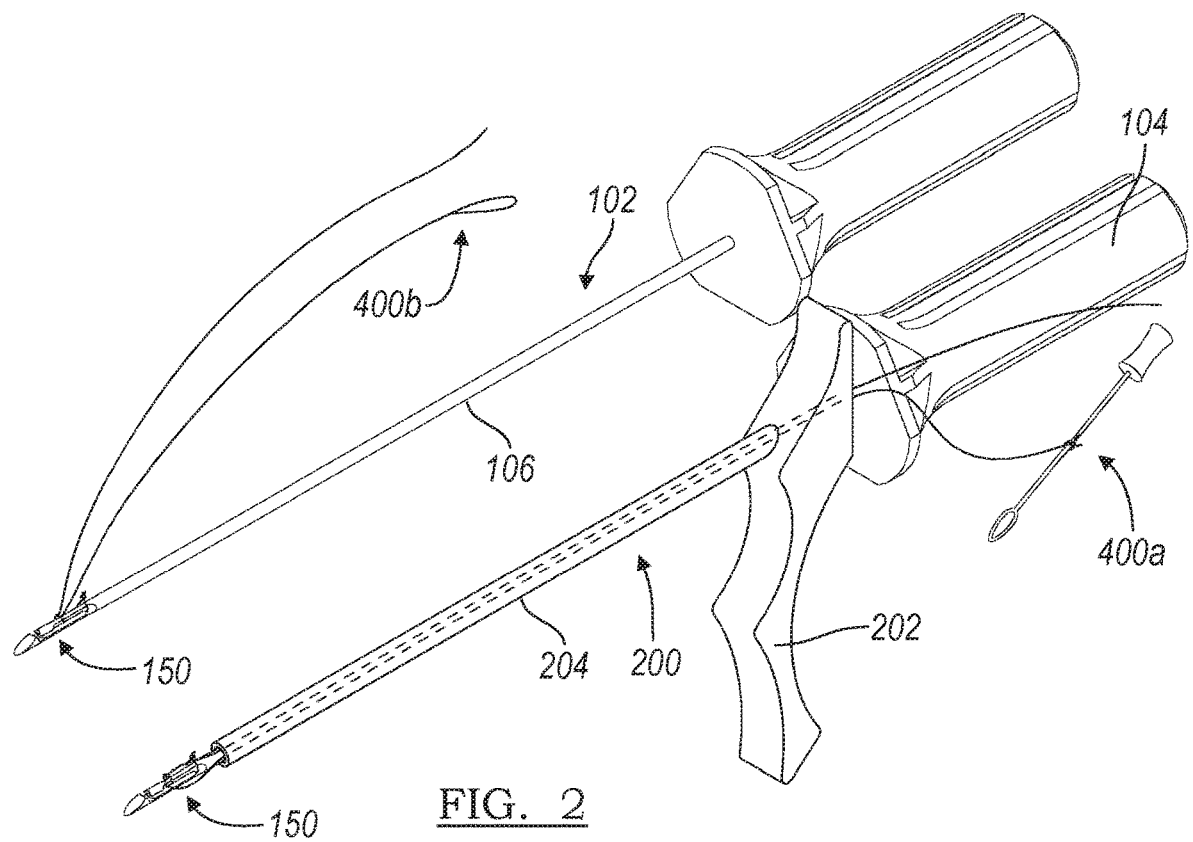
FIG. 2 is a perspective view of a tissue repair device according to the present teachings.
Figure 3:
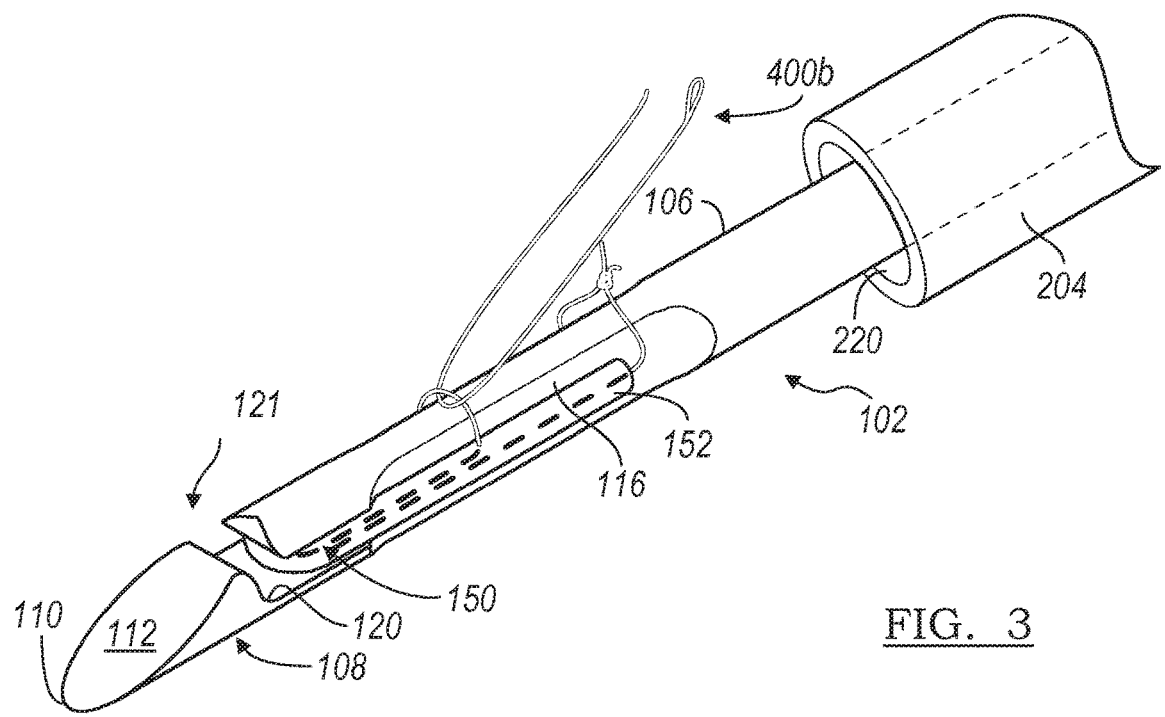
FIG. 3 is an enlarged perspective view of a tissue repair device according to the present teachings.

An exemplary tissue repair device 100 according to the present teachings is illustrated in FIG. 1, and in a kit form in FIG. 1A. The device 100 can include one or more inserters 102 and a cannula 200. The inserters 102 can be single-use, disposable, or sterilizable inserters. Each inserter 102 can be externally pre-loaded on its outer or external surface 121 with a single flexible anchor 150, as described below. The inserter 102 can include a handle 104 and a solid shaft 106 having a solid distal portion 108.

Figure 6:
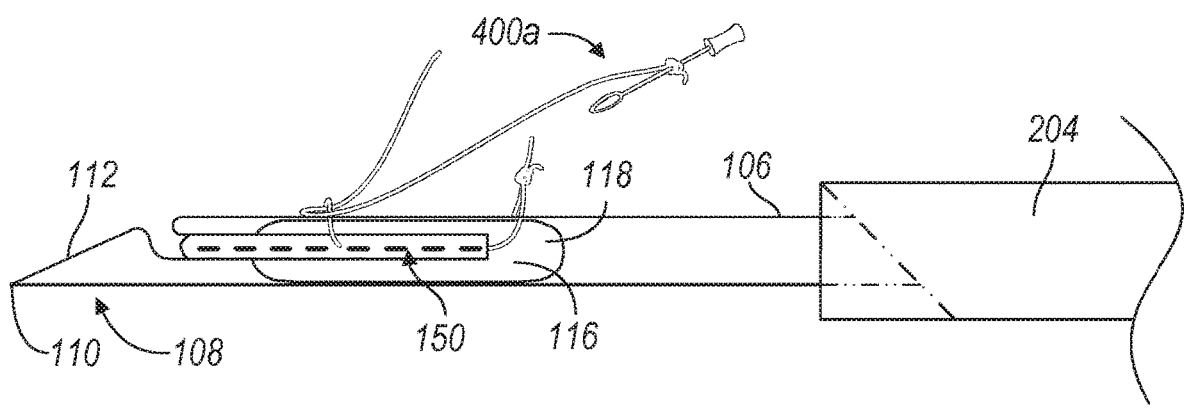
FIG. 6 is an enlarged side view of a tissue repair device according to the present teachings.
Figure 7:
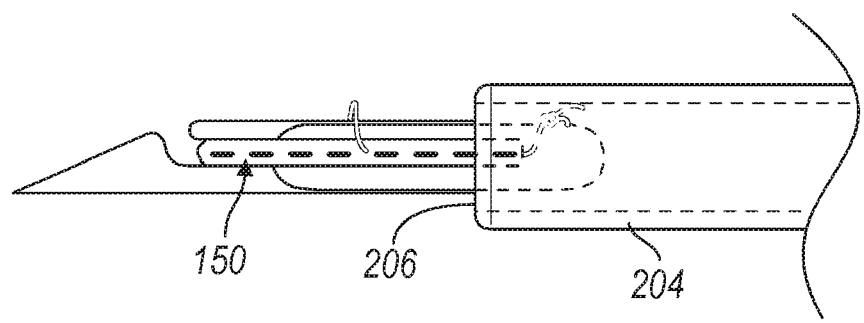
FIG. 7 is an enlarged side view of a tissue repair device according to the present teachings.
Figure 8:
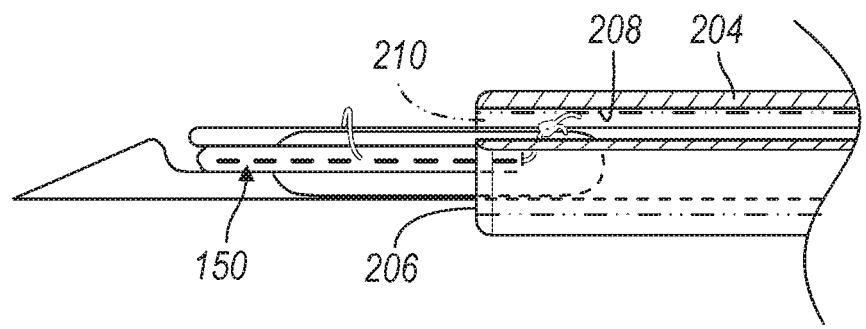
FIG. 8 is an enlarged side view of a tissue repair device according to the present teachings.

Referring to FIGS. 6-8, the distal portion 108 can include a sharp edge 110 defined by an inclined surface 112. The distal portion 108 can also include an external groove or slot 120 which is formed in a direction that is transverse or substantially perpendicular to the shaft 106. The distal portion 108 can also include two opposing substantially planar surfaces 116 defining a buttress 118. It will be appreciated that the outer or external surface 121 of the distal portion 108 incorporates the external groove 120, the planar surfaces 116 and the buttress 118.

The flexible anchor 150 can be an elongated member having first and second ends 152, 154. The flexible anchor 150 can be made of resorbable or non-resorbable materials, including braided suture, sponges and sponge-like materials in solid form, perforated materials, woven/braided from biocompatible materials or fibers, such as, for example, polymer, polyester, polyethylene, cotton, silk, or other natural or synthetic materials, including sponges and sponge-like materials. The flexible anchor 150 can also be an elongated tubular or solid member or a two-dimensional member with or without internal bores. The flexible anchor 150 can have any properties that allow the flexible anchor 150 to change shape. The flexible anchor 150 can be, for example, compliant, flexible, foldable, squashable, squeezable, deformable, limp, flaccid, elastic, low-modulus, soft, spongy, perforated or any other flexible member which can change shape. In some aspects, the flexible anchor 150 can be coated with biological or biocompatible coatings, and it can also be soaked in platelets and other biologics, which can be easily absorbed by the flexible anchor 150 in particular when, for example, the flexible anchor 150 is made from spongy, absorbent material.

Figure 9A:
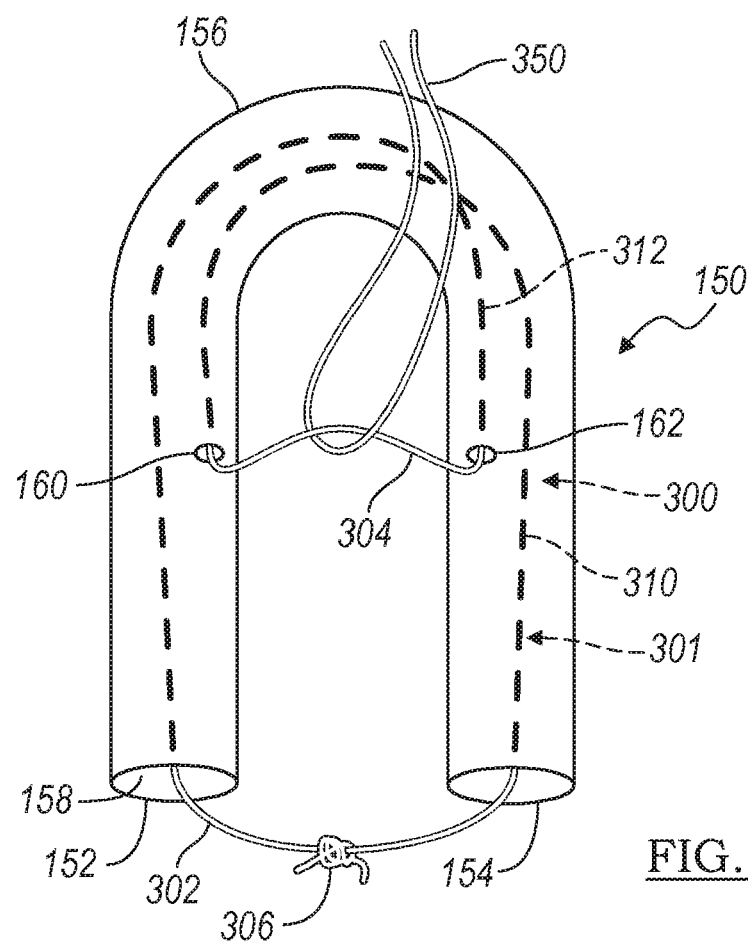
FIGS. 9A-C are perspective views of a flexible anchor shown with flexible strand arrangements according to the present teachings.

It should be understood by the above description that the flexible anchor 150 cannot pierce or otherwise penetrate tissue either with the first and second ends 152, 154 or with any portion thereof. The flexible anchor 150 can be loaded solely on the external surface 121 of the distal portion 108 of the shaft 106 in a folded configuration, such at the first and second ends 152, 154 are facing each other. Accordingly, no portion of the anchor 150 is received even partially in or within the inserter, in contrast to prior art hollow needles and tubes that define an interior tubular surface within which one or more anchors are held substantially in their entirety. More specifically, an intermediate portion 156 of the flexible anchor 150 can be smoothly bent in a substantially U-shape, and draped over the external groove 120, while the first and second ends 152, 154 extend along the flat portions 116 of the shaft 106 of the inserter 102. The flexible anchor 150 can be in the form of an elongate flexible tube defining a bore 158 along its length, as shown in FIG. 9A. The flexible anchor 150 can be formed of suture braided without a core.

Referring to FIGS. 1, 1A, and 6-8, the cannula 200 can include a handle 202 and a tubular or hollow shaft 204. The shaft 204 of the cannula 200 can have a longitudinal bore 220 having an inner diameter sized to receive the shaft 106 of the inserter 102. The shaft 204 of the cannula 200 can have a distal end 206 which can be perpendicular relative to the shaft 204, although it can be also be slanted relative to the shaft 204 as shown in phantom line in FIG. 6. The distal end 206 of the cannula 200 has a rounded, blunt or smooth edge, which is not intended to or capable of piercing or otherwise penetrating tissue, whether the distal end 206 is slanted or perpendicular to the shaft 204.

Referring to FIG. 8, the cannula shaft 204 can include a cut-away slot 208 defining a viewing window 210. The window 210 can be covered with clear plastic, for example in the form of a tubular member 212 received in the bore 220 of the cannula shaft 204.

Figure 4:
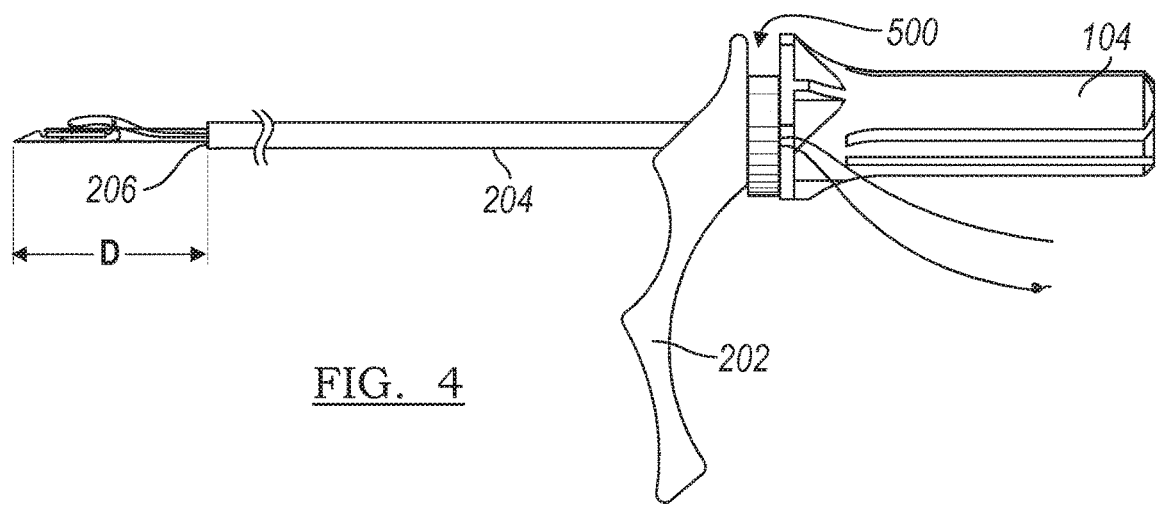
FIG. 4 is a side view of a tissue repair device according to the present teachings shown in a first position.
Figure 5:
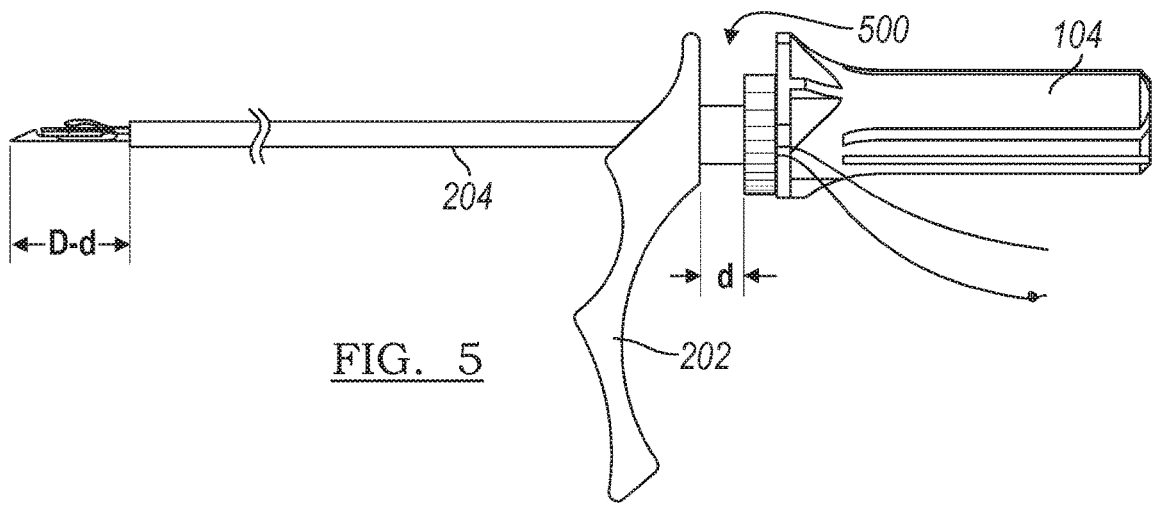
FIG. 5 is a side view of the device of FIG. 4 shown in a second position.

Referring to FIGS. 4 and 5, the soft tissue repair device 100 can be used with a depth limiter 500. The depth limiter 500 can be installed over the shaft 106 of the inserter 102 and between the handle 104 of the inserter 102 and the handle 204 of the cannula 200. The depth limiter can operate as an actuator using, for example, a rack-and-gear mechanism to move the shaft 106 of the inserter 102 relative to the shaft 204 of the cannula 200 between the position shown in FIG. 4, and the position shown in FIG. 5. In the position of FIG. 4, the inserter 102 extends a distance "D" beyond the distal end 206 of the cannula 200. In the position of FIG. 5, the inserter 102 extends a distance "D-d" beyond the distal end 206 of the cannula 200, where "d" is a retraction distance of the depth limiter 500. Alternatively, a separate disposable depth limiter in the form of a plastic tube 200' that can be cut to a desired depth by removing a portion of length "d" can also be used over the shaft 106 of the inserter 102, as shown in FIG. 1A. The cannula 200, on the other and, can be reusable.

Referring to FIGS. 1A and 9A-9C, the flexible anchor 150 can be assembled bent in a U-shape form on the inserter 102 with a continuous strand loop 300 attached thereon. The strand loop 300 can be formed by a single segment of flexible strand 301 passing through the bore 158 of the anchor 150, such that the strand loop 300 includes a first external segment or portion 302 outside the bore 158 and between the ends 152, 154, and a second external segment portion 304 located outside the bore 158 and exiting the bore 158 from exit positions or openings 160, 162 on opposite sides of the bent U-shape of the flexible anchor 150. The flexible strand 301 can be made of braided filaments or fibers of biocompatible material, including natural and synthetic fibers, such as cotton, silk, polymer, polyester, polyethylene, thin wire, suture, and other materials.

Figure 9B:
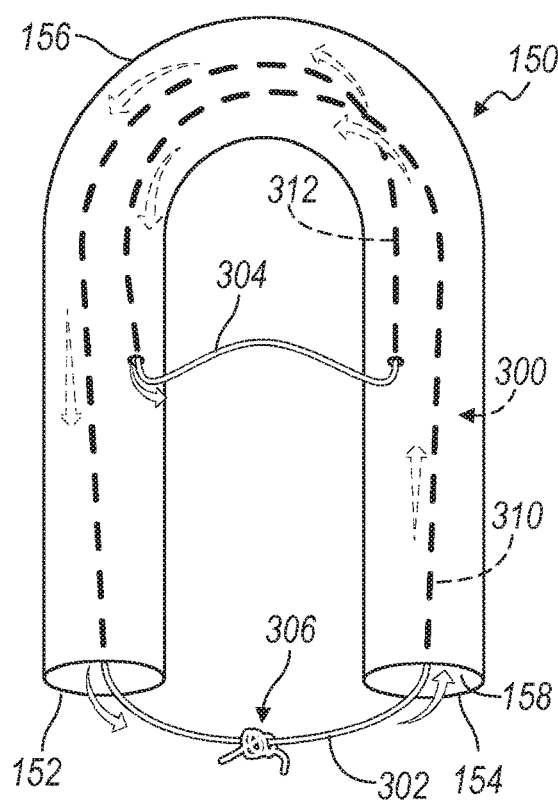
Figure 9C:
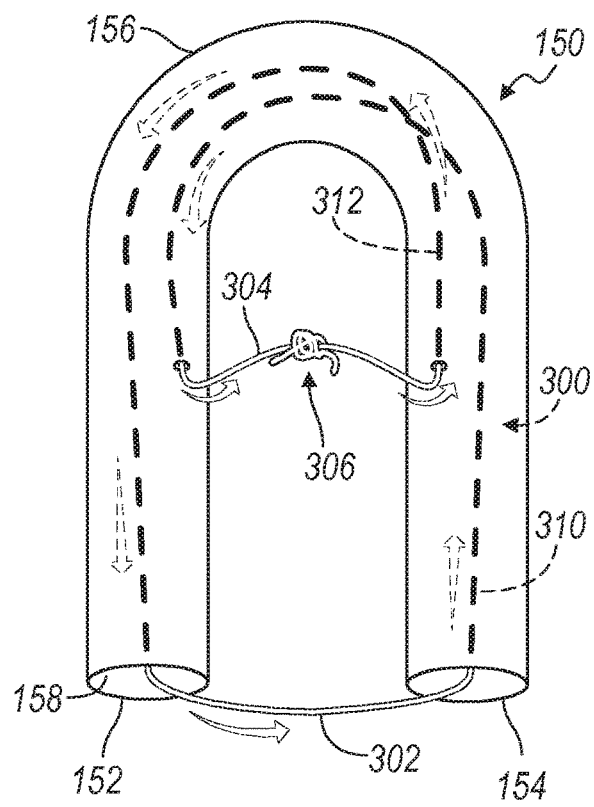

The strand loop 300 can be formed by tying the ends of the segment with a knot 306 which can be positioned on either the first external portion 302 or the second external portion 304, as shown in FIGS. 9B and 9C respectively. It will be appreciated that the loop 300 can define first and second secondary loops or sub-loops 310, 312. The first sub-loop 310 can include the first external portion 302, and the second sub-loop can include the second external portion 304. The first and second sub-loops 310, 312 can intersect each other, and each sub-loop 310, 312 can pass through the bent portion of the bore 158 corresponding to the intermediate portion 156 of the flexible anchor 150.

Figure 10:
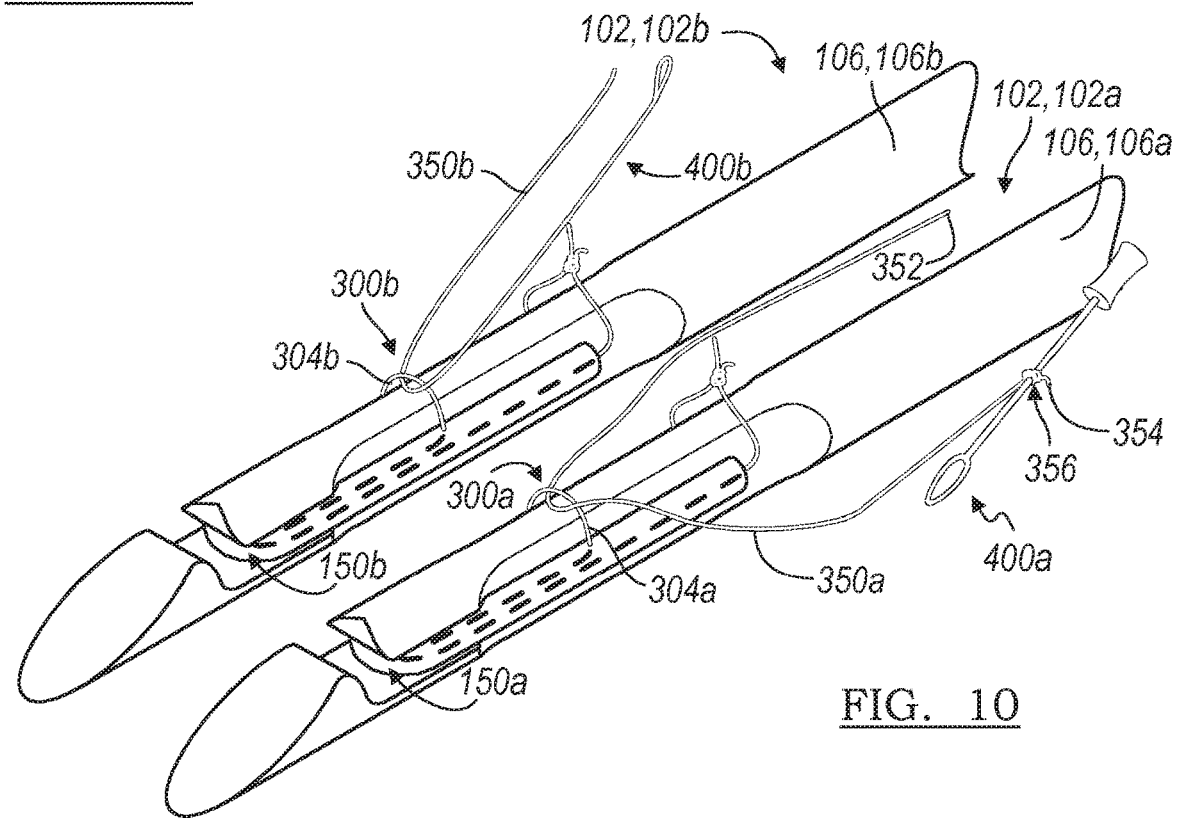
FIG. 10 is a perspective of two pre-loaded inserters according to the present teachings.
Figure 11:
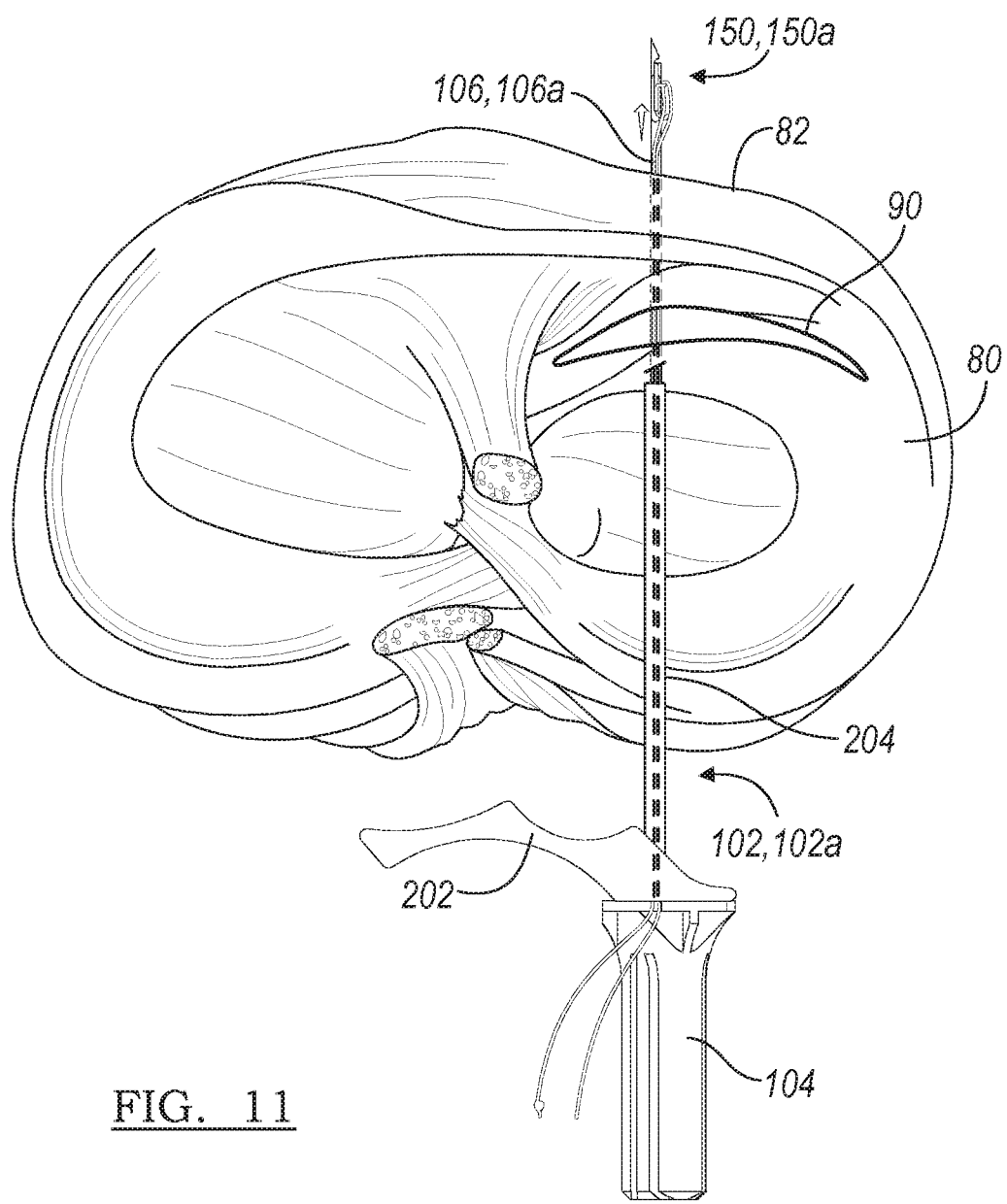
FIG. 11 is an environmental view illustrating inserting a first anchor through soft tissue according to the present teachings.

Referring to FIGS. 10-15, the soft tissue repair device 100 can be used to repair a soft tissue defect 90, such as, for example, a tear, or other weakness in fibrous soft tissue 80, such as in meniscal tissue, cartilage, muscle or other fibrous tissue under the skin. After an outer incision is made through the skin to access the soft tissue 80, the cannula 200 can be positioned through the incision without cutting or piercing any tissue and placed adjacent the soft tissue 80, such as fibrous meniscal tissue, and operate as an access portal for the inserter 102, as shown in FIG. 11. In the following exemplary procedure, the kit of FIG. 1A that includes first and second inserters 102 can be used with the cannula 200 to repair the soft tissue 80. The first and second inserters 102 and their respective features, although identical, will be distinguished for descriptive clarity by appending the letters "a" and "b", e.g. inserters 102a, 102b, shafts 106a, 106b, etc., when desirable for further clarity. Similarly, the associated anchors 150 and their features, as well as other devices used in the procedure will also be distinguished, by appending the letters "a" and "b", when desirable for further descriptive clarity.

Referring to FIG. 10, the first inserter 102a can be assembled with the first anchor 150a externally coupled thereon, as shown. A first flexible strand 350a having a first "free" end 352 and a second end 354 can be coupled on a first threader 400a with a slip knot 356. The first strand 350a can pass through the first strand loop 300a at the second external portion 304a. The second inserter 102b can be assembled with the second anchor 150b externally coupled thereon, as shown. A second strand 350b coupled to a second threader 400b can pass through the second strand loop 300b at the second external portion 304b of the second anchor 150b. Accordingly, the first and second inserters 102a, 102b can be independently pre-assembled, such that the first and second anchors 150a, 150b are only connectable to each other intra-operatively.

Figure 12:
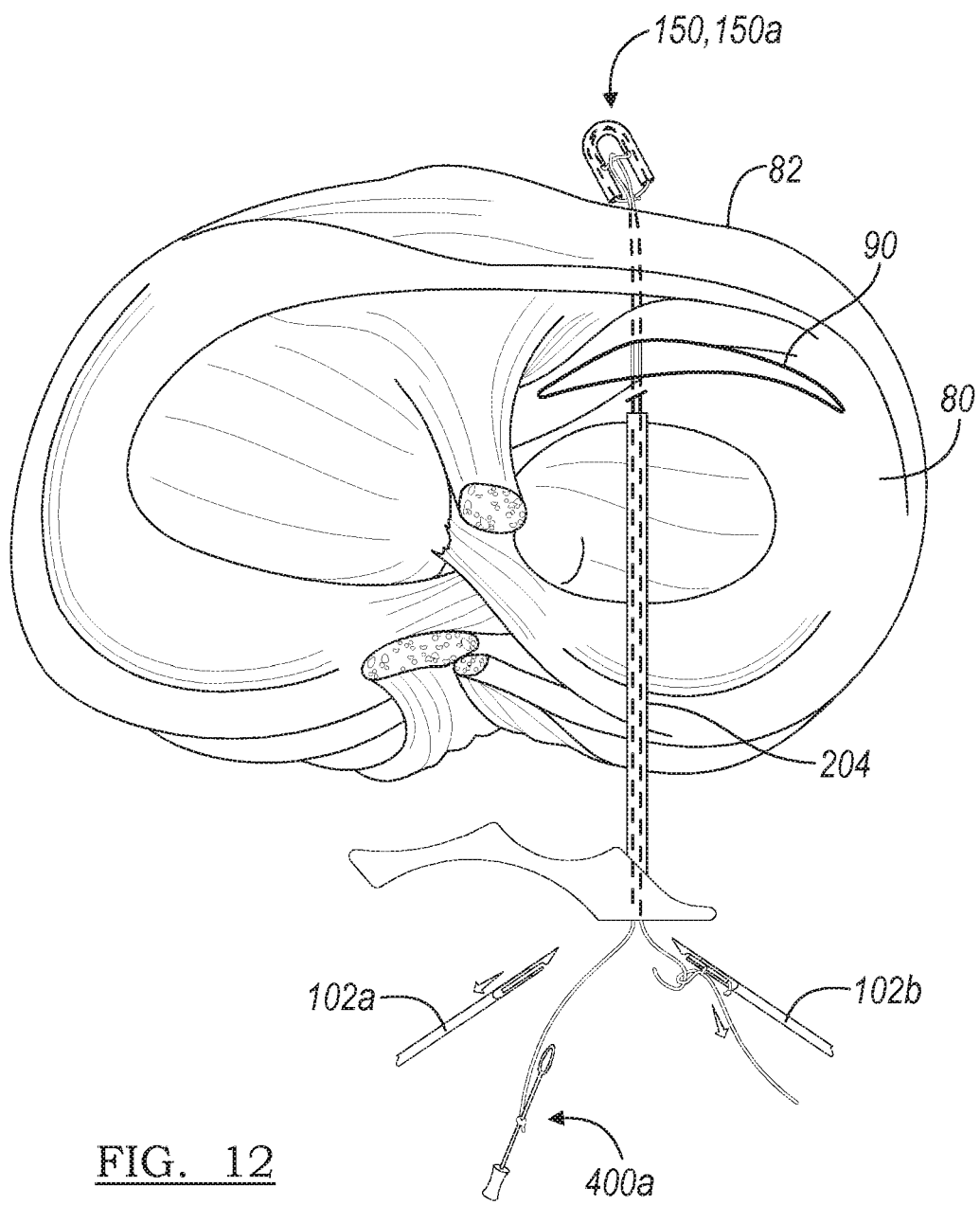
FIG. 12 is an environmental view illustrating delivering a first anchor on an outer surface of soft tissue according to the present teachings.

Referring to FIGS. 11-14, in an exemplary meniscal repair of a knee joint, the cannula 200 can be passed through the incision into the knee joint without piercing any fibrous tissue, except the tissue of the knee joint capsule, and positioned adjacent the meniscus. The first inserter 102a can be passed through the cannula 200 and into the soft tissue 80 or meniscus from a first side of the defect 90 until the shaft 106a of the first inserter 102a can exit a second side 82 of the soft tissue 80, such as an outer surface or back side of the meniscus of the knee joint or other outer surface of a fibrous tissue, for example. The shaft 106a of the first inserter 102a can be sufficiently pushed through the second side 82 of the soft tissue 80 such that upon retraction of the first shaft 106a, the first anchor 150a can be pulled off the first shaft 106a by the spontaneously closing tissue and remain on the second side 82 of the soft tissue 80 at a first location, as shown in FIG. 12. The first inserter 102a can then be removed and discarded.

Figure 9D:
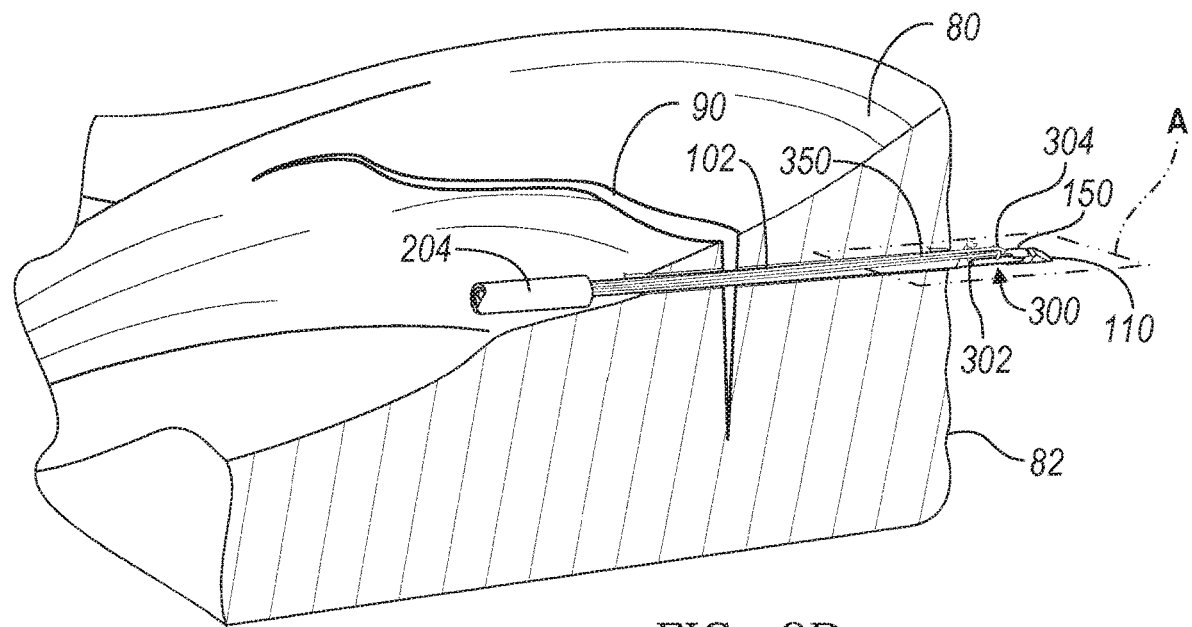
FIG. 9D is a perspective view illustrating a first configuration and a first orientation of an anchor relative to soft tissue according to the present teachings.
Figure 9E:
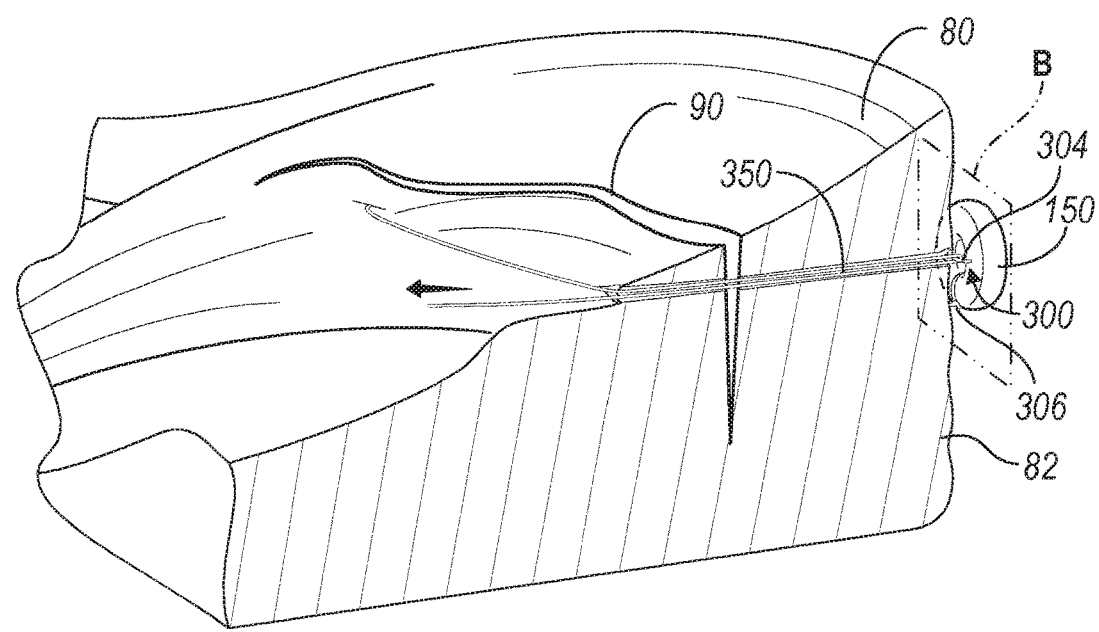
FIG. 9E is a perspective view illustrating a second configuration and a second orientation of the anchor of FIG. 9E relative to soft tissue according to the present teachings.

It will be appreciated that the manner and structure of the pre-assembled inserter 102 and anchor 150 allows the anchor 150 to pass through a narrow opening or slit formed in the tissue 80 by the edge 110 of the inserter 102 in a first low-profile folded configuration defining a plane "A", as shown in FIG. 9D, and deposited in that configuration outside the tissue 80. It will be appreciated that the flexible anchor 150 is deployed in its U-shape configuration with the first and second ends 152, 154 being delivered substantially simultaneously. Further, it will be understood that tightening the first strand loop 300 by pulling on the second external portion 304 can cause the anchor 150 to deform to a second configuration having a substantially flat round-like or knurled shape. Further pulling on the second external portion 304 can rotate the first anchor 150a from a first orientation defined by plane A and substantially perpendicular to the outer surface 82 to a second orientation such that the deformed anchor 150 can define a plane "B" substantially parallel to and lying on the outer surface 82 of the soft tissue 80 in a substantially flat shape, as shown in FIG. 9E.

Figure 13:
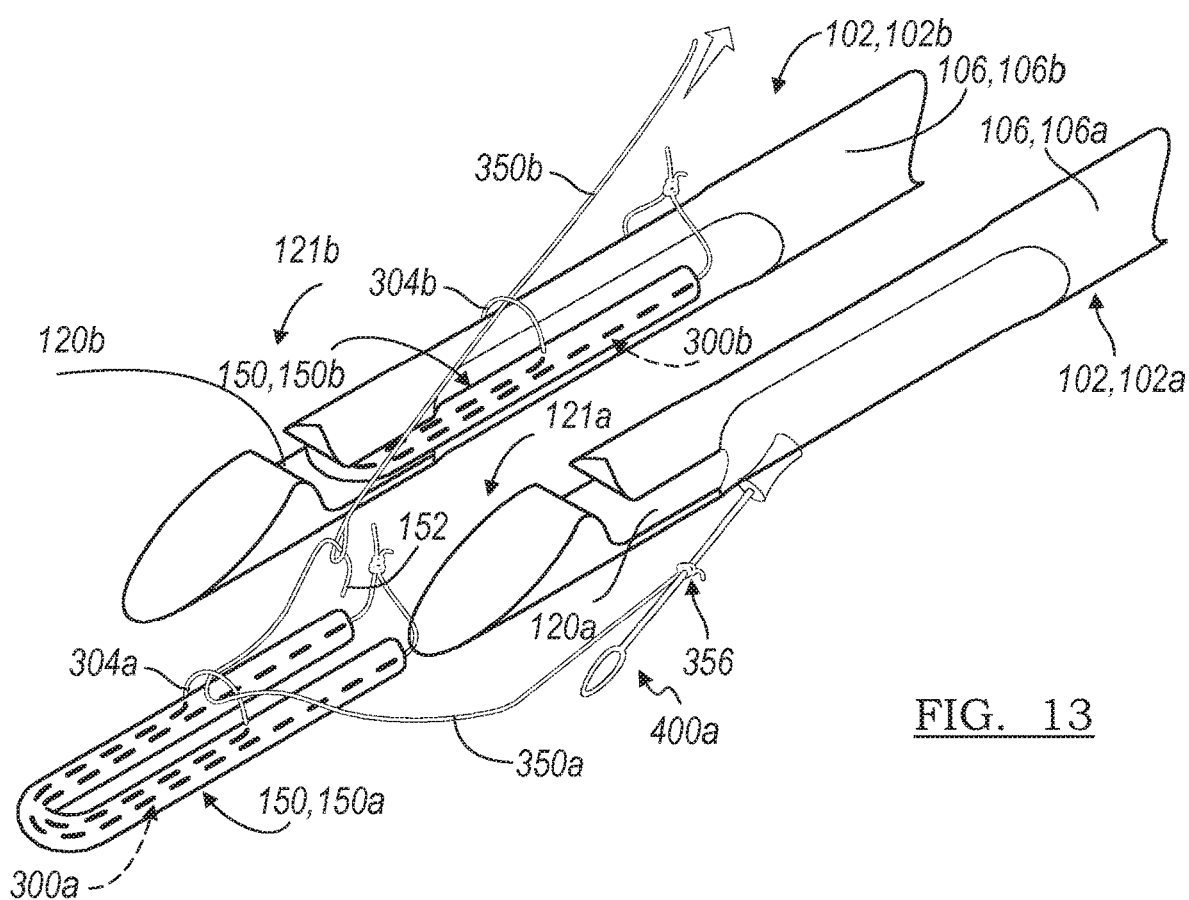
FIG. 13 is a perspective view illustrating connecting a flexible strand between first and second anchors according to the present teachings.
Figure 14:
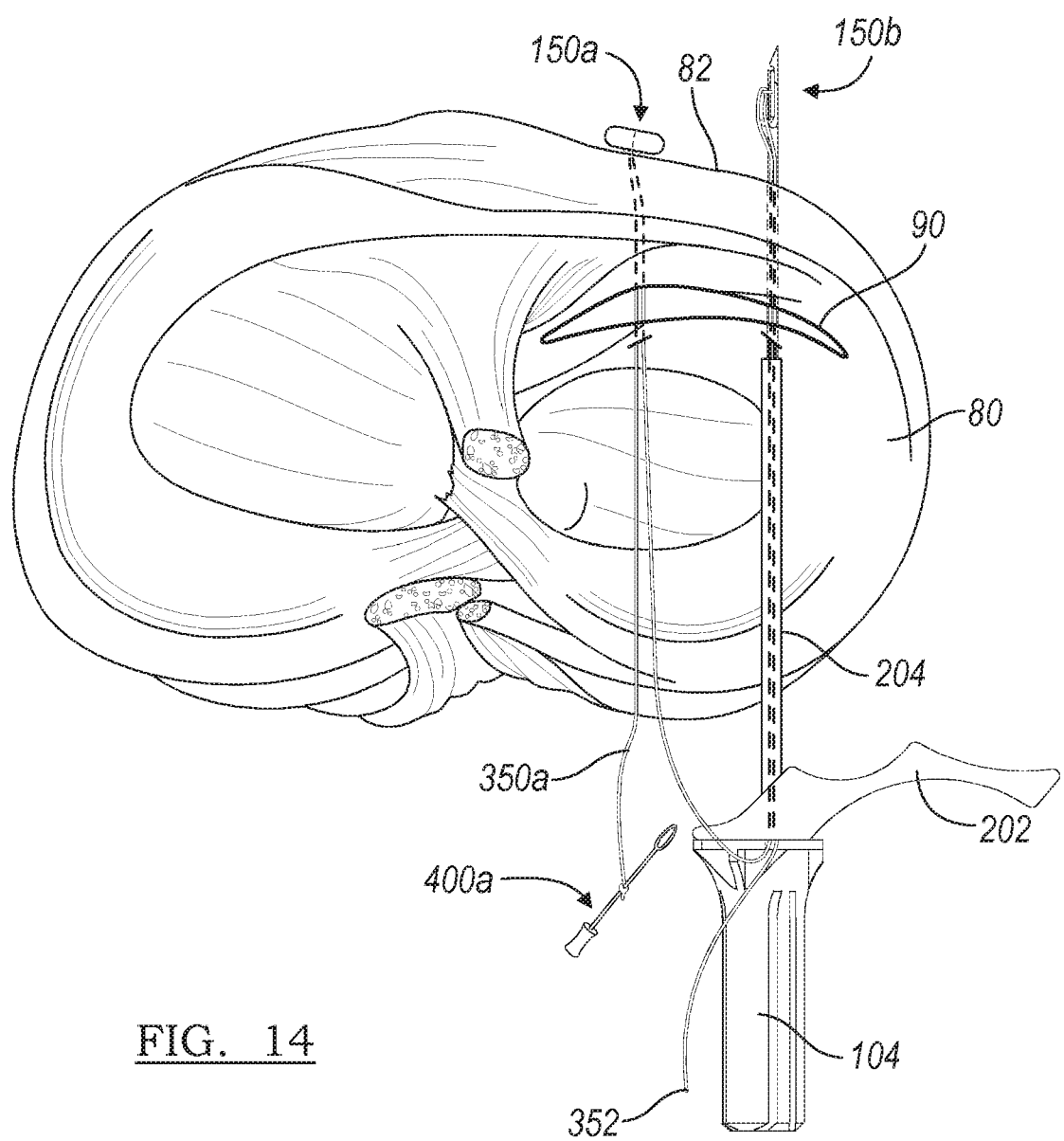
FIG. 14 is an environmental view illustrating delivering a second anchor on an outer surface of soft tissue according to the present teachings.

Referring to FIGS. 13 and 14, the first strand 350a can be captured by the second threader 400 and passed through the second external portion 304b of the second strand loop 300b of the second anchor 150b, which is pre-loaded on the second inserter 102b, as shown in FIG. 13. The second inserter 102b can be inserted through the cannula 200 which is positioned adjacent but without piercing the fibrous tissue as described above, and the second anchor 150b can be delivered to the second side 82 of the soft tissue 80 at a second location, as shown in FIG. 14. The second inserter 102b can then be removed and discarded.

Figure 15:
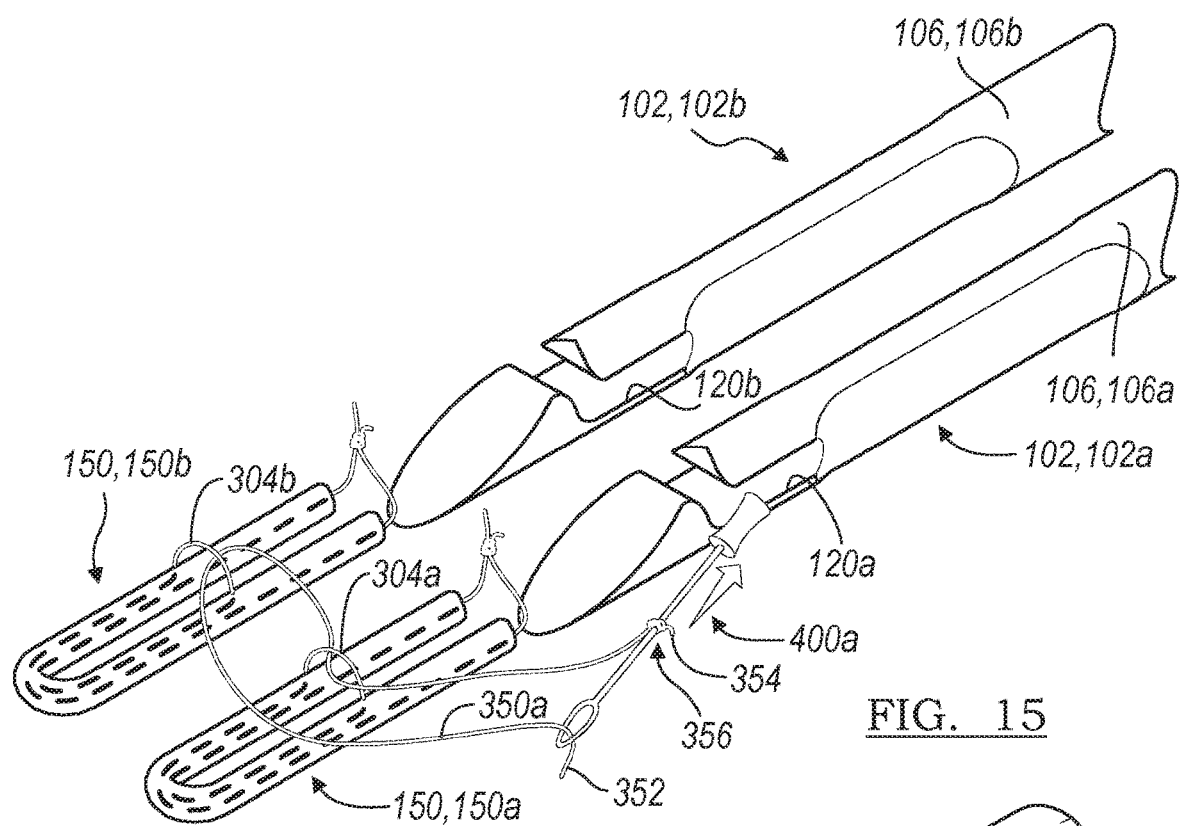
FIG. 15 is a perspective view illustrating passing a free end of flexible strand connecting first and second anchors through a slip knot according to the present teachings.
Figure 16:
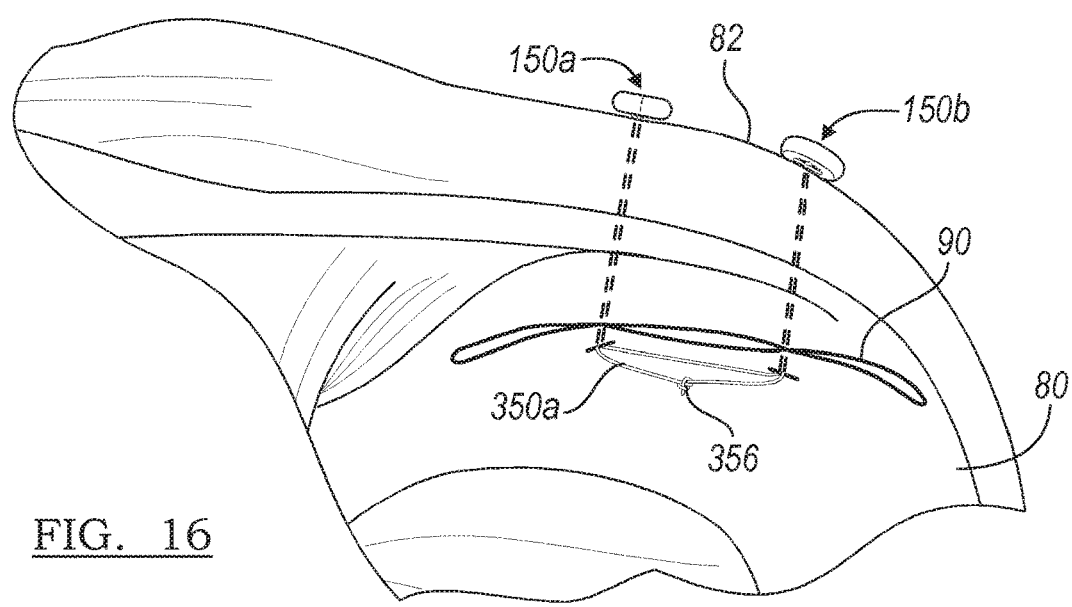
FIG. 16 is an environmental view illustrating a soft tissue defect repair with two anchors according to the present teachings.

Referring to FIG. 15, the first strand 350a can be captured by the first threader 400a, and the free end 352 can be passed through the slip knot 356. The free end 352 of the first strand 350a can be tensioned, thereby deforming each of the anchors 150a, 150b to a substantially flat round-like or knurled shape that can lie substantially flat on the second side 82 of the soft tissue, and compressing the defect 90. Any excess portion of the first strand 350a can be cut off, as shown in FIG. 16. It will be appreciated that more than two anchors 150 can be deployed using a corresponding number of inserters 102. The additional anchors 150 can be connected with the first strand 350a after the second anchor 150b is deployed in the manner described above. Alternatively, additional anchors 150 can be connected independently of the first and second anchors 150a, 150b, either in pairs or singly.

Figure 15A:
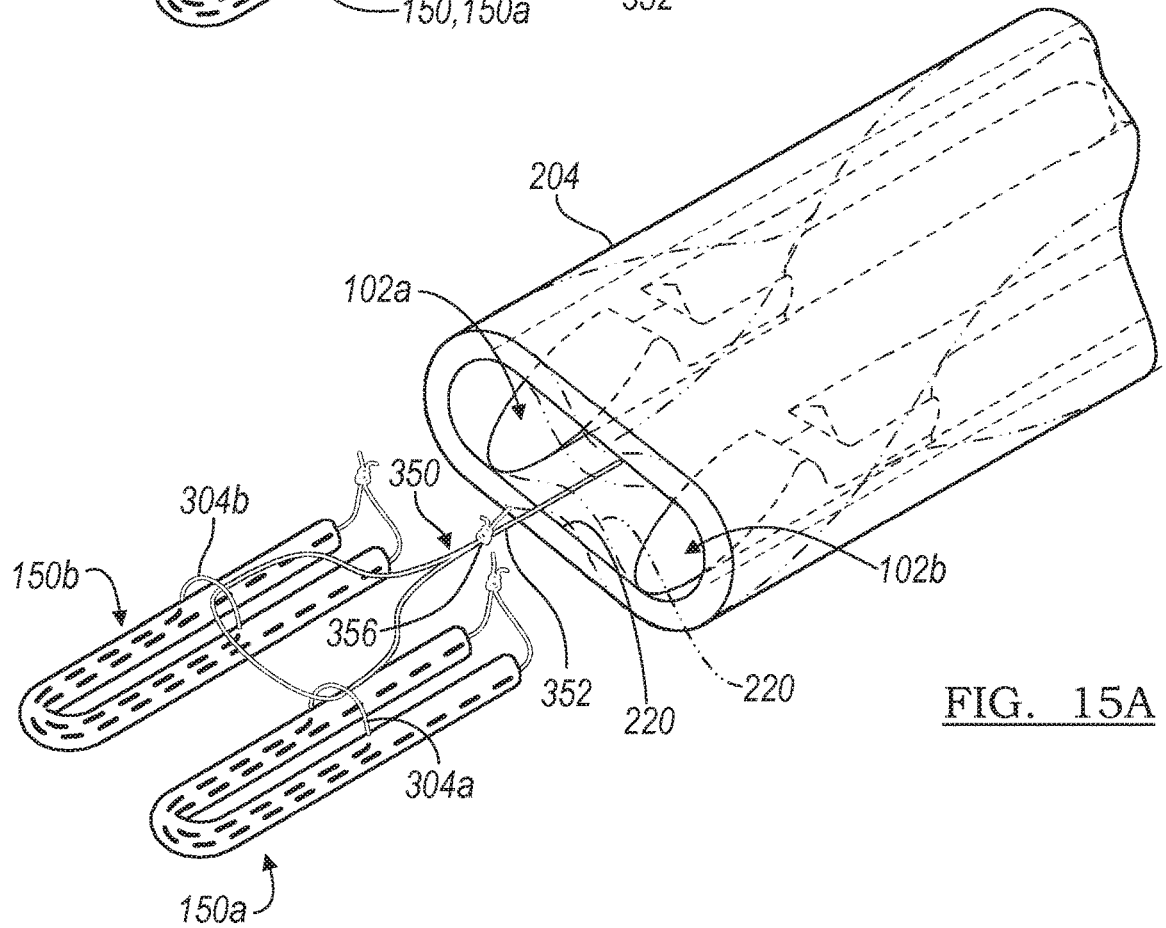
FIG. 15A is a perspective view illustrating first and second anchors connected by a flexible strand according to the present teachings.
Figure 15B:
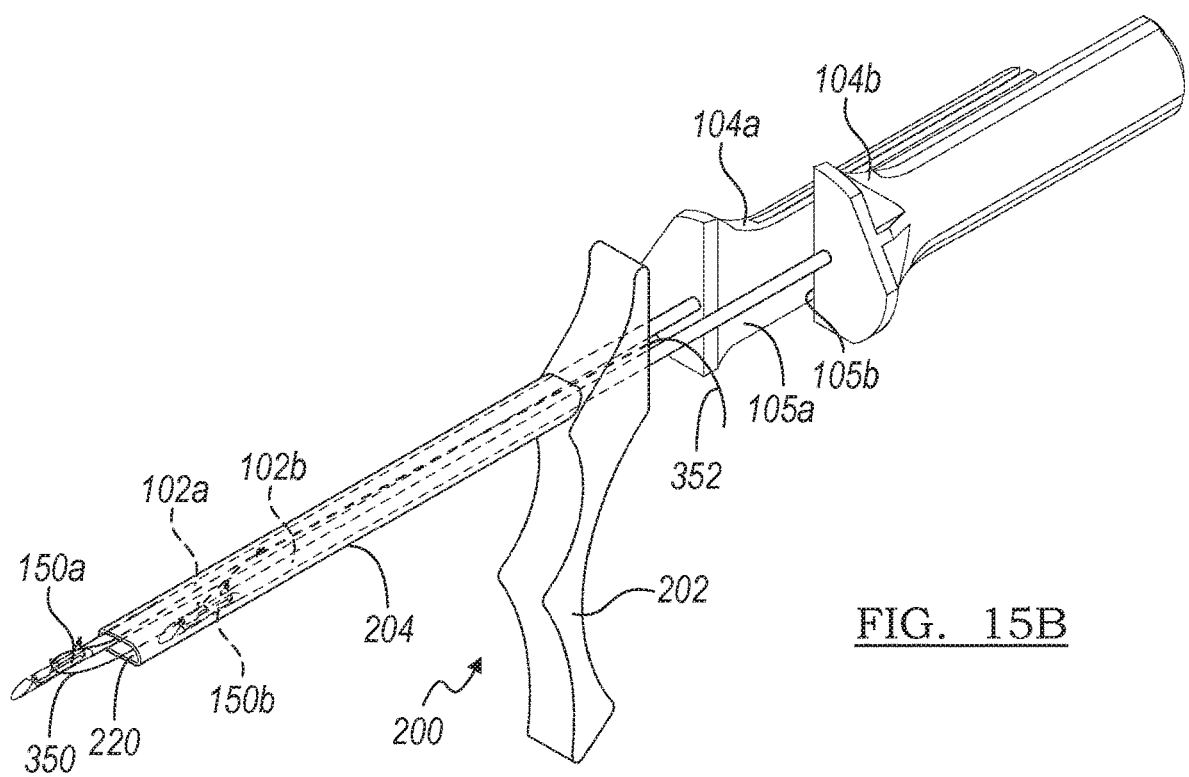
FIG. 15B is a perspective view of a soft tissue repair device according to the present teachings.

Referring to FIGS. 15A and 15B, the flexible strand 350 can be pre-loaded on the first and second anchors 150, 150b, with the free end 352 passing through the slip knot 356, as shown. The first and second anchors 150a, 150b can be deployed as described above using the first and second inserters 102a, 102b with the interconnected anchors 150a, 150b assembled thereon. The bore 220 of the hollow shaft 204 of the cannula 200 can have an elongated shape, or an eight-like shape shown in phantom lines in FIG. 15A, for receiving both the first and second inserters 102a, 102b sequentially or simultaneously. The handles 104a, 104b of the first and second inserters 102a, 102b can have corresponding flat surfaces 105a, 105b, facing one another and slidable relative to one another, such that each of the first and second inserters 102a, 102b can be independently inserted into or retracted from the cannula bore 220 without interference or obstruction from the other.

Alternative loop arrangements for coupling and deforming flexible anchors 150a, 150b are discussed below in reference with FIGS. 33-38.

Figure 18:
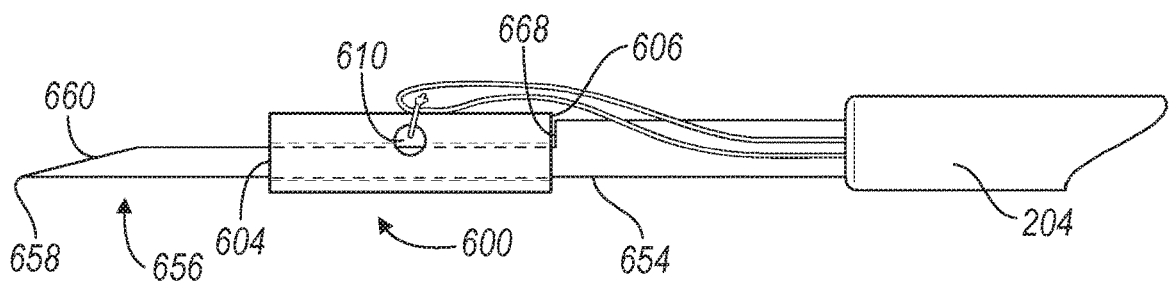
FIG. 18 is an enlarged side view of the device of FIG. 17.
Figure 19:
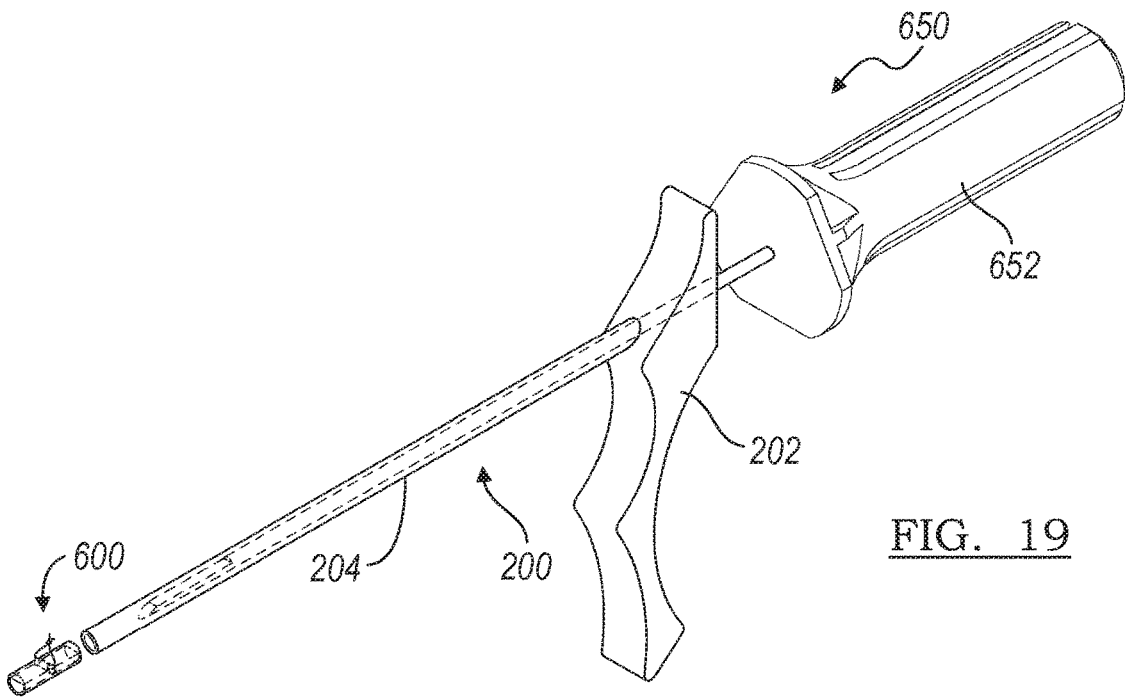
FIG. 19 is an exploded view of FIG. 17.
Figure 20:
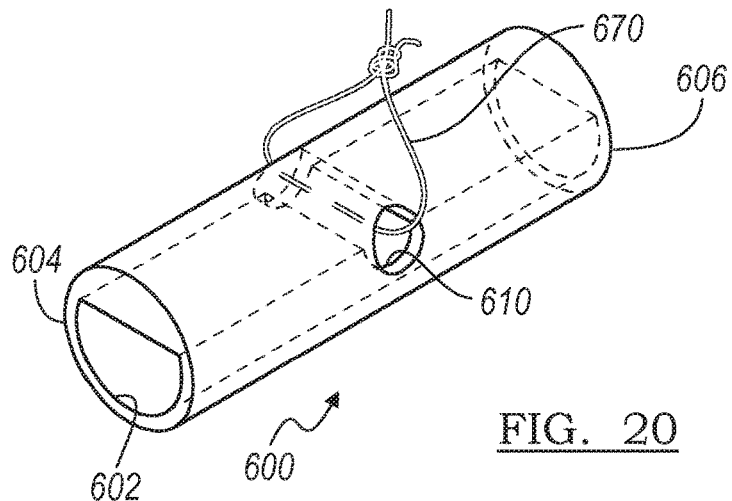
FIG. 20 is a perspective view of an anchor according to the present teachings.

Referring to FIGS. 17-26, a similar procedure can be used to repair a defect 90 in soft tissue 80 using a non-deformable or substantially rigid anchor 600. The anchor 600 can be made of any biocompatible material, such as, for example, titanium or other non-resorbable or resorbable material, including polymeric materials and Lactosorb® commercially available from Biomet, Inc., Warsaw, Ind. Referring to FIG. 20, the anchor 600 can be tubular defining a longitudinal bore 602 that extends between first and second ends 604, 606 of the anchor 600. The longitudinal bore 602 can be substantially D-shaped. The ends 604, 606 of the anchor 600 have blunt rounded edges substantially perpendicular to the anchor 600, such that the ends 604, 606 are not capable and not intended for piercing or penetrating tissue. The anchor 600 can further define a transverse bore 610 oriented at an angle to the longitudinal bore 602, such as, for example, 90-degrees or other suitable angle relative to the longitudinal bore 602. A flexible strand loop 620 can be passed through the transverse bore 610.

Alternative non-deformable anchors and loop arrangements are discussed below in reference with FIGS. 39A-41.

Figure 17:
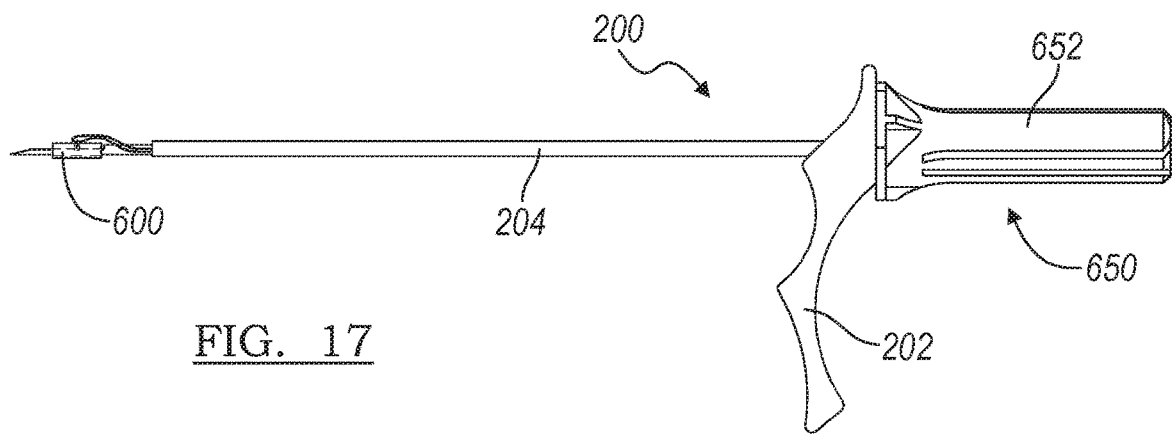
FIG. 17 is side view of a tissue repair device according to the present teachings.

Referring to FIG. 17-19, the anchor 600 can be inserted in tissue using an inserter 650 similar to the inserter 102 shown in FIG. 1A, but configured to be coupled with the anchor 600. The inserter 650 can be used with the cannula 200, as described above. The inserter 650 can include a handle 652, and a solid shaft 654 having a solid distal portion 656. The distal portion 656 can terminate at a sharp edge 658 defined by a slanted surface 660. The distal portion 656 can include a buttress or stop 668 on which the second end 606 of the anchor 600 can abut, as shown in FIG. 18. The distal portion 656 that extends between the slanted surface 660 and the buttress 668 can have a D-shaped cross-section configured to be received in the D-shaped longitudinal bore 602 of the anchor 600 in a keyed manner that does not permit relative rotation between the anchor 600 and the shaft 654.

The inserter 650 and anchor 600 can be used for fibrous tissue repair as described above in reference to FIGS. 10-16. In one exemplary procedure, illustrated in FIGS. 21-23, first and second disposable inserters 650a and 650b independently pre-assembled with first and second anchors 600a, 600b, respectively, can be used. Each anchor 600a, 600b can include a corresponding strand loop 670a, 670b passing through each transverse bore 610a, 610b. A first flexible strand 680 having a first or free end 682 and a second end 684 can be passed through the first strand loop 670a and coupled with a slip knot 686 to a first threader 400a. Similarly, a second flexible strand 680b coupled to a second threader 400b can pass through the second strand loop 670b.

Figure 27:
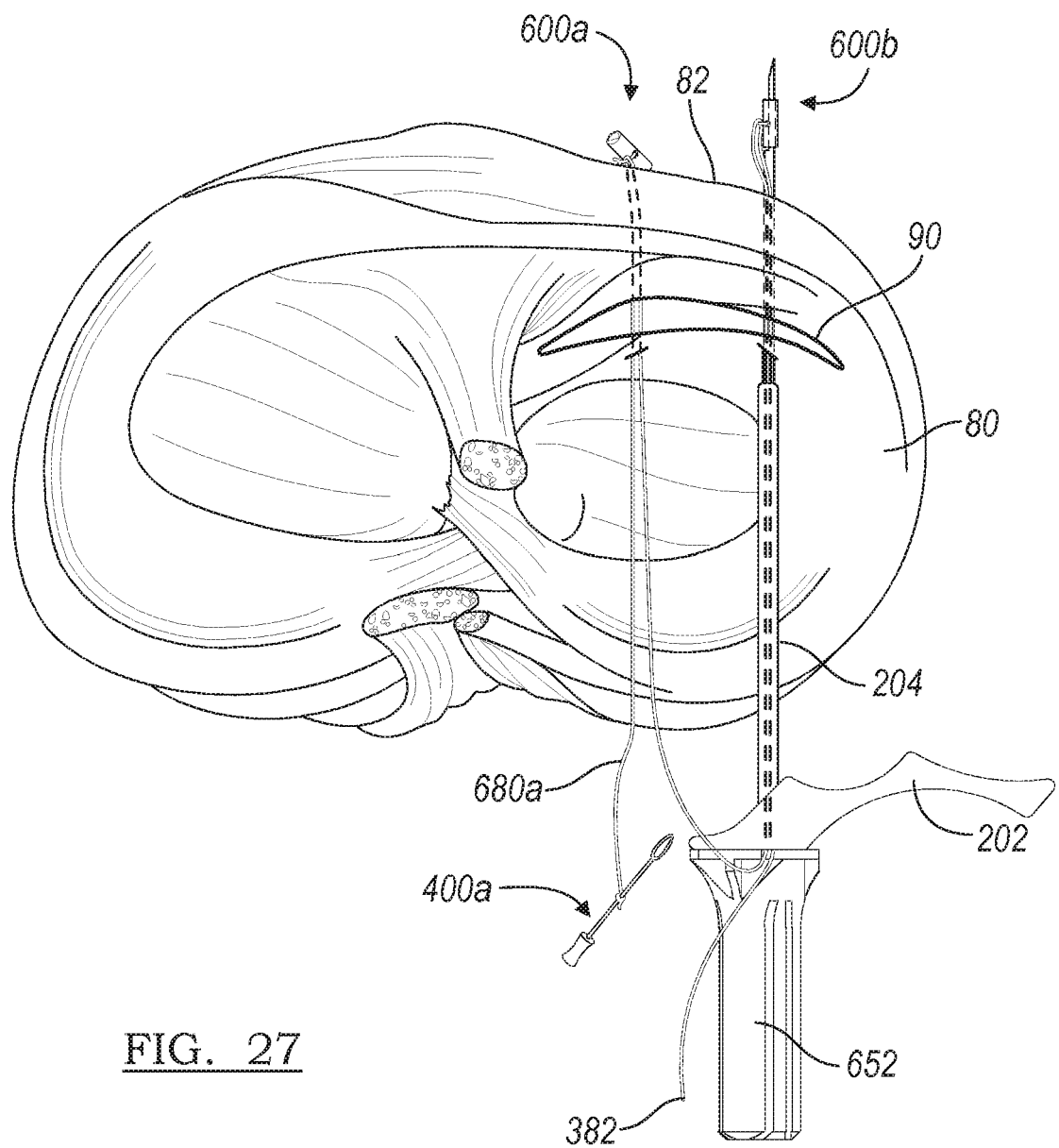
FIG. 27 is an environmental view illustrating delivering a second anchor on an outer surface of soft tissue according to the present teachings.

The first inserter 650a can be passed through the cannula 200 into the soft tissue 80 from a first side of the defect 90 until the shaft 654a of the first inserter 650a can exit the second side 82 of the fibrous soft tissue 80, such that upon retraction of the first shaft 654a, the first anchor 650a can be pulled off the first shaft 654a by the closing tissue and remain on the second side 82 of the soft tissue 80 at a first location, as shown in FIG. 27. The first inserter 650a can then be removed and discarded.

Figure 22:
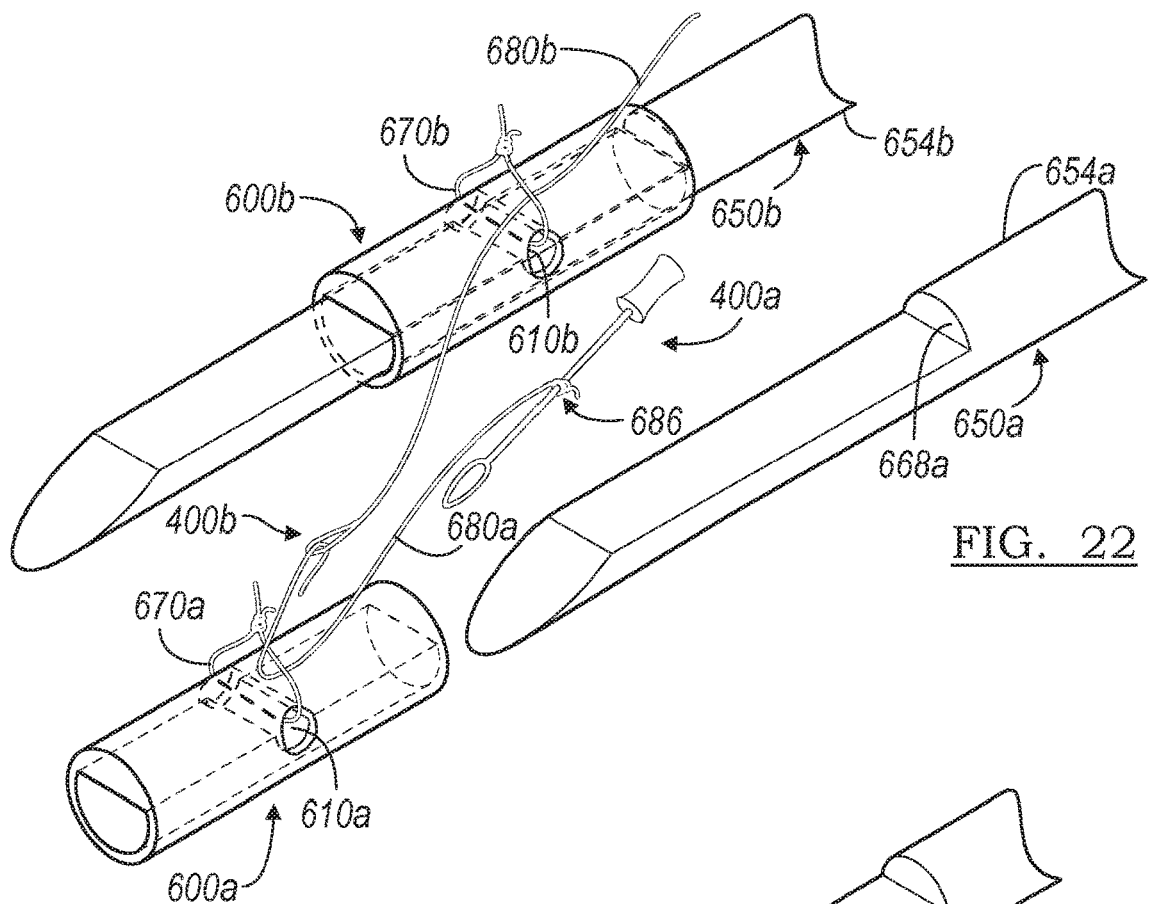
FIG. 22 is a perspective view illustrating connecting a flexible strand between first and second anchors according to the present teachings.

The first strand 680a can be captured intra-operatively by the second threader 400b and passed through the second strand loop 670b of the second anchor 600b which is pre-loaded on the second inserter 650b, as shown in FIG. 22. The second inserter 650b can be inserted through the cannula 200 and the second anchor 600b can be delivered to the second side 82 of the soft tissue 80 at a second location, as shown in FIG. 27. The second inserter 650b can be removed and discarded.

Figure 23:
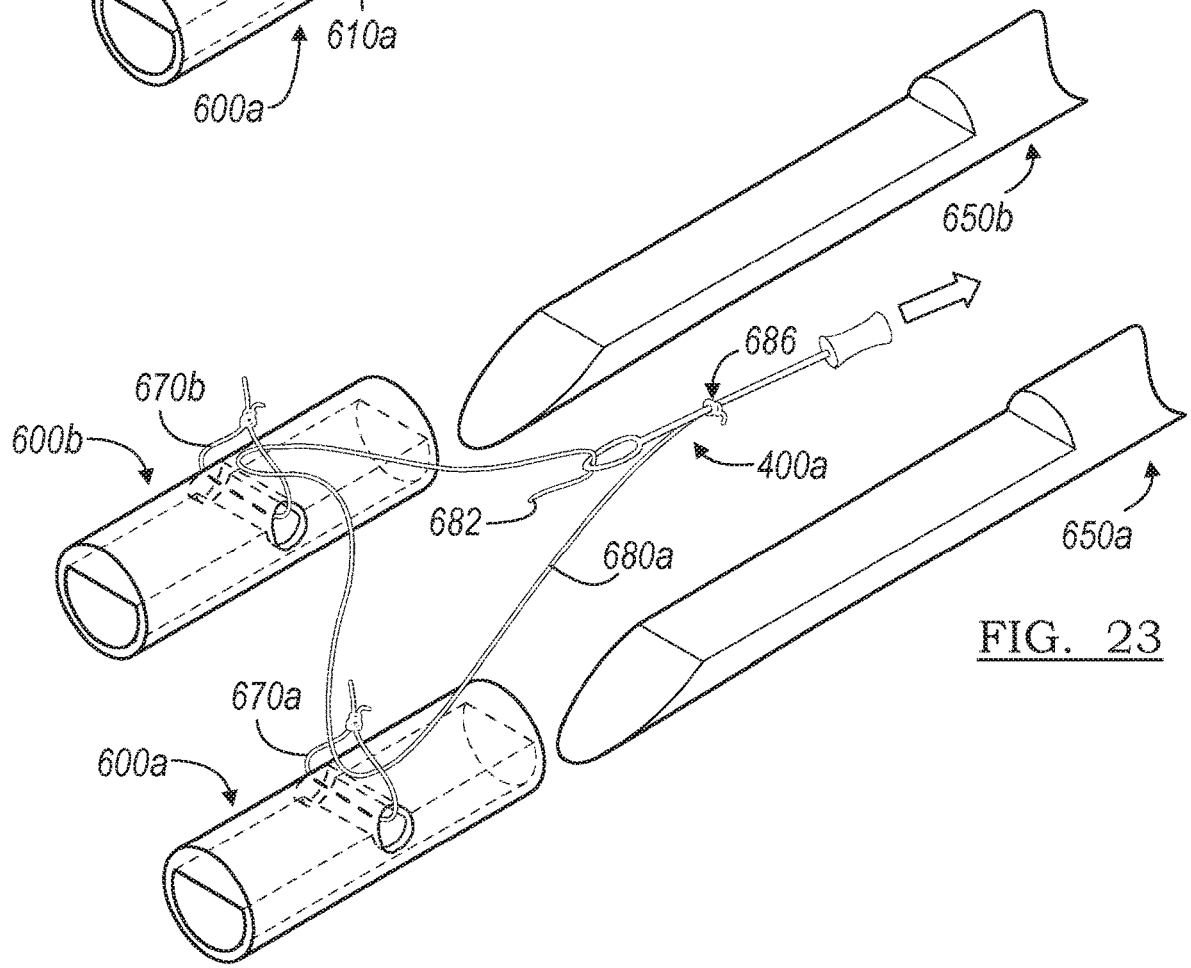
FIG. 23 is a perspective view illustrating passing a free end of flexible strand connecting first and second anchors through a slip knot according to the present teachings.

Referring to FIG. 23, the first strand 680a can be captured by the first threader 400a and the free end 682 can be passed through the slip knot 686. The free end 682 of the first strand 680a can be tensioned, thereby rotating the anchors 600a, 600b such that each anchor 60a, 600b is positioned with its longitudinal axis parallel to the surface of the second side 82 of the soft tissue 80. Tensioning the first strand 680a further can compress the defect 90. Any excess portion of the first strand 680a can be cut off, as shown in FIG. 27.

Figure 21:
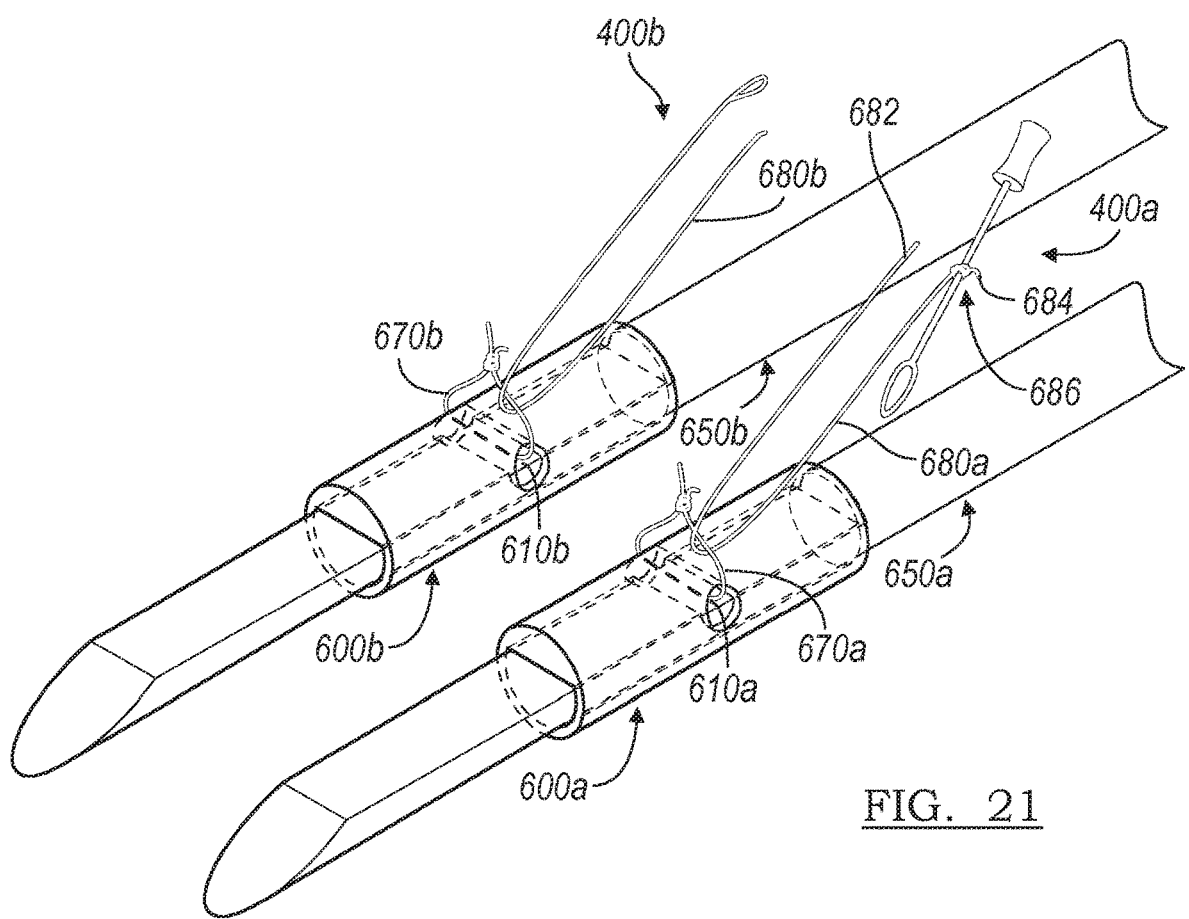
FIG. 21 is a perspective view of two pre-loaded inserters according to the present teachings.
Figure 24:
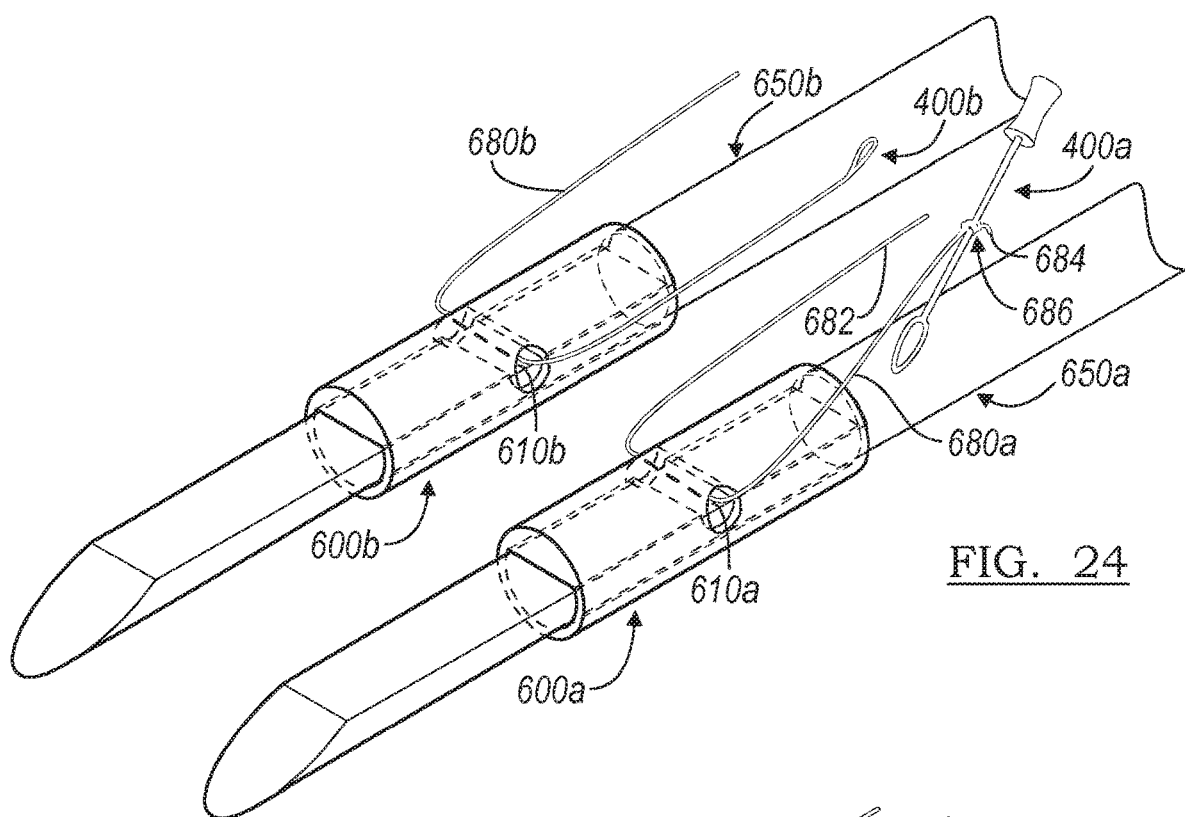
FIG. 24 is a perspective view of two pre-loaded inserters according to the present teachings.
Figure 25:
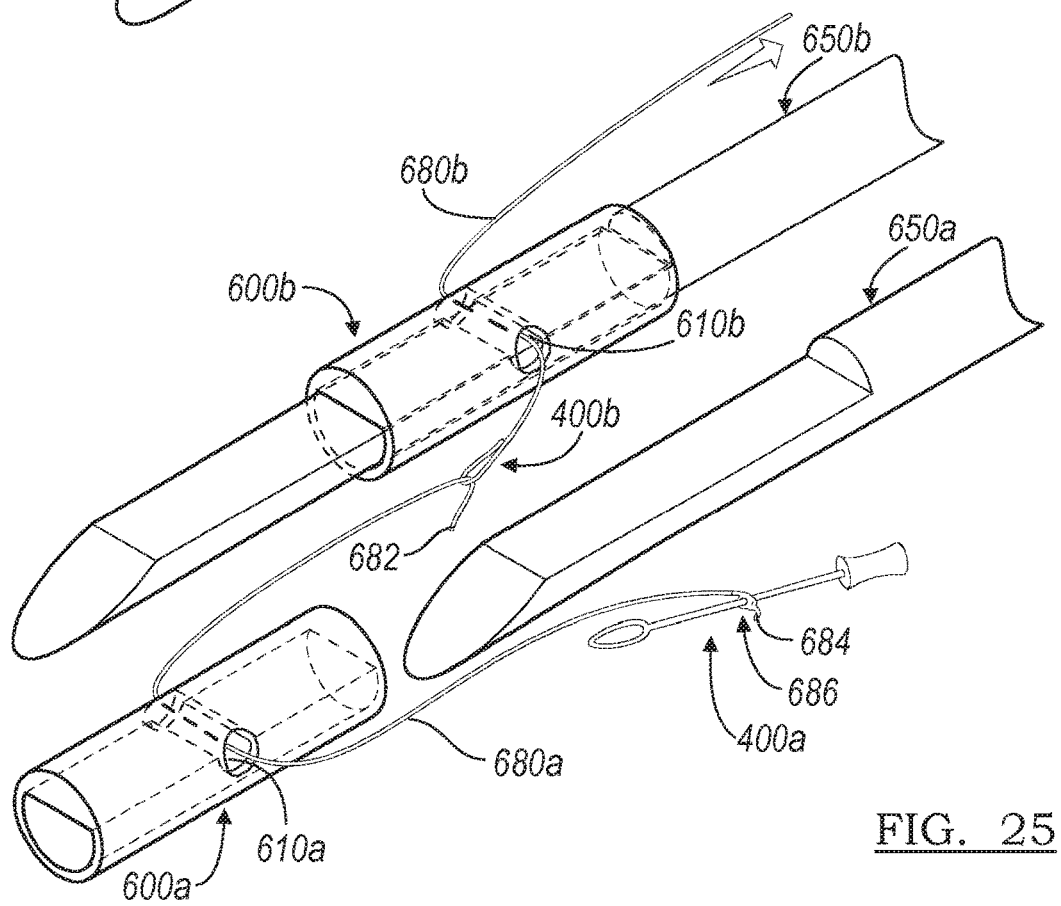
FIG. 25 is a perspective view illustrating connecting a flexible strand between first and second anchors according to the present teachings.
Figure 26:
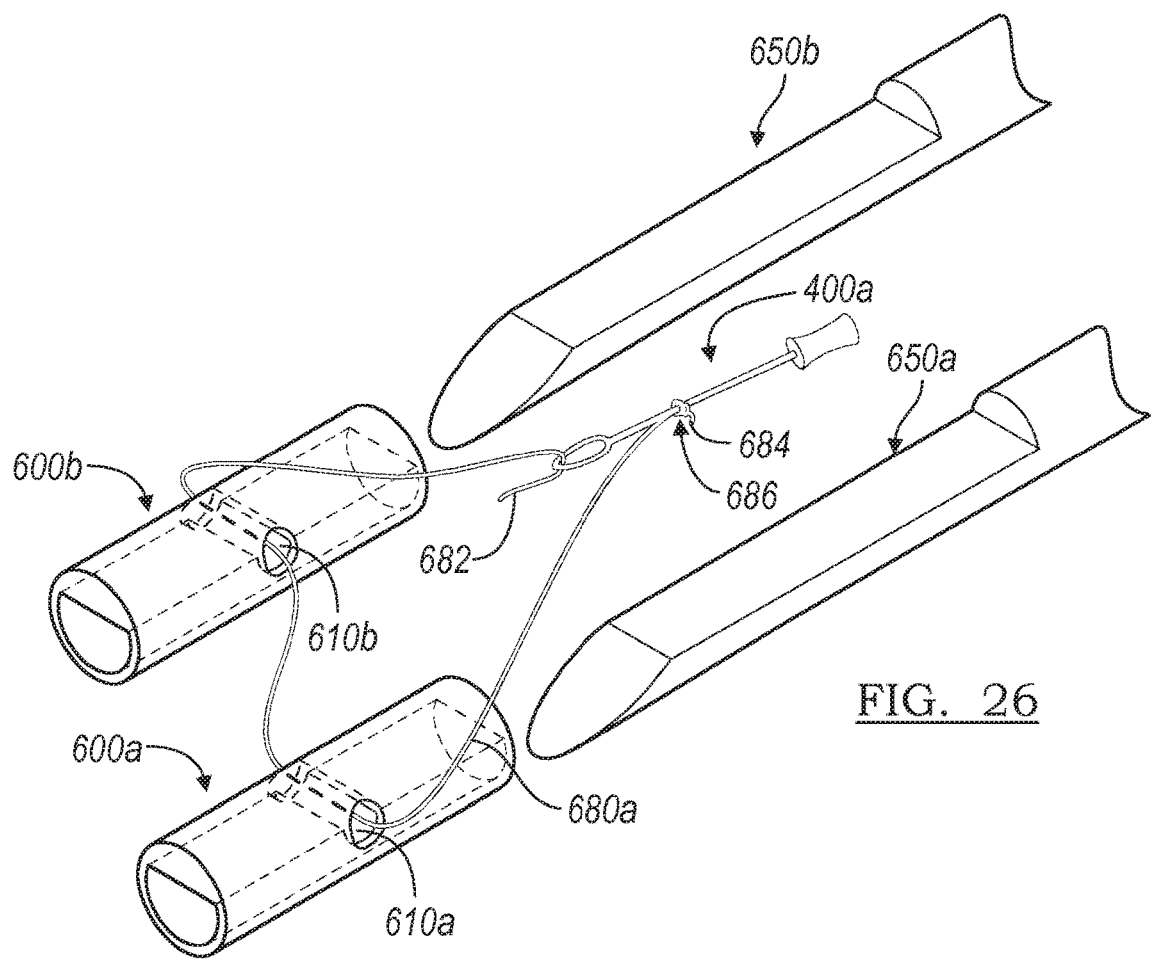
FIG. 26 is a perspective view illustrating passing a free end of flexible strand connecting first and second anchors through a slip knot according to the present teachings.
Figure 28A:
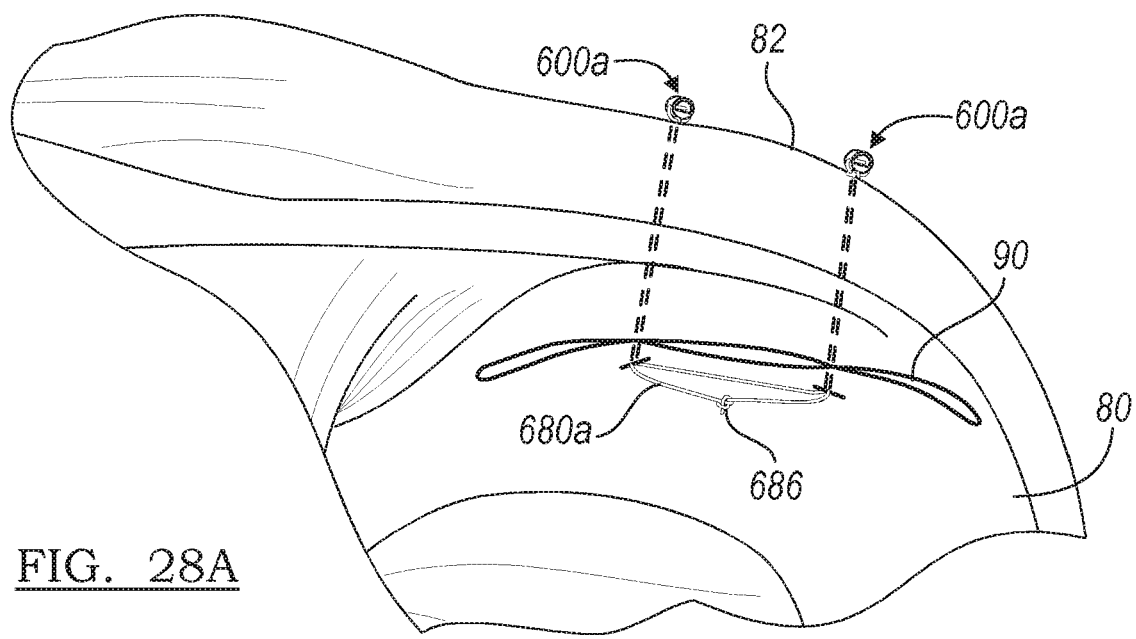
FIGS. 28A and 28B are environmental views illustrating a soft tissue defect repair with two anchors according to the present teachings.
Figure 28B:
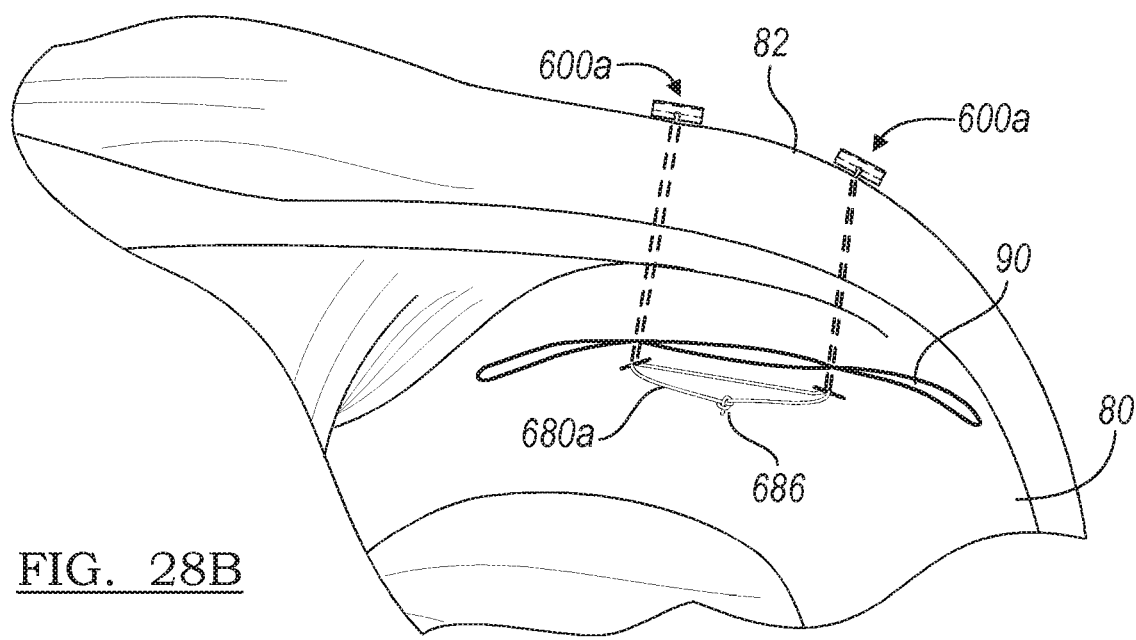

Referring to FIGS. 24-26, an alternative intra-operative strand connection for the first and second anchors 600a, 600b is illustrated in which strand loops such as loops 670a, 670b shown in FIGS. 21-23 are not used. Rather, the first inserter 650a can be assembled with the first strand 680a passing through the transverse bore 610a of the first anchor 600a and coupled to the first threader 600a, as shown in FIG. 24. Similarly, the second inserter 650b can be also assembled with the second strand 680b passing through the transverse bore 610b of the second anchor 600b and coupled to the second threader 400b. After the first anchor 600a is implanted on the second side 82 of the soft tissue 80 and the first inserter 650a is removed and discarded, the first strand 680a can be pulled by the second threader 400b through the transverse bore 610b of the second anchor 600b, as shown in FIG. 25. After the second anchor 600b is also implanted and the second inserter 650b removed and discarded, the free end 682 of the first strand 680a can be captured by the first threader 400a and passed through the slip knot 686, as shown in FIG. 26. The first strand 680 is then tensioned to reduce the defect 90, as described above and shown in FIGS. 28A and 28B.

Figure 26A:
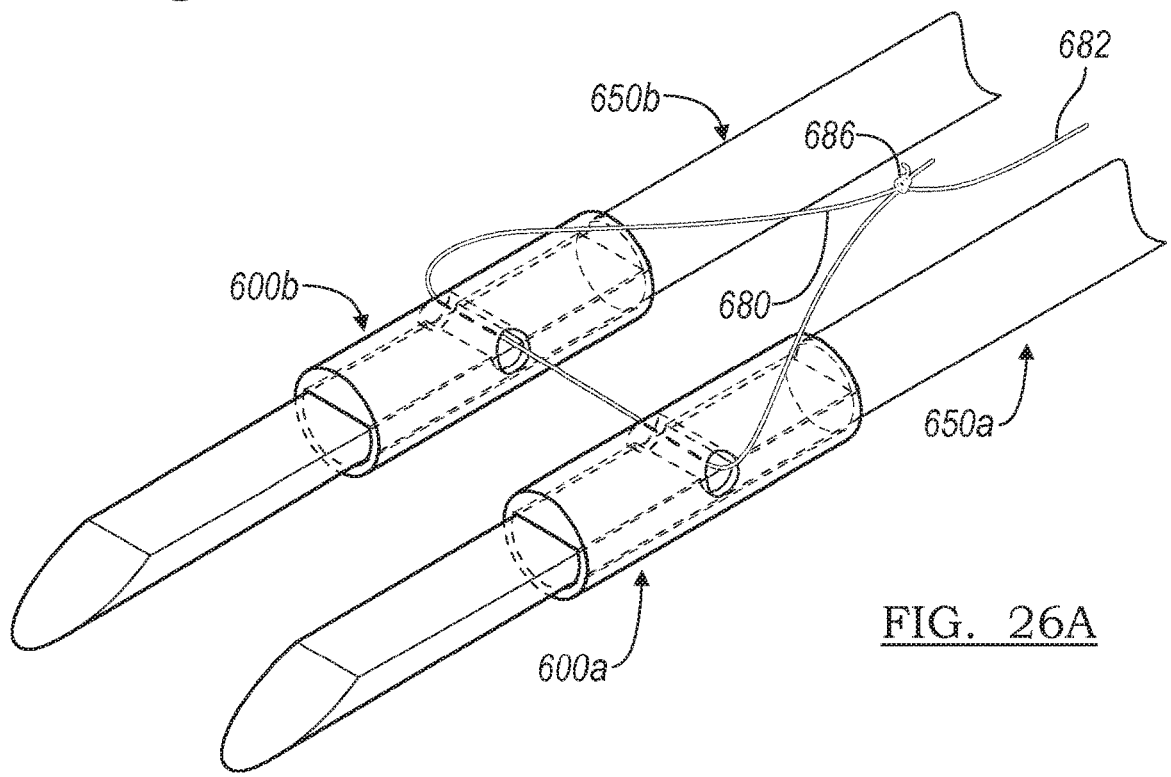
FIG. 26A is a perspective view illustrating first and second anchors connected by a flexible strand according to the present teachings.
Figure 26B:
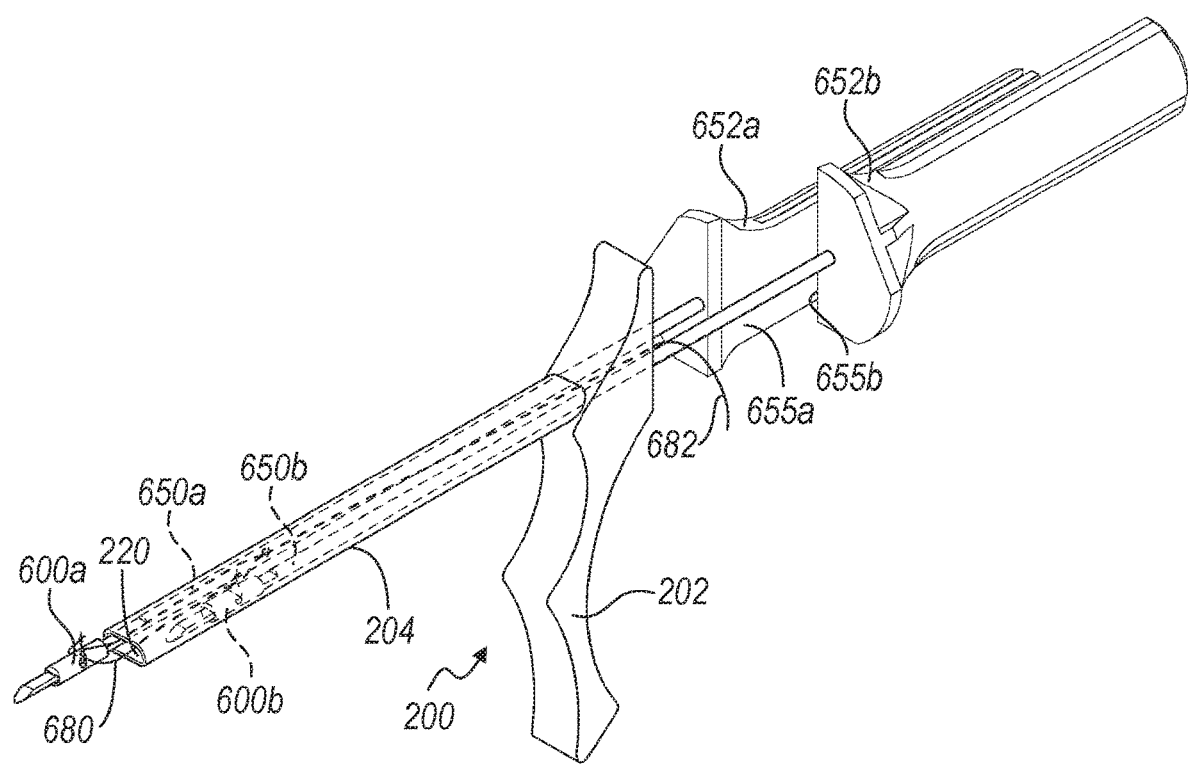
FIG. 26B is a perspective view of a soft tissue repair device according to the present teachings.

Referring to FIGS. 26A and 26B, the flexible strand 680 can be pre-loaded on the first and second anchors 600a, 600b with the free end 682 passing through the slip knot 686, as shown. The first and second anchors 600a, 600b, can be deployed as described above using the first and second inserters 650a, 650b with the interconnected anchors 600a, 600b assembled thereon. The bore 220 of the hollow shaft 204 of the cannula 200 can have an elongated shape, or an eight-like shape as described in connection with FIG. 15B above. The cannula 200 can be used for receiving both the first and second inserters 650a, 650b sequentially or simultaneously, as shown in FIG. 26B. The handles 652a, 652b of the first and second inserters 650a, 650b can have corresponding flat surfaces 655a, 655b, facing one another and slidable relative to one another, such that each of the first and second inserters 650a, 650b can be independently inserted into or retracted from the cannula bore 220 without interference or obstruction from the other.

Referring to FIGS. 29-32 and 37, various views of an inserter assembly 800 carrying first and second inserters 102a, 102b, such as those described above, are illustrated. The inserter assembly 800 can be optionally used with a cannula. The inserter assembly 800 can include a handle 802 and first and second sliders 804a, 804b operable for selectively and separately moving the corresponding inserters 102a, 102b, as described below. The handle 802 can be constructed from first and second handle portions 802a, 802b that are bonded or otherwise attached to one another.

Figure 29:
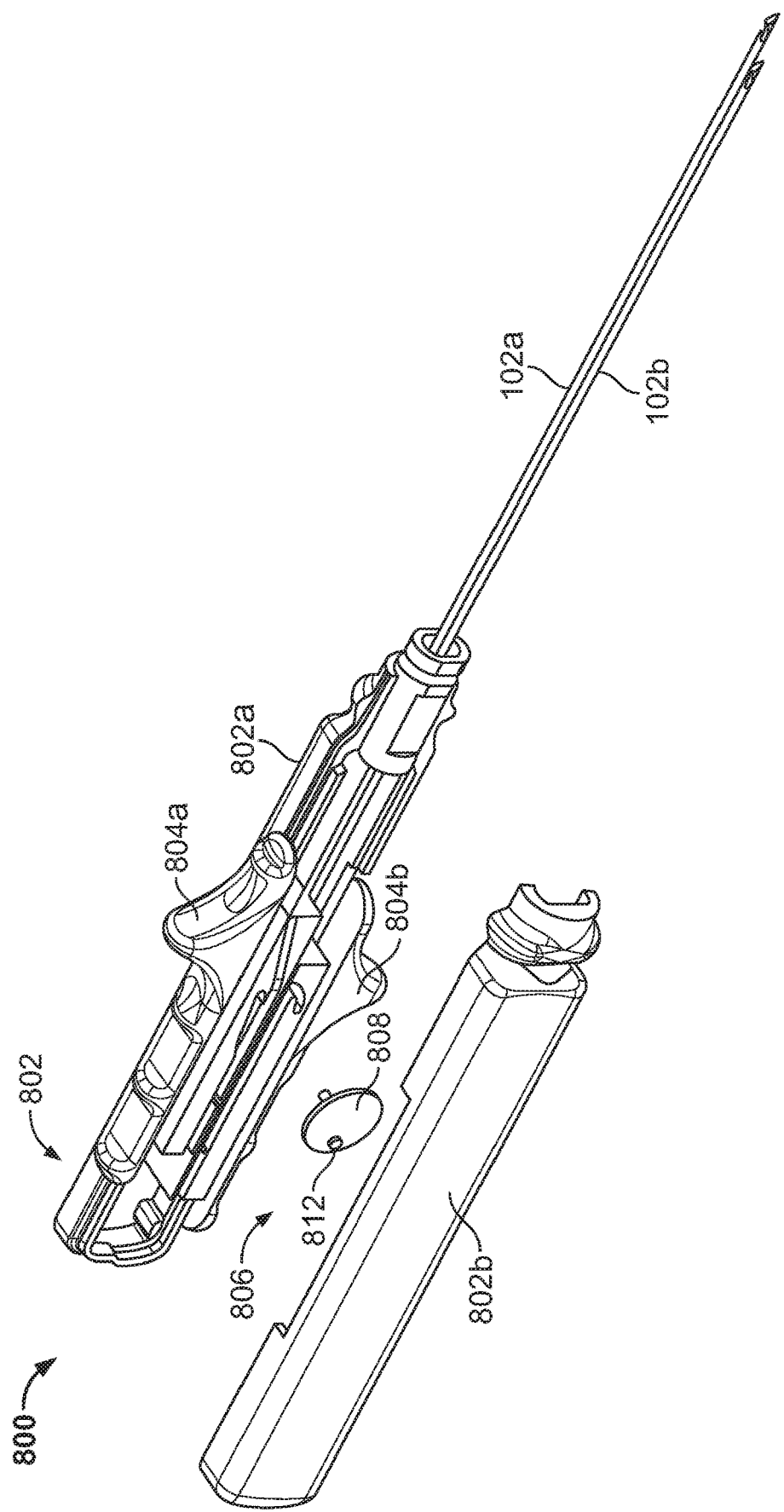
FIG. 29 is partially exploded perspective view of an inserter assembly according to the present teachings.
Figure 30:
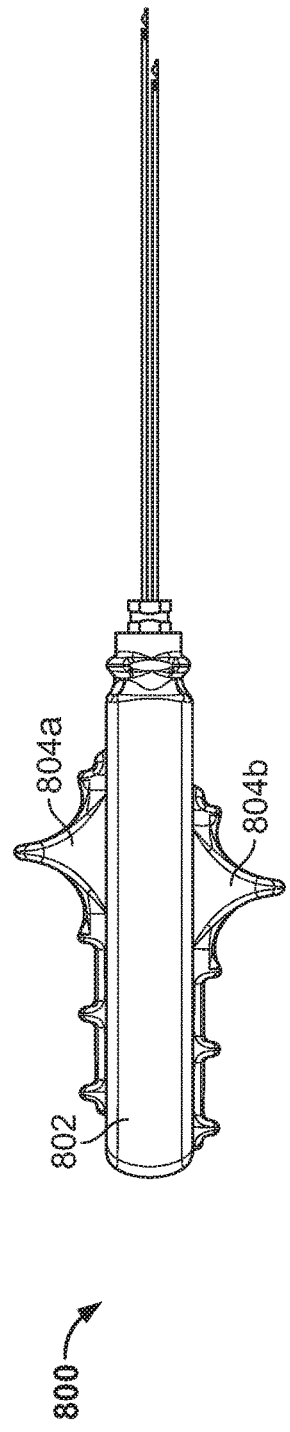
FIG. 30 is a plan view of the inserter assembly of FIG. 29.
Figure 31:
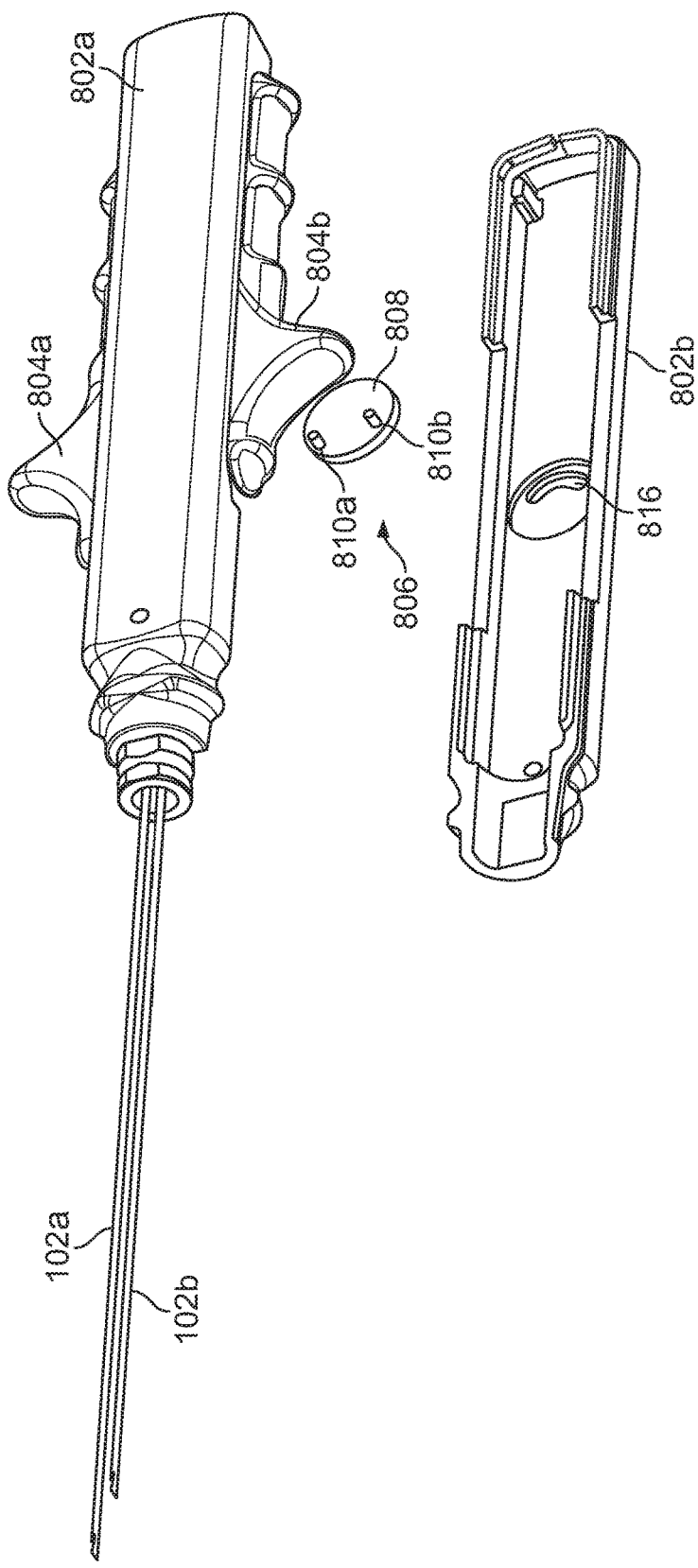
FIG. 31 is another partially exploded view of the inserter assembly of FIG. 29.
Figure 32:
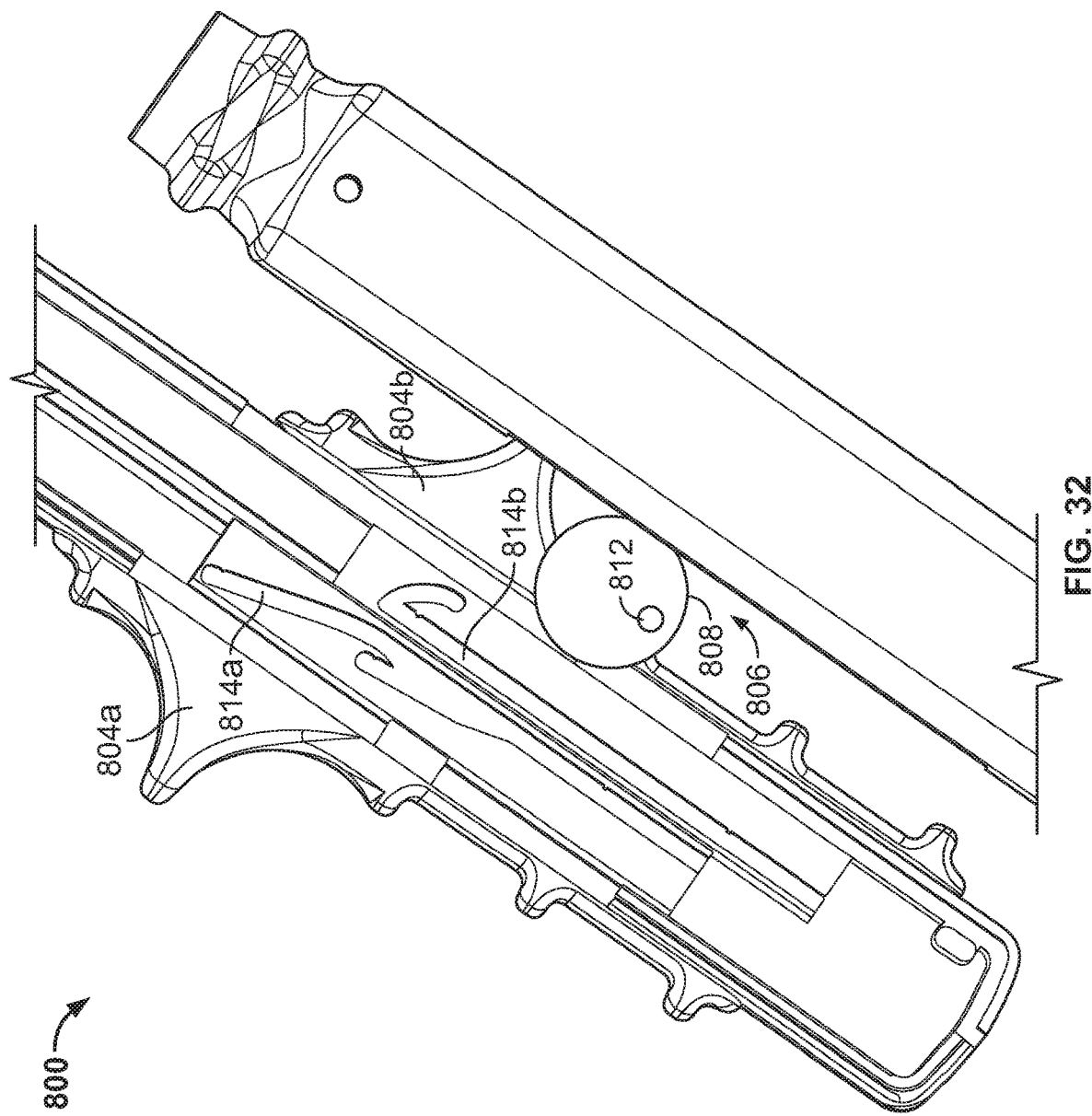
FIG. 32 is a detail of a partially exploded view of the inserter assembly of FIG. 29.
Figure 33:
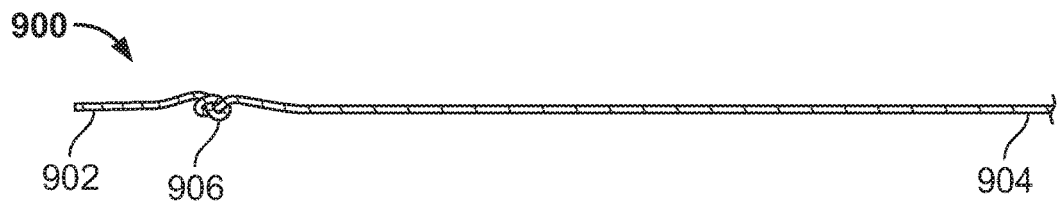
FIGS. 33, 34, 35 and 36 are sequential views illustrating an exemplary method of coupling first and second flexible anchors with a flexible strand.

In one aspect, the inserter assembly 800 can also include a slider control mechanism 806 between the first and second handle portions 802a, 802b. The slider control mechanism 806 can be coupled to the first and second sliders 804a, 805b and is operable to prioritize the separate deployment of the first and second flexible anchors 150a, 150b, which are loaded on the respective first and second inserters 102a, 102b. The slider control mechanism 806 can include a pivotable disc 808 having first and second posts or pins 810a, 810b on a first side and a third post or pin 812 on a second side opposite the first side, as shown in FIGS. 29, 31, and 32. The first and second posts 810a, 810b can move along respective first and second curved tracks 814a, 814b, respectively associated with the first and second sliders 804a, 804b. The third post 812 can move along an associated third curved track or groove 816 defined on an inner surface of the second handle portion 802b.

In one aspect, by the cooperation of the first and second tracks 804a, 804b, and the disc 808, the slider control mechanism 806 can enable a forward or deployment motion of the first inserter 102a, before enabling a retraction motion of the first inserter 102a and a subsequent forward or deployment motion of the second inserter 102b. The preferential deployment of the first inserter 102a ensures that the first anchor 150a will be deployed before the second anchor 150b, although the first and second flexible anchors 150a, 150b are substantially identical. The second anchor 150b is the anchor associated with the adjustment portion 908 and from which the free second end 904 of the flexible strand 900 exits. As discussed above, each anchor 150a, 150b can be sleeve-like having first and second ends 152, 154 and a longitudinal bore 158 extending between the first and second ends 152, 154. See also FIG. 38.

Figure 34:
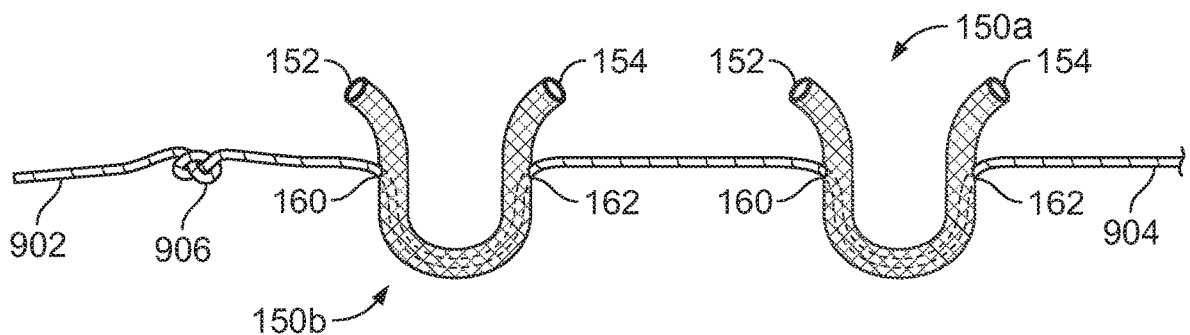

Referring to FIGS. 33-38, another aspect of coupling the flexible anchors 150a, 150b with a flexible strand 900 is illustrated. The flexible strand 900 can have first and second ends 902, 904 and can be made of materials similar to those discussed above in reference to the flexible strand 301. The flexible strand 900 can be braided in a tubular or hollow form such that it forms an internal passage 901 along the first and second ends 902, 904. A small knot or other retaining device 906 can be optionally formed adjacent the first end 902. It will be appreciated that the knot 906 can be entirely omitted. The flexible strand 900 can be passed through a first opening 160 of each flexible anchor 150a, 150b, guided along the bore 158 and exit through a second opening 162 of each flexible anchor 150a, 150b, as shown in FIG. 34. The openings 160, 162 can be positioned between the first and second ends 152, 154 of each flexible anchor 150a, 150b, at a distance of, for example one-quarter length from the ends 152, 154. Furthermore, it will be appreciated that the openings 160, 162 can be voids in the woven fabric of the flexible anchors 150a, 150b, such that the openings 160, 162 do not disrupt or break the weave of flexible anchors 150a, 150b, when the flexible anchors 150a, 150b are made of braided or woven material.

Figure 35:
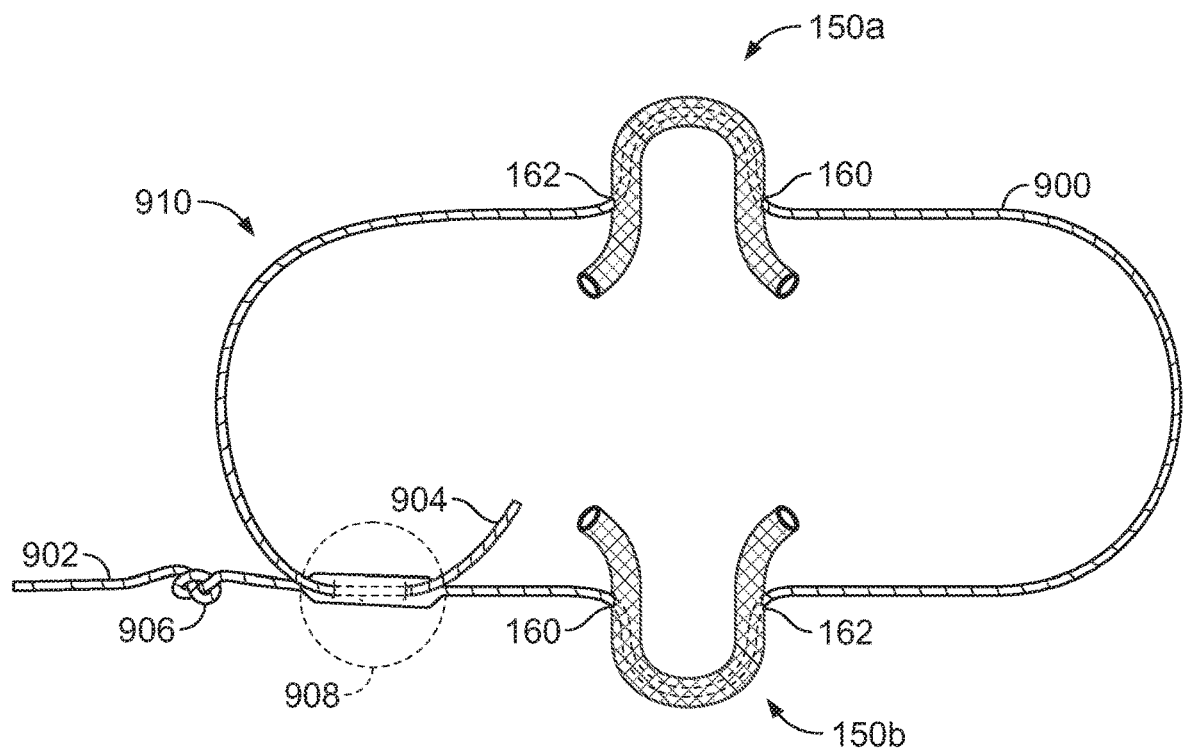
Figure 35A:
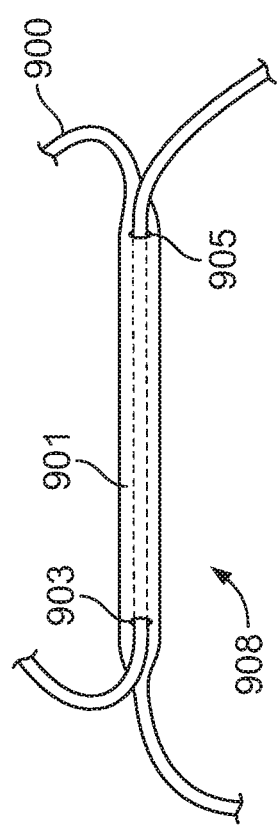
FIG. 35A shows a detail of FIG. 35.
Figure 36:
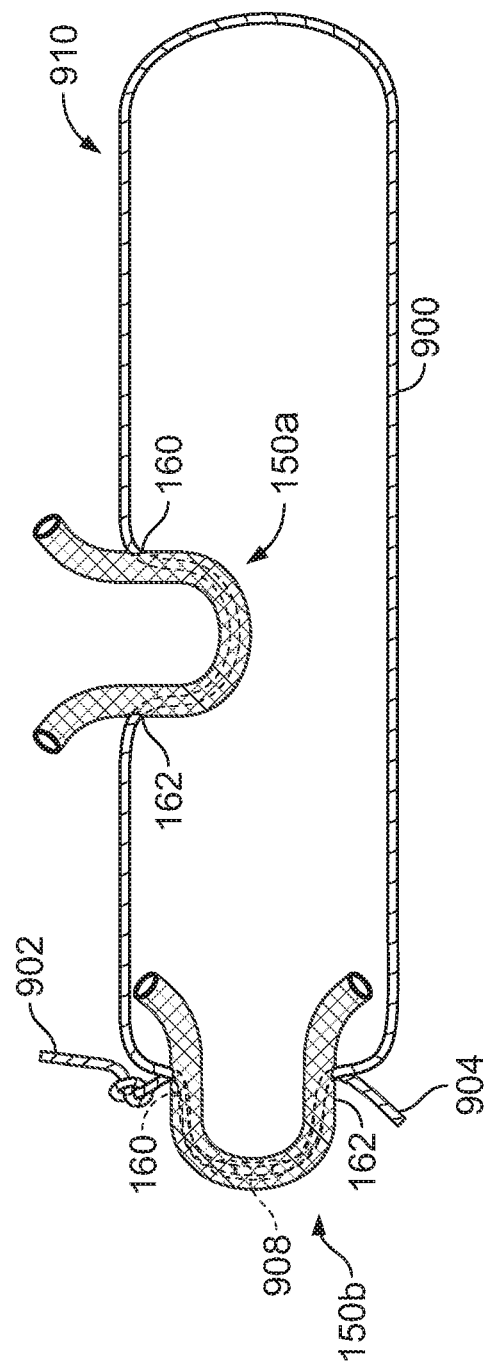

After the flexible anchors 150a, 150b are mounted on the flexible strand 900, the second end 904 of the flexible strand 900 can be passed into the internal passage 901 of the flexible strand 900 at an aperture 903, guided longitudinally along the passage 901, and guided out of the flexible strand 900 at an aperture 905. The portion of the flexible strand 900 between apertures 901 and 905 can form an adjustment portion 908 between the knot 906 and the opening 162 of the second flexible anchor 150b, such that the flexible strand 900 defines a single adjustable knotless loop 910, as shown in FIGS. 35 and 35A. The second flexible anchor 150b can be slidably moved along the flexible strand 900 until the adjustment position 908 is within the bore 158 of the second flexible anchor 150b and the knot 906 is adjacent the opening 160 second flexible anchor 150b, as shown in FIG. 36. It will be appreciated, however, that the adjustment portion 908 can remain in the position shown in FIG. 35. The adjustable knotless loop 910 is self-locking and does not require the surgeon to tie a knot during the surgical procedure for securing the flexible strand 900. Further, once the adjustable knotless loop 910 is self-locked by pulling the second end 904 of the flexible strand 900 and tensioning the flexible strand 900, friction prevents the adjustable knotless loop 910 from being loosened, thereby providing a secure lock. Additional details regarding forming the knotless adjustable loop 910 and other adjustable knotless loop configurations are disclosed in co-pending and commonly assigned U.S. patent application Ser. No. 11/541,506, filed on Sep. 29, 2006, the disclosure of which is incorporated herein by reference.

Figure 37:
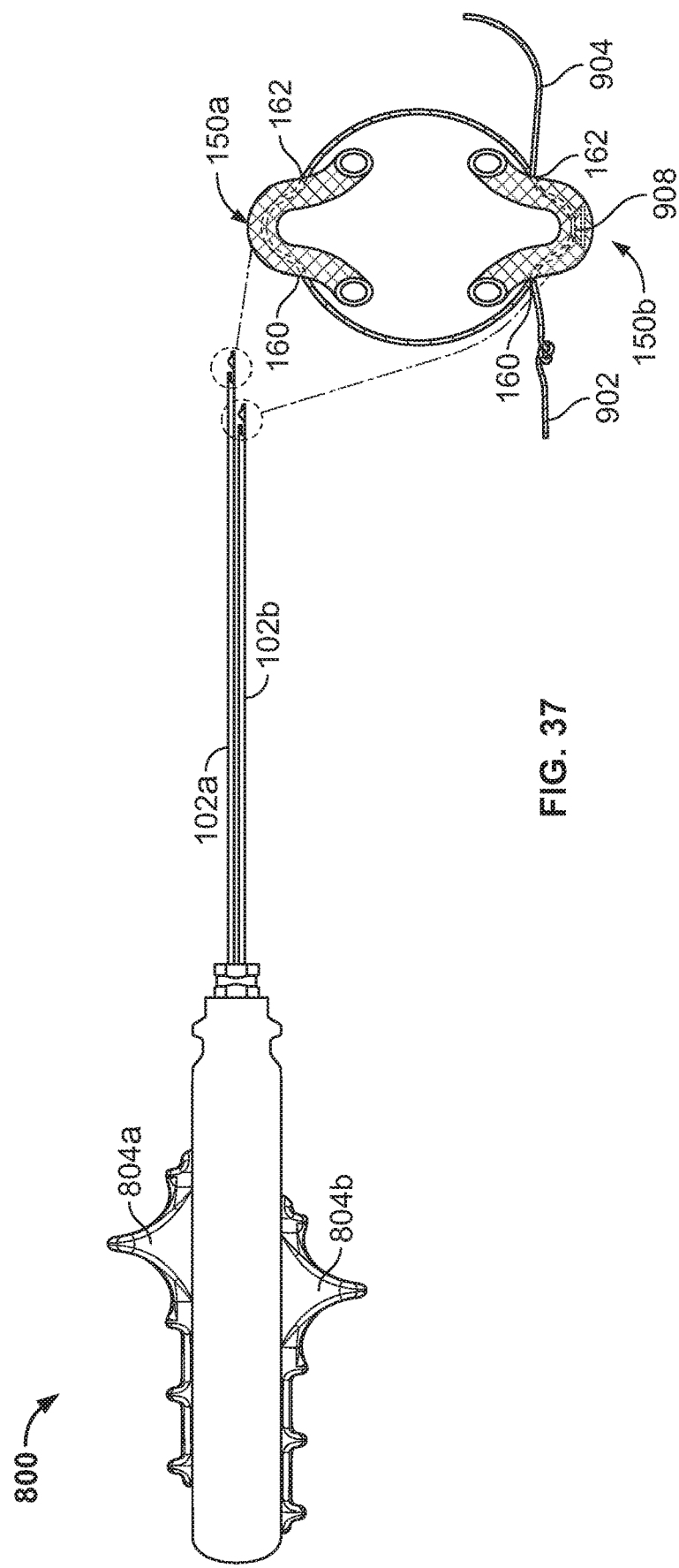
FIG. 37 is a view illustrating loading first and second flexible anchors on the inserter assembly of FIG. 29.
Figure 39A:
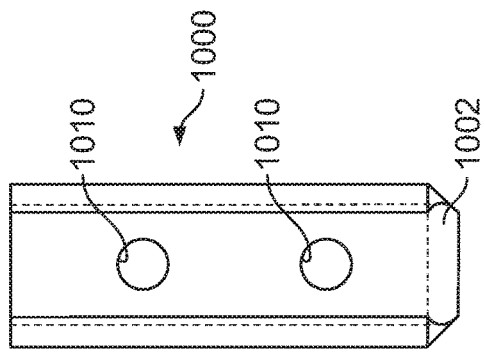
FIG. 39A is a bottom view of an anchor according to the present teachings.
Figure 39B:
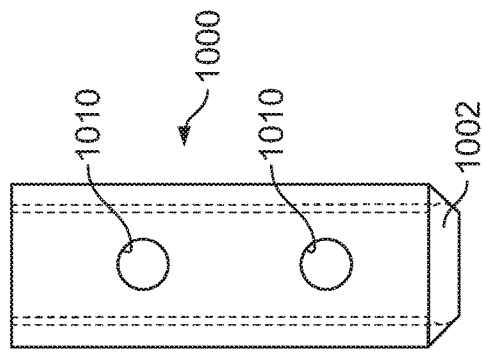
FIG. 39B is a top view of the anchor of FIG. 39A.
Figure 38:
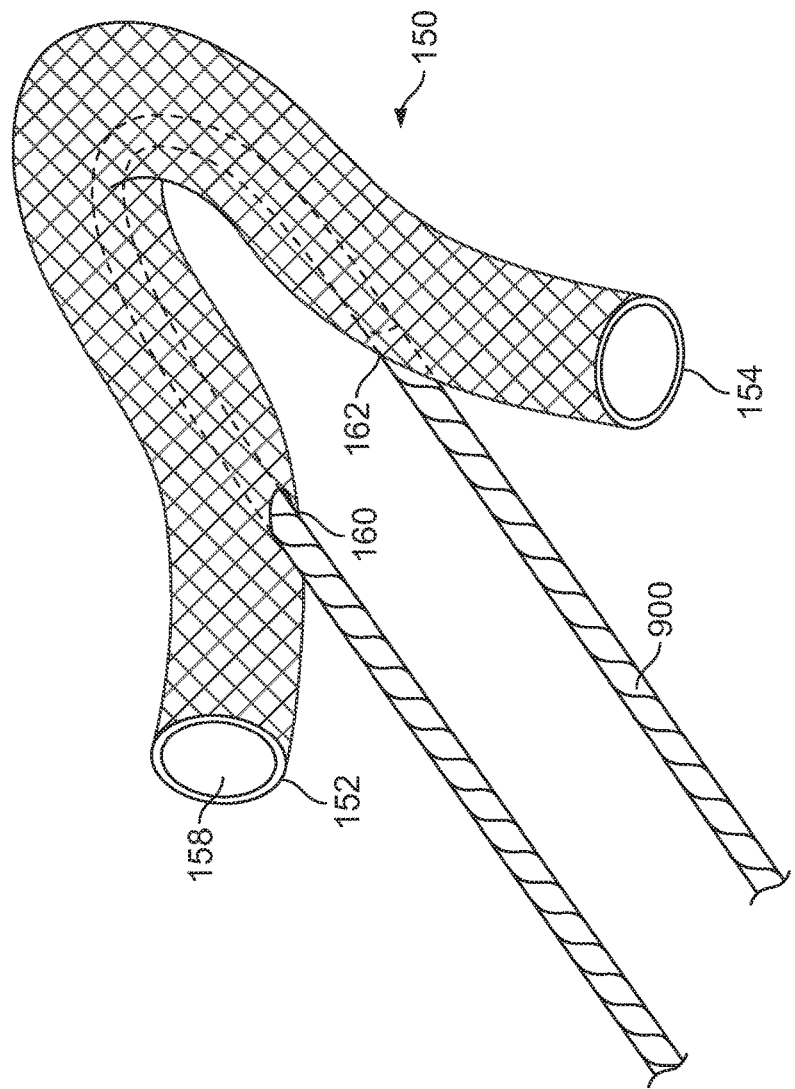
FIG. 38 is a perspective view of a flexible anchor coupled with a flexible strand.

The first flexible anchor 150a can be loaded on the first inserter 102a, and second flexible anchor 150b can be loaded on the second inserter 102b, as shown in FIG. 37. The first and second anchors 150a, 150b can be loaded externally on their respective inserters in the manner discussed in reference with FIG. 13, above. Specifically, each of the first and second flexible anchors 150a, 150b can be draped over the external groove 120 in the distal portion of the corresponding inserter 102a, 102b. The inserter assembly 800 can be loaded with the first and second flexible anchors 150a, 150b coupled with the flexible strand 900, which forms the closed adjustable knotless loop 910. The adjustable knotless loop 910 allows tightening the strand 900, deforming the first and second flexible anchors 150a, 150b for anchoring and shortening the length of the adjustable knotless loop 910 without using a slipknot. The inserter assembly 800 can be used for repairing soft tissue 80, such as a meniscus tear 90, in a similar manner as discussed with reference to FIG. 14. The first slider 804a can be moved forward to deploy the first flexible anchor 150a at an outer surface 82 of the soft tissue. The first slider 804a can then be moved backward, enabling the second slider 804b to be moved forward to deploy the second flexible anchor 150b at the outer surface 82 of the soft tissue, and adjacent the first flexible anchor 150a. Pulling the second end 904 of the flexible strand 900 tightens the adjustable knotless loop 910, secures the first and second flexible anchors 150a, 150b against the outer surface 82 of the soft tissue 80 and reduces the defect 90. Further, the portions of the sleeve between the first and second ends 152, 154 of each of the flexible anchors 150a, 150b and the corresponding first and second openings 160, 162, define anchoring leg portions that provide additional resistance for securing the flexible anchors 150a, 150b on the outer surface 82 of the soft tissue 80, as these leg portions are forced against the outer surface 82 for anchoring.

Figure 40:
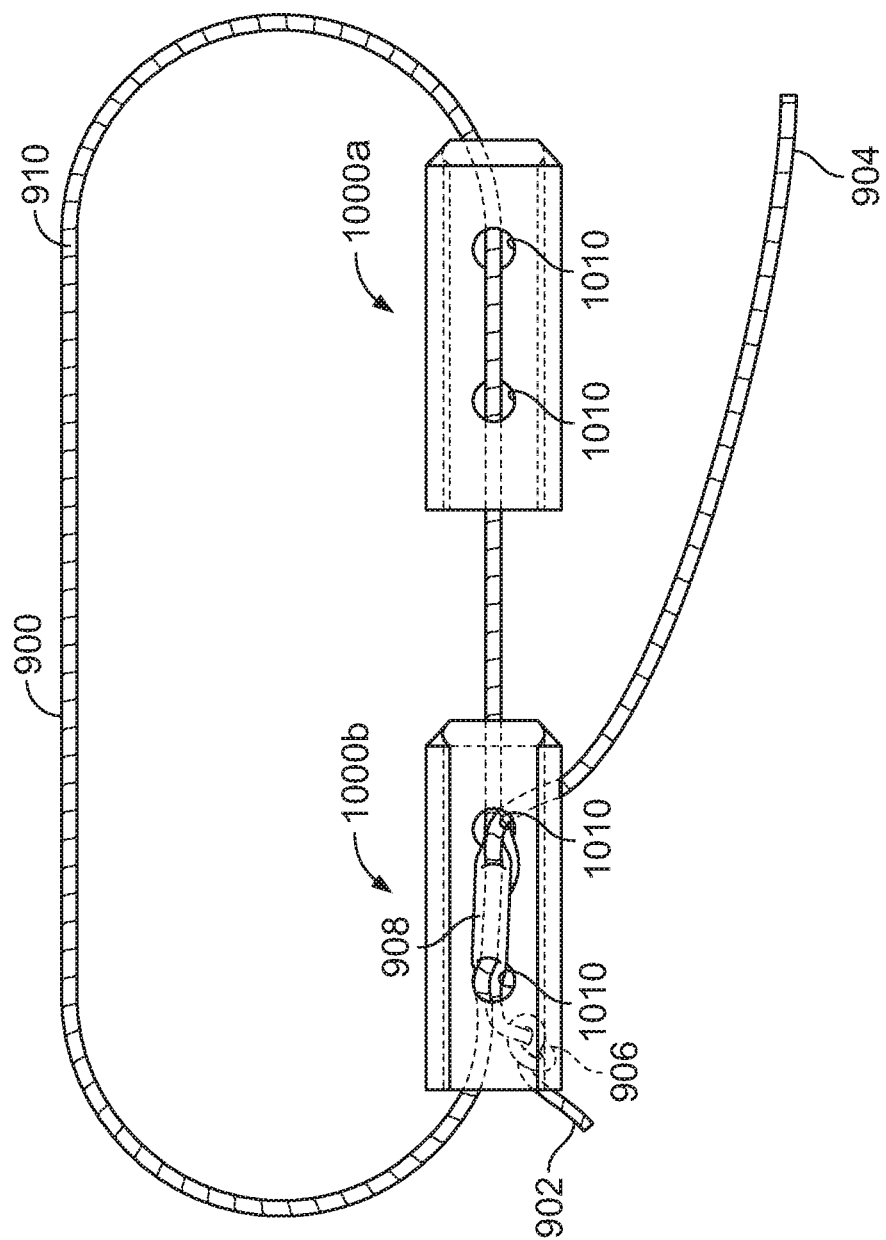
FIG. 40 is a view illustrating coupling first and second anchors with a flexible strand according to the present teachings.

Referring to FIGS. 39A-41, another non-deformable or substantially rigid anchor 1000 is illustrated. Similarly to the anchor 600 illustrated in FIG. 20, the anchor 1000 can be made of any biocompatible material, such as, for example, titanium or other non-resorbable or resorbable material, including polymeric materials and Lactosorb® commercially available from Biomet, Inc., Warsaw, Ind., and can be used in a similar manner to repair a soft tissue defect 90. The anchor 1000 can be tubular defining a longitudinal bore 1002 that extends between first and second ends 1004, 1006 of the anchor 600 and has an open, channel-like cross-section defining an arc of 180 degrees or more. The ends 1004, 1006 of the anchor 1000 have blunt rounded edges substantially perpendicular to the anchor 1000, such that the ends 1004, 1006 are not capable and not intended for piercing or penetrating tissue. The anchor 1000 can further define first and second transverse through bores 1010 oriented substantially perpendicularly to the anchor 1000. A flexible strand 900 can be passed through the transverse bores 1010 and couple first and second anchors 1000a, 1000b, as shown in FIG. 40. The strand 900 can be tightened with an adjustable knotless loop 910 by pulling on free end 904 and without the use of slipknot, as discussed above.

Figure 41:
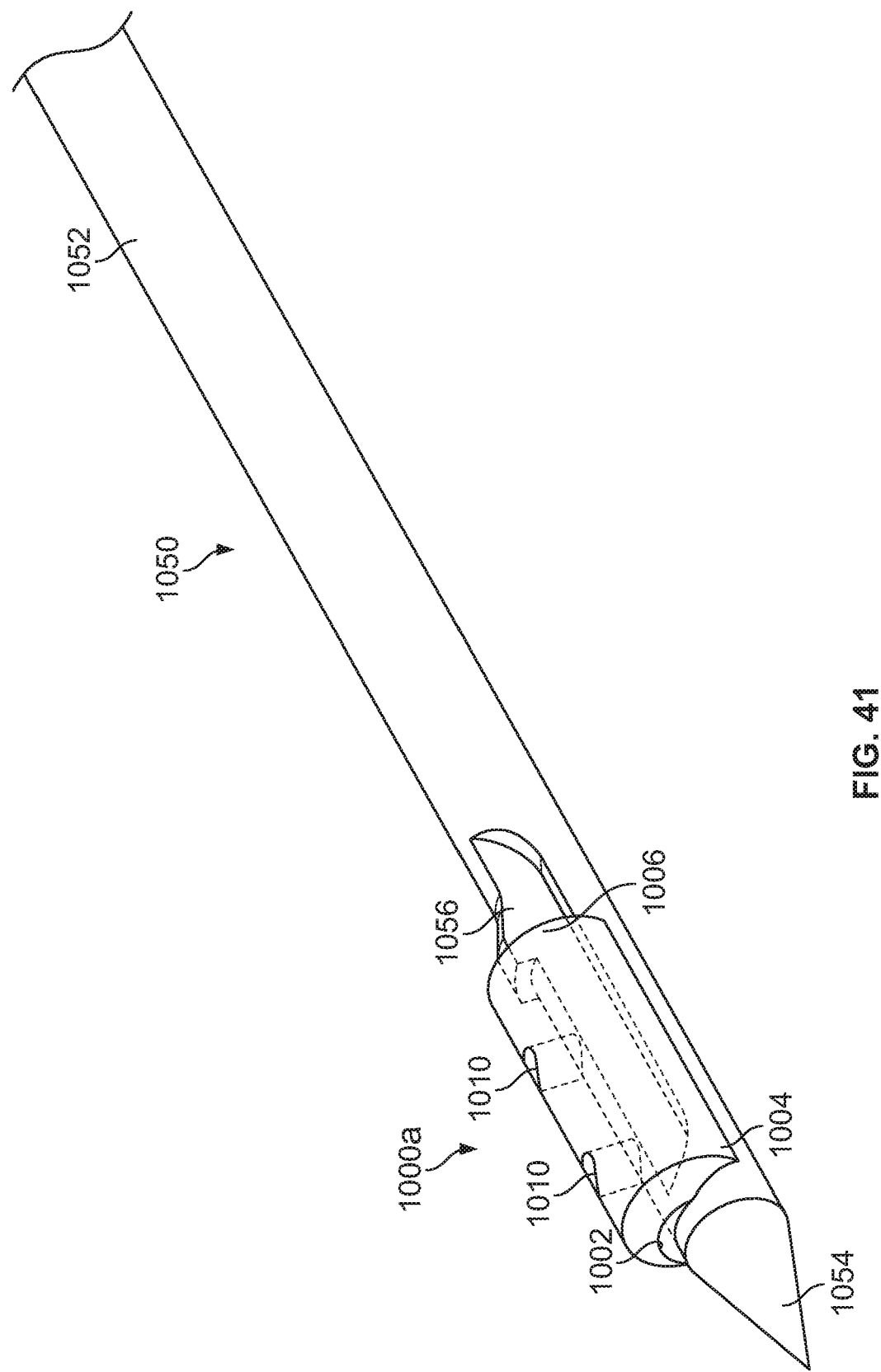
FIG. 41 is a perspective view showing an anchor loaded onto an inserter according to the present teachings.

The first and second anchors 1000a, 1000b, coupled with the flexible strand 900, can be mounted on two separate inserters, as described above in connection with anchors 600. An exemplary inserter 1050 loaded with the anchor 1000a is shown in FIG. 41. Two such inserters 1050 can be used with the inserter assembly 800 of FIG. 29, replacing the inserters 102a, 102b. Each inserter 1050 can have a cylindrical body 1052, a pointed tip 1054, and a stop 1056. The first anchor 1000a can be mounted externally onto the body 1052 of the inserter 1050 between the tip 1054 and the stop 1056, such that that a portion of the inserter 1050 is received in the longitudinal bore 1002 of the first anchor 1000a. The second anchor 1000b can be similarly mounted on another inserter 1050. Each anchor 1000a and 1000b can be optionally mounted in a keyed manner onto the corresponding inserter 1050, such that accidental relative rotation is substantially prevented.

It will be appreciated from the above description and drawings that the present teachings provide anchors of versatile configurations that can be passed through fibrous tissue easily in a compact or low profile configuration and or orientation and then positioned outside the fibrous tissue in a second orientation that provides anchoring without tissue penetration, prevents withdrawal from the tissue and reduces tissue injury. Additionally, the inserter of the present teachings does not require an active expeller or other additional pusher rod to deploy the anchor. Rather, and because the anchor is carried solely on the external surface of the inserter, the anchor is deployed passively outside fibrous tissue upon retraction of the inserter. Further, the use of a disposable or single use inserter provided with a preassembled anchor can help reduce the time length of the procedure and simplify manipulations required during the procedure.

It will be further understood that the various embodiments of the inserters, anchors and coupling arrangements can be mixed and matched or combined in ways other than those explicitly discussed above, without departing from the scope of the present teachings.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

The invention claimed is:

1. A method for repairing a tear in a meniscus, the method comprising:

deploying a first deformable tube anchor and a second deformable tube anchor at a first location and a second location, respectively, along an outer surface of a meniscus with an adjustable suture construct extending from the deployed first deformable tube anchor, through a tear in a meniscus along a first pathway, and back through the tear in the meniscus along a second pathway to the deployed second deformable tube anchor so as to connect the deployed first deformable tube anchor to the deployed second deformable tube anchor, the first deformable tube anchor providing a first longitudinal bore extending through the first deformable tube anchor, the second deformable tube anchor providing a second longitudinal bore extending through the second deformable tube anchor, wherein the adjustable suture construct includes a suture with a first free end that passes longitudinally through a longitudinal passage in the suture to form a first self-locking adjustable loop, wherein the adjustable suture construct being connected to the first deformable tube anchor and to the second deformable tube anchor includes the suture extending through at least part of the first longitudinal bore in the first deformable tube anchor and through at least part of the second longitudinal bore in the second deformable tube anchor, respectively, so that the first deformable tube anchor and the second deformable tube anchor are both received on the first self-locking adjustable loop, wherein the longitudinal passage in the suture is at least partially received in the first longitudinal bore in the first deformable tube anchor; and pulling on the first free end of the suture so as to reduce a size of the first self-locking adjustable loop.

2. The method of claim 1, wherein said pulling reduces the tear in the meniscus.

3. The method of claim 1, wherein the first free end of the suture extends into the suture through a first aperture in the suture, longitudinally within the suture along the longitudinal passage, and out of the suture through a fourth aperture in the suture to form the first self-locking adjustable loop, and wherein the first aperture and the fourth aperture in the suture are both received in the first longitudinal bore in the first deformable tube anchor.

4. The method of claim 1, wherein the first deformable tube anchor and the second deformable tube anchor are slidably received on the first self-locking adjustable loop.

5. A method for repairing a tear in a meniscus, the method comprising:

advancing a first deformable tube anchor along a first pathway through a tear in a meniscus to an outer surface of the meniscus for deployment at a first location along the outer surface of the meniscus, wherein the first deformable tube anchor provides a first longitudinal bore extending through the first deformable tube anchor, wherein, during said advancing, an adjustable suture construct connected to the first deformable tube anchor extends back through the first pathway and again through the tear in the meniscus along a second pathway to connect to a second deformable tube anchor deployed at a second location along the outer surface of the meniscus, wherein the adjustable suture construct includes a suture with a first free end that passes longitudinally through a longitudinal passage in the suture to form a first self-locking adjustable loop, wherein the adjustable suture construct being connected to the first deformable tube anchor includes the first self-locking adjustable loop extending through at least part of the first longitudinal bore in the first deformable tube anchor so that the first deformable tube anchor is received on the adjustable suture construct, wherein the longitudinal passage in the suture is at least partially received in the first longitudinal bore in the first deformable tube anchor; and pulling on the first free end of the suture so as to reduce a size of the first self-locking adjustable loop.

6. The method of claim 5, wherein said pulling reduces the tear in the meniscus.

7. The method of claim 5, wherein the first free end of the suture extends into the suture through a first aperture in the suture, longitudinally within the suture along the longitudinal passage, and out of the suture through a fourth aperture in the suture to form the first self-locking adjustable loop, and wherein the first aperture in the suture is received in the first longitudinal bore in the first deformable tube anchor.

8. The method of claim 5, wherein the first deformable tube anchor is slidably received on the first self-locking adjustable loop.

9. The method of claim 5, wherein the second deformable tube anchor provides a second longitudinal bore extending through the second deformable tube anchor, and wherein the adjustable suture construct being connected to the second deformable tube anchor includes the first self-locking adjustable loop extending through at least part of the second longitudinal bore in the second deformable tube anchor so that the second deformable tube anchor is received on the adjustable suture construct.

10. The method of claim 5, wherein the first deformable tube anchor is deformable from a first condition to a second condition, the first condition permitting said advancing of the first deformable tube anchor along the first pathway through the tear in the meniscus to the outer surface of the meniscus, the second condition having a different shape than the first condition for inhibiting movement of the first deformable tube anchor back through the meniscus for providing anchoring for the adjustable suture construct along the outer surface of the meniscus.

11. The method of claim 5, wherein the adjustable suture construct includes only a single self-locking adjustable loop which is said first self-locking adjustable loop.

12. A method for repairing a tear in a meniscus, the method comprising:

advancing a first deformable tube anchor along a first pathway through a tear in a meniscus to an outer surface of the meniscus, wherein the first deformable tube anchor provides a first longitudinal bore extending through the first deformable tube anchor, wherein, during said advancing, an adjustable suture construct connected to the first deformable tube anchor extends back through the first pathway and connects to a second deformable tube anchor that is waiting outside the tear in the meniscus for a deployment subsequent to that of the first deformable tube anchor, wherein the adjustable suture construct includes a suture with a first free end that extends into the suture through a first aperture in the suture, longitudinally within the suture along a longitudinal passage, and out of the suture through a fourth aperture in the suture to form a first self-locking adjustable loop, wherein the adjustable suture construct being connected to the first deformable tube anchor includes the first self-locking adjustable loop extending through at least part of the first longitudinal bore in the first deformable tube anchor so that the first deformable tube anchor is received on the first self-locking adjustable loop, wherein the first aperture in the suture and at least part of the longitudinal passage in the suture are received in the first longitudinal bore in the first deformable tube anchor; and deploying the first deformable tube anchor along the outer surface of the meniscus.

13. The method of claim 12 further comprising pulling on the first free end of the suture so as to reduce a size of the first self-locking adjustable loop.

14. The method of claim 13, wherein said pulling reduces the tear in the meniscus.

15. The method of claim 12, wherein the fourth aperture in the suture is also received in the first longitudinal bore in the first deformable tube anchor.

16. The method of claim 12, wherein the second deformable tube anchor provides a second longitudinal bore extending through the second deformable tube anchor, and wherein the adjustable suture construct being connected to the second deformable tube anchor includes the first self-locking adjustable loop extending through at least part of the second longitudinal bore in the second deformable tube anchor so that the second deformable tube anchor is received on the adjustable suture construct.

17. A method for repairing a tear in a meniscus, comprising:

obtaining a tissue repair assembly, comprising:
a suture;

a first deformable tube anchor received on the suture such that the suture extends a first time longitudinally through a first longitudinal bore in the first deformable tube anchor and a second time longitudinally through the first longitudinal bore in the first deformable tube anchor with a second free end of the suture remaining outside the first deformable tube anchor and extending away from a second end portion of the first deformable tube anchor, wherein the suture extending said first time and said second time longitudinally through the first longitudinal bore in the first deformable tube anchor has the suture extending longitudinally past itself in the first longitudinal bore and leaves an adjustable loop portion of the suture positioned outside the first deformable tube anchor; and a second deformable tube anchor received on the adjustable loop portion of the suture;

deploying the first deformable tube anchor and the second deformable tube anchor at a first location and a second location, respectively, along an outer surface of a meniscus with the adjustable loop portion of the suture extending from the deployed first deformable tube anchor, through a tear in a meniscus along a first pathway, and back through the tear in the meniscus along a second pathway to the deployed second definable tube anchor so as to connect the deployed first deformable tube anchor to the deployed second deformable tube anchor; and pulling on the second free end of the suture so as to reduce a size of the adjustable loop portion.

18. The method of claim 17, wherein said pulling reduces the tear in the meniscus.

19. The method of claim 17, wherein, in the tissue repair assembly, a first free end of the suture remains outside the first deformable tube anchor and extends away from a first end portion of the first deformable tube anchor.

20. The method of claim 17, wherein, in the tissue repair assembly, the adjustable loop portion includes a length of suture extending longitudinally through a second longitudinal bore in the second deformable tube anchor.

21. The method of claim 17, wherein, in the tissue repair assembly, a retaining device is located along the suture proximate a first free end of the suture.

22. The method of claim 21, wherein the retaining device comprises a knot formed in the suture.

23. The method of claim 17, wherein, in the tissue repair assembly, a first free end of the suture passes longitudinally through a longitudinal passage in the suture to form a self-locking adjustable loop that comprises the adjustable loop portion.

24. The method of claim 23, wherein, in the tissue repair assembly, the longitudinal passage in the suture is at least partially received in the first longitudinal bore in the first deformable tube anchor.

* * * * *